US009354224B2

(12) United States Patent
D'Andrea et al.

(10) Patent No.: US 9,354,224 B2
(45) Date of Patent: May 31, 2016

(54) METHODS AND COMPOSITIONS FOR THE DIAGNOSIS OF CANCER SUSCEPTIBILITIES AND DEFECTIVE DNA REPAIR MECHANISMS AND TREATMENT THEREOF

(71) Applicants: DANA-FARBER CANCER INSTITUTE, INC., Boston, MA (US); Oregon Health and Science University, Portland, OR (US)

(72) Inventors: Alan D. D'Andrea, Winchester, MA (US); Toshiyasu Taniguchi, Boston, MA (US); Edward A. Fox, Boston, MA (US); Cynthia Timmers, Columbus, OH (US); Markus Grompe, Portland, OR (US)

(73) Assignees: Dana-Farber Cancer Institute, Inc., Boston, MA (US); Oregon Health and Science University, Portland, OR (US)

( * ) Notice: Subject to any disclaimer, the term of this patent is extended or adjusted under 35 U.S.C. 154(b) by 0 days.

(21) Appl. No.: 14/520,055

(22) Filed: Oct. 21, 2014

(65) Prior Publication Data
US 2016/0084821 A1 Mar. 24, 2016

Related U.S. Application Data

(63) Continuation of application No. 13/654,243, filed on Oct. 17, 2012, now abandoned, which is a continuation of application No. 12/749,419, filed on Mar. 29, 2010, now abandoned, which is a continuation of application No. 10/165,099, filed on Jun. 6, 2002, now abandoned, which is a continuation-in-part of application No. 09/998,027, filed on Nov. 2, 2001, now abandoned.

(60) Provisional application No. 60/245,756, filed on Nov. 3, 2000.

(51) Int. Cl.
G01N 33/53 (2006.01)
G01N 33/50 (2006.01)

(52) U.S. Cl.
CPC ........ G01N 33/5011 (2013.01); G01N 2333/47 (2013.01); G01N 2800/52 (2013.01)

(58) Field of Classification Search
None
See application file for complete search history.

(56) References Cited

U.S. PATENT DOCUMENTS

| 5,252,479 | A | 10/1993 | Srivastava |
| 5,709,999 | A | 1/1998 | Shattuck-Eidens et al. |
| 5,710,001 | A | 1/1998 | Skolnick et al. |
| 5,776,925 | A | 7/1998 | Young et al. |
| 5,821,328 | A | 10/1998 | King et al. |
| 5,965,377 | A | 10/1999 | Adams et al. |
| 5,981,218 | A | 11/1999 | Rio et al. |
| 5,989,815 | A | 11/1999 | Skolnick et al. |
| 6,033,857 | A | 3/2000 | Tavtigian et al. |
| 6,037,129 | A | 3/2000 | Cole et al. |
| 6,056,690 | A | 5/2000 | Roberts |
| 6,124,104 | A | 9/2000 | Tavtigian et al. |
| 6,162,897 | A | 12/2000 | Skolnick et al. |
| 6,200,756 | B1 | 3/2001 | Herman et al. |
| 6,218,529 | B1 | 4/2001 | An et al. |
| 6,251,594 | B1 | 6/2001 | Gonzalgo et al. |
| 6,268,184 | B1 | 7/2001 | Gray et al. |
| 6,280,935 | B1 | 8/2001 | Macevicz |
| 6,281,010 | B1 | 8/2001 | Gao et al. |
| 6,287,557 | B1 | 9/2001 | Boursnell et al. |
| 6,287,772 | B1 | 9/2001 | Stefano et al. |
| 6,297,010 | B1 | 10/2001 | Stefano |
| 6,300,076 | B1 | 10/2001 | Koster |
| 6,303,379 | B1 | 10/2001 | Selden et al. |
| 6,331,393 | B1 | 12/2001 | Laird et al. |

FOREIGN PATENT DOCUMENTS

| WO | WO 89/10412 A1 | 11/1989 |
| WO | WO 91/09311 A1 | 6/1991 |
| WO | WO 93/07282 A1 | 4/1993 |
| WO | WO 95/00530 A1 | 1/1995 |
| WO | WO 02/36761 A2 | 5/2002 |

OTHER PUBLICATIONS

Alter. "Fanconi's Anemia and Malgnancies." Am. J. Hematol. 53(1996):99-110.
Bagby et al. "Cisplatin and the Sensitive Cell." Nat. Med. 9(2003):513-514.
Bodnar et al. "Extension of Life-Span by Introduction of Telomerase Into Normal Human Cells." Science. 279(1998):349-352.
Bowie et al. "Deciphering the Message in Protein Sequences:Tolerance to Amino Acid Substitions." Science. 247(1990):1306-1310.
Brunn et al. "Overexpression of a FANCD-EGFP Fusion Protein Leads to Accumulation in the Nucleus and Rapid Cell Death." Am. J. Hum. Genet. 65.4(1993):A183.
Brunn et al. "Identification of a Domain of the FANCD2 Protein Rhat is Toxic to Cells When Overexpressed." Am. J. Hum. Genet. 67.4, Suppl. 2(2000):181.
Chen et al. "Inactivation of Fac in Mice Produces Inducible Chromosomal Instability and Reduced Fertility Reminiscent of Fanconi Anaemia." Nat. Genet. 12(1996):448-451.

(Continued)

Primary Examiner — Laura B Goddard
(74) Attorney, Agent, or Firm — Cooley LLP; Ivor R. Elrifi; Cynthia A. Kozakiewicz

(57) ABSTRACT

Methods and compositions for the diagnosis of cancer susceptibilities, defective DNA repair mechanisms and treatments thereof are provided. Among sequences provided here, the FANCD2 gene has been identified, and probes and primers are provided for screening patients in genetic-based tests and for diagnosing Fanconi Anemia and cancer. The FANCD2 gene can be targeted in vivo for preparing experimental mouse models for use in screening new therapeutic agents for treating conditions involving defective DNA repair. The FANCD2 polypeptide has been sequenced and has been shown to exist in two isoforms identified as FANCD2-S and the monoubiquinated FANCD-L form. Antibodies including polyclonal and monoclonal antibodies have been prepared that distinguish the two isoforms and have been used in diagnostic tests to determine whether a subject has an intact Fanconi Anemia/BRCA pathway.

2 Claims, 50 Drawing Sheets

(56) References Cited

OTHER PUBLICATIONS

D'Andrea et al. "Molecular Biology of Fanconi Anemia: Implications for Diagnosis and Therapy." *Blood*. 90.5(1997):1725-1736.
D'Andrea et al. "The Fanconi Anaemia/BRCA Pathway." *Nat. Rev. Cancer*. 3(2003):23-34.
D'Andrea. "Fanconi Anaemia Forges a Novel Pathway." *Nat. Genet*. 14(1996):240-242.
de Winter et al. "Isolation of a cDNA Representing the Fanconi Anemia Complementation Group E Gene." *Am. J. Hum. Genet*. 67.5(2000):1306-1308.
de Winter et al. "The Fanconi Anaemia Group G Gene FANCG is Identical With XRCC9." *Nat. Genet*. 20(1990):281-283.
Dermer. "Another Anniversary for the War on Cancer." *Bio/Technol*. 12(1994):320.
Dijit et al. "Formation and Repair of Cisplatin-Induced Adducts to DNA in Cultured Normal and Repair-Deficient Human Fibroblasts." *Cancer Res*. 48(1988):6058-6062.
Drexler. "Recent Results on the Biology of Hodgkin and Reed-Sternberg Cells." *Leuk. Lymph*. 9(1993):1-25.
EMBL Database Accession No. AA172276, Dec. 24, 1996.
EMBL Database Accession No. AK022613, Sep. 29, 2000.
Ferrer et al. "FANCD2 Expression in Advanced Non-Small-Cell Lung Cancer and Response to Platinum-Based Chemotherapy." *Clin. Lung Cancer*. 6(2005):250-254.
Freshney. *Culture of Animal Cells, A Manual of Basic Technique*. New York: Alan R. Liss, Inc. (1983):4.
Garcia-Higuera et al. "Fanconi Anemia Proteins FANCA, FANC-C, and FANCG/XRCC9 Interact in a Functional Nuclear Complex." *Mol. Cell. Biol*. 19(1999):4866-4873.
Garcia-Higuera et al. "Interaction of the Fanconi Anemia Proteins and BRCA1 in a Common Pathway." *Mol. Cell*. 7(2001):249-262.
Garcia-Higuera et al. "Regulated Binding of the Fanconi Anemia Proteins, FANCA and FANCC." *Blood*. 93.4(1999):1430-1432.
Garcia-Higuera et al. "The Molecular and Cellular Biology of Fanconi Anemia." *Curr. Opin. Hematol*. 6.2(1999):83-88.
GenBank Accession No. BC000032, Jul. 15, 2006.
GenBank Accession No. NM_000135, May 28, 2011.
GenBank Accession No. NM_000136, Apr. 9, 2011.
GenBank Accession No. NM_021922, Apr. 9, 2011.
GenBank Accession No. NM_022725, Apr. 9, 2011.
GenBank Accession No. NM_033084, Jun. 4, 2011.
GenBank Accession No. U14680, Jun. 10, 2002.
GenBank Accession No. U33841, Nov. 29, 1995.
GenBank Accession No. U43746, Sep. 3, 1996.
Giangrande et al. "The A and B Isoforms of the Human Progesterone Receptor: Two Functionally Different Transcription Factors Encoded by a Single Gene." *Recent Prog. Horm. Res*. 54(1999):291-314.
Grompe et al. "Fanconi Anemia and DNA Repair." *Hum. Mol. Genet*. 10.20(2001): 2253-2259.
Haining et al. "Rapid Assessment of Fanconi Pathway Function: A New Diagnostic Approach to Fanconi Anemia." *Blood*. 96.11(2000):229a. (Abstract Only).
Hejna et al. "Localization of the Fanconi Anemia Complementation Group D Gene to a 200-kb Region on Chromosome 3p25.3." *Am. J. Hum. Genet*. 66.5(2000):1540-1551. (Abstract Only).
Jakobs et al. "Complementation Group Assignments in Fanconi Anemia Fibroblast Cell Lines From North America." *Somat. Cell Mol. Genet*. 23.1(1997):1-7.
Jakobs et al. "Immortalization of Four New Fanconi Anemia Fibroblast Cell Line by an Improved Procedure." *Somat. Cell Mol. Genet*. 22.2(1996):151-157.
Joenje et al. "Complementation Analysis in Fanconi Anemia: Assignment of the Reference FA-H Patient to Group A." *Am. J. Hum. Genet*. 67(2000):759-762.
Joenje et al. "Connecting Fanconi Anemia to BRCA1." *Nat. Med*. 7.4(2001):406-407.
Joenje et al. "Evidence for at Least Eight Fanconi Anemia Genes." *Am. J. Hum. Genet*. 61(1997):940-944.

Kachnic et al. "Fanconi Anemia Pathway Heterogeneity Revealed by Cisplatin and Oxaliplatin Treatments." *Cancer Lett*. 292(2010):73-79.
Kupfer et al. "A Patient-Derived Mutant Form of the Fanconi Anemia Protein, FANCA, is Defective in Nuclear Accumulation." *Exp. Hematol*. 27(1997):587-593.
Kupfer et al. "The Fanconi Anaemia Proteins, FAA and FAC, Interact to Form a Nuclear Complex." *Nat. Genet*. 17(1997):487-490.
Kupfer et al. "The Fanconi Anemia Polypeptide, FAC, Binds to the Cyclin-Dependent Kinase, cdc2." *Blood*. 90.3(1997):1047-1054.
Morgan et al. "High Frequency of Large Intragenic Deletions in the Fanconi Anemia Group A. Gene." *Am. J. Hum. Genet*. 65(1999):1330-1341.
Nakanishi et al. "Interaction of FANCD2 and NBS1 in the DNA Damage Response." *Nat. Cell Biol*. 4(2002):913-920.
Scully et al. "Genetic Analysis of CRCA1 Function in a Defined Tumor Cell Line." *Mol. Cell*. 4.6(1999):1093-1099.
Sekine et al. "Localization of a Novel Susceptibility for Familial Ovarian Cancer to Chromosome 3p22-25." *Hum. Mol. Genet*. 10(2001):1421-1429.
Slamon et al. "Studies of the HER2/neu Protoncogene in Human Breast Cancer." *Cancer Cells 7-Molecular Diagnostics of Human Cancer*. Furth et al., eds. Cold Spring Harbor, New York: Cold Spring Harbor Lab. Press. 7(1989):371-384.
Slamon et. al. "Human Breast Cancer: Correlation of Relapse and Survival With Amplification of the HER-2/neu Oncogene." *Science*. 235(1987):177-182.
Taniguchi et al. "DNA Damage-Induced Association of the Fanconia Anemia Protein, FANCD2, with BRCA1 Nuclear Foci." *Blood*. 96.11(2000):559a. (Abstract Only).
Timmers et al. "Positional Cloning of a Novel Fanconi Anemia Gene, FANCD2." Mol. Cell. 7(2001):241-248.
Timmers et al. "Positional Cloning of the Fanconi Anemia Complementation Group D (FANCD) Gene." *Am. J. Hum. Genet*. 65.4(1999):A20. (Abstract Only).
Tockman et al. "Considerations in Bringing a Cancer Biomarker to Clinical Application." *Cancer Res*. 52(1992):2711s-2718s.
Todd et al. "Homozygous Deletions of Human Chromosome 3p in Lung Tumors." *Cancer Res*. 57(1997):1344-1352.
Toshiyasu et al. "DNA Damage-Induced Association of the Fanconi Anemia Protein, FANCD2, with BRCA1 Nuclear foci." *Blood*. 96.11(2000):559A. (Abstract Only).
van den Hoff et al. "Electroporation in 'Intracellular' Buffer Increases Cell Survival." *Nucl. Acids Res*. 20.11(1992):2902.
Wang et al. "BASC, a Super Complex of BRCA1-Associated Proteins Involved in the Recognition and Repair and Aberrant DNA Structures." *Genes Dev*. 14(2000):927-939.
Whitney et al. "Germ Cell Defects and Hematopoietic Hypersensitivity to Gamma-Interferon in Mice with a Targeted Disruption of the Fanconi Anemia C Gene." *Blood*. 88(1996):49-58.
Whitney et al. "Microcell Mediated Chromosome Transfer Maps the Fanconi Anaemia Group D Gene to Chromosome 3p." *Nat. Genet*. 11(1995):341-343.
Wilson et al. "The Chinese Hamster FANCG/XRCC9 Mutant NM3 Fails to Express the Monoubiquitinated Form of the FANCD2 Protein, is Hypersensitive to a Range of DNA Damaging Agents and Exhibits a Normal Level of Spontaneous Sister Chromatid Exchange." *Carcinogenesis*. 22.12(2001):1939-1946.
Yamashita et al. "The Fanconi Anemia Pathway Requires FAA Phosphorylation and FAA/FAC Nuclear Accumulation." *PNAS*. 95(1998):13085-13090.
Yamashita et al. "The Fanconi Anemia Polypeptide FACC is Localized to the Cytoplasm." *PNAS*. 91(1994):6712-6716.
Yang et al. "Targeted Disruption of the Murine Fanconi Anemia Gene, Fancg/Xrcc9." *Blood*. 98(2001):3435-3440.
Yokota. "Illustrated Series in Medicine & Science: Solves the Mechanism of Canceration." *Yodosha Co., Ltd*. 2(1998):70-76.
Zellner et al. "Disparity in Expression of Protein Kinase C α in Human Glioma Versus Glioma-Derived Primary Cell Lines: Therapeutic Implications." *Clin. Can. Res*. 4(1998):1797-1802.

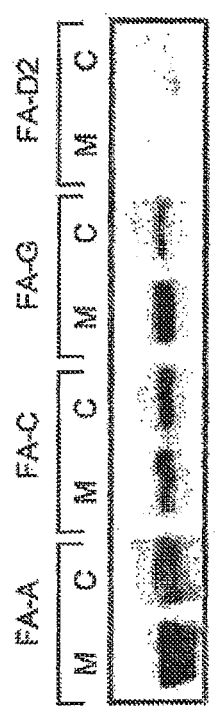
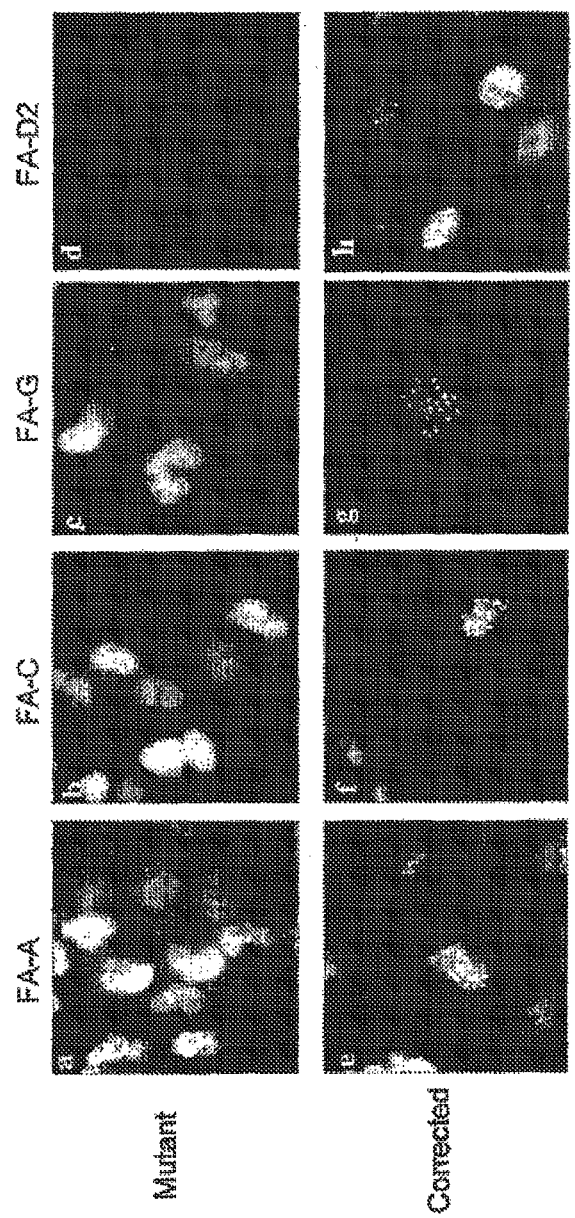
FIG. 2A
FIG. 2B

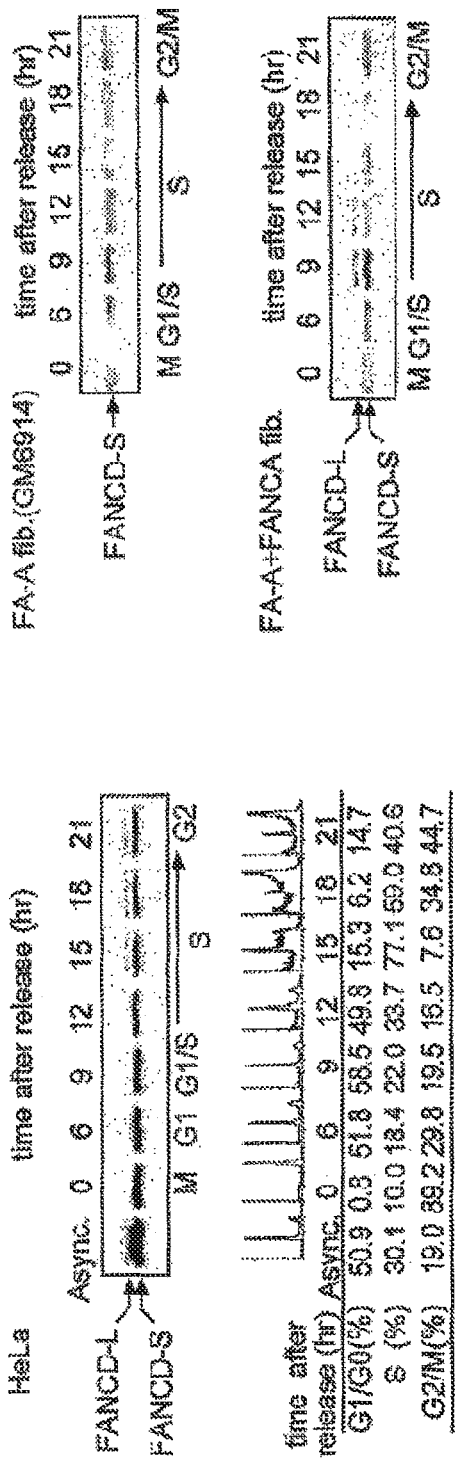
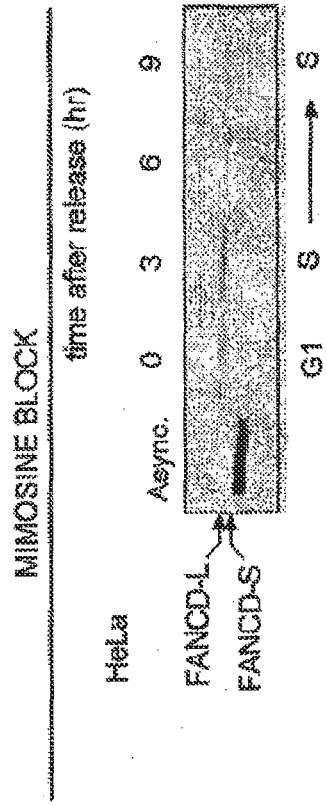
FIG. 3B
FIG. 3C

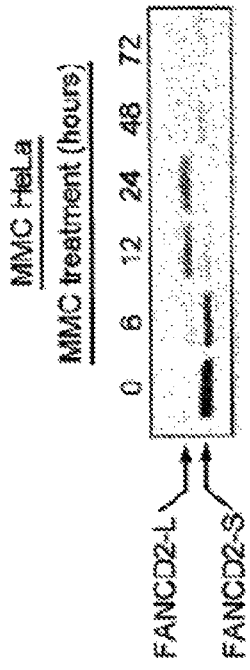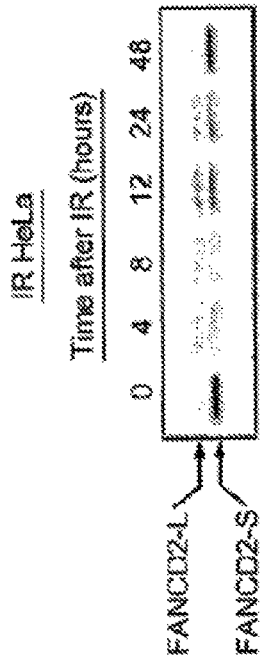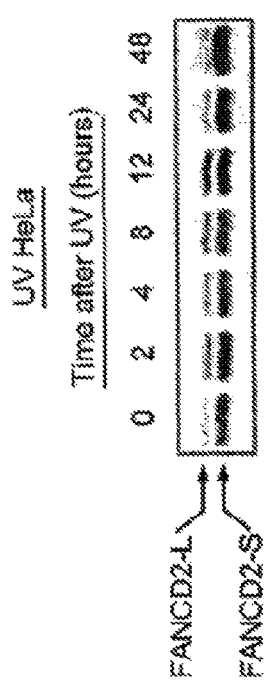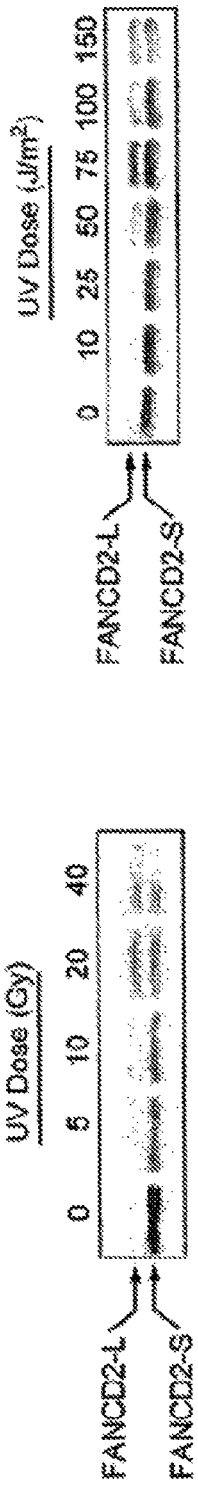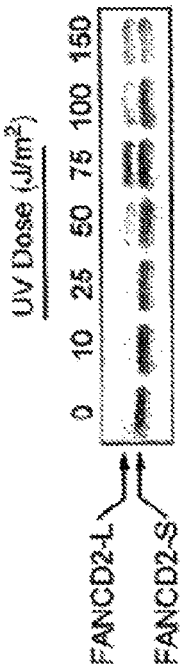
FIG. 4A
FIG. 4B
FIG. 4C
FIG. 4D
FIG. 4E

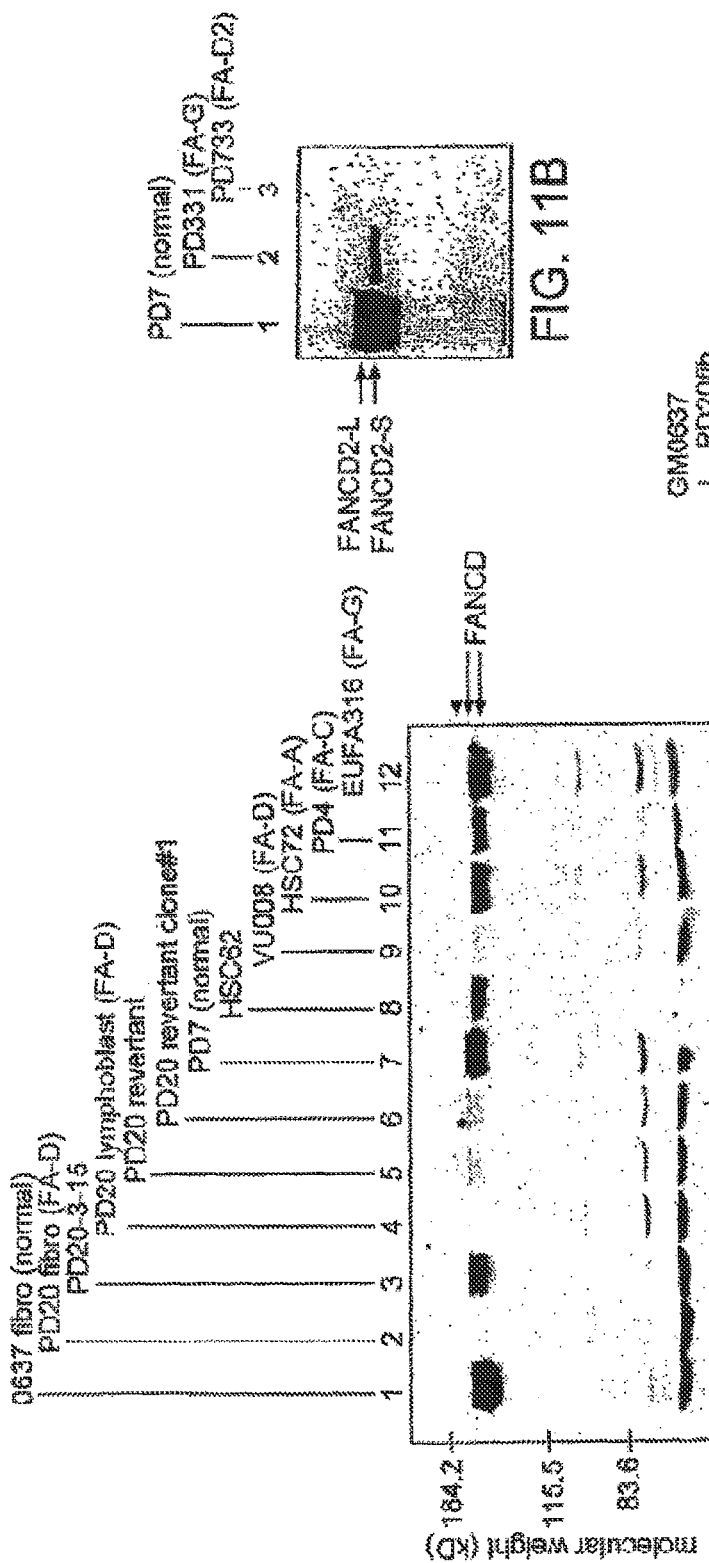
FIG. 11A
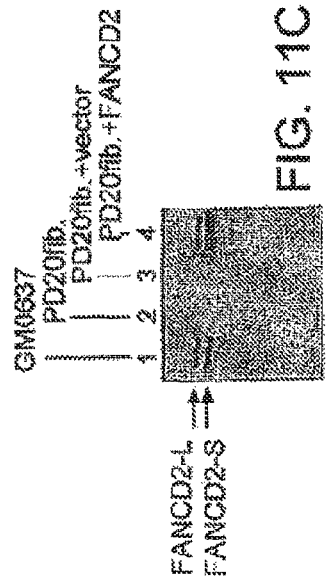
FIG. 11B
FIG. 11C

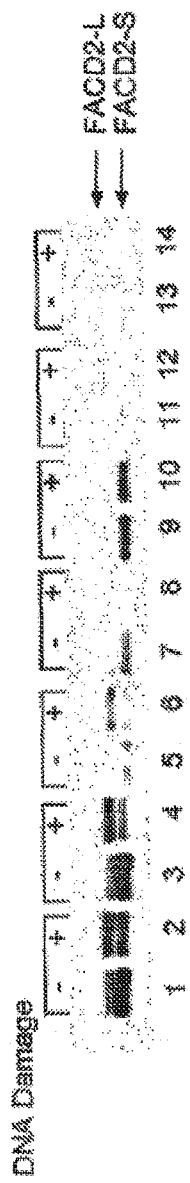

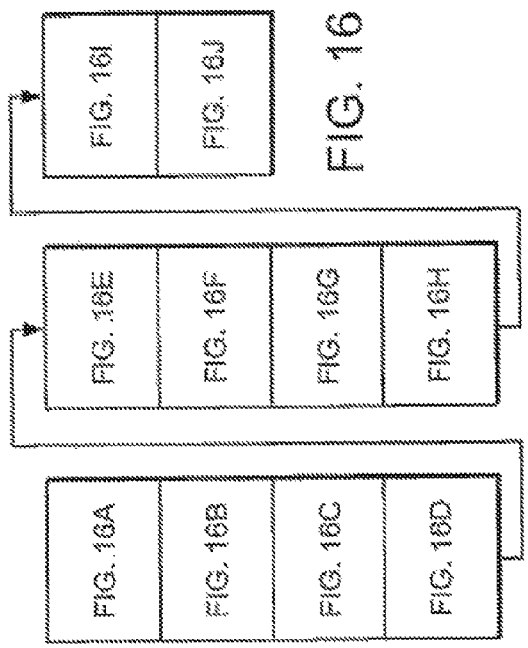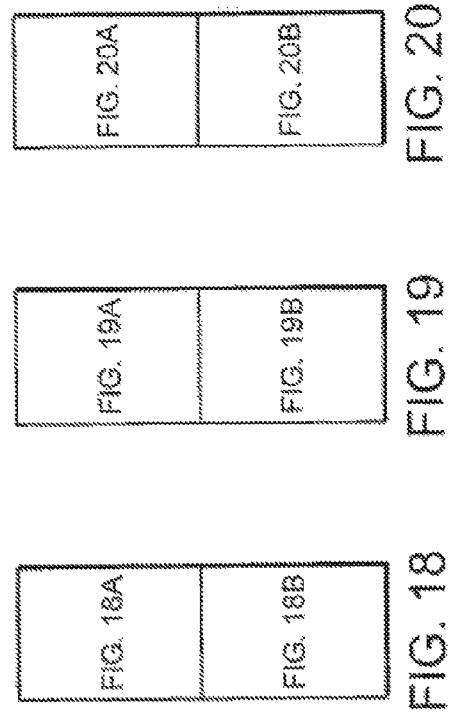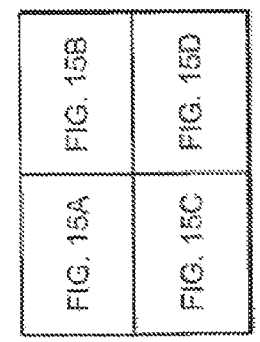

SEQ ID NOS: 4-5

FANCD cDNA SEQUENCE

```
-53       5'-TCGAAAACTACGGGGCGGCGACGGCTTCTCGGAAGTAATTAAGTGCACAAGACATTGGTCAAA  -1

1 ATG GTT TCC AAA AGA AGA CTG TCA AAA TCT GAT GAT AAA GAG AGC CTC ACA GAA GAT CCC   50
4-1 M   V   S   K   R   R   L   S   K   S   D   D   K   E   S   L   T   E   D   A    20

51 TCC AAA ACC AGG AAG CAA CCA CTT TCC AAA AAG ACA AAG AAA TCT CAT ATT GCT AAT GAA  120
 21 S   K   T   R   K   Q   P   L   S   K   K   T   K   K   S   H   I   A   N   E     40

121 GTT CAA GAA AAT GAC AGC ATC TTT GTA AAG CTT CTT AAG ATA TCA GGA ATT ATT CTT AAA  180
 41 V   Q   E   N   D   S   I   F   V   K   L   L   K   I   S   G   I   I   L   K     60
```

| | | | | | | | | | | | | | | | | | | | |
|---|---|---|---|---|---|---|---|---|---|---|---|---|---|---|---|---|---|---|---|
|1801|AAC|CTG|AGC|GAT|GAG|CAG|TGC|ACA|CAG|GTG|ACC|TCC|TTG|TTG|CAG|GTT|CAT|TCC|TGC|1860|
|601|N|L|S|D|E|Q|C|T|Q|V|T|S|L|L|Q|V|H|S|C|620|
|1861|AGT|GAG|CAG|TCT|CCT|CAG|GCC|TCT|CAG|GCC|CTT|GCA|TAC|TAT|GAT|GAA|TTT|GCC|ATC|CAA|1920|
|621|S|E|Q|S|P|Q|A|S|Q|A|L|A|Y|Y|D|E|F|A|I|Q|640|
|1921|CAT|GAA|AAG|CTG|GAT|CCA|AAA|GCC|CTG|GAA|TGG|GTT|GAA|AAG|ATG|TGG|AAT|CTG|ATC|AAT|1980|
|641|H|E|K|L|D|P|K|A|L|E|W|V|E|K|M|W|N|L|I|N|660|
|1981|CAG|GAT|GCC|TTC|GTA|GTG|GAC|TCC|TGT|GTT|CCG|GAA|GGT|GAC|TTT|CCA|AAT|GAT|CCT|GTG|2040|
|661|Q|D|A|F|V|V|D|S|C|V|P|E|G|D|F|P|N|D|P|V|680|
|2041|AAA|GCA|CTG|TAC|CGA|CTG|GAG|TAC|GAC|ACT|CAG|GAT|GGG|ATT|GCC|AAA|ACA|CAG|CTG|AGC|2100|
|681|K|A|L|Y|R|L|E|Y|D|T|Q|D|G|I|A|K|T|Q|L|S|700|
|2101|CCG|CTG|TGT|TCT|CAG|GAC|TTT|GCA|AAA|GAT|GGG|GGT|CCG|GTC|ACC|TCA|CAG|GAA|TCA|2160|
|701|P|L|Y|S|Q|D|F|A|K|D|G|G|P|V|T|S|Q|E|S|720|
|2161|GGC|CAA|AAA|TTC|CTC|CCT|CCG|TGC|CTC|CCT|CCC|TAT|TTC|CGG|TTA|CTC|AGA|CTT|TGT|2220|
|721|G|Q|K|F|L|V|S|P|L|A|P|Y|F|R|L|L|R|L|C|740|
|2221|GTG|CAG|AGA|CAG|GAT|AAC|TGA|GAG|ATT|GAT|GCC|CTA|CTA|GAT|TGT|CCT|ATA|2280|
|741|V|E|R|Q|M|N|E|E|I|D|G|L|L|D|C|F|I|760|
|2281|TTC|CAT|ACT|GAC|CTG|AAG|CCT|GGA|GAG|AAG|TTC|GAG|CCT|GGA|ACG|TGT|CGT|AAA|GAG|TCA|2340|
|761|F|H|T|D|L|K|P|G|E|K|F|E|R|G|M|S|A|K|S|780|

FIG. 16E

```
2341 TTC ATG TGT TCT CTC ATA TTT CTT ACT CTC AAC TGG TTC CGA GAG ATT GTA AAT GCC TTC 2400
 781 F   M   C   S   L   I   F   L   T   L   N   W   F   R   E   I   V   N   A   F    800

2401 TGC CAG GAA ACA TCA GCT GAG ATG AAG GGG CTC ACT CGG TTA AAG CAC ATT GTA 2460
 801 G   Q   E   T   S   A   E   M   K   G   L   T   R   L   K   H   I   V    820

2461 GAA TTG CAA ATA ATC CTG GAA AAG TAC TTG GCA GTC ACC CCA GAC GTC CCT CTT 2520
 821 E   L   Q   I   I   L   E   K   Y   L   A   V   T   P   D   V   P   L    840

2521 GGA AAC TTT GAT GTG GAA ACT TTA GAT ATA ACA CGT CAT ACT GCT ACT GTT TCA GCA 2580
 841 G   N   F   D   V   E   T   L   D   I   T   R   H   T   A   T   V   S   A    860

2581 AAA ATC AGA AAG GCA AAA ATA GAA AGG AAA ACA GAT GGC AGC AAG ACA TCC 2640
 861 K   I   R   K   A   K   I   E   R   K   T   D   G   S   K   T   S    880

2641 TCT GAC ACA GTT TCA GAA GAG AAA AAT TCA GAA TGT GAC CCT ACG CCA TCA CAT AGA 2700
 881 S   D   T   V   S   E   E   K   N   S   E   C   D   P   T   P   S   K   R    900

2701 GGC CAG CTA AAG AAG GAG TTC ACA AAG TCA GAA TTG TTA CTA CAT AAT 2760
 901 G   Q   L   K   K   E   T   G   K   S   E   L   L   L   H   N    920

2761 TCC CAT GCT TTT TTC CGA GAG CTG GAC ATT CAG GTC TCT ATT CTA CAT TGT GGA CTT 2820
 921 S   H   A   F   F   R   E   L   D   I   Q   V   S   I   L   H   C   G   L    940

2821 GTG ACG AAG TTC ATC TTA GAT ACT GAA ATG CAC ACT GAA GCT ACA GAA GTT GTG CAA CTT 2880
 941 V   T   K   F   I   L   D   T   E   M   H   T   E   A   T   E   V   V   Q   L    960
```

FIG. 16F

```
2881 GGG CCC CCT GAG CTG CTT TTC TTG GAA GAT CTC TCC CAG AAG CTG GAG AGT ATG CTG  2940
 961  G   P   P   E   L   L   F   L   E   D   L   S   Q   K   L   E   S   M   L    980

2941 ACA CCT CCT ATT GCC AGG AGA GTC CCC TTT CTC AAG AAC AAA GAA AGC CGG AAT ATT GGA 3000
 981  T   P   P   I   A   R   R   V   P   F   L   K   N   K   E   S   R   N   I   G  1000

3001 TTC TCA CAT CTC CAA CAG AGA TCT GCC CAA GAA ATT GTT CAT TGT GTT CAA CTG CTG  3060
1001  F   S   H   L   Q   Q   R   S   A   Q   E   I   V   H   C   V   Q   L   L   1020

3061 ACC CAA ATG TGT AAC CAC CTG GAG AAC ATT CAC AAC TAC TTT CAG TGT TTT GCT GCT GAG 3120
1021  T   Q   M   C   N   H   L   E   N   I   H   N   Y   F   Q   C   F   A   A   E  1040

3121 AAT CAC CGA GTT GAT GGA CCA CAG AAA GTG AAA CAG GTT CAG GGA ATA ATG TCT TCC  3180
1041  N   H   R   V   D   G   P   Q   N   V   K   Q   V   Q   G   I   M   S   S   1060

3181 TGC TAT CAG AGG CTG CTG CAG ATT TTT CAT GCC CTT TTT GCT TGG AGT CGA CTT CAA  3240
1061  C   Y   Q   R   L   L   Q   I   F   H   A   L   F   A   W   S   R   L   Q   1080

3241 CCT GAA AAT CAG AAT TTA TCA GAA CAG CCT CTT AGC GCC CTT CAT AGC AGT ATC CAG AAA CAG 3300
1081  P   E   N   Q   N   L   S   E   Q   P   L   S   A   L   H   S   S   R   L   Q  1100

3301 GGA GAA CAG AGC CAG CCT TTG GAG GAA CTC CTC CAG CAG CAT CAT TAC TTC CAG AAT  3360
1101  G   E   Q   S   Q   P   L   E   E   L   L   Q   Q   H   Y   F   Q   N   1120
```

SEQ ID NOS: 187-188

FANCD-S,ORF,s  GGAGAACACAGCAGCCAGCCTTGAGGAACTACTCAGCGAGGCGAGCGTCCATT
FANCD cDNA,OR  GGAGAACACAGCAGCCAGCCTTGAGGAACTACTCAGCGAGGCGAGCGTCCATT
                3310      3320      3330      3340      3350

FANCD-S,ORF,s  TTTGATCGTTATTTGCAGAAATCAACAGCTTCTGCTCAGAACAAGAA
FANCD cDNA,OR  TTTGATCGTTATTTGCAGAAATCAACAGCTTCTGCTCAGAACAAGAA
                3420      3430      3440      3450      3460

FANCD-S,ORF,s  AGAGCAACATCCTAATGACCAGTTCATGCTTGCTCTGTATCTACCT
FANCD cDNA,OR  AGAGCAACATCCTAATGACCAGTTCATGCTTGCTCTGTATCTACCT
                3530      3540      3550      3560      3570

FANCD-S,ORF,s  CTGATCAACTCTCCTAAGATGCATTCTTCCACATTCCTACACTGA
FANCD cDNA,OR  CTGATCAACTCTCCTAAGATGCATTCTTCCACATTCCTACACTGA
                3640      3650      3660      3670      3680

```
FANCD-S,ORF,s  AAAAATTGAGCCTGGCAGCAGACTCGCAGCAGATTCATGAAGAG
                3750      3760      3770      3780      3790
FANCD,cDNA,OR  AAAAATTGAGCCTGGCAGCAGACTCGCAGCAGATTCATGAAGAG

FANCD-S,ORF,s  TATTTGATAGTCATCCTGTTCGCATGTATGTTTGAAGTATGGCGGTGT
                3860      3870      3880      3890      3900
FANCD,cDNA,OR  TATTTGATAGTCATCCTGTTCGCATGTATGTTGAAGTATGGCGGCT

FANCD-S,ORF,s  CGGGAAGATGTTCTGAGCTTACTGGAAACCTTCCAGTTGCACACAGGC
                3970      3980      3990      4000      4010
FANCD,cDNA,OR  CGGGAAGATGTTCTGAGCTTACTGGAAACCTTCCAGTTGCACACAGGC

FANCD-S,ORF,s  GCCCTCTGCTCAAAAGACCCTGGAACTTTTGTTTGCAGAGTCAAAGCT
                4080      4090      4100      4110      4120
FANCD,cDNA,OR  GCCCTCTGCTCAAAAGACCCTGGAACTTTTGTTTGCAGAGTCAAAGCT
```

```
FANCD-S, ORF, s  TGCAGGCGTGAAGAGATTAAGTCCCAAAATTCCAGGAGAGCACAGCAGA
FANCD cDNA, OR   TGCAGGCGTGAAGAGATTAAGTCCCAAAATTCCAGGAGAGCACAGCAGA
                      4190      4200      4210      4220      4230

FANCD-S, ORF, s  GAAGACGCGTAGTAGTTCTGCGCTGATGGTTCGTTTTTTGTGTTT
FANCD cDNA, OR   GAAGACGGAGTAGTTCTGGAGAAAAGGAGCAAGATAGTGATAGTT
                      4300      4310      4320      4330      4340

FANCD-S, ORF, s  
FANCD cDNA, OR   CAAAACCCACCAGTCTGGCACTCGATCTTGCATTTCCTTCCATAA
                                 4410                      4392
                                                           4416
```

FIG. 17 (CONT.)

TGAGAGTGAGGATGACATGTCATCCCAGGCCTCCAAGAGCAAGCCACTCGAGGTATCTCTA
4230        4240        4250        4260        4270        4280        4290
TGAGAGTGACGATGACATGTCATCCCAGGCCTCCAAGAGCAAGCCACTCGAGGTATCTCTA 4290
TGAGAGTGAGGATGACATGTCATCCCAGGCCTCCAAGAGCAAGCCACTCGAGGTATCTCTA 4290

TTCGTTCGTGCGTTGGGACTTGGGCTACTTTTTTTCTGTGTTTCTAXXXXXXXX
4340        4350        4360        4370        4380        4390        4400
ATCATGACTTCGATTAGACCCAGATAAATTGTGCCCTCTTCTGTGTCTCAA           4392
TAAGTTGGTTGGAGAGCAGAACTTTAGTTTATTGCCTACTTGTGCAATGCTTCTATGCCCATT 4400

FIG. 17 (CONT.)

tagaatcgaa aactacgggc ggcgacggct tctcggaagt aattaagtg cacaagacat
tggtcaaaat ggtttccaaa agaagactgt caaaatctga ggataaagag agcctgacag
aagatgcctc caaaaccagg aagcaaccac ttccaaaaa gacaaagaaa tctcatattg
ctaatgaagt tgaagaaaat gacagcatct ttgtaaagct tcttaagata tcaggaatta
ttcttaaaac gggagagagt cagaatcaac tagctgtgga tcaaatagct ttccaaaaga
agctctttca gaccctgagg agacaccctt cctatcccaa aataatagaa gaatttgtta
gtggcctgga gtcttacatt gaggatgaag acagtttcag gaactgcctt ttgtcttgtg
agcgtctgca ggatgaggaa gccagtatgg gtgcatctta ttctaagagt ctcatcaaac
tgcttctgag gattgacata ctgcagcctg ccattatcaa aaccttattt gagaagttgc
cagaatattt tttgaaaaac aagaacagtg atgaaatcaa catacctcga ctcattgtca
gtcaactaaa atggcttgac agagtgtgg atggcaagga cctcaccacc aagatcatgc
agctgatcag tattgctcca gagaacctgc agcatgacat catcaccagc ctacctgaga
tcctagggga ttcccagcac gctgatgtgg ggaagaact cagtgaccta ctgatagaga
atacttcact cactgtccca atcctggatg tccttcaag cctccgactt gacccaaact
tcctattgaa ggttcgccag ttggtgatgg ataagttgtc gtctattaga ttggaggatt
tacctgtgat aataaagttc attcttcatt ccgtaacagc catggataca cttgaggtaa
tttctgagct tcggagaag ttggatctga agcattgtgt ttgccatca cggtacagg
cttcccaagt aaagttgaaa agtaaaggac gagcaagttc ctcaggaaat caagaaagca
gcggtcaagg ctgtattatt ctcctcttg atgtaatana gtcagctatt agatatgaga
aaaccattc agaagcctgg attaaggcaa ttganaacac tgcctcagta tctgaacaca
aggtgtttga cctggtgatg ctttcatca tctatagcac caatactcag acaaagnagt
acattgacag ggtgctaaga aataagatcc gatcaggctg cattcaagaa cagctgctcc
agagtacatt ctctgttcat tacttagttc ttaaggatat gtgttcatcc attctgtcgc
tggctcagag tttgcttcac tctctagacc agagtataat ttcattggc agtctcctat
acaaatatgc attaagttt ttgacacgt actgccagca ggaagtggtt ggtgcttag
tgacccatat ctgcagtggg aatgaagctg aagttgatac tgccttagat gtccttctag
agttggtagt gttaaaccca tctgctatga tgatgaatgc tgtctttgta aagggcatt
tagattatct ggataacata tcccctcagc aaatacgaaa actctctat gtctcagca
cactggcatt tagcaaacag aatgaagcca gcagccacat ccaggatgac atgcacttgg
tgataagaaa gcagctctct agcacacgta tcaagtacaa gctcattggg attattggtg
ctgtgaccat ggctggcatc atgcggcag acagaagtga atcacctagt tgacccaag
agagagccaa cctgagcgat gagcagtgca cacaggtgac ctccttgttg cagttggttc
attcctgcag tgagcagtct cctcaggcct ctgactttta ctatgatgaa tttgccaacc
tgatccaaca tgaaaagctg gatccaaaag ccctggaatg ggttgggcat accatctgta
atgatttcca ggatgcctc gtagtggact cctgtgttgt tccggaaggt gacttccat
ttcctgtgaa agcactgtac ggactggaag aaatacgacac tcaggatgg attgccataa
acctcctgcc gctgctgttt tctcaggact ttgcaaaaga tggggtccg gtgacctcac
aggaatcagg ccaaaaattg gtgtctccgc tgtgcctggc tccgtattc cggttactga
gactttgtgt ggagagacag cataacggaa acttggagga gattgatggt ctactagatt
gtcctatatt cctaactgac ctggagcctg gagagaagtt ggagtccatg tctgctaaag
agcgttcatt catgtgttct ctcatattc ttactctcaa ctggttccga gagattgtaa
atgccttctg ccaggaaaca tcacctgaga tgaagggaa ggtgctcact cggttaaagc
acattgtaga attgcaaata atcctggaaa agtactgggc agtcacccca gactatgtcc
ctcctcttgg aaactttgat gtgggaaactt tagatataac acctcatact gttactgcta

FIG. 18A ttcagcaaaa aatcagaaag aaaggaaaaa tagaaaggaa acaaaaaaca gatggcagca
agacatcctc ctctgacaca ctttcagaag agaaaaattc agatgtgac cctacgccat
ctcatagagg ccagctaaac aaggagttca cagggaagga agaaaagaca tcattgttac
tacataattc ccatgctttt ttcgagagc tggacatga ggtcttctct attctacatt
gtggacttgt gacgaagtc atcttagata ctgaaatgca cactgaagct acagaagttg
tgcaacttgg gccccctgag ctgcttttct tgctggaaga tctctcccag aagctggaga
gtatgctgac acctcctatt gccaggagag tccccttct caagaacaa ggaagccgga
atattggatt ctcacatctc caacagagat ctgcccaaga aattgttcat tgtgttttc
aactgctgac cccaatgtgt aaccacctgg agaacattca caactatttt cagtgtttag
ctgctgagaa tcacggtgta gttgatggac caggagtgaa agttcaggag taccacataa
tgtcttcctg ctatcagagg ctgctgcaga ttttcatgg gcttttgct tggagtggat
tttctcaacc tgaaaatcag aatttactgt attcagccct ccatgtcctt agtagccgac
tgaaacaggg agaaacacagc cagcctggga aggaactact cagccagagc gtccattact
tgcagaattt ccatcaaagc attcccagtt tccagtgtgc tcttatctc atcagactt
tgatggttat tttggagaaa tcaacagctt ctgctcagaa caaagaaaaa attgcttccc
ttgccagaca attcctctgt cgggtgtggc caagtgggga taagagaag agcaacatct
ctaatgacca gctccatgct ctgctctgta tctacctgga gcacacagag agcattctga
aggccataga ggagattgct ggtgttggtg tccagaact gatcaactct cctaaagatg
catcttcctc cacattccct acactgacca ggcatacttt tgttgttc ttccgtgtga
tgatggctga actagagaag acggtgaaaa aaattgagcc tggcacagca gcagctcgc
agcagattca tgaagagaaa ctccctctact ggaacatggc tgttcgagac ttcagtatcc
tcatcaactt gataaaggta tttgatagtc a tcctgttct gcatgtatgt ttgaagtatg
ggcgtctctt tgtggaagca tttctgaagc aatgtatgcc gctcctagac ttcagtttta
gaaaacaccg ggaagatgtt ctgagcttac tggaaaactt ccagttggac acaaggctgc
ttcatcacct gtgtgggcat tccaagattc accaggacac gagactcacc caacatgtgc
ctctgctcaa aaagaccctg gaac tttag tttgcagagt caaagctatg ctcactctca
acaattgtag agaggcttc tggctggaca atctaaaaaa ccgggacttg cagggtgaag
agattaagtc ccaaaattcc caggagagca cagcagatga gagtgaggat gacatgtcat
cccaggcctc caagagcaaa gccactgagg tatctctaca aaaccaccca gagtctggca
ctgatggttg cattttg tta attgttctaa gttggtggag cagaacttg cctacttatg
ttattgtca aatgcttcta tgcccatttc cattccctc ataacagctt ctgtgcttat
ataattttg ggacccaagaa gaaacaaaga cacaatctta gaatcactcc tgagtatctc
gagtgtggc attgttata gagttgacaa ttttctgcat tatagcctct cattttccat
gaattcatat ctgaaaccat ttagaaggg agaagtcatc gaagtatttt ctgagtgtg
agaagaatga gttaaaccat ttaaacacat ttgaaacata caaaaataga aatgtgaaag
cattggtga aagccaaagc acagagtcag aagctgccac cttagagaac tgaaataaaa
atagaagttc ttacgctttt ttgtggtaca gatgcttcg acaatttaaa gaaagctaaa
taaaaatgta gacatggctg gcgcagtggc tcatgcttgt aatcctagca ctttgagg
ccaaggtagg aggattgctt gagtccggga gctcaaggca agctgcaca acataacaag
accctatctc cacaaaaaaa atgaaaaata aacctgggtg cggtggctca cacctgtaat
cccagcactt tgggaggccg atgtgggcag atcacaaggt caggagttca agaccagcct
ggccaacata gtgaaacccc atctctactg aaaatacaaa aattagctgg gtgtggtggc
acgtgcctgt tatctcagct acttgggaag ctga

FIG. 18B tcgaaaacta cggggggcga cggcttctcg gaagtaattt aagtgcacaa gacattggtc
aaaatggttt ccaaaagaag actgtcaaaa tctgaggata aagagagcct gacagaagat
gcctccaaaa ccaggaagca accacttcc aaaaagacaa agaaatctca tattgctaat
gaagttgaag aaaatgacag catctttgta aagcttctta agatatcagg aattattctt
aaaacgggag agagtcagaa tcaactagct gtggatcaaa tagctttcca aaagaagctc
ttcagaccc tgaggagaca cccttcctat cccaaaataa tagaagaatt tgttagtggc
ctggagtctt acattgagga tgaagacagt ttcaggaact gcctttgtc ttgtgagcgt
ctgcaggatg aggaagccag tatgggtgca tctatatcta agagtctcat caaactgctt
ctggggattg acatactgca gcctgccatt atcaaaacct tatttgagaa gttgccagaa
tattttttg aaaacaagaa cagtgatgaa atcaacatac ctcgactcat tgtcagtcaa
ctaaaatggc ttgacagagt tgtggatggc aaggacctca ccaccaagat catgcagctg
atcagtattg ctccagagaa cctgcagcat gacatcatca ccagcctacc tgagatccta
ggggattccc agcacgctga tgtgagggaaa gaactcagtg acctactgat agagaatact
tcactcactg tcccaatcct ggatgtcctt tcaagcctcc gacttgaccc aaacttccta
ttgaaggttc gccagttggt gatggataag ttgtcgtcta ttagattgga ggatttacct
gtgataataa agttcattct tcattccgta acagccatgg atacacttga ggtaatttct
gagcttcggg agaagttgga tctgcagcat tgtgttttgc catcacggtt acaggcttcc
caagtaaagt tgaaaagtaa aggacgagca agttcctcag gaaatcaaga aagcagcggt
cagagctgta ttattctcct ctttgatgta ataaagtcag ctattagata tgagaaaacc
attcagaag cctggattaa ggcaattgaa aacactgcct cagtatctga acacaaggtg
tttgacctgg tgatgctttt catcatctat agcaccaata ctcagacaaa gaagtacatt
gacagggtgc taagaaataa gattcgatca ggctgcattc aagaacagct gctccagagt
acattctctg ttcattact agttcttaag gatatgtgtt catccattct gtcgctggct
cagagtttgc ttcactctct agaccagagt ataatttcat ttggcagtct cctatacaaa
tatgcatta agttttttga cacgtactgc cagcaggaag tggttggtgc cttagtgacc
catatctgca gtgggaatga agctgaagtt gatactgcct tagatgtcct tctagagttg
gtagtgttaa acccatctgc tatgatgatg aatgctgtct ttgtaaaggg catttagat
tatctggata acatatcccc tcagcaaata cgaaaactct tctatgttct cagcacactg
gcatttagca aacagaatga agccagcagc cacatccagg atgacatgca cttggtgata
agaaagcagc tctctagcac cgtattcaag tacaagctca ttgggattat tggtgctgtg
accatggctg gcatcatggc ggcagacaga agtgaatcac ctagtttgac ccaagagaga
gccaacctga gcgatgagca gtgcaacacag gtgacctcct tgttgcagtt ggttcattcc
tgcagtgagc agtctcctca ggcctctgca cttactatg atgaatttgc caacctgatc
caacatgaaa agctggatcc aaaagccctg gaatgggttg ggcataccat ctgtaatga
ttccaggatg cctcgtagt ggactccgt gttgttccgg aaggtgactt tccattcct
gtgaaagcac tgtacggact ggaagaatac gacactcagg atgggattgc cataaacctc
ctgccgctgc tgtttctca ggactttgca aaagatgggg gtccggtgac ctcacaggaa
tcaggccaaa aattggtgtc tccgctgtgc ctggctccgt atttccggtt actgagactt tgtgtggaga gacagcataa cggaaacttg gaggagattg atggtctact agattgtcct
atattcctaa ctgacctgga gcctggagag aagttggagt ccatgtctgc taaagagcgt
tcattcatgt gttctctcat atttcttact ctcaactggt tccgagagat tgtaaatgcc
ttctgccagg aaacatcacc tgagatgaag gggaaggtgc tcactcggtt aaagcacatt
gtagaattgc aaataatcct ggaaaagtac ttggcagtca cccagacta tgtccctcct
cttggaaact ttgatgtgga aactttagat ataacacctc atactgttac tgctatttca
gcaaaaatca gaaagaaagg aaaaatagaa aggaaacaaa aaacagatgg
cagcaagaca tcctcctctg acacactttc agaagagaaa aattcagaat gtgacctac
gccatctcat agaggccagc taaacaagga gttcacaggg aaggaagaaa agacatcatt
gttactacat aattcccatg ctttttccg agagctggac attgaggtct tctctattctacattgtgga
cttgtgacga agttcatctt agatactgaa atgcacactg aagctacaga agttgtgcaa
cttgggccc ctgagctgct ttcttgctg gaagatctct cccagaagct ggagagtatg
ctgacacctc ctattgccag gagagtcccc ttctcaaga acaaaggaag cggaatatt
ggattctcac atctccaaca gagatctgcc caagaaattg ttcattgtgt tttcaactg
ctgaccccaa tgtgtaacca cctggagaac atcacaact attttcagtg tttagctgct
gagaatcacg gtgtagttga tggaccagga gtgaaagttc aggagtacca cataatgtct
tcctgctatc agaggctgct gcagattttt catgggcttt ttgcttggag tggattttct
caacctgaaa atcagaattt actgtattca gccctccatg tccttagtag ccgactgaaa
cagggagaac acagccagcc tttggaggaa ctactcagcc agagcgtcca ttacttgcag
aattccate aaagcattcc cagttccag tgtgctctt atctcatcag acttttgatg
gttatttgg agaaatcaac agcttctgct cagaacaaag aaaaaattgc ttccctgcc
agacaattcc tctgtcgggt gtggccaagt ggggataaag agaagagcaa catctctaat
gaccagctcc atgctctgct ctgtatctac ctggagcaca cagagagcat tctgaaggcc
atagaggaga ttgctggtgt tggtgtccca gaactgatca actctcctaa agatgcatct
tcctccacat tccctacact gaccaggcat actttgttg tttcttccg tgtgatgatg
gctgaactag agaagacggt gaaaaaaatt gagcctggca cagcagcaga ctggcagcag
attcatgaag agaaactcct ctactggaac atggctgttc gagacttcag tatcctcatc
aacttgataa aggtatttga tagtcatcct gttctgcatg tatgtttgaa gtatgggcgt
ctctttgtgg aagcatttct gaagcaatgt atgccgctcc tagacttcag ttttagaaaa
cacggggaag atgttctgag cttactggaa accttccagt tggacacaag gctgcttcat
cacctgtgtg ggcattccaa gattccag gacacgagac tcaccaaca tgtgcctctg
ctcaaaaaga ccctggaact tttagttgc agagtcaaag ctatgctcac tctcaacat
tgtagagagg cttttctggct gggcaatcta aaaaaccggg acttgcaggg tgaagagatt
aagtcccaaa attcccagga gagcacagca gatgagagtg aggatgacat gtcatccag
gcctccaaga gcaaagccac tgaggatggt gaagaagacg aagtaagtgc tggagaaaag
gagcaagata gtgatgagag ttatgatgac tctgattaga cccagataa attgttgcct
gcttctgtgt ctcaa

FIG. 19B ggaaagtcga aaacgaaggg aagcaactgg cgggtccccaa ggaagtaata taagtggcag
aagacgttag tcaaaatgat ttccaaaaga cgtcggctag attctgagga taaagaaaac
ctgacagaag atgcctccaa aaccatgccc cttccaagc tggcaaagaa gtctcacaat
tctcatgaag ttgaagaaaa tggcagtgtc tttgtaaagc ttcttaaggc ttcaggactc
actcttaaaa ctggagagaa ccaaaatcag ctaggtgtgg atcaggtaat cttccaaagg
aagctcttc aggccttgag gaagcatcct gcttatccca aagtaataga agagtttgtt
aatggcctgg agtcctacac tgaggacagt gagagtctca ggaactgcct gctgtcttgt
gagcgcctgc aggatgagga agccagcatg ggcacatttt actccaagag tctgatccag
ctacttctgg ggattgacat ttacagcct gccattatca aaatgttatt tgaaaaagtg
cctcagttc ttttgaaag tgagaacaga gatggaatca acatggccag actcattatc
aatcaactaa aatggctgga tagaattgtg gatggcaagg acctcacggc ccagatgatg
cagttgatca gtgttgctcc cgtgaactta cagcatgact tcatcacgag cctcctgaa
atcctagggg attccagca tgctaatgtg gggaaagagc ttggcgagct gctggtgcag
aatacttccc tgactgtcc aattttggat gtcttttcca gtctccgact tgacccaac
ttcctgtcca agatccgcca gttgatgatg ggcaagctgt catctgtccg tctagaggat
ttccctgtga ttgtaaagtt ccttcttcat tctgtaacag acaccactc ccttgaggtc
attgccgagc ttcgggagaa cttgaacgtc cagcagttta tttgccgtc acgaatcag
gcttcccaaa gcaatattgaa aaglaaagga ctagcaagct cttcaggaaa tcaagagaac
agtgataaag actgtattgt tcttgtcttt gatgtaataa agtcagccat tagatatgag
aaaaccattt cagaggcctg gttaaggca attgaacgca ttgagtccgc ggctgaacat
aaggcttgg acgtggtcat gctgctcatc atctacagca ccagcacgca gaccaagaag
ggcgtggaga agctgctgag aaacaagatt cagtcgaact gcattcaaga acagctgctt
gacagtgcgt tctctacaca ttacctggtt cttaaggata tttgcccatc tattcttttg
ctggctcaga ctttgttca ctctcaagac cagaggatca tttgttggg cagtcttctg
tacaaatatg ctttaagtt ttttgatact tactgccagc aggaagtggt tggtgccata
gtcacccatg tctgcagtgg gactgaggct gaagtcgaca ctgactgga tgtcctcctg
gagctgattg tgctaaaacg ctctgctatg aggctcaatg ctgctttgt taagggcatc
ttagattatt tggaaaatat gtccccctcag caaatacgaa aaatcttctg tattctcagc
actcttgcat ttgccatca gcccggtacc agcaaccatc tccaggacga catgcaactg
gtgatccgga agcagctctc tagcactgtg ttcaagtaca agctcattgg gatcattggt
gcagtcacca tggccggcat catggcggaa gacagaagtg taccatcta ctcatcccag
aggagcgcca atgtgagcag tgagcagcgc acacaggtga cttctttgct acaactagtt
cattcttgca ctgagcactc tcctggggcc tctctctgt attatgatga atttgccatc
ctgatccaag aaaggaagtt ggctccaaaa acttggagt gggttgggca gaccatcttc
aatgatttcc aagatgcctt tgtggtagac ttctgtgctg ctccagaggg tgactttcca
tttcctgtga aagcgctcta tggactggaa gagtacagca ctcaagacgg catgtcatc
aacctcctgc cgctgttcta tcaggaatgt gcaaagaatg ccagtcgagc gacatcacaa
gaatcgagcc agagatcaat gtcttcttg tgcctggctt cccattccg gctgctgaga
ctttgcgtgg caagacaaca tgatggaaac ttgatgaga tcgatgggct cttagattgt
cccctgtcc tcctgacctt ggaactgga gagaaactgg agtccatgtc tgctaaagac
cgttcgctta tgtgttcgct cacaattccta acttcaaact gttccgaga ggttgtgaat
gccttctgcc aacaaacatc tcctgagatg aaggcgaagg ttcttagtcg gctaaaggac
ctgtagaaac ttcagggaat cctagagaag tacttggcag tcatcccaga ctatgttccg
cctttcgcaa gcgttgactt ggacactttta gtgatgatgc ctaggagcag ttctgctgtt
gcagcaaaaa acagaaacaa ggggaagacg gggggaaaga aacaaaagc tgatagcaac
aaagcatcct gttcggacac acttctaaca gaagacactt cagagtgtga catggcgcca

FIG. 20A

```
tctggagaaa gccacgtaga caaggagtcc acagggaagg aaggaaagac gtttgtgtca
ctgcagaatt accgcgcttt ttccgagag ctggacattg aggtcttctc tattctacat
tctggacttg tgaccaagtt catcttagac actgaaatgc acactgaagc tacagaggtc
gtacagctgg ggcctgctga gctgctcttc ttgctggaag atctttcccca gaagctagag
aatatgctga ctgctccttt tgccaagaga atctgctgct ttaagaataa aggaaggcag
aatattggct tctcacatct tcatcagaga tctgtccagg acattgtgca ctgtgtggtt
cagctgctaa cccegatgtg taaccatctg gagaacattc acaacttctt tcagtgctta
ggtgctgage atctcagtge agatgacaag gcgagagcga cagetcagga gcagcacacc
atggcctgct gctaccagaa gctgctgcag gtcttgcacg cgctctttgc gtggaagggga
tttactcacc aatcaaagca ccgcctcctg cactcagccc ttgaggtcct ctgaaccga
ctaaagcaga tggaacagga ccagcccttg gaggaactgg tcagccagag cttcagttac
ttgcagaact tccaccatag tgttccagt ttccagtgtg gtctctacct tctcagactt
ctgatggccc ttctggagaa gtctgcagta cctaaccaga agaaagaaaa acttgcctct
ctggccaaac agctgctttg ccgagcatgg cctcatgggg aaaaagagaa gaacccccact
tttaatgacc acctgcatga tgtgctttac atctactgg agcacacaga caatgttctg
aaggccatag aggagatyac tggtgttggt gtccagaac tggtcagtgc tccgaaagac
gccgcctcct ctacattccc tacgttgacc grgcacacct ttgtcatatt cttccgtgtg
atgatggctg aactcgagaa gacggtgaag ggtctycagg ctggcacagc agcagattcg
cagcaggttc acgaagagaa gctcctctat tkgaacatgg ctgtccgaga tttcagyatc
cttytcaatc tgatgaaagt atttgacagt tatcctgttc tgcatgtgtg tttaaagtat
ggccgtcgct ttgtggaggc atttctgaag caatgtatgc cactcctcga cttcagcttt
agaaagcatc gggaagatgt tctgagcttg ctgcaaaccc ttcagttgaa cacgaggcta
cttcatcacc tttgtggaca ctccaagatt cgccaggaca caagactcac caagcaygtg
cctttactca aaaagtcact ggaactgtta gtttgcagag tcaaagccat gcttgtcctc
aacaactgta gagaggcttt ctggttgggt actctcaaaa accgagactt acagggtgaa
gaaattattt cccaggatcc ctcttcctca gagagcaatg cagaggacag tgaggatggc
gtgacatctc acgtctccag gaacagagca acagaggatg gggaagatga agcaagtgat
gaacagaagg accaggacag tgatgaaagt gacgacagct ccagttagag ccgagtggca
tggctgccct gctcacctct gacagactct catctctttg gggtttgaag tcagatgtct
gtttttctag tcagaagcat cctgtttgtc catcaagaag gggtgtttat ttaattcccc
agtgggtttc acaggttgtc taacctccag gtccctggtt caggagtcca gtgtagcatc
catcgttgac taggaygaac atggctgggc tgcagtgcag tkcagtgcag gtgccctagc
tgggccttgg ggttttgaaa ctaaaattta ggcttataat agctttgtaa ataaatctgt
ttcagagttt tgcctcagct accttttcc tcactttaga tgtgattatt caaggatctc
attattcaag gattaggtaa tattgagttg aggtttgtgc aatcgtactg gtggcctaaa
agtatgttcc gtactgttat cttcctggag gaatgaccca actttcttat caatgatcaa
gtgtttgatt tggtctgtgt cagggtctct ttacatagtc ctggctggtg tgttattaga
tatgtgacc aggagggtct tgaacattac tttgaattt taaacatttt tgtacatatg
tgtatgggca tatatgtgcc actgtgcata tgtgtaggtc agaggatagc ttatgggagt
gagctctctc cttccaccat gtgggttcca gggttcaaac tctagacctt cacctgctca
gccaccttac cctttaaaa tgttggtta ttaatatata aaaggaagga agacaacatc
aaacatgtgc tggctttgta tgtatatata gttttattt ccacattaat ttgaattatg
cctataatat atttgtaata atcatacaaa ataattgtaa tttattagaa atagaacatc
aggagttaaa ataggggatt cttctgtctt ctgccaggaa gccagtctc agagatgctg
ccaggctctt cctcgctgtg ccattaagat tatttaattt ttgttaatat tttactcaat
accggtatta aagttatgtt ttgttggaaa aaaaaaaaa aaaaaaaaaa aaaaaa
```

FIG. 20B

METHODS AND COMPOSITIONS FOR THE DIAGNOSIS OF CANCER SUSCEPTIBILITIES AND DEFECTIVE DNA REPAIR MECHANISMS AND TREATMENT THEREOF

RELATED APPLICATIONS

This application is a continuation of U.S. application Ser. No. 13/654,243, filed Oct. 17, 2012, which is a continuation of U.S. application Ser. No. 12/749,419, filed Mar. 29, 2010, pending, which is a continuation of U.S. application Ser. No. 10/165,099, filed Jun. 6, 2002, abandoned, which is a continuation-in-part of U.S. application Ser. No. 09/998,027, filed Nov. 2, 2001, which in turn claims priority from U.S. Provisional Application No. 60/245,756, filed Nov. 3, 2000. The entire contents of each of the above applications are incorporated herein by reference.

GOVERNMENT SUPPORT

The work described herein was supported by the National Institute of Health, NIH Grant No. Health grants RO1HL52725-04, RO1DK43889-09, 1PO1HL48546, and PO1HL54785-04. The US Government has certain rights to the claimed invention.

INCORPORATION-BY-REFERENCE OF SEQUENCE LISTING

The contents of the text file named "Sequence_Listing_C03US.txt", which was created on Oct. 21, 2014 and is 132 KB in size, are hereby incorporated by reference in their entirety.

BACKGROUND

The present invention relates to the diagnosis of cancer susceptibilities in subjects having a defect in the FANCD2 gene and the determination of suitable treatment protocols for those subjects who have developed cancer. Animal models with defects in the FANCD2 gene can be used to screen for therapeutic agents.

Fanconi Anemia (FA) is an autosomal recessive cancer susceptibility syndrome characterized by birth defects, bone marrow failure and cancer predisposition. Cells from FA patients display a characteristic hypersensitivity to agents that produce interstrand DNA crosslinks such as mitomycin C or diepoxybutane. FA patients develop several types of cancers including acute myeloid leukemias and cancers of the skin, gastrointestinal; and gynecological systems. The skin and gastrointestinal tumors are usually squamous cell carcinomas. At least 20% of patients with FA develop cancers. The average age of patients who develop cancer is 15 years for leukemia, 16 years for liver tumors, and 23 years for other tumors. (D'Andrea et al., Blood, (1997) Vol. 90, p. 1725, Garcia-Higuera et al., Curr. Opin. Hematol., (1999) Vol. 2, pp. 83-88 and Heijna et al., Am. J. Hum. Genet. Vol. 66, pp. 1540-1551).

FA is genetically heterogeneous. Somatic cell fusion studies have identified at least seven distinct complementation groups (Joenje et al., (1997) Am. J. Hum. Genet., Vol. 61, pp. 940-944 and Joenje et al., (2000) Am. J. Hum, Genet, Vol. 67, pp. 759-762). This observation has resulted in the hypothesis that the FA genes define a multicomponent pathway involved in cellular responses to DNA cross-links. Five of the FA genes (FANCA, FANCC, FANCE, FANCF and FANCG) have been cloned and the FANCA, FANCC and FANCG proteins have been shown to form a molecular complex with primarily nuclear localization. FANCC also localizes in the cytoplasm. Different FA proteins have few or no known sequence motifs with no strong homologs of the FANCA, FANCC, FANCE, FANCF, and FANCG proteins in non-vertebrate species. FANCF has weak homology of unknown significance to an *E. coli* RNA binding protein. The two most frequent complementation groups are FA-A and FA-C which together account for 75%-80% of FA patients. Multiple mutations have been recognized in the FANCA gene that span 80 kb and consists of at least 43 exons. FANCC has been found to have 14 exons and spans approximately 80 kb. A number of mutations in the FANCC gene have been identified which are correlated with FA of differing degrees of severity. FA-D has been identified as a distinct but rare complementation group. Although FA-D patients are phenotypically distinguishable from patients from other subtypes, the FA protein complex assembles normally in FA-D cells (Yamashita et al., (1998) P.N.A.S., Vol. 95, pp. 13085-13090).

The cloned FA proteins encode orphan proteins with no sequence similarity to each other or to other proteins in Germanic and no functional domains are apparent in the protein sequence. Little is known regarding the cellular or biochemical function of these proteins.

Diagnosis of FA is complicated by the wide variability in FA patient phenotype. Further confounding diagnosis, approximately 33% of patients with FA have no obvious congenital abnormalities. Moreover, existing diagnostic tests do not differentiate FA carriers from the general population. The problems associated with diagnosis are described in D'Andrea et al., (1997). Many cellular phenotypes have been reported in FA cells but the most consistent is hypersensitivity to bifunctional alkylating agents such as mitomycin C or diepoxybutane. These agents produce interstrand DNA cross-links (an important class of DNA damage).

Diagnosing cancer susceptibility is complicated because of the large number of regulatory genes and biochemical pathways that have been implicated in the formation of cancers. Different cancers depending on how they arise and the genetic lesions involved may determine how a subject responds to any particular therapeutic treatments. Genetic lesions that are associated with defective repair mechanisms may give rise to defective cell division and apoptosis which in turn may increase a patient's susceptibility to cancer. FA is a disease condition in which multiple pathological outcomes are associated with defective repair mechanisms in addition to cancer susceptibility.

An understanding of the molecular genetics and cell biology of Fanconi Anemia pathway can provide insights into prognosis, diagnosis and treatment of particular classes of cancers and conditions relating to defects in DNA repair mechanisms that arise in non-FA patients as well as FA patients.

SUMMARY OF THE INVENTION

The invention features a method of diagnosing or determining if a patient has cancer or is at increased risk of cancer, where the method includes testing a Fanconi Anemia/BRCA pathway gene for the presence of a cancer-associated defect, where said presence of one or more cancer-associated defects is indicative of cancer or an increased risk of cancer in said patient. The cancer can be breast, ovarian, or prostate cancer, or other forms of cancer. The cancer-associated defect can be one which results in a reduction in the ratio of FANC D2-L relative to FANC D2-S as compared to the ratio in a patient without one or more cancer-associated defects in a Fanconi Anemia/BRCA pathway gene.

The invention also features a method of diagnosing or determining if a patient has cancer or is at increased risk of cancer, where the method includes testing a Fanconi Anemia/BRCA pathway protein for the presence, of a cancer-associated defect, where said presence of a cancer-associated defect is indicative of cancer or an increased risk of cancer in said patient. The cancer can be breast, ovarian, or prostate cancer, or other forms of cancer.

An another aspect, the invention features a method of diagnosing or determining if a patient is at increased risk of developing cancer, where the method includes the steps of (a) providing a tissue sample from said patient; (b) inducing DNA damage in the cells of said tissue sample; and (c) assaying for the presence of FANC D2-S and FANC D2-L proteins in said cells; wherein a reduction in the ratio of FANC D2-L to FANC D2-S is indicative that said patient is at increased risk of developing cancer. The cancer can be breast, ovarian, or prostate cancer, or other forms of cancer. The patient can be known or not known to have any previously-known cancer-associated defects in the BRCA-1 or BRCA-2 genes. A plurality of such tissue samples can be distributed on or in an array.

An another aspect, the invention features a method of determining if a patient has cancer, or is at increased risk of developing cancer, where the patient has no known cancer causing defect in the BRCA 1 or BRCA-2 genes, where the method comprises the steps of: (a) providing a DNA sample from said patient; (b) amplifying the FANC D2 gene from said patient with the FANC D2 gene-specific polynucleotide primers of SEQ ID NOs:115-186; (c) sequencing the amplified FANC D2 gene; and (d) comparing the FANC D2 gene sequence from said patient to a reference FANC D2 gene sequence, where a discrepancy between the two gene sequences indicates the presence of a cancer-associated defect; where the presence of one or more cancer-associated defects indicates said patient has cancer or is at an increased risk of developing cancer. The cancer can be breast, ovarian, or prostate cancer, or other forms of cancer. The patient can be known or not known to have any previously-known cancer-associated defects in the BRCA-1 or FANC-D1/BRCA-2 genes. A plurality of such tissue samples can be distributed on or in an array. SEQ ID NOs: 115-186 are matched sets of primers, as shown in Table 7, with the odd-numbered primers being forward primers, and the even-numbered primers being reverse primers. Primers can also be used from different pairs, to make new pairings of primers, e.g., SEQ ID NO:115 can be used with SEQ ID NO:118, etc. By "discrepancy" is meant a difference between the two sequences, where the difference is know to be associated with cancer.

In a further aspect, the invention features a method of screening for a chemosensitizing agent, where the method comprises the steps of (a) providing a potential inhibitor of the Fanconi Anemia/BRCA pathway; (b) providing a tumor cell line that is resistant to one or more anti-neoplastic agents; (c) contacting said tumor cell line and said potential inhibitor of the Fanconi Anemia/BRCA pathway and said one or more anti-neoplastic agents; and (d) measuring the growth rate of said tumor cell line in the presence of said inhibitor of the Fanconi Anemia/BRCA pathway and said anti-neoplastic agent; where a reduced growth rate of the tumor cell line, relative to cells of the tumor cell line in the presence of the anti-neoplastic agent and the absence of said inhibitor of the Fanconi Anemia/BRCA pathway, is indicative that the potential inhibitor is a chemosensitizing agent. The potential inhibitors of the Fanconi Anemia/BRCA pathway can be screened on a microarray, where the microarray contains addresses containing one or more cells that are resistant to one or more anti-neoplastic agents. The potential inhibitor of the Fanconi Anemia/BRCA pathway can be an inhibitor of the ubiquitination of the FANC D2 protein. The anti-neoplastic agent can be cisplatin. The tumor cell line can be an ovary cancer cell line.

In another aspect, the invention features a method of treating a patient having a cancer, where the cancer is resistant to a anti-neoplastic agent, where the method comprises the step of administering a therapeutically effective amount of an inhibitor of the Fanconi Anemia/BRCA pathway together with said anti-neoplastic agent. The anti-neoplastic agent can be cisplatin. The potential inhibitor of the Fanconi Anemia/BRCA pathway can be an inhibitor of the ubiquitination of the FANC D2 protein. The tumor cell line can be an ovary cancer cell line.

In an additional aspect, the invention features a method for screening for a cancer therapeutic, where the method comprises the steps of (a) providing one or more cells containing a Fanconi Anemia/BRCA pathway gene having one or more cancer associated defects; (b) growing said cells in the presence of a potential cancer therapeutic; and (e) determining the rate of growth of said cells in the presence of said potential cancer therapeutic relative to the rate of growth of equivalent cells grown in the absence of said potential cancer therapeutic; where a reduced rate of growth of said cells in the presence of said potential cancer therapeutic, relative to the rate of growth of equivalent cells grown in the absence of said potential cancer therapeutic, indicates that the potential cancer then is a cancer therapeutic. The cells can contain a Fanconi Anemia/BRCA pathway gene having one or more cancer associated defects are distributed in a array, or several such genes.

The invention also features a method of predicting the efficacy of a therapeutic agent in a cancer patient, where the method comprises the steps of: (a) providing a tissue sample from said cancer patient who is being treated with said therapeutic agent; (b) inducing DNA damage in the cells of said tissue sample; and (c) detecting the presence of FANC D2-L protein in said cells; where the presence of FANC D2-L is indicative of a reduced efficacy of said therapeutic agent in said cancer patient. The therapeutic agent can be an anti-neoplastic agent, e.g., can be cisplatin. Alternatively, in step (c), one can detect both FANC-D2-S and FANC-D2-L, where a reduction in the ratio of FANC D2-L relative to FANC D2-S as compared to the ratio in a non-cancer patient indicates reduced efficacy.

The invention also features a method of determining resistance, of tumor cells to an anti-neoplastic agent, comprising the steps of (a) providing a tissue sample from a patient who is being treated with an anti-neoplastic agent; (b) inducing DNA damage in the cells of said tissue sample; and (c) determining the methylation state of a Fanconi Anemia/BRCA pathway gene; where methylation of a Fanconi Anemia/BRCA gene is indicative of resistance of the tumor cells to an anti-neoplastic agent. The Fanconi Anemia/BRCA gene can be the FANC F gene. The anti-neoplastic agent can be cisplatin.

The invention also features a kit for detecting defects in the FANC D2 gene, comprising a polynucleotide primer pair specific for the FANC D2 gene, a reference FANC D2 gene sequence and packaging materials therefore.

The invention also features a kit for detecting the presence of FANC D2-L, comprising a FANC D2-L-specific antibody and packaging materials therefore.

The invention also features a kit for determining the methylation state of a Fanconi Anemia/BRCA pathway gene, comprising FANC D2 polynucleotide primer pairs and probes, a control unmethylated reference FANC D2 gene sequence and packaging materials therefore.

The invention also features a kit for screening for a chemosensitizing agent, comprising a tumor cell line that is resistant to one or more anti-neoplastic agents and packaging materials therefore. The tumor cell line can be an ovary tumor cell line, e.g., a cisplatin resistant ovary tumor cell line. The anti-neoplastic agent can be cisplatin.

The invention also features a microarray containing one or more nucleic acid sequences from one or more Fanconi Anemia/BRCA pathway genes. The genes can be selected from the group consisting of: ATM, FANC A, FANC B, FANC C, FANC D1, FANC D2, FANC E, FANC F and FANC G.

The invention also features the use of such a microarray in a method of determining if a patient has cancer, or is at increased risk of developing cancer, where the method comprises the steps of (a) providing the microarray; (b) providing a nucleic acid sample from said patient; (c) hybridizing said nucleic acid sample to said nucleic acid sequences from the Fanconi Anemia/BRCA pathway on said microarray; and (d) detecting the presence of mutations in the Fanconi Anemia/BRCA pathway genes in the nucleic acid sample from said patient; where detecting the presence of mutations is indicative of a patient who has cancer, or is at increased risk of developing cancer.

In a one embodiment of the invention there is provided an isolated nucleic acid molecule that includes a polynucleotide selected from (a) a nucleotide sequence encoding a polypeptide having an amino acid sequence as shown in SEQ ID NO:4; (b) a nucleotide sequence at least 90% identical to the polynucleotide of (b); (a) a nucleotide sequence complementary to the polynucleotide of (b); (d) a nucleotide sequence at least 90% identical to the nucleotide sequence shown in SEQ ID NO:5-8, 187-188; and (e) a nucleotide sequence complementary to the nucleotide sequence of (d). The polynucleotide may be an RNA molecule or a DNA molecule, such as a cDNA.

In another embodiment of the invention, an isolated nucleic acid molecule is provided that consists essentially of a nucleotide sequence encoding a polypeptide having an amino acid sequence sufficiently similar to that of SEQ ID NO:4 to retain the biological property of conversion from a short form to a long form of FANCD2 in the nucleus of a cell for facilitating DNA repair. Alternately, the isolated nucleic acid molecule consists essentially of a polynucleotide having a nucleotide sequence at least 90% identical to SEQ ID NO:9-191 or complementary to a nucleotide sequence that is at least 90% identical to SEQ ID NO:9-191.

In an embodiment, a method is provided for making a recombinant vector that includes inserting any of the isolated nucleic acid molecules described above into a vector. A recombinant vector product may be made by this method and the vector may be introduced to form a recombinant host cell into a host cell.

In an embodiment of the invention, a method is provided for making an FA-D2 cell line, that includes (a) obtaining cells from a subject having a biallelic mutation in a complementation group associated with FA-D2; and (b) infecting the cells with a transforming virus to make the FA-D2 cell line where the cells may be selected from fibroblasts and lymphocytes and the transforming virus selected from Epstein Barr virus and retrovirus. The FA-D2 cell line may be characterized by determining the presence of a defective FANDC2 in the cell line for example by performing a diagnostic assay selected from (i) a Western blot or nuclear immunofluorescence using an antibody specific for FANCD2 and (ii) a DNA hybridization assay.

In an embodiment of the invention, a recombinant method is provided for producing a polypeptide, that includes culturing a recombinant host cell wherein the host cell includes any of the isolated nucleic acid molecules described above.

In an embodiment of the invention, an isolated polypeptide, including an amino acid sequence selected from (a) SEQ ID NO:4; (b) an amino acid sequence at least 90% identical to (a); (c) an amino acid sequence which is encoded by a polynucleotide having a nucleotide sequence which is at least 90% identical to at least one of SEQ ID NO:5-8, 187-188; (d) an amino acid sequence which is encoded by a polynucleotide having a nucleotide sequence which is at least 90% identical to a complementary sequence to at least one of SEQ ID NO:5-8, 187-188; and (e) a polypeptide fragment of (a)-(d) wherein the fragment is at least 50 aminoacids in length.

The isolated polypeptide may be encoded by a DNA having a mutation selected from nt 376A to G, nt 3707G to A, nt 904C to T and nt 958C to T. Alternatively, the polypeptide may be characterized by a polymorphism in DNA encoding the polypeptide, the polymorphism being selected from nt 1122A to O, nt 1440T to C, nt 1509C to T, nt 2141C to T, nt 2259T to C, nt 4098T to G, nt 4453G to A. Alternatively, the polypeptide may be characterized by a mutation at amino acid 222 or amino acid 561.

In an embodiment of the invention, an antibody preparation is described having a binding specificity for a FANCD2 protein where the antibody may be a monoclonal antibody or a polyclonal antibody and wherein the FANCD2 may be FANCD2-S or FANCD2-L.

In an embodiment of the invention, a diagnostic method is provided for measuring FANCD2 isoforms in a biological sample where the method includes (a) exposing the sample to a first antibody for forming a first complex with FANCD2-L and optionally a second antibody for forming a second complex with FANCD2-S; and (b) detecting with a marker, the amount of the first complex and the second complex in the sample. The sample may be intact cells or lysed cells in a lysate. The biological sample may be from a human subject with a susceptibility to cancer or having the initial stages of cancer. The sample may be from a cancer in a human subject, wherein the cancer is selected from melanoma, leukemia, astocytoma, glioblastoma, lymphoma, glioma, Hodgkins lymphoma, chronic lymphocyte leukemia and cancer of the pancreas, breast, thyroid, ovary, uterus, testis, pituitary, kidney, stomach, esophagus and rectum. The biological sample may be from a human fetus or from an adult human and may be derived from .any of a blood sample, a biopsy sample of tissue from the subject and a cell line. The biological sample may be derived from heart, brain, placenta, liver, skeletal muscle, kidney, pancreas, spleen, thymus, prostate, testis, uterus, small intestine, colon, peripheral blood or lymphocytes. The marker may be a fluorescent marker, the fluorescent marker optionally conjugated to the FANCD2-L antibody, a chemiluminescent marker optionally conjugated to the FANCD2-L antibody and may bind the first and the second complex to a third antibody conjugated to a substrate. Where the sample is a lysate, it may be subjected to a separation procedure to separate FANCD2 isoforms and the separated isoforms may be identified by determining binding to the first or the second FANCD2 antibody.

In an embodiment of the invention, a diagnostic test is provided for identifying a defect in the Fanconi Anemia pathway in a cell population from a subject, that includes selecting an antibody to FANCD2 protein and determining whether the amount of an FAND2-L isoform is reduced in the cell population compared with amounts, in a wild type cell population; such that if the amount of the FANCD2-L protein is reduced, then determining whether an amount of any of FANCA, FANCB, FANCC, FANCD1, FANCE, FANCF or FANCG protein is altered in the cell population compared with the wild type so as to identify the defect in the Fanconi Anemia pathway in the cell population. In one example, the amount of an isoform relies on a separation of the FANCD2-L and FANCD2-S isoforms where the separation may be achieved by gel electrophoresis or by a migration binding banded test strip.

In an embodiment of the invention, a screening assay for identifying a therapeutic agent, is provided that includes selecting a cell population in which FAND2-L is made in reduced amounts; exposing the cell population to individual members of a library of candidate therapeutic molecules; and identifying those individual member molecules that cause the amount of FANCD2-L to be increased in the cell population. In one example, the cell population is an in vitro cell population. In another example, the cell population is an in vivo cell population, the in vivo population being within an experimental animal, the experimental animal having a mutant FANCD2 gene. In a further example, the experimental animal is a knock-out mouse in which the mouse FAND2 gene has been replaced by a human mutant FANCD2 gene. In another example, a chemical carcinogen is added to the cell population in which FANCD2 is made in reduced amounts, to determine if any member molecules can cause the amount of FANCD2-L to be increased so as to protect the cells form the harmful effects of the chemical carcinogen.

In an embodiment of the invention, an experimental animal model is provided in which the animal FANCD2 gene has been removed and optionally replaced by any of the nucleic acid molecules described above.

In an embodiment of the invention, a method is provided for identifying in a cell sample from a subject, a mutant FANCD2 nucleotide sequence in a suspected mutant FANCD2 allele which comprises comparing the nucleotide sequence of the suspected mutant FANCD2 allele with the wild type FANCD2 nucleotide sequence wherein a difference between the suspected mutant and the wild type sequence identifies a mutant FANCD2 nucleotide sequence in the cell sample, In one example, the suspected mutant allele is a germline allele. In another example, identification of a mutant FANCD2 nucleotide sequence is diagnostic for a predisposition for a cancer in the subject or for an increased risk of the subject bearing an offspring with Fanconi Anemia. In another example, the suspected mutant allele is a somatic allele in a tumor type and identifying a mutant FANCD2 nucleotide sequence is diagnostic for the tumor type. In another example, the nucleotide sequence of the wild type and the suspected mutant FANCD2 nucleotide sequence is selected from a gene, a mRNA and a cDNA made from a mRNA. In another example, comparing the polynucleotide sequence of the suspected mutant FANCD2 allele with the wild type FANCD2 polynucleotide sequence, further includes selecting a FANCD2 probe which specifically hybridizes to the mutant FANCD2 nucleotide sequence, and detecting the presence of the mutant sequence by hybridization with the probe. In another example, comparing the polynucleotide sequence of the suspected mutant FANCD2 allele with the wild type FANCD2 polynucleotide sequence, further comprises amplifying all or part of the FANCD2 gene using a set of primers specific for wild type FANCD2 DNA to produce amplified FANCD2 DNA and sequencing the FANCD2 DNA so as to identify the mutant sequence. In another example, where the mutant FANCD2 nucleotide sequence is a germline alteration in the FANCD2 allele of the human subject, the alteration is selected from the alterations set forth in Table 3 and where the mutant FANCD2 nucleotide sequence is a somatic alteration, in the FANCD2 allele of the human subject, the alteration is selected from the alterations set forth in Table 3.

In an embodiment of the invention, a method is provided for diagnosing a susceptibility to cancer in a subject which comprises comparing the germline sequence of the FANCD2 gene or the sequence of its mRNA in a tissue sample from the subject with the germline sequence of the FANCD2 gene or the sequence of its mRNA wherein an alteration in the germline sequence of the FANCD2 gene or the sequence of its mRNA of the subject indicates the susceptibility to the cancer. An alteration may be detected in a regulatory region of the FANCD2 gene. An alteration in the germline sequence may be determined by an assay selected from the group consisting of (a) observing shifts in electrophoretic mobility of single-stranded DNA on non-denaturing polyacrylamide gels, (b) hybridizing a FANCD2 gene probe to genomic DNA isolated from the tissue sample, (c) hybridizing an allele-specific probe to genomic DNA of the tissue sample, (d) amplifying all or part of the FANCD2 gene from the tissue sample to produce an amplified sequence and sequencing the amplified sequence, (e) amplifying all or part of the FANCD2 gene from the tissue sample using primers for a specific FANCD2 mutant allele, (f) molecularly cloning all or part of the FANCD2 gene from the tissue sample to produce a cloned sequence and sequencing the cloned sequence, (g) identifying a mismatch between (i) a FANCD2 gene or a FANCD2 mRNA isolated from the tissue sample, and (ii) a nucleic acid probe complementary to the human wild-type FANCD2 gene sequence, when molecules (i) and (ii) are hybridized to each other to form a duplex, (h) amplification of FANCD2 gene sequences in the tissue sample and hybridization of the amplified sequences to nucleic acid probes which comprise wild-type FANCD2 gene sequences, (i) amplification of FANCD2 gene sequences in the tissue sample and hybridization of the amplified sequences to nucleic acid probes which comprise mutant FANCD2 gene sequences, (j) screening for a deletion mutation in the tissue sample, (k) screening for a point mutation in the tissue sample, (l) screening for an insertion mutation in the tissue sample, and (m) in situ hybridization of the FANCD2 gene of said tissue sample with nucleic acid probes which comprise the FANCD2 gene.

In an embodiment of the invention, a method is provided for diagnosing a susceptibility for cancer in a subject, includes: (a) accessing genetic material from the subject so as to determine defective DNA repair; (b) determining the presence of mutations in a set of genes, the set comprising FAND2 and at least one of FANCA, FANCB, FANCC, FANCD1, FANCDE, FANDF, FANDG, BRACA1 and ATM; and (c) diagnosing susceptibility for cancer from the presence of mutations, in the set of genes.

In an embodiment of the invention, a method is provided for detecting a mutation in a neoplastic lesion at the FANCD2 gene in a human subject which includes: comparing the sequence of the FANCD2 gene or the sequence of its mRNA in a tissue sample from a lesion of the subject with the sequence of the wild-type FANCD2 gene or the sequence of its mRNA, wherein an alteration in the sequence of the FANCD2 gene or the sequence of its mRNA of the subject indicates a mutation at the FANCD2 gene of the neoplastic lesion. A therapeutic protocol may be provided for treating the neoplastic lesion according to the mutation at the FANCD2 gene of the neoplastic lesion.

In an embodiment of the invention, a method is provided for confirming the lack of a FANCD2 mutation in a neoplastic lesion from a human subject which comprises comparing the sequence of the FANCD2 gene or the sequence of its mRNA in a tissue sample from a lesion of said subject with the sequence of the wild-type FANCD2 gene or the sequence of its RNA, wherein the presence of the wild-type sequence in the tissue sample indicates the lack of a mutation at the FANCD2 gene.

In an embodiment of the invention, a method is provided for determining a therapeutic protocol for a subject having a cancer, that includes (a) determining if a deficiency in FANCD2-L occurs in a cell sample from the subject by measuring FANCD2 isoforms using specific antibodies; (b) if a deficiency is detected in (a), then determining whether the deficiency is a result of genetic defect in non-cancer cells; and (c) if (b) is positive, reducing the use of a therapeutic protocol that causes increased. DNA damage so as to protect normal tissue in the subject and if (b) is negative, and the deficiency is contained within a genetic defect in cancer cells only, then increasing the use of a therapeutic protocol that causes increased DNA damage so as to adversely affect the cancer cells.

In an embodiment of the invention, a method of treating a FA pathway defect in a cell target is provided that includes: administering an effective amount of FANCD2 protein or an exogenous nucleic acid to the target. The FA pathway defect may be a defective FANCD2 gene and the exogenous nucleic acid vector may further include introducing a vector according to those described above. The vector may be selected from a mutant herpes virus, a E1/E4 deleted recombinant adenovirus, a mutant retrovirus, the viral vector being defective in respect of a viral gene essential for production of infectious new virus particles. The vector may be contained in a lipid micelle.

In an embodiment of the invention, a method is provided for treating a patient with a defective FANCD2 gene, that includes providing a polypeptide 'described in SEQ ID NO:4, for functionally correcting a defect arising from a condition arising from the defective FANCD2 gene.

In an embodiment of the invention, a cell based assay for detecting a FA pathway defect is provided that includes obtaining a cell sample from a subject; exposing the cell sample to DNA damaging agents; and detecting whether FANCD2-L is upregulated, the absence of upregulation being indicative of the FA pathway defect. In the cell-based assay, amounts of FANCD2 may be measured by an analysis technique selected from: immunoblotting for detecting nuclear foci; Western blots to detect amounts of FANCD2 isoforms and quantifying mRNA by hybridizing with DNA probes.

In an embodiment of the invention, a kit is provided for use in detecting a cancer cell in a biological sample, that includes (a) primer pair which binds under high stringency conditions to a sequence in the FANCD2 gene, the primer pair being selected to specifically amplify an altered nucleic acid sequence described in Table 7; and containers for each of the primers.

As used herein, the "Fanconi Anemia/BRCA pathway" or "Fanconi Anemia Pathway" refers to the genes within the 7 complementation groups (FA-A to FA-G), the BRCA-1 gene and the ATM gene and their respective proteins that interact in a pathway referred herein as the Fanconi Anemia/BRCA pathway and regulate the cellular response to DNA damage (see FIG. 22).

The genes of the Fanconi Anemia/BRCA pathway are:
1) FANC-A (e.g., Genbank Accession No.: NM_000135)
2) FANC-B (not yet cloned)
3) FANC-C (e.g., Genbank Accession No.: NM_000136)
4) FANC-D1/BRCA-2 (e.g., Genbank Accession No.: U43746)
5) FANC-D2 (e.g., Genbank Accession No.: NM_033084)
6) FANC-E (e.g., Genbank Accession No.: NM_021922)
7) FANC-F (e.g., Genbank Accession No.: N4_022725)
8) FANC-G (e.g., Genbank Accession No.: BC000032)
9) BRCA-1 (e.g., Genbank Accession No.: U14680)
10) ATM (e.g., Genbank Accession No.: U33841)

As used herein, "testing a Fanconi Anemia/BRCA pathway protein for the presence of a cancer-associated defect" refers to the method of determining if a protein encoded by a Fanconi Anemia/BRCA pathway gene, as defined herein, harbors a defect, as defined herein, that can cause or is associated with a cancer in a patient.

As used herein, the term "defect" refers to any alteration of a gene or protein within the Fanconi Anemia/BRCA pathway, and/or proteins, with respect to any unaltered gene or protein within the Fanconi Anemia/BRCA pathway.

"Alteration" of a gene includes, but is not limited to: a) alteration of the DNA sequence itself, i.e., DNA mutations, deletions, insertions, substitutions; b) DNA modifications affecting the regulation of gene expression such as regulatory region mutations, modification in associated chromatin, modifications of intron sequences affecting mRNA splicing, modification affecting the methylation/demethylation state of the gene sequence; c) mRNA modifications affecting protein translation or mRNA transport or mRNA splicing.

"Alteration" of a protein includes, but is not limited to, amino acid deletions, insertions, substitutions; modification affecting protein phosphorylation or glycosylation; modifications affecting protein transport or localization; modifications affecting the ability to form protein complexes with one or more associated proteins or changes in the amino acid sequence caused by changes in the DNA sequence encoding the amino acid.

As used herein, the term "increased risk" or "elevated risk" refers to the greater incidence of cancer in those patients having altered Fanconi Anemia/BRCA genes or proteins as compared to those patients without alterations in the Fanconi Anemia/BRCA pathway genes or proteins. "Increased risk" also refers to patients who are already diagnosed with cancer and may have an increased incidence of a different cancer form. According to the invention, "increased risk" of cancer refers to cancer-associated defects in a Fanconi Anemia/BRCA pathway gene that contributes to a 50%, preferably 90%, more preferably 99% or more increase in the probability of acquiring cancer relative to patients who do not have a cancer-associated defect in a Fanconi Anemia/BRCA pathway gene.

As used herein, an "inhibitor of the Fanconi Anemia/BRCA pathway", according to the invention, refers to any compound that disrupts FANC D2-L protein function either directly or indirectly. Disruption of FANC D2-L protein function can be achieved either through disruption of any of the other FANC proteins upstream of the FANC D2 protein within the pathway, inhibition of the ubiquitination of the FANC D2-S to the FANC D2-L isoform, inhibition of subsequent nuclear transport of the FANC D2-L protein or disruption of the association of the FANC D2-L protein with the nuclear BRCA DNA repair protein complex. An "inhibitor" according to the invention can be nucleic acids (anti-sense RNA or DNA oligonucleotides), proteins (humanized antibodies), peptides or small molecule drugs that specifically bind to FANC D2-L and disrupt FANC D2-L protein function. In a most preferred embodiment, the inhibitor of the Fanconi Anemia/BRCA pathway is a small molecule inhibitor of the mono-ubiquitination of the FANC D2 protein.

As used herein, a "reduction in the ratio of FANC D2-L, relative to FANC D2-S" refers to a decrease in the percentage of the total amount of FANC D2 protein that is in the FANC D2-L isoform. In a preferred embodiment, the total amount of FANC D2 protein that is in the FANC D2-L isoform is at most 25%, preferably 10%, more preferably 1% and most preferably 0%. Such a reduction indicates a defect in one or more genes or proteins of the Fanconi Anemia/BRCA pathway, as defined herein.

As used herein, "testing a Fanconi Anemia/BRCA pathway protein for the presence of a cancer-associated defect" refers to the method of determining if a protein encoded within the 7 complementation groups (A, B, C, D, E, F and G) that comprise the Fanconi Anemia/BRCA gene pathway, harbor a defect or other mutation, as defined herein, that can cause or contribute to a cancer in a patient.

As used herein, the term "inducing DNA damage" refers to both chemical and physical methods of damaging DNA. Chemicals that damage DNA include, but are not limited to, acids/bases and various mutagens, such as ethidium bromide, acridine orange, as well as free radicals. Physical methods include, but are not limited to, ionizing radiation, such as X rays and gamma rays, and ultraviolet (UV) radiation. Both methods of "inducing DNA damage" can result in DNA mutations that typically include, but, are not limited to, single-strand breaks, double-strand breaks, alterations of bases, insertions, deletions or the cross-linking of DNA strands.

As used herein, the term "tissue biopsy" refers to a biological material, which is isolated from a patient. The term "tissue", as used herein, is an aggregate of cells that perform a particular function in an organism and encompasses, cell lines and other sources of cellular material including, but not limited to, a biological fluid for example, blood, plasma, sputum, urine, cerebrospinal fluid, lavages, and leukophoresis samples.

As used herein, the term "amplifying", when applied to a nucleic acid sequence, refers to a process whereby one or more copies of a particular nucleic acid sequence is generated from a template nucleic acid, preferably by the method of polymerase chain reaction (Mullis and Faloona, 1987, Methods Enzymol., 155:335). "Polymerase chain reaction" or "PCR" refers to an in vitro method for amplifying a specific nucleic acid template sequence. The PCR reaction involves a repetitive series of temperature cycles and is typically performed in a volume of 50-100 41. The reaction mix comprises dNTPs (each of the four deoxynucleotides dATP, dCTP, dGTP, and dTTP), primers, buffers, DNA polymerase, and nucleic acid template. The PCR reaction comprises providing a set of polynucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of polynucleotide primers" or "a set of PCR primers" can comprise two, three, four or more primers.

Other methods of amplification include, but are not limited to, ligase chain reaction (LCR), polynucleotide-specific base amplification (NSBA), or any other method known in the art.

As used herein, the term "polynucleotide primer" refers to a DNA or RNA molecule capable of hybridizing to a nucleic acid template and acting as a substrate for enzymatic synthesis under conditions in which synthesis of a primer extension product which is complementary to a nucleic acid template is catalyzed to produce a primer extension product which is complementary to the target nucleic acid template. The conditions for initiation and extension include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer is preferably single-stranded for maximum efficiency in amplification. "Primers" useful in the present invention are generally between about 10 and 35 nucleotides in length, preferably between about 15 and 30 nucleotides in length, and most preferably between about 18 and 25 nucleotides in length.

As defined herein, "a tumor" is a neoplasm that may either be malignant or non-malignant. Tumors of the same tissue type originate in the same tissue, and may be divided into different subtypes based on their biological characteristics.

As used herein, the term "cancer" refers to a malignant disease caused or characterized by the proliferation of cells which have lost susceptibility to normal growth control. "Malignant disease" refers to a disease caused by cells that have gained the ability to invade either the tissue of origin or to travel to sites removed from the tissue of origin.

As used herein, the term "antibody" refers to an immunoglobulin having the capacity to specifically bind a given antigen. The term "antibody" as used herein is intended to include whole antibodies of any isotype (IgG, IgA, IgM, IgE, etc), and fragments thereof which are also specifically reactive with a vertebrate, e.g., mammalian, protein. Antibodies can be fragmented using conventional techniques and the fragments screened for utility in the same manner as whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab, Fv, and single chain antibodies (scFv) containing a V[L] and/or V[H] domain joined by a peptide linker. The scFv's may be covalently or non-covalently linked to form antibodies having two or more binding sites. Antibodies may be labeled with detectable moieties by one of skill in the art. In some embodiments, the antibody that binds to an entity one wishes to measure (the primary antibody) is not labeled, but is instead detected by binding of a labeled secondary antibody that specifically binds to the primary antibody.

A patient is "treated" according to the invention if one or preferably more symptoms of cancer as described herein are eliminated or reduced in severity, or prevented from progressing or developing further.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions.

As used herein, the term "cancer therapeutic" refers to a compound that prevents the onset or progression of cancer or prevents cancer metastasis or reduces, delays, or eliminates the symptoms of cancer.

As used herein, the term "inhibitor of the mono-ubiquitination" refers to a compound that prevents or inhibits the ubiquitination of the FANC D2 gene. "Ubiquitination" is defined as the covalent linkage of ubiquitin to a protein by a E3 mono-ubiquitin ligase. In a preferred embodiment, the "inhibitor of the mono-ubiquitination" refers to any inhibitor of a FANC protein complex with E3 FANC D2 monoubiquitin ligase activity such that FANC D2 monoubiquitin ligase activity is inhibited.

As used herein, the term "cisplatin" refers to an agent with the following chemical structure:

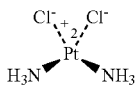

Cisplatin, also called cis-diamminedichloroplatinum(II), is one of the most frequently used anticancer drugs. It is an effective component of several different combination drug protocols used to treat a variety of solid tumors. These drugs are used in the treatment of testicular cancer (with bleomycin and vinblastine), bladder cancer, head and neck cancer (with bleomycin and fluorouracil), ovarian cancer (with cyclophosphamide or doxorubicin) and lung cancer (with etoposide). Cisplatin has been found to be the most active single agent against most of these tumors; Cisplatin is commercially available as 'Platinol' from Bristol Myers Squibb Co. Cisplatin, is one of a number of platinum coordination complexes with antitumor activity. The platinum compounds are DNA cross-linking agents similar to but not identical to the alkylating agents. The platinum compounds exchange chloride ions for nucleophilic grows of various kinds. Both the cis and trans isomers do this but the trans isomer is known to be biologically inactive for reasons not completely understood. To possess antitumor activity a platinum compound must have two relatively labile cis-oriented leaving groups. The principal sites of reaction are the N7 atoms of guanine and adenine. The main interaction is formation of intrastrand cross links between the drug and neighboring guanines. Intrastrand cross linking has been shown to correlate with clinical response to cisplatin therapy. DNA/protein cross linking also occurs but this does not correlate with cytotoxicity. Cross-resistance between the two groups of drugs is usually not seen indicating that the mechanisms of action are not identical. The types of cross linking with DNA may differ between the platinum compounds and the typical alkylating agents.

As used herein, "resistance to one or more anti-neoplastic agents" refers the ability of cancer cells to develop resistance to anticancer drugs. Mechanisms of drug resistance include decreased intracellular drug levels caused by an increased drug efflux or decreased inward transport, increased drug inactivation, decreased conversion of drug to an active form, altered amount of target enzyme or receptor (gene amplification), decreased affinity of target enzyme or receptor for drug, enhanced repair of the drug-induced defect, decreased activity of an enzyme required for the killing effect (topoisomerase II). In a preferred embodiment of the invention, drug resistance refers to the enhanced repair of DNA damage induced by one or more anti-neoplastic agents. In another preferred embodiment of the invention, the enhanced repair of DNA damage induced by one or more anti-neoplastic agents is due to a constitutively active Fanconi Anemia/BRCA DNA repair pathway.

As used herein, the term "anti-neoplastic agent" refers to a compound that is used to treat cancer. According to the invention, an "anti-neoplastic agent" encompasses chemotherapy compounds as well as other anti-cancer agents known in the art. In a preferred embodiment, the "anti-neoplastic agent" is cisplatin. Anti-neoplastic agents according to the invention also include cancer therapy protocols using chemotherapy compounds in conjunction with radiation therapy and/or surgery. Radiation therapy relies on the local destruction of cancer cells through ionizing radiation that disrupts cellular DNA. Radiation therapy can be externally or internally originated, high or low dose, and delivered with computer-assisted accuracy to the site of the tumor. Brachytherapy, or interstitial radiation therapy, places the source of radiation directly into the tumor as implanted "seeds."

As used herein, the term "a reduced growth rate" refers to a decrease of 50%, preferably 90%, more preferably 99% and most preferably 100% in the rate of cellular proliferation of a tumor cell line that is being treated with a potential inhibitor of the Fanconi Anemia/BRCA pathway and one or more chemotherapy compounds relative to cells of a tumor cell line that is not being treated with a potential inhibitor of the Fanconi Anemia/BRCA pathway and one or more chemotherapy compounds.

As used herein, the term "chemosensitizing agent" refers to any compound that renders a cell or cell population sensitive to a chemotherapy compound and results in a "reduced growth rate" as defined herein. A chemosensitizing agent is a compound that is generally not cytotoxic in itself, but modifies the host or tumor cells to enhance anticancer therapy. According to the invention, cellular resistance to a chemotherapy compound is reversed in the presence of a chemosensitizing agent. In a preferred embodiment, the chemosensitizing agent is an inhibitor of the Fanconi Anemia/BRCA pathway. In a most preferred embodiment, the chemosensitizing agent is an inhibitor of the mono-ubiquitination of the FANC D2 protein.

As used herein, the "methylation state of a Fanconi Anemia/BRCA pathway gene" refers to the presence of one or more methylated cytosines (5 m-C) within a Fanconi Anemia/BRCA pathway gene and results in a decrease or inhibition of gene expression of 90%, 99% or preferably 100% relative to a gene that is not methylated. In a preferred embodiment, the methylated cytosines reside within CpG islands. According to the invention, a gene is said to be "methylated" when one or more of CpG residues is methylated.

As used herein, "microarray", or "array", refers to a plurality of unique biomolecules attached to one surface of a solid support. Preferably, a biomolecule of the invention a potential inhibitor of the Fanconi Anemia/BRCA pathway as described herein. In this embodiment, the microarray of the invention comprises nucleic acids, proteins, polypeptides, peptides, fusion proteins or small molecules that are immobilised on a solid support, generally at high density. Each of the biomolecules is attached to the surface of the solid support in a pre-selected region. Suitable solid supports are available commercially, and will be apparent to the skilled person. The supports may be manufactured from materials such as glass, ceramics, silica and silicon. The supports usually comprise a flat (planar) surface, or at least an array in which the molecules to be interrogated are in the same plane. In one embodiment, the array is on microbeads. In one embodiment, the array comprises at least 10, 500, 1000, 10,000 different biomolecules attached to one surface of the solid support.

BRIEF DESCRIPTION OF THE DRAWINGS

The foregoing features of the invention will be more readily understood by reference to the following detailed description, taken with reference to the accompanying drawings, in which:

FIGS. 2A and 2B demonstrates that the Fanconi Anemia pathway is required for the formation of FANCD2 nuclear foci. Top panel shows anti-FANCD2 immunoblots of SV40 transformed fibroblasts prepared as whole cell extracts. Panels 2A-2H show immunofluorescence with the affinity-purified anti-FANCD2 antiserum. The uncorrected (mutant, M) FA fibroblasts were FA-A (GM6914), FA-G (FAG326SV), FA-C (PD426), and FAD (PD20F). The FA-A, FA-G, and FA-C fibroblasts were functionally complemented with the corresponding FA cDNA. The FA-D cells were complemented with neomycin-tagged human chromosome 3p (Whitney et al., 1995).

FIGS. 3A-3E show the cell cycle dependent expression of the two isoforms of the FANCD2 protein. (a) HeLa cells, SV40 transformed fibroblasts from an FA-A patient (GM6914), and GM6914 cells corrected with FANCA cDNA were synchronized by the double thymidine block method. Cells corresponding to the indicated phase of the cell cycle were lysed, and processed for FANCD2 immunoblotting (b) Synchrony by nocodazole block (c) Synchrony by mimosine block (d) HeLa cells were synchronized in the cell cycle using nocodazole or (e) mimosine, and cells corresponding to the indicated phase of the cell cycle were immunostained with the anti-FANCD2 antibody and analyzed by immunofluorescence.

FIGS. 4A-4J show the formation of activated FANCD2 nuclear foci following cellular exposure to MMC, Ionizing Radiation, or Ultraviolet Light. Exponentially-growing HeLa cells were either untreated or exposed to the indicated DNA damaging agents, Mitomycin C (MMC) (FIG. 4A), γ-irradiation (IR) (FIG. 4B), or Ultraviolet Light (UV) (FIGS. 4C-4E), and processed for FANCD2 immunoblotting or FANCD2 immunostaining. FIG. 4A depicts cells that were continuously exposed to 40 ng/ml MMC for 0-72 hours as indicated, or treated for 24 hours and fixed for immunofluorescence. FIGS. 4B-4E show cells that were exposed to γ-irradiation (10 Gy) or UV light (60 J/m2) and collected after the indicated time (FIGS. 4B and 4C) or irradiated with the indicated doses and harvested one hour later (FIGS. 4D and 4E). For immunofluorescence analysis cells were fixed 8 hours after treatment. The indicated EBV-transformed lymphoblast lines from a normal individual (PD7) or from various Fanconi Anemia patients were either treated with 40 ng/ml of Mitomycin C continuously (lanes 1-21; FIGS. 4G and 4H) or exposed to 15 Gy of γ-irradiation (lanes 22-33; FIG. 4I)) and processed for FANCD2 immunoblotting. FIG. 4F depicts the effect of DNA damage on FA cells as assessed by the presence or absence activated FANCD2-L isoform and FANCD2 nuclear foci. The upregulation of FANCD-L after MMC or IR treatment was seen in PD7 (lanes 2-5; FIG. 4G) and in the corrected FA-A cells (lanes 28-33; FIG. 4I), but was not observed in any of the mutant Fanconi Anemia cell lines. Similarly, IR-induced FANCD2 nuclear foci were not detected in PA fibroblasts (FA-G+IR; FIG. 4J) but were restored after functional complementation (PA-G+FANCG; FIG. 4J).

FIGS. 11A-11C show a Western blot analysis of the FANCD2 protein in human Fanconi Anemia cell lines. Whole cell lysates were generated from the indicated fibroblast and lymphoblast lines. Protein lysates (70 g) were probed directly by immunoblotting with the anti-FANCD2 antiserum. The FANCD2 proteins (155 kD and 162 kD) are indicated by arrows. Other bands in the immunoblot are non-specific. (a) Cell lines tested included wild-type cells (lanes 1,7), PD20 Fibroblasts (lane 2), PD20 lymphoblasts (lane 4), revertant. MMC-resistant PD20 lymphoblasts (lane 5, 6), and chromosome 3p complemented PD20 fibroblasts (lane 3). Several other FA group D cell lines were analyzed including HSC62 (lane 8) and VU008 (lane 9). FA-A cells were HSC72 (lane 10), FA-C cells were PD4 (lane 11), and PA-G cells were EUFA316 (lane 12). (b) Identification of a third FANCD2 patient. FANCD2 protein was readily detectable in wild-type and FA group G cells but not in PD733 cells. (c) Specificity of the antibody. PD20i cells transduced with a retroviral FANCD2 expression vector displayed both isoforms of the FANCD2 protein (lane 4) in contrast to empty vector controls (lane 3) and untransfected PD20i cells (lane 2). In wild-type cells the endogenous FANCD2 protein (two isoforms) was also immunoreactive with the antibody (lane 1).

FIGS. 13A and 13B show a molecular basis for the reversion of PD20 Lymphoblasts. (a) PCR primers to exons 5 and 6 were used to amplify cDNA. Control samples (right lane) yielded a single band of 114 bp, whereas PD20 cDNA (left lane) showed 2 bands, the larger reflecting the insertion of 13 bp of intronic sequence into the maternal allele. Reverted, MMC resistant lymphoblasts (middle lane) from PD20 revealed a third, inframe splice variant of 114+36 bp (b) Schematic representation of splicing at the FANCD2 exon 5/intron 5 boundary. In wild-type cDNA 100% of splice events occur at the proper exon/intron boundary (SEQ ID NO:189), whereas the maternal A→G mutation (indicated by arrow) leads to aberrant splicing, also in 100% (SEQ ID NO:190). In the reverted cells all cDNAs with the maternal mutation also had a second sequence change (fat arrow) and showed a mixed splicing pattern with insertion of either 13 by (~40% of mRNA) or 36 by (~60% of mRNA) (SEQ ID NO:191).

FIG. 14 shows an FANCD2 Western blot of cancer cell lines derived from patients with ovarian cancer.

Figure 15A:
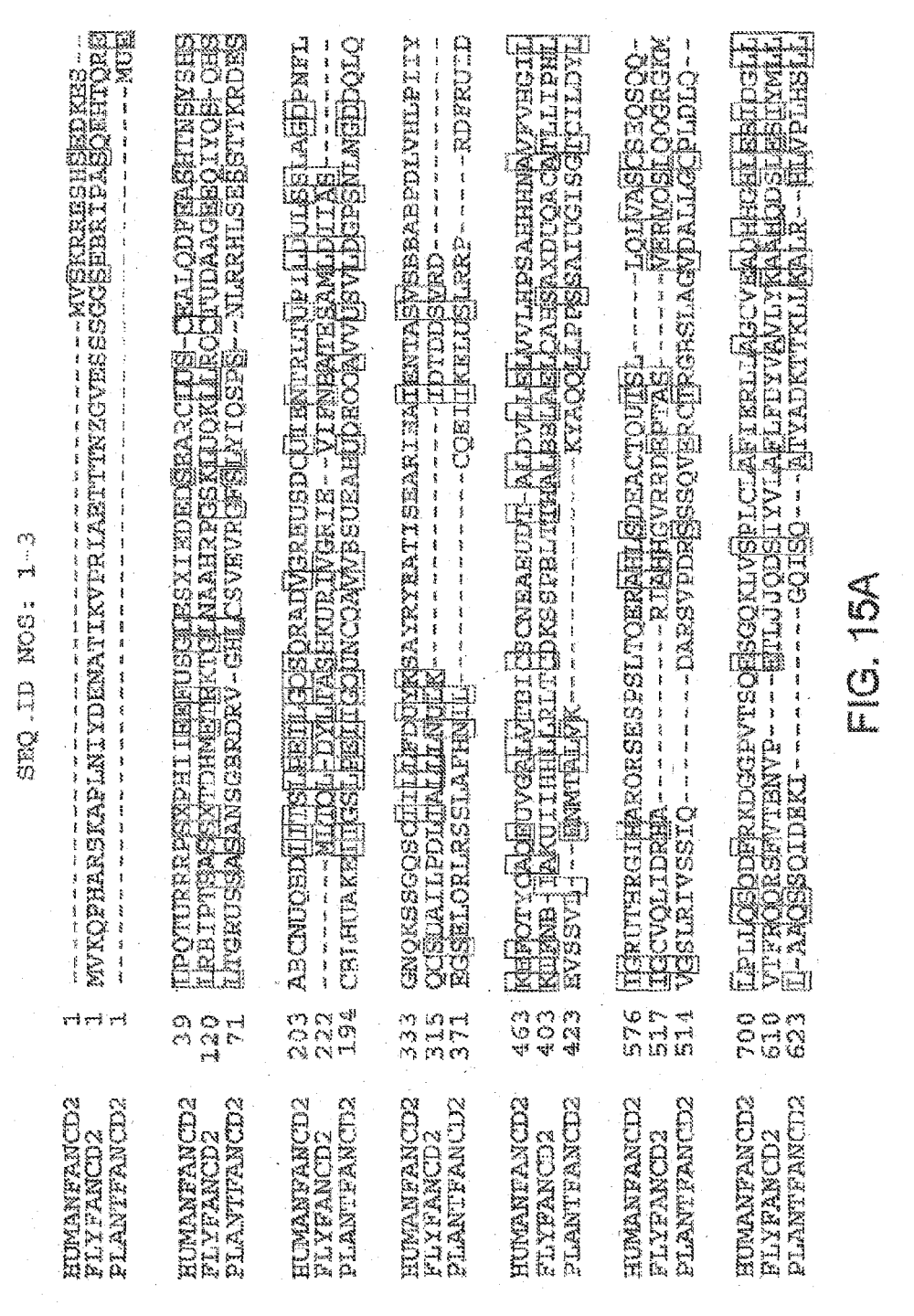
Figure 15B:
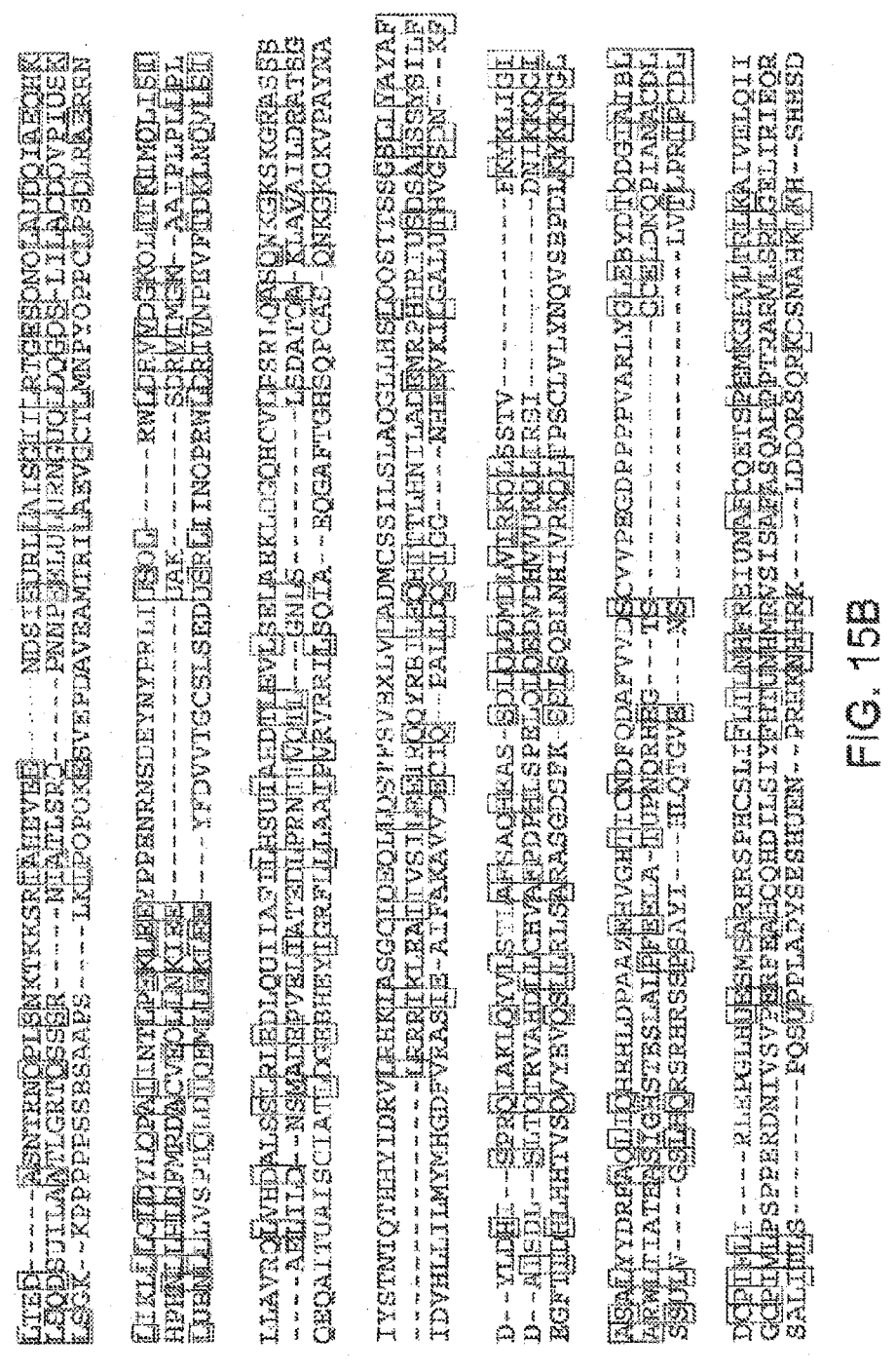
Figure 15C:
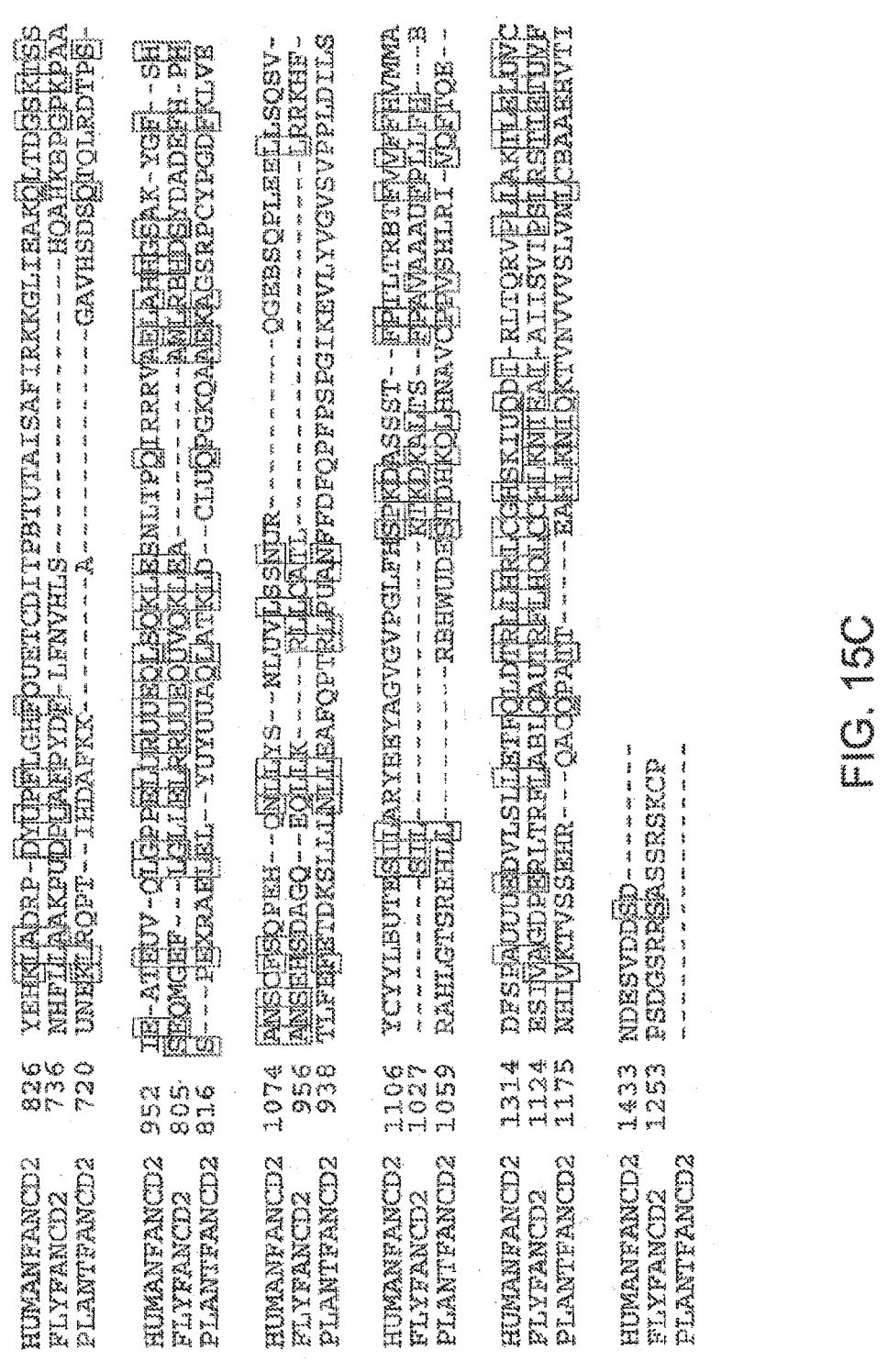
Figure 15D:
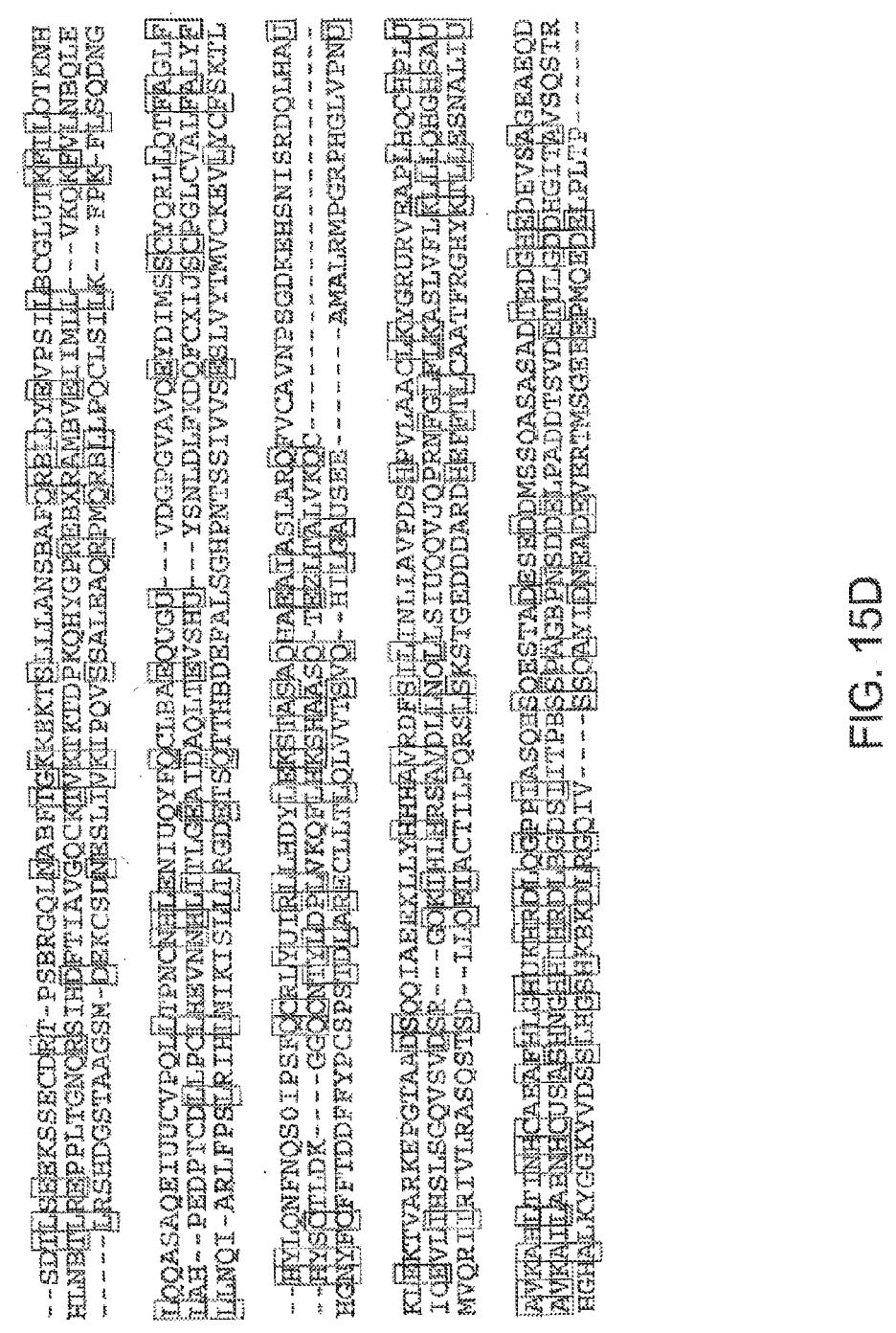

FIGS. 15A-15D show a sequence listing for amino acid sequence of human FANCD2 (SEQ ID NO:1) and alignment with fly (SEQ ID NO:2) and plant (SEQ ID NO:3) homologues using the BEAUTY algorithm (Worley et al., (1995) Genome Res. Vol. 5, pp. 173-184). Black boxes indicate amino acid identity and gray similarity. The best alignment scores were observed with hypothetical proteins in *D. melanogaster* (p=8.4×10-58, accession number AAF55806) and *A. thaliana* (p=9.4×10-45, accession number B71413).

Figure 16B:
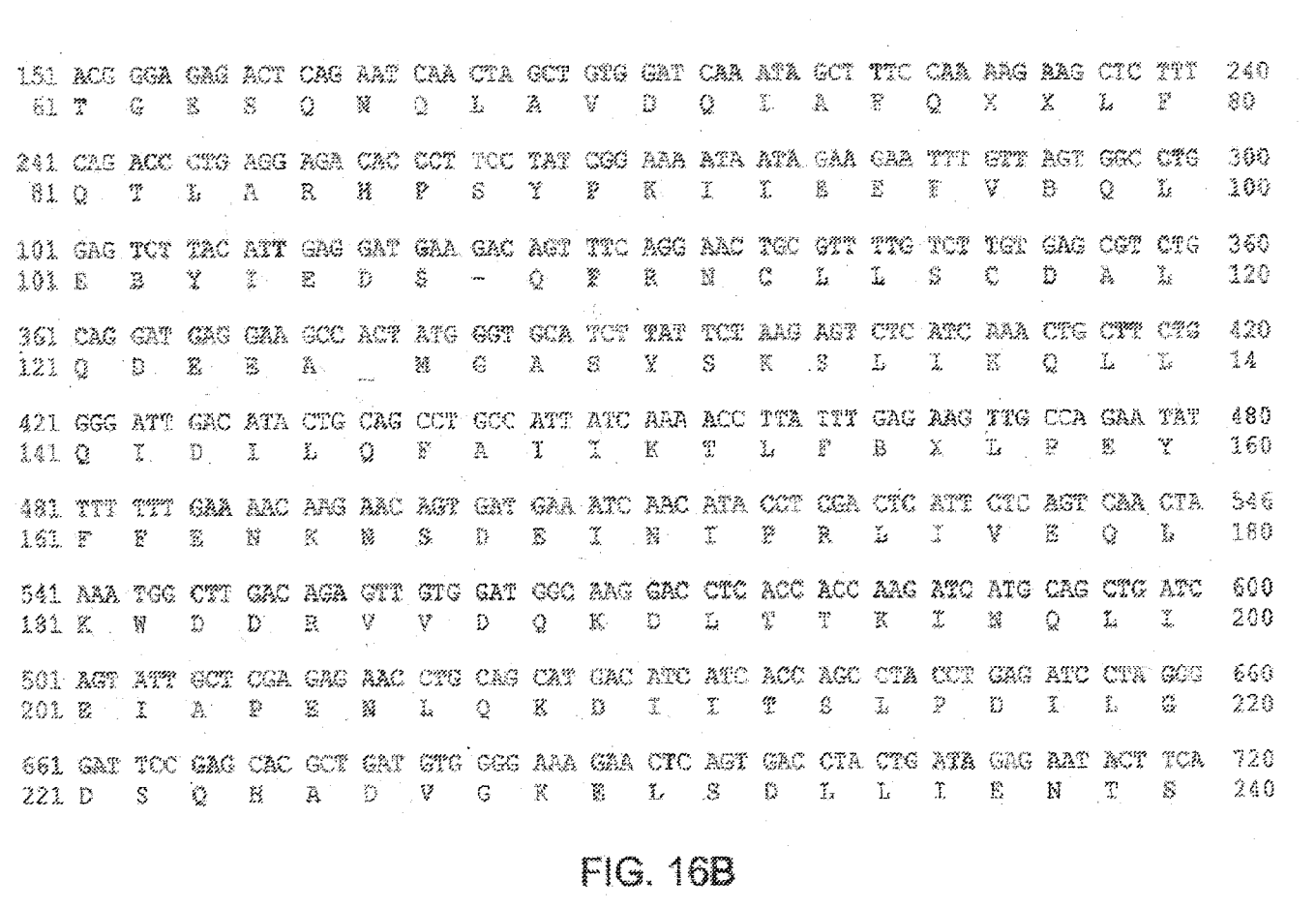
Figure 16C:
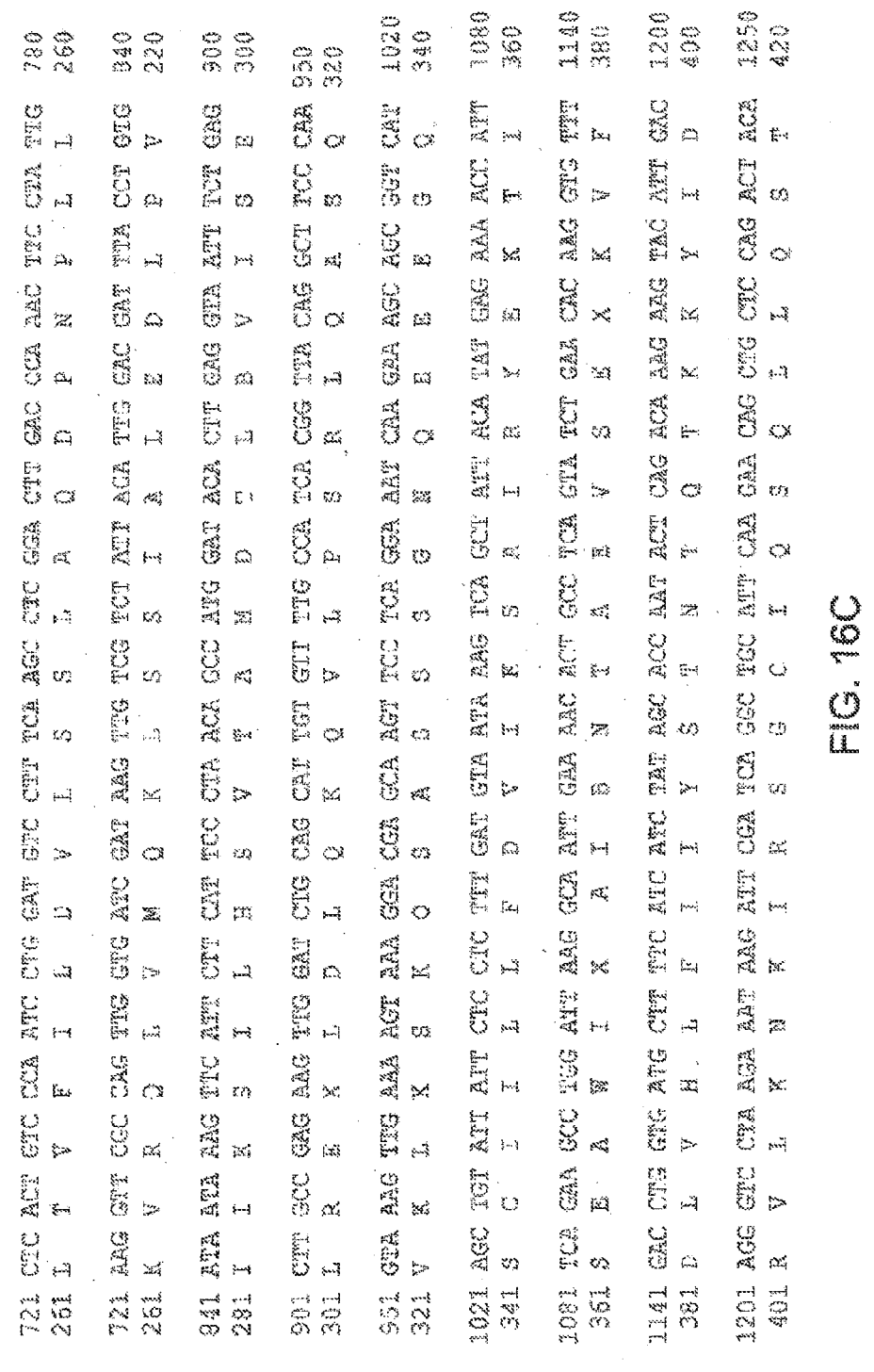
Figure 16D:
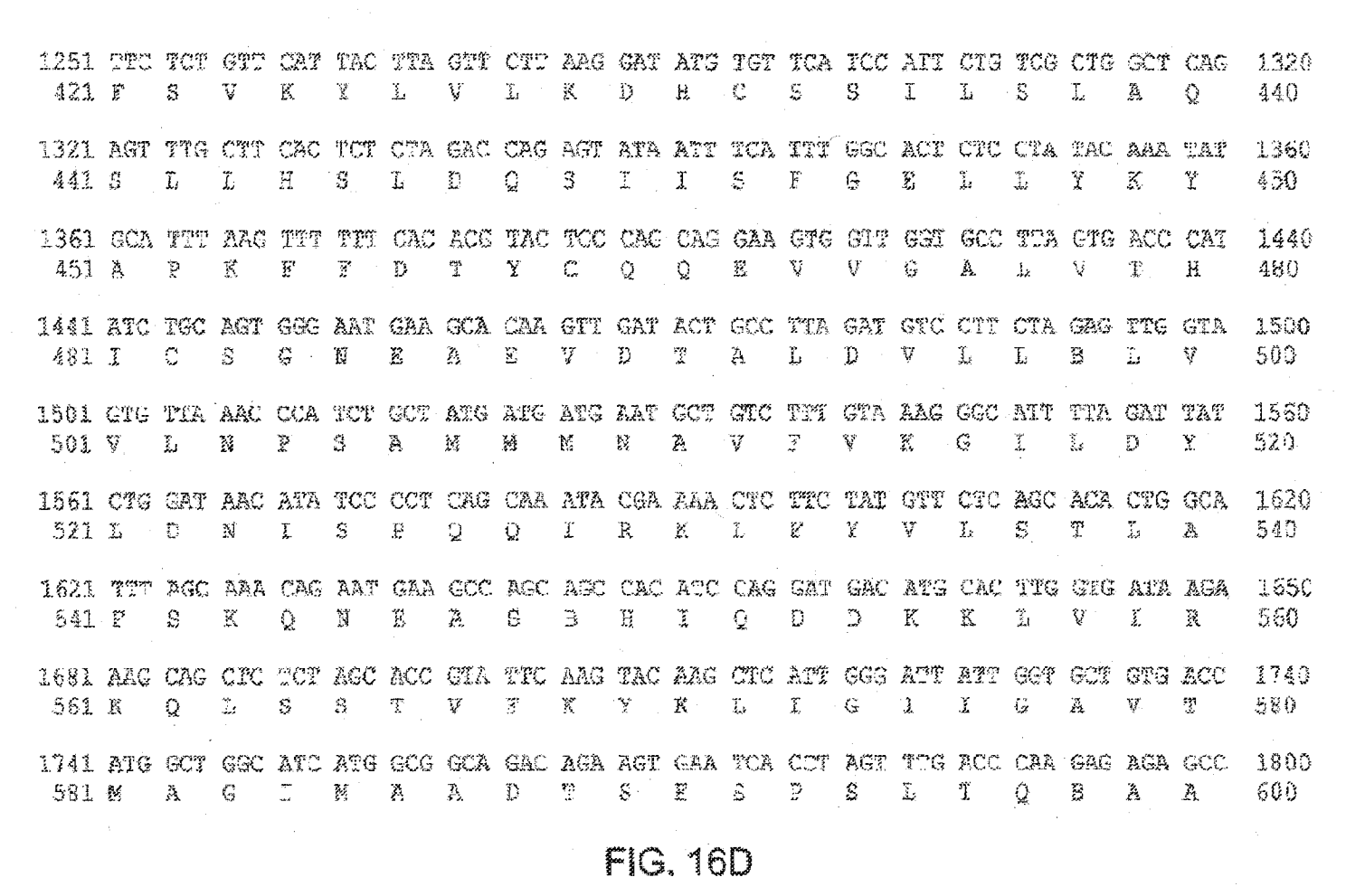
Figure 16H:
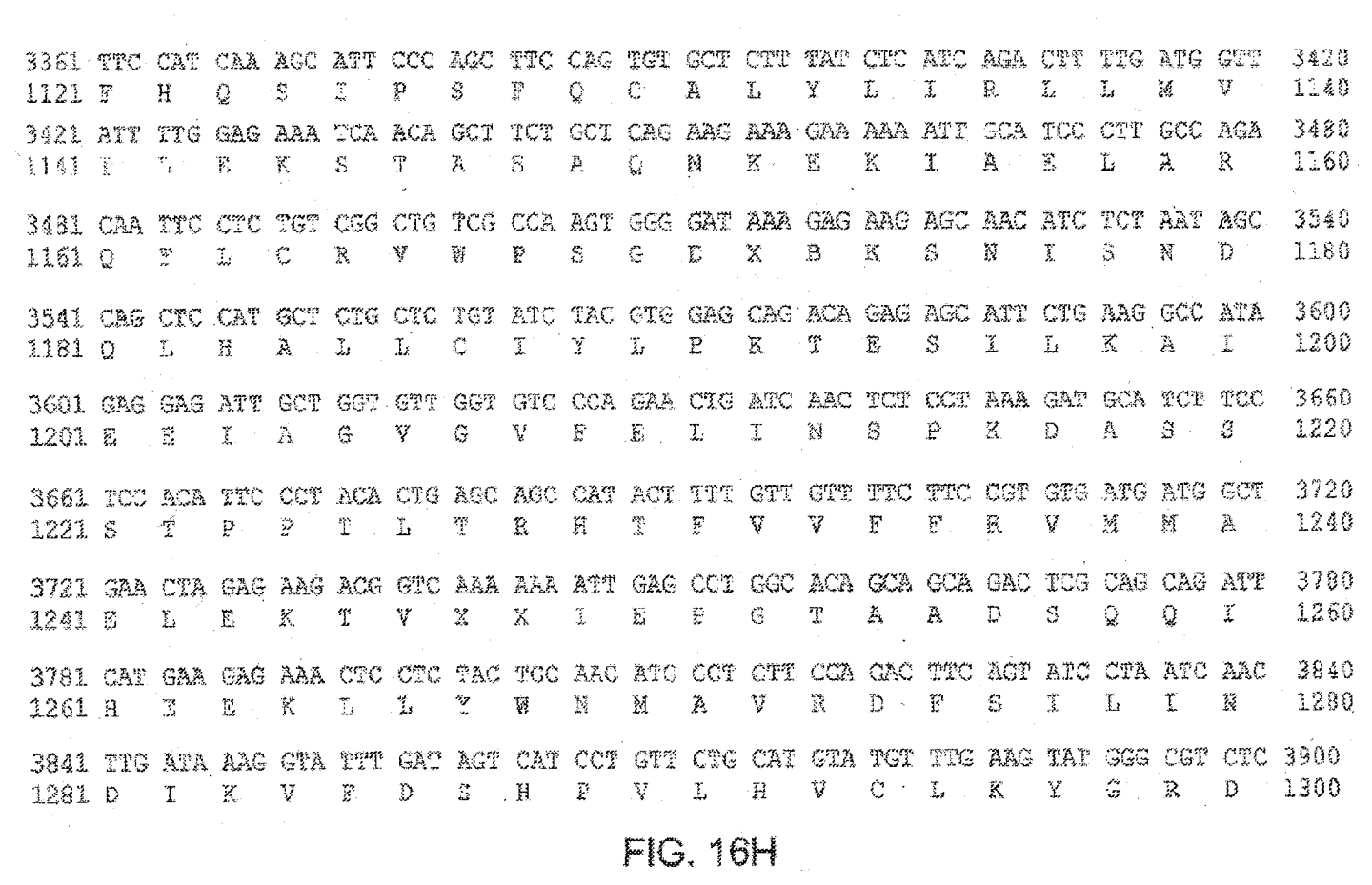
Figure 16I:
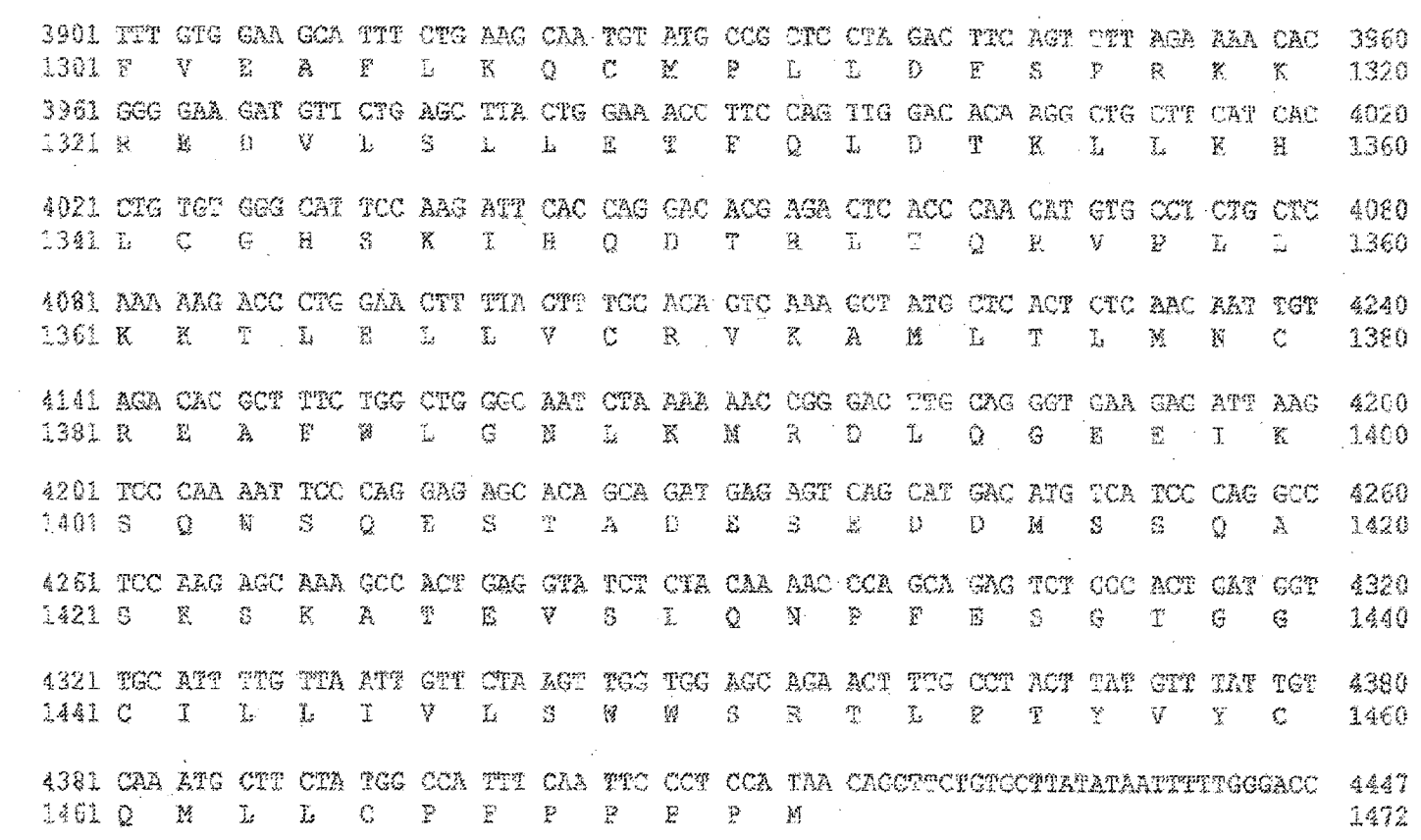
Figure 16J:
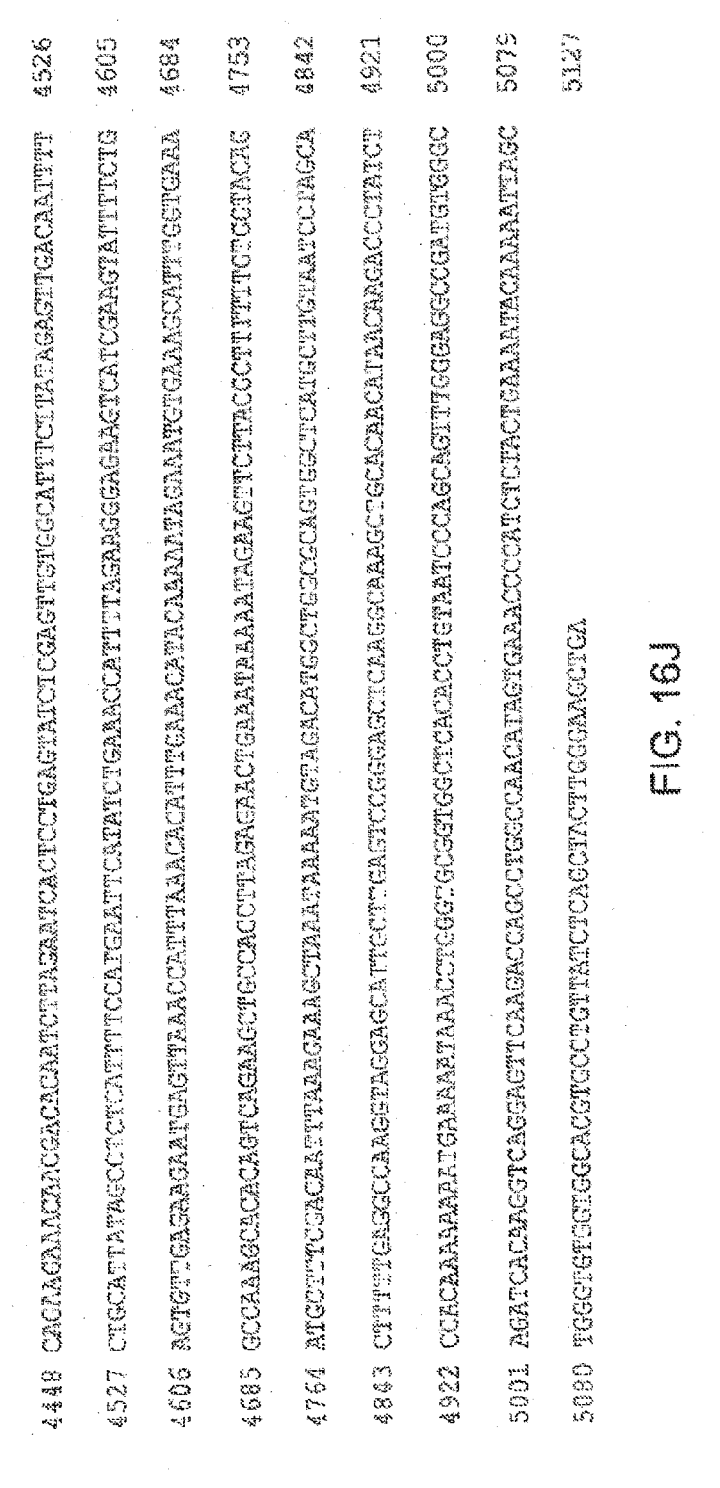

FIGS. 16A-16J are the FANCD cDNA sequence −63 to 5127 nucleotides (SEQ ID NO:5) and polypeptide encoded by this sequence from amino acid 1 to 1472 (SEQ ID NO:4).

Figure 17:
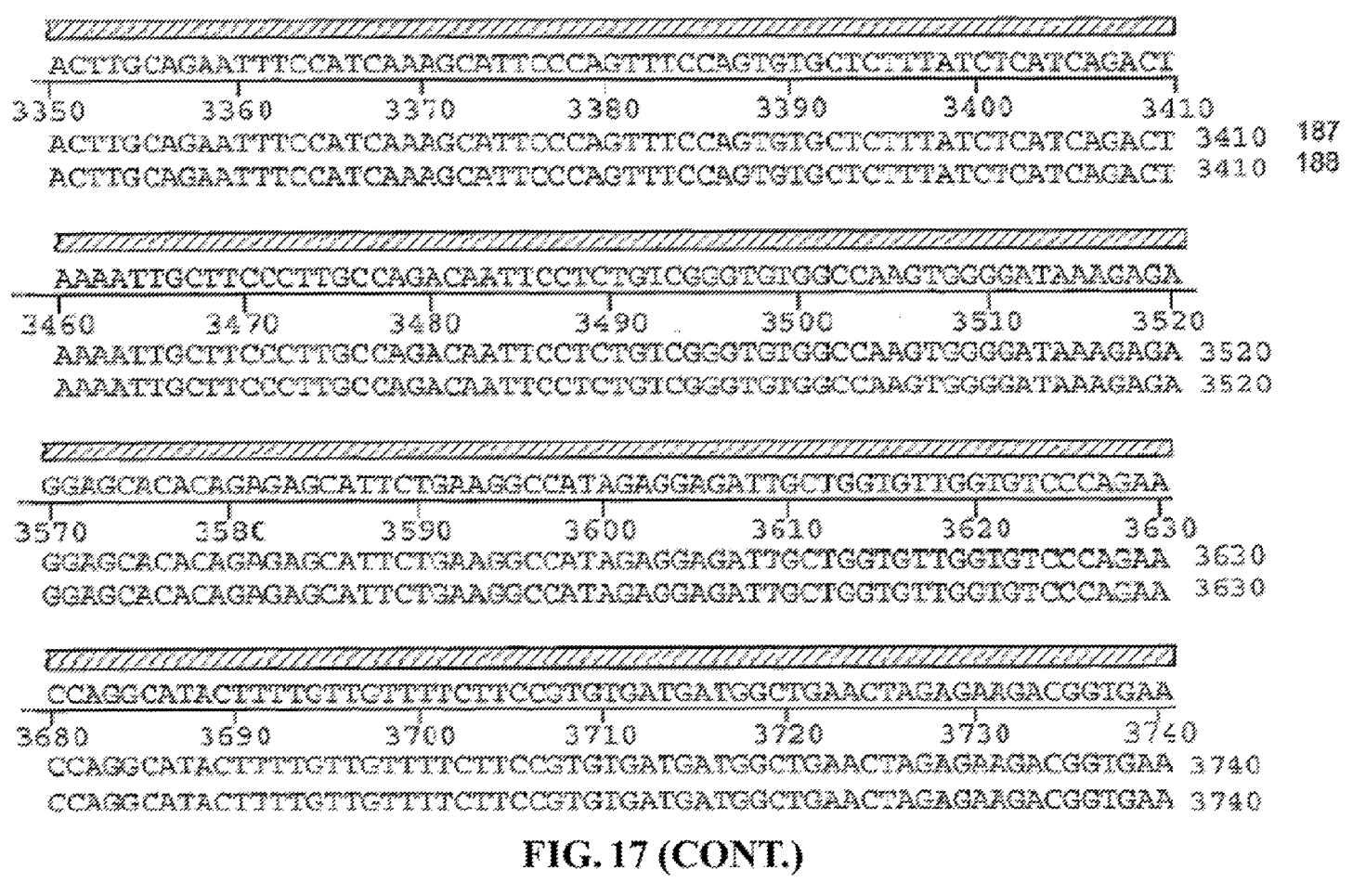
Figure 17:
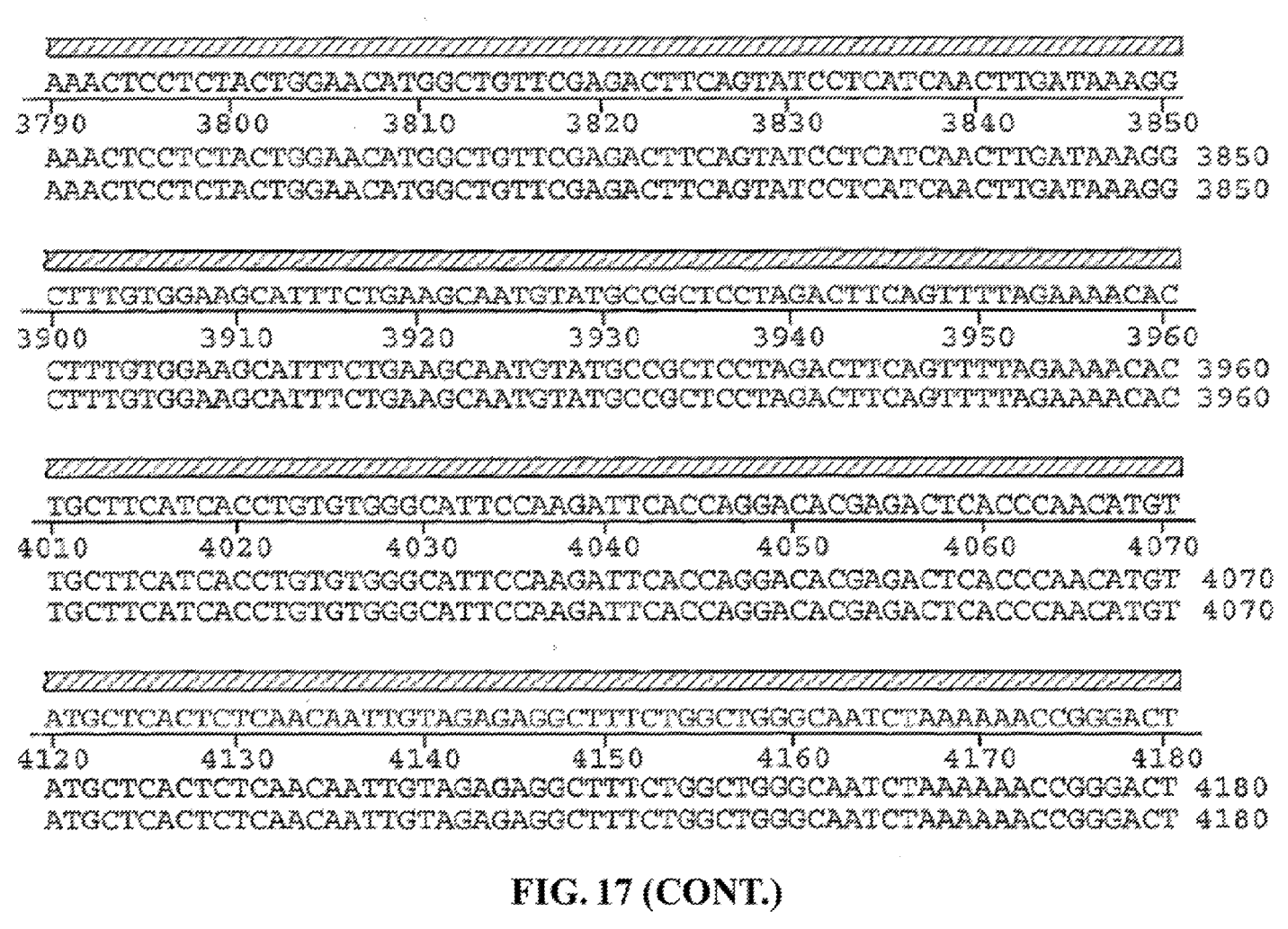

FIG. 17 is the nucleotide sequence for FANCD-S ORF (SEQ ID NO:187) compared with FANCD cDNA (SEQ ID NO:188).

FIGS. 18A and 18B are the nucleotide sequence for human FANCD2-L (SEQ ID NO:6).

FIG. 19A and 19B are the nucleotide sequence for human FANCD2-S(SEQ ID NO:7).

FIGS. 20A and 20B is the nucleotide sequence for mouse FANCD2 (SEQ ID NO:8).

DETAILED DESCRIPTION

Figure 1A:
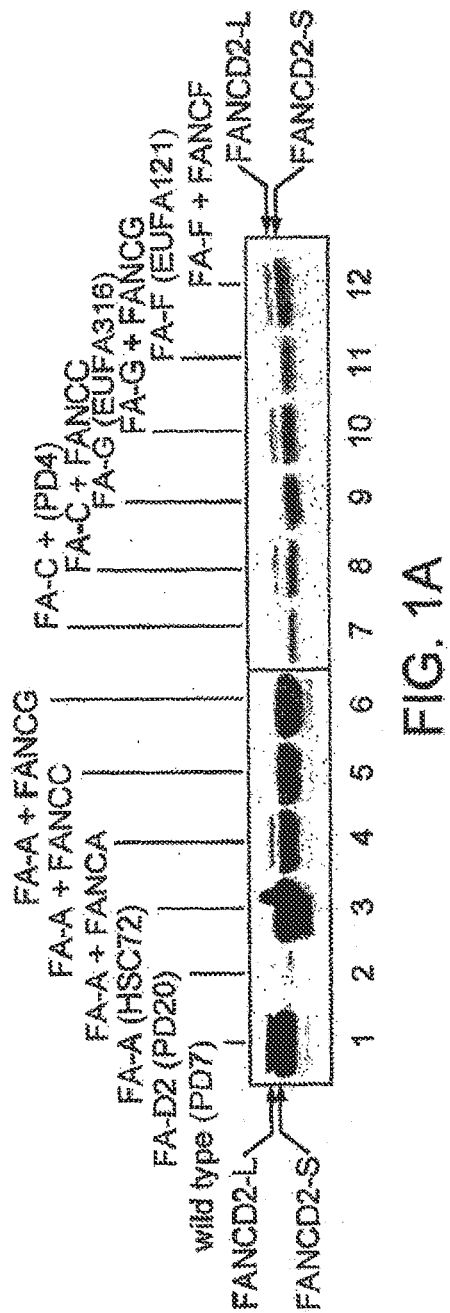
FIG. 1A provides a Western blot demonstrating that the Fanconi Anemia protein complex is required for the monoubiquitination of FANCD2. Normal (WT) cells (lane 1) express two isoforms of the FANCD2 protein, a low molecular weight isoform (FANCD2-S) (155 kD) and a high molecular weight isoform (FANCD2-L) (162 kD). Lanes 3, 7, 9, 11 show that FA cell lines derived from type A, C, G, and F patients only express the FANCD2-S isoform. Lanes 4, 8, 10, 12 show the restoration of the high molecular weight isoform FANCD2-L following transfection of cell lines with corresponding FAcDNA.

"FANCD2-L therapeutic agent" shall mean any of a protein isoform, and includes a peptide, a peptide derivative, analogue or isomer of the FANCD2-L protein and further include any of a small molecule derivative, analog, isomer or agonist that is functionally equivalent to FANCD2-L. Also included in the definition is a nucleic acid encoding FANCD2 which may be a full length or partial length gene sequence or cDNA or may be a gene activating nucleic acid or a nucleic acid binding molecule including an aptamer of antisense molecule which may act to modulate gene expression.

"Nucleic acid encoding FANCD-2" shall include the complete cDNA or genomic sequence of FANCD2 or portions thereof for expressing FANCD2-L protein as defined above. The nucleic acid may further be included in a nucleic acid carrier or vector and includes nucleic acid that has been suitably modified for effective delivery to the target site.

"Stringent conditions of hybridization" will generally include temperatures in excess of 30° C., typically in excess of 37° C., and preferably in excess of 45° C. Stringent salt conditions will ordinarily be less than 1000 mM, typically less than 500 mM, and preferably less than 200 mM.

"Substantial homology or similarity" for a nucleic acid is when a nucleic acid or fragment thereof is "substantially homologous" (or "substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80.

"Antibodies" includes polyclonal and/or monoclonal antibodies and fragments thereof including single chain antibodies and including single chain antibodies and Fab fragments, and immunologic binding equivalents thereof, which have a binding specificity sufficient to differentiate isoforms of a protein. These antibodies will be useful in assays as well as pharmaceuticals.

"Isolated" is used to describe a protein, polypeptide or nucleic acid which has been separated from components which accompany it in its natural state. An "isolated" protein or nucleic acid is substantially pure when at least about 60 to 75% of a sample exhibits a single amino acid or nucleotide sequence.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Polynucleotide" includes RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric nucleic acids, etc.). Also included are synthetic molecules that mimic nucleic acids in their ability to bind to a designated sequence via hydrogen bonding and other chemical interactions.

"Mutation" is a change in nucleotide sequence within a gene, or outside the gene in a regulatory sequence compared to wild type. The change may be a deletion, substitution, point mutation, mutation of multiple nucleotides, transposition, inversion, frame shift, nonsense mutation or other forms of aberration that differentiate the nucleic acid or protein, sequence from that of a normally expressed gene in a functional cell where expression and functionality are within the normally occurring range.

"Subject" refers to an animal including mammal, including human.

"Wild type FANCD2" refers to a gene that encodes a protein or an expressed protein capable of being monoubiquinated to form FANCD2-L from FANCD-S within a cell.

We have found that some Fanconi Anemia has similarities with a group of syndromes including ataxia telangiectasia (AT), Xeroderma pigmentosum (XP), Cockayne syndrome (CS), Bloom's syndrome, myelodysplastic syndrome, aplastic anemia, cancer susceptibility syndromes and HNPCC (see Table 2). These syndromes have an underlying defect in DNA repair and are associated with defects in maintenance of chromosomal integrity. Defects in pathways associated with DNA repair and maintenance of chromosomal integrity result in genomic instability, and cellular sensitivity to DNA damaging agents such as bifunctional alkylating agents that cause intrastrand crosslinking. Moreover, deficiencies in DNA repair mechanisms appear to substantially increase the probability of initiating a range of cancers through genetic rearrangements. This observation is pertinent with regard to the clinical use of DNA cross-linking drugs including mitomycin C, cisplatin, cyclophosphamide, psoralen and UVA irradiation.

Although Fanconi Anemia is a rare disease, the pleiotropic effects of FA indicate the importance of the wild type function of FA proteins in the pathway for diverse cellular processes including genome stability, apoptosis, cell cycle control and resistance to DNA crosslinks. The cellular abnormalities in FA include sensitivity to cross-linking agents, prolongation of G2 phase of cell cycle, sensitivity to oxygen including poor growth at ambient 02, overproduction of 02 radicals, deficient 02 radical defense, deficiency in superoxide dismutase; sensitivity to ionizing radiation (G2 specific); overproduction of tumor necrosis factor, direct defects in DNA repair including accumulations of DNA adducts, and defects in repair of DNA cross-links, genomic instability including spontaneous chromosome breakage, and hypermutability by deletion mechanism, increased aptosis, defective p53 induction, intrinsic stem cell defect, including decreased colony growth in vitro; and decreased gonadal stem cell survival.

Figure 8:
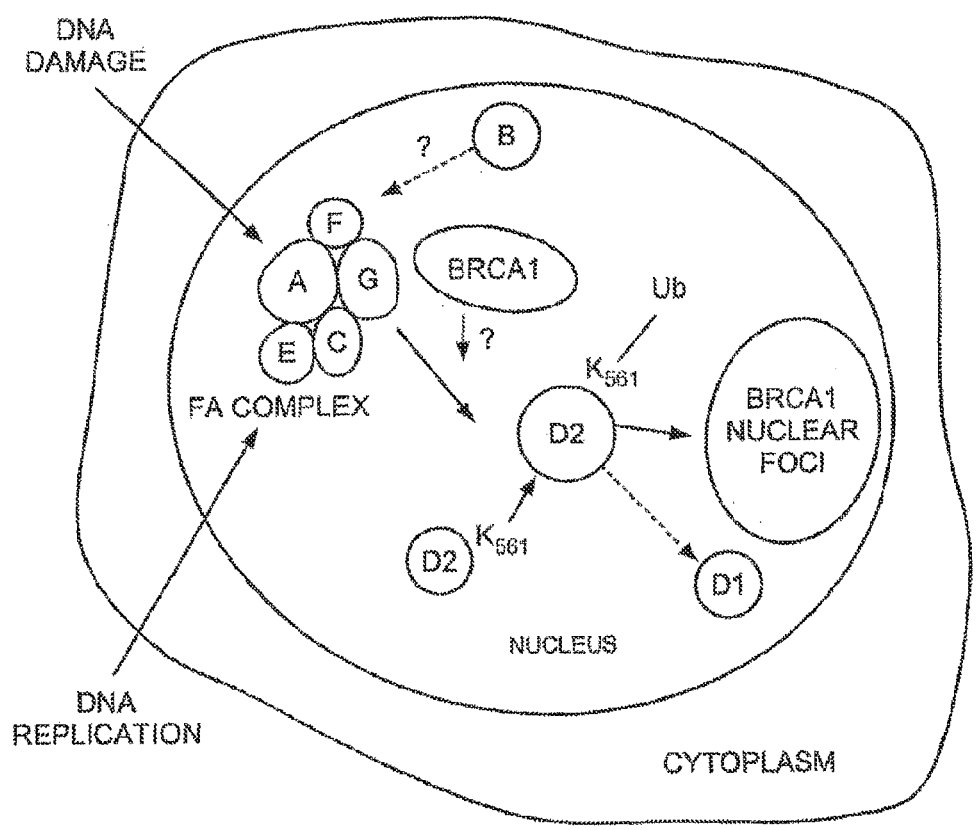
FIG. 8 provides a schematic interaction of the FA proteins in a cellular pathway. The FA proteins (A, C, and G) bind in a functional nuclear complex. Upon activation of this complex, by either S phase entry or DNA damage, this complex enzymatically modifies (monoubiquitinates) the D protein. According to this model, the activated D protein is subsequently targeted to nuclear foci where it interacts with the BRCA1 protein and other proteins involved in DNA repair.
Figure 9:
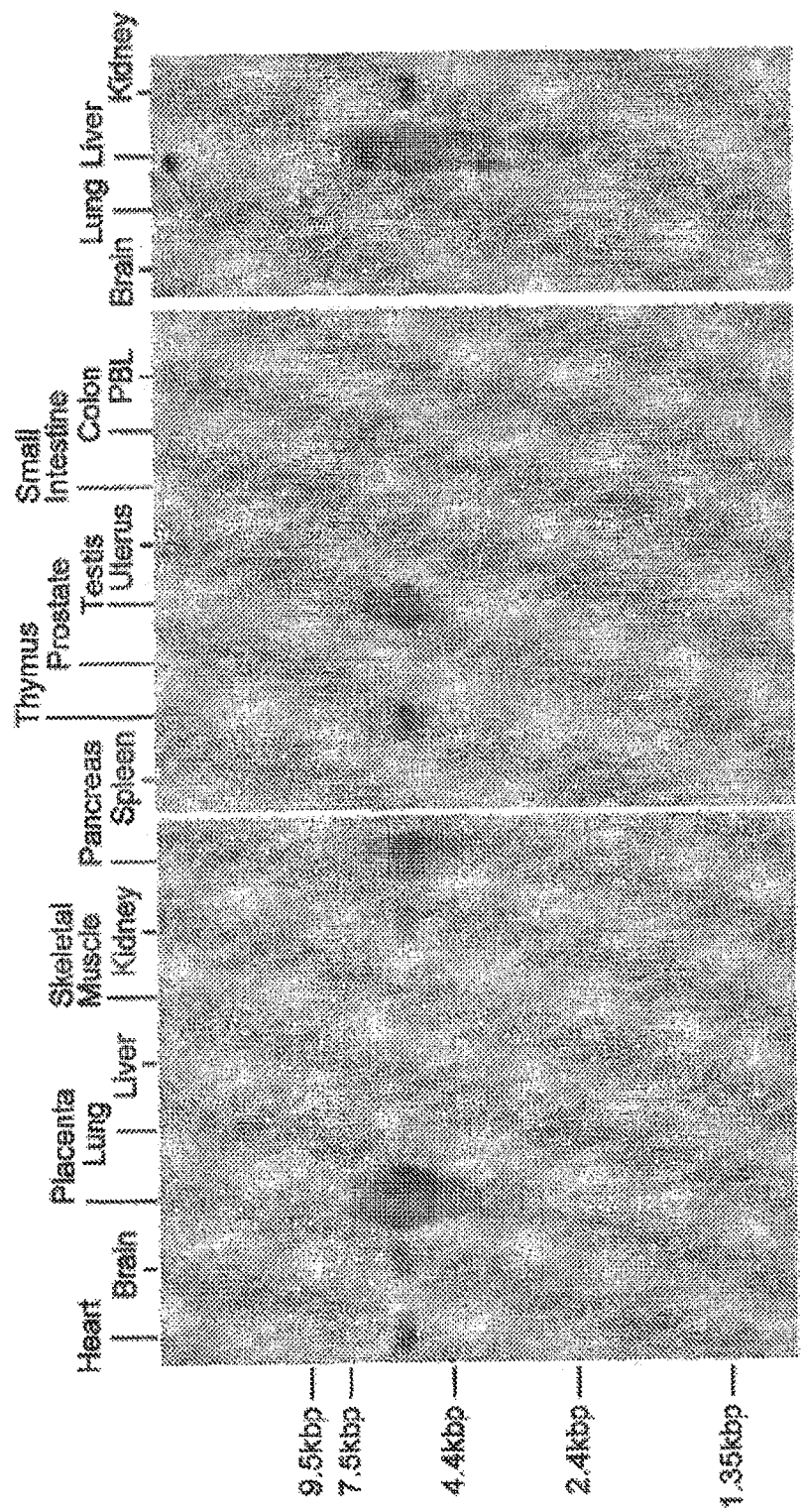
FIG. 9 shows a Northern blot of cells from heart, brain, placenta, liver, skeletal muscle, kidney, pancreas, spleen, thymus, prostate, testis, uterus, small intestine, colon and peripheral blood lymphocytes from a human adult and brain, lung, liver and kidney from a human fetus probed with a full-length FANCD2 cDNA and exposed for 24 hours.
Figure 10A:
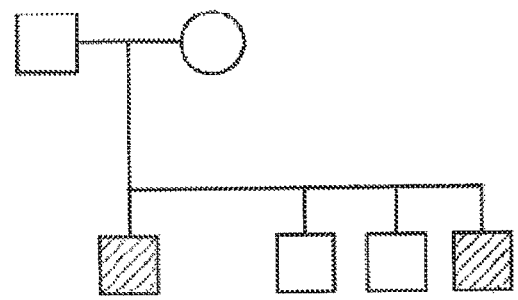
FIGS. 10A-10F show allele specific assays for mutation analysis of 2 FANCD2 families where the family pedigrees (a, d) and panels b, c, e and f are vertically aligned such that the corresponding mutation analysis is below the individual in question. Panels a-c depict the PD20 and panels d-f the VU008 family. Panels b and e show the segregation of the maternal mutations as detected by the creation of a new MspI site (PD20) or DdeI site (VU008). The paternally inherited mutations in both families were detected with allele specific oligonucleotide hybridization (panels c and f).
Figure 10B:
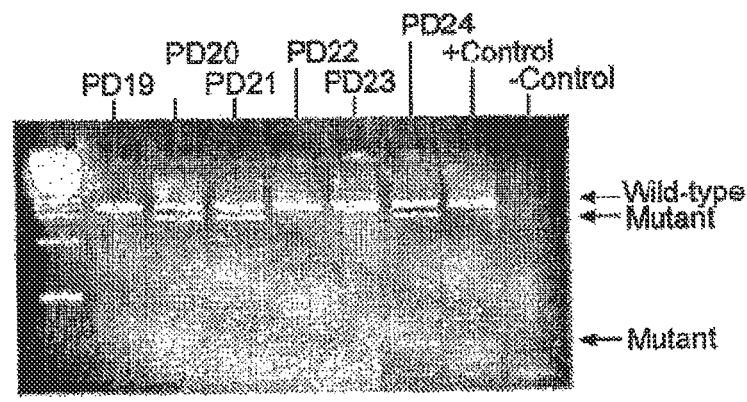
Figure 10C:
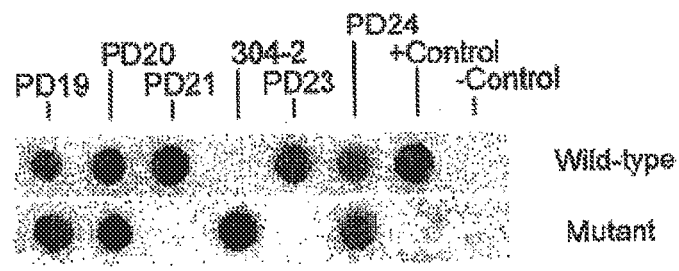
Figure 10D:
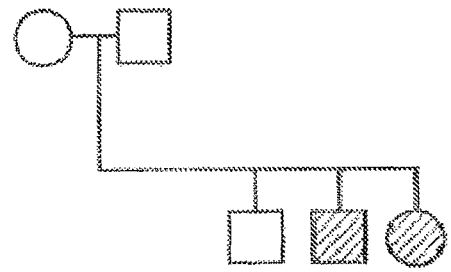
Figure 10E:
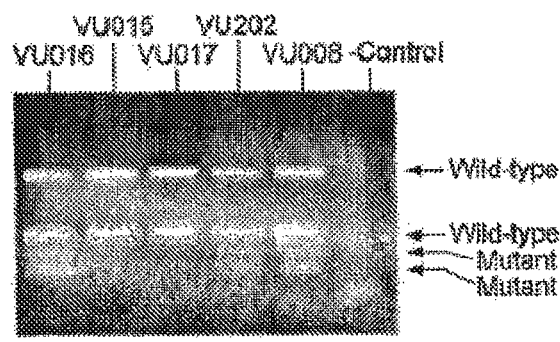
Figure 10F:
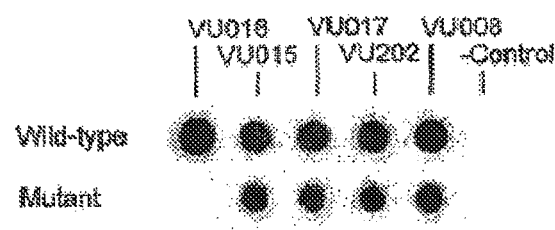

These features are reflective of the involvement of FA in maintenance of hematopoietic and gonadal stein cells, as well as the normal embryonic development of many different structures, including the skeleton and urogenital systems. Cell samples from patients were analyzed to determine defects in the FA complementation group D. Lymphoblasts from one patient gave rise to the PD20 cell line which was found to be mutated in a different gene from HSC62 derived from another patient with a defect in the D complementation group Mutations from both patients mapped to the D complementation group but to different genes hence the naming of two FANCD proteins-FANCD1 (HSC62) and FANCD2 (PD20) (Timmers et al., (2001) Molecular Cell, Vol. 7, pp. 241-248). We have shown that FANCD2 is the endpoint of the FA pathway and is not part of the FA nuclear complex nor required for its assembly or stability and that FANCD2 exists in two isoforms, FANCD2-S and FANCD2-L. We have also shown that transformation of the protein short form (FAND2-S) to the protein long form (FANCD2-L) occurs in response to the FA complex (FIG. 8). Defects in particular proteins associated with the FA pathway result in failure to make an important post translationally modified form of FANCD2 identified as FANCD2-L. The two isoforms of FANCD2 are identified as the short form and the long form.

Failure to make FANCD2-L correlates with errors in DNA repair and cell cycle abnormalities associated with diseases listed above.

To understand more about the role of FANCD2 in the aforementioned syndromes, we cloned the FANCD2 gene and determined the protein sequence. The FANCD2 gene has an open reading frame of 4,353 base pairs and forty four exons which encodes a novel 1451 amino acid nuclear protein, with a predicted molecular weight of 166 kD. Western blot analysis revealed the existence of 2 protein isoforms of 162 and 155 kD. The sequence corresponding to the 44 Intron/Exon Junctions are provided in Table 6 (SEQ ID NO:9-94).

Unlike previously cloned FA proteins, FANCD2 proteins from several nonvertebrate eukaryotes showed highly significant alignment scores with proteins in *D. melanogaster, A. thaliana*, and *C. elegans*. The *drosophila* homologue, has 28% amino acid identity and 50% similarity to FANCD2 (Figure and SEQ ID NO:1-3) and no functional studies have been carried out in the respective species. No proteins similar to FANCD2 were found in *E. coli* or *S. cerevisiae*.

We obtained the FANCD2 DNA sequence (SEQ ID NO:5) by analyzing the chromosome 3p locus in PD20 and VU008, two FA cell lines having biallelic mutations in the FANCD2 gene (FIGS. 10A-10F). The cell lines were assigned as complementation group D because lymphoblasts from the patients failed to complement HSC62, the reference cell line for group D. FANCD2 mutations were not detected in this group D reference cell line which indicates that the gene mutated in HSC62 is the gene encoding FANCD1 and in PD20 and VU008 is FANCD2 (FIG. 11). Microcell mediated chromosome transfer was used to identify the mutations (Whitney et al., Blood, (1995) Vol. 88, 49-58). Detailed analysis of five microcell hybrids containing small overlapping deletions encompassing the locus narrowed the candidate region of the FANCD2 gene to 200 kb. The FANCD2 gene was isolated as follows: Three candidate ESTs were localized in or near this FANCD2 critical region. Using 5' and 3' RACE to obtain full-length cDNAs, the genes were sequenced, and the expression pattern of each was analyzed by northern blot. EST SCC34603 had ubiquitous and low level expression of a 5 kb and 7 kb mRNA similar to previously cloned FA genes. Open reading frames were found for TIGR-A004X28, AA609512 and SGC34603 and were 234, 531 and 4413 by in length respectively. All 3 were analyzed for mutations in PD20 cells by sequencing cloned RT-PCR products. Whereas no sequence changes were detected in TIGR-A004X28 and AA609512, five sequence changes were found in SGC34603. Next, we determined the structure of the SGC34603 gene by using cDNA sequencing primers on BAC 177N7 from the critical region.

Based on the genomic sequence information, PCR primer pairs were designed (Table 7), the exons containing putative mutations were amplified, and allele-specific assays were developed to screen the PD20 family as well as 568 control chromosomes. Three of the alleles were common polymorphisms; however, 2 changes were not found in the controls and thus represented potential mutations (Table 3). The first was a maternally inherited A→G change at nt 376. In addition to changing an amino acid (S126G), this alteration was associated with mis-splicing and insertion of 13 bp from intron 5 into the mRNA. 43/43 (100%) independently cloned RT-PCR products with the maternal mutation contained this insertion, whereas only 3% (1/31) of control cDNA clones displayed mis-spliced mRNA. The 13 bp insertion generated a frameshift and predicts a severely truncated protein only 180 aminoacids in length. The second alteration was a paternally inherited missense change at position 1236 (R1236H). The segregation of the mutations in the PD20 core family is depicted in FIGS. 10A-F. Because the SGC34603 gene of PD20 contained both a maternal and a paternal allele not present on 568 control chromosomes and because the maternal mutation was associated with mis-splicing in 100% of cDNAs analyzed, we concluded that SGC34603 is the FANCD2 gene.

The protein encoded by FANCD2 is absent in PD20: To further confirm the identity of SGC34603 as FANCD2, an antibody was raised against the protein, and Western blot analysis was performed (FIGS. 11A-11C). The specificity of the antibody was shown by retroviral transduction and stable expression FANCD2 in PD20 cells (FIGS. 11A-11C). In wild-type cells this antibody detected two bands (155 and 162 kD) which we call FANCD2-S and -L (best seen in FIGS. 11A-11C). FANCD2 protein levels were markedly diminished in all MMC-sensitive cell lines from patient PD20 (FIG. 11*a*, lanes 2, 4) but present in all wild-type cell lines and FA cells from other complementation groups. Furthermore, PD20 cells corrected by microcell-mediated transfer of chromosome 3 also made normal amounts of protein (FIG. 11*a*, lane 3).

Figure 12A:
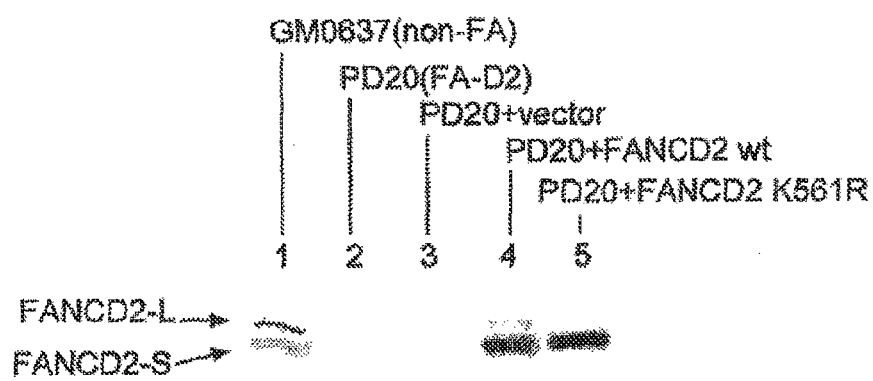
FIGS. 12A-12C show functional complementation of FA-D2 cells with the cloned FANCD2 cDNA. The SV40-transformed FA-D2 fibroblast line, PD20i, was transduced with pMMP-puro (PD20+vector) or pMMP-FANCD2 (PD20 FANCD2 wt). Puromycin-selected cells were subjected to MMC sensitivity analysis. Cells analyzed were the parental PD20F cells (Δ), PD20 corrected with human chromosome 3p (○), and PD20 cells transduced with either pMMP-puro ● or pMMP-FANCD2(wt)-puro (◆).
Figure 12B:
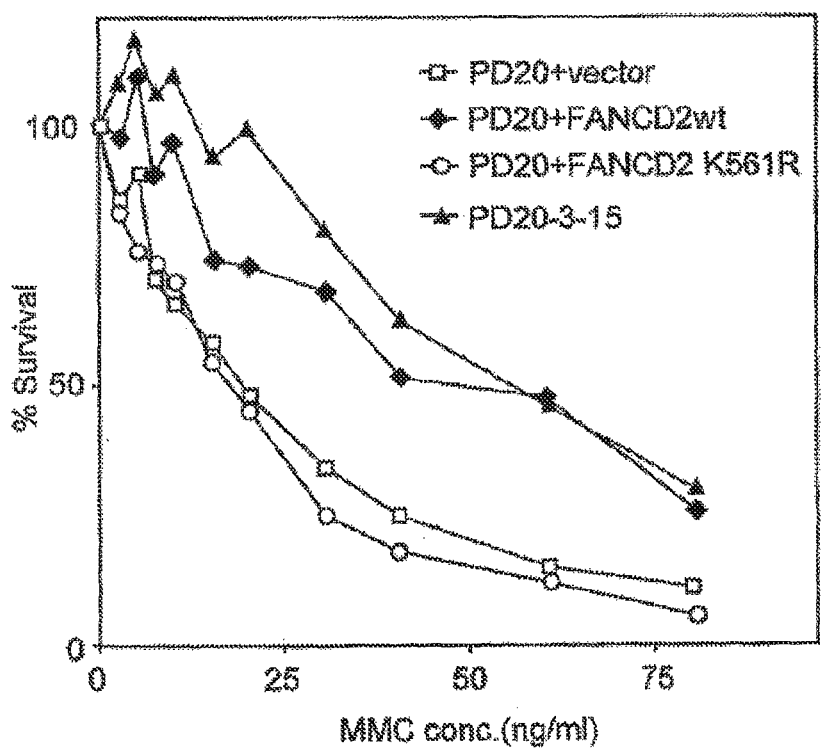
Figure 12C:
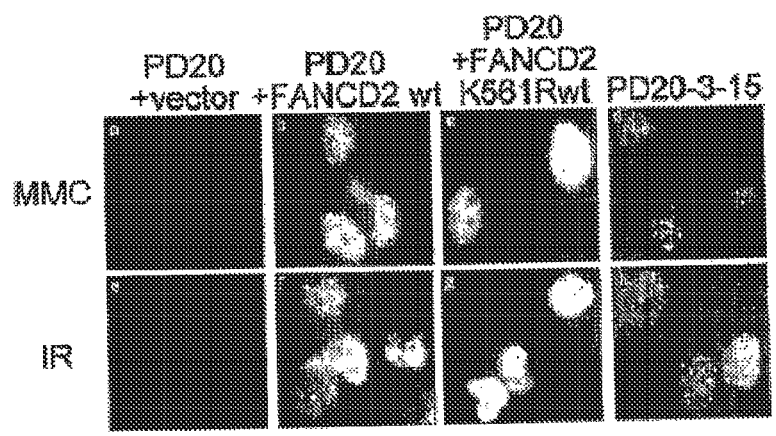

Functional complementation of FA-D2 cells with the FANCD2 cDNA: We next assessed the ability of the cloned FANCD2 cDNA to complement the MMC sensitivity of FA-D2 cells (FIGS. 12A-12C). The full length FANCD2 cDNA was subcloned into the retroviral expression vector, pMMP-puro, as previously described (Pulsipher et al. (1998), Mol. Med., Vol. 4, pp. 468-479). The transduced PD-20 cells expressed both isoforms of the FANCD2 protein, FANCD2-S and FANCD2-L (FIG. 12*c*). Transduction of PA-D2 (PD20) cells with pMMP-FANCD2 corrected the MMC sensitivity of the cells. These results further show that the cloned FANCD2 cDNA encodes the FANCD2-S protein, which can be post-translationally-modified to the FANCD2-L isoform. This important modification is discussed in greater detail below.

Figure 13A:
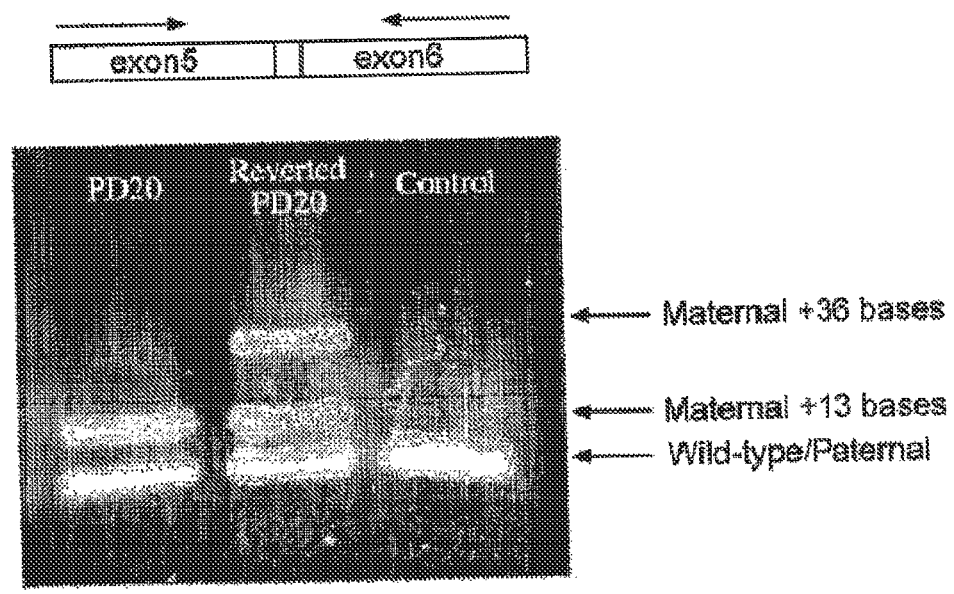

Analysis of a phenotypically reverted PD20 clone: We next generated additional evidence demonstrating that the sequence variations in PD20 cells were not functionally neutral polymorphisms. Towards this end we performed a molecular analysis of a revertant lymphoblast clone (PD20-cl.1) from patient PD20 which was no longer sensitive to MMC. Phenotypic reversion and somatic mosaicism are frequent findings in FA and have been associated with intragenic events such as mitotic recombination or compensatory frameshifts. Indeed, −60% of maternally derived SGC34603 cDNAs had a novel splice variant inserting 36 by of intron 5 sequence rather than the usually observed 13 by (FIGS. 13A and 13B). The appearance of this in-frame splice variant correlated with a de novo base change at position IVS5+6 from G to A (FIGS. 13A and 13B) and restoration of the correct reading frame was confirmed by Western blot analysis. In contrast to all MMC sensitive fibroblasts and lymphoblasts from patient PD20, PD20-cl.1 produced readily detectable amounts of FANCD2 protein of slightly higher molecular weight than the normal protein.

Analysis of cell lines from other "FANCD" patients: The antibody was also used to screen additional FA patient cell lines, including the reference cell line for FA group D, HSC and 2 other cell lines identified as group D by the European Fanconi Anemia Registry (EUFAR). VU008 did not express the FANCD2 protein and was found to be a compound heterozygote, with a missense and nonsense mutation, both in exon 12, and not found on 370 control chromosomes (Table 3, FIGS. 11A-11C). The missense mutation appears to destabilize the FANCD2 protein, as there is no detectable FANCD2 protein in lysates from VU008 cells. A third patient PD733 also lacked FANCD2 protein (FIG. 11*b*, lane 3) and a splice mutation leading to absence of exon 17 and an internal deletion of the protein was found. The correlation of the mutations with the absence of FANCD2 protein in cell lysates derived from these patients substantiates the identity of FANCD2 as a FA gene. In contrast, readily detectable amounts of both isoforms of the FANCD2 protein were found in HSC62 (FIG. 11a, lane 8) and VU423 cDNA and genomic DNA from both cell lines were extensively analyzed for mutations, and none were found. In addition, a whole cell fusion between VU423 and PD20 fibroblasts showed complementation of the chromosome breakage phenotype (Table 5). Taken together these data show that FA group D are genetically heterogeneous and that the gene(s) defective in HSC62 and VU423 are distinct from FANCD2.

The identification and sequencing of the FANCD2 gene and protein provides a novel target for therapeutic development, diagnostic tests and screening assays for diseases associated with failure of DNA repair and cell cycle abnormalities including but not limited to those listed in Table 2.

The following description provides novel and useful insights into the biological role of FANCD2 in the FA pathway which provides a basis for diagnosis and treatment of the aforementioned syndromes.

Evidence that FA cells have an underlying molecular defect in cell cycle regulation include the following: (a) FA cells display a cell cycle delay with 4N DNA content which is enhanced by treatment with chemical crosslinking agents, (b) the cell cycle arrest and reduced proliferation of FA cells can be partially corrected by overexpression of a protein, SPHAR, a member of the cyclin family of proteins and (c) caffeine abrogates the G2 arrest of FA cells. Consistent with these results, caffeine constitutively activates cdc2 and may override a normal G2 cell cycle checkpoint in FA cells. Finally, the FANCC protein binds to the cyclin dependent kinase, cdc2. We propose that the FA complex may be a substrate or modulator of the cyclinB/cdc2 complex.

Additionally, evidence that FA cells have an underlying defect in DNA repair is suggested by (a) FA cells that are sensitive to DNA cross-linking agents and ionizing radiation (IR), suggesting a specific defect in the repair of cross-linked DNA or double strand breaks; (b) DNA damage of FA cells which results in a hyperactive p53 response, suggesting the presence of defective repair yet intact checkpoint activities; and (c) FA cells with a defect in the fidelity of non-homologous end joining and an increased rate of homologous recombination (Garcia-Higuera et al, Mel. Cell., (2001) Vol. 7, pp. 249-262), (Grompe et al., Hum. Mol. Genet., (2001) Vol. 10, pp. 1-7).

Despite these general abnormalities in cell cycle and DNA repair, the mechanism by which FA pathway regulates these activities has remained elusive. Here we show that the FANCD2 protein functions downstream of the FA protein complex. In the presence of the assembled FA protein complex, the FANCD2 protein is activated to a high molecular weight, monoubiquitinated isoform which appears to modulate an S phase specific DNA repair response. The activated FANCD2 protein accumulates in nuclear foci in response to DNA damaging agents and co-localizes and coimmunmoprecipitates with a known DNA repair protein, BRCA1. These results resolve previous conflicting models of the FA pathway (D'Andrea et al., 1997) and demonstrate that the FA proteins cooperate in a cellular response to DNA damage.

The FA pathway includes the formation of the FA multi-subunit nuclear complex which in addition to A/C/G, we have shown also includes FANCF as a subunit of the complex (FIG. 8). The FA pathway becomes "active" during the S phase to provide S phase specific repair response or checkpoint response. The normal activation of the FA pathway which relies on the FA multisubunit complex results in the regulated monoubiquitination of the phosphoprotein-FANCD2 via a phosphorylation step to a high molecular weight activated isoform identified as FANCD-2L (FIG. 1). Monoubiquitination is associated with cell trafficking. FANCD2-L appears to modulate an S phase specific DNA repair response (FIGS. 3A-3E). The failure of FA cells to activate the S phase specific activation of FANCD2 is associated with cell cycle specific abnormalities. The activated FANCD2 protein accumulates in nuclear foci in response to the DNA damaging agents, MMC and LR, and co-localizes and co-immunoprecipitates with a known DNA repair protein, BRCA1 (FIGS. 4-6). These results resolve previous conflicting models of FA protein function (D'Andrea et al., 1997) and strongly support a role of the FA pathway in DNA repair.

We have identified for the first time, an association between FANCD2 isoforms with respect to the FA pathway and proteins that are known diagnostic molecules for various cancers. A similar pathway with respect to DNA damage for the BRCA1 protein which is activated to a high molecular weight, post-translationally-modified isoform in S phase or in response to DNA damage suggests that activated FANCD2 protein interacts with BRCA1. More particularly, the regulated monoubiquitination of FANCD2 appears to target the FANCD2 protein to nuclear foci containing BRCA1. FANCD2 co-immunoprecipitates with BRCA1, and may further bind with other "dot" proteins, such as RAD50, Mre11, NBS, or RAD51. Recent studies demonstrate that BRCA1 foci are composed of a large (2 Megadalton) multi-protein complex (Wang et al., Genes Dev., (2001) Vol. 14, pp. 927-939). This complex includes ATM, ATM substrates involved in DNA repair functions (BRCA1), and ATM substrates involved in checkpoint functions (NBS). It is further suggested that damage recognition and activation of the FA pathway involve kinases which respond to DNA damage including ATM, ATR, CHK1, or CHK2.

We have found that the DNA damaging reagents, IR and MMC, activate independent post-translational modifications of FANCD2 result in distinct functional consequences. IR activates the ATM-dependent phosphorylation of FANCD2 at Serine 222 resulting in an S phase checkpoint response. MMC activates the BRACA-1 dependent and FA pathway dependent monoubiquitination of FANCD2 at lysine 561, resulting in the assembly of FANCD2/BRCA1 nuclear foci and MMC resistance. FANCD2 therefore has two independent functional roles in the maintenance of chromosomal stability resulting from two discrete post-translational modifications provide a link between two additional cancer susceptibility genes (ATM and BRCA1) in a common pathway. Several additional lines of evidence support an interaction between FANCD2 and BRCA1. First, the BRCA1 (−/−) cell line, HCC1937 (Scully et al., Mol. Cell, (1999) Vol. 4, pp. 1093-1099) has a "Fanconi Anemia-like" phenotype, with chromosome instability and increased tri-radial and tetra-radial chromosome formations. Second, although FA cells form BRCA1 foci (and RAD51 foci) normally in response to IR, BRCA1 (−/−) cells have no detectable BRCA1 foci and a greatly decreased number of FANCD2 foci compared to normal cells. Functional complementation of BRCA1 (−/−) cells restored BRCA1 foci and FANCD2 foci to normal levels, and restored normal MMC resistance.

The amount of FANCD2-L is determined in part by the amount of FAND2-S that is synthesized from the fancd2 gene and in part by the availability of the FA complex to monoubiquinated FANCD2-S to form FANCD2-L. The association of FANCD2-L with nuclear foci including BRCA and ATM and determining the role of FANCD2-L in DNA repair make this protein a powerful target for looking at potential cancer development in patients for a wide range of cancers. Such cancers include those that arise through lesions on chromosome 3p as well as cancers on other chromosomes such that mutations result in interfering with production of upstream members of the FA pathway such as FANCG, FANCC or FANCA. Cancer lines and primary cells from cancer patients including tumor biopsies are being screened for FANCD-L and abnormal levels of this protein is expected to correlate with early diagnosis of disease. Because FANCD2 protein is a final step in a pathway to DNA repair, it is envisaged that any abnormality in a protein in the one or more pathways that lead to the conversion of FANCD2-S to FANCD-L will be readily detected by measuring levels of FANCD2. Moreover, levels of FANCD2 affect how other proteins such as BRCA and ATM functionally interact in the nucleus with consequences for the patient. Analysis of levels of FANCD2 in a patient is expected to aid a physician in a clinical decision with respect to understanding the class of cancer presented by the patient. For instance, if a cancer cell fails to generate the monoubiquinated FANCD2-L isoform, the cell may have increased chromosome instability and perhaps increased sensitivity to irradiation or chemotherapeutic agents. This information will assist the physician in procedure improved treatment for the patient.

Fanconi Anemia is associated not only with a broad spectrum of different cancers but also with congenital abnormalities. Development of the fetus is a complex but orderly process. Certain proteins have a particularly broad spectrum of effects because they disrupt this orderly progression of development. The FA pathway plays a significant role in development and disruption of the FA pathway results in a multitude of adverse effects. Errors in the FA pathway are detectable through the analysis of the FAND2-L protein from fetal cells. FANCD2 represents a diagnostic marker for normal fetal development and a possible target for therapeutic intervention.

Figure 7:
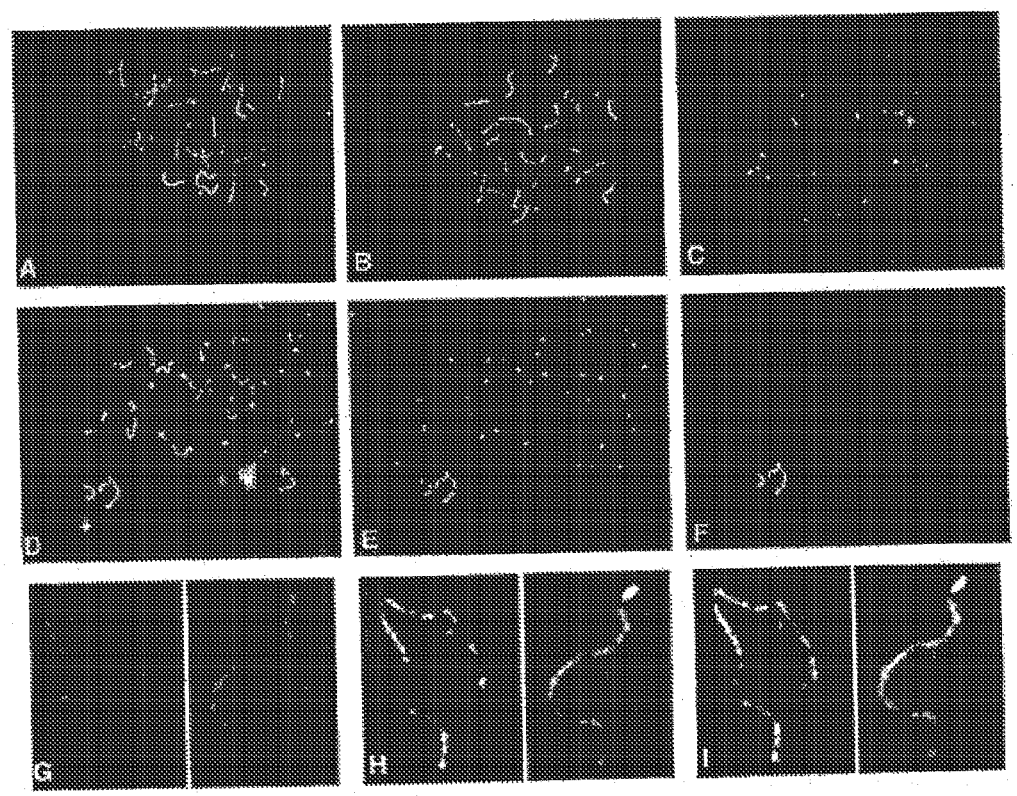
FIG. 7 shows that FANCD2 forms foci on synaptonemal complexes that can co-localize with BRCA1 during meiosis I in mouse spermatocytes. (a) Anti-SCP3 (white) and, anti-FANCD2 (red) staining of synaptonemal complexes in a late pachytene mouse nucleus. (b) SCP3 staining of late pachytene chromosomes. (c) Staining of this spread with preimmune serum for the anti-FANCD2 E35 antibody. (d) Anti-SCP3 staining of synaptonemal complexes in a mouse diplotene nucleus. (e) Costaining of this spread with E35 anti-FANCD2 antibody. Note staining of both the unpaired sex chromosomes and the telomeres of the autosomes with anti-FANCD2. (f) Costaining of this spread with anti-BRCA1 antibody. The sex chromosomes are preferentially stained. (g) Anti-FANCD2 staining of late pachytene sex chromosome synaptonemal complexes. (h) Anti-BRCA1 staining of the same complexes. (i) Anti-FANCD2 (red) and anti-BRCA1 (green) co-staining (co-localization reflected by yellow areas).

Consistent with the above, we have shown that FANCD2 plays a role in the production of viable sperm. FANCD2 forms foci on the unpaired axes of chromosomes XY bivalents in late pachytene and in diplotene murine spermatocytes (FIG. 7). Interestingly, FANCD2 foci are also seen at the autosomal telomeres in diplonema. Taken together with the known fertility defects in FA patients and FA-C knockout mice, our observations suggest that activated FANCD2 protein is required for normal progression of spermatocytes through meiosis I. Most of the FANCD2 foci seen on the XY axes were found to co-localize with BRCA1 foci, suggesting that the two proteins may function together in meiotic cells. Like BRCA1, FANCD2 was detected on the axial (unsynapsed) elements of developing synaptonemal complexes. Since recombination occurs in synapsed regions, FANCD2 may function prior to the initiation of recombination, perhaps to help prepare chromosomes for synapsis or to regulate subsequent recombinational events. The relatively synchronous manner in which FANCD2 assembles on meiotic chromosomes, and forms dot structures in mitotic cells, suggests a role of FANCD2 in both mitotic and meiotic cell cycle control.

Embodiments of the invention are directed to the use of the post translationally modified isoform: FANCD-2L as a diagnostic target for determining the integrity of the FA pathway. Ubiquitination of FANCD2 and the formation of FANCD2 nuclear foci are downstream events in the FA pathway, requiring the function of several FA genes. We have found that biallelic mutations of any of the upstream FA genes (FANCA, FANCB, FANCC, FANCE, FANCF and FANCG) block the posttranslational modification of FANCD2 the unubiquitinated FANCD2 (FANCD2-S) form to the ubiquitinated (FANCD2-L). Any of these upstream defects can be overridden by transfecting cells with FANCD2 cDNA (FIG. 1a).

We have demonstrated for the first time the existence of FANCD2 and its role in the FA pathway. We have shown that FANCD2 accumulates in nuclear foci in response to DNA damaging agents where it is associated with other DNA repair proteins such as BRCA1 and ATM. We have also demonstrated that FANCD2 exists in two isoforms in cells where a reduction in one of the two isoforms, FANCD2-L is correlated with Fanconi Anemia and with increased cancer susceptibility. We have used these findings to propose a number of diagnostic tests for use in the clinic that will assist with patient care.

These tests include: (a) genetic and prenatal counseling for parents concerned about inherited Fanconi Anemia in a future offspring or in an existing pregnancy; (b) genetic counseling and immunodiagnostic tests for adult humans to determine increased susceptibility to a cancer correlated with a defective FA pathway; and (c) diagnosing an already existing cancer in a subject to provide an opportunity for developing treatment protocols that are maximally effective for the subject while minimizing side effects.

The diagnostic tests described herein rely on standard protocols known in the art for which we have provided novel reagents to test for FANCD2 proteins and nucleotide sequences. These reagents include antibodies specific for FANCD2 isoforms, nucleotide sequences from which vectors, probes and primers have been derived for detecting genetic alterations in the FANCD2 gene and cells lines and recombinant cells for preserving and testing defects in the FA pathway.

We have prepared monoclonal and polyclonal, antibody preparations as described in Example 1 that are specific for FANCD2-L and FANCD2-S proteins. In addition, FANCD2 isoform specific antibody fragments and single chain antibodies may be prepared using standard techniques. We have used these antibodies in wet chemistry assays such as immunoprecipitation assays, for example Western blots, to identify FANCD2 isoforms in biological samples (FIG. 1). Conventional immunoassays including enzyme linked immunosorbent assays (ELISA), radioimmune assays (RIA), immunoradiometric assays (IRMA) and immunoenzymatic assays (IEMA) and further including sandwich assays may also be used. Other immunoassays may utilize a sample of whole cells or lysed cells that are reacted with antibody in solution and optionally analyzed in a liquid state within a reservoir. Isoforms of FANCD2 can be identified in situ in intact cells including cell lines, tissue biopsies and blood by immunological techniques using for example fluorescent activated cell sorting, and laser or light microscopy to detect immunofluorescent cells (FIGS. 1-7, 9-14). For example, biopsies of tissues or cell monolayers, prepared on a slide in a preserved state such as embedded in paraffin or as frozen tissue sections can be exposed to antibody for detecting FANCD2-L and then examined by fluorescent microscopy.

In an embodiment of the invention, patient-derived cell lines or cancer cell lines are analyzed by immunoblotting and immunofluorescence to provide a novel simple diagnostic test for detecting altered amounts of FANCD2 isoforms. The diagnostic test also provides a means to screen for upstream defects in the FA pathway and a practical alternative to the currently employed DEB/MMC chromosome breakage test for FA, because individuals with upstream defects in the FA pathway are unable to ubiquitinate FANCD2. Other assays may be used including assays that combine retroviral gene transfer to form transformed patient derived cell lines (Pulsipher et al., Mol. Med., (1998) Vol. 4, pp. 468-79) together with FANCD2 immunoblotting to provide a rapid subtyping analysis of newly diagnosed patients with any of the syndromes described in Table 2, in particular, that of FA.

The above assays may be performed by diagnostic laboratories, or, alternatively, diagnostic kits may be manufactured and sold to health care providers or to private individuals for self-diagnosis. The results of these tests and interpretive information are useful for the healthcare provider in diagnosis and treatment of a patient's condition.

Genetic tests can provide for a subject, a rapid reliable risk analysis for a particular condition against an epidemiological baseline. Our data suggests that genetic heterogeneity occurs in patients with FA within the FANCD2 complementation group. We have found a correlation between genetic heterogeneity and disease as well as genetic heterogeneity and abnormal post-translational modifications that result in the presence or absence of FANCD2-L. This correlation provides the basis for prognostic tests as well as diagnostic tests and treatments for any of the syndromes characterized by abnormal DNA repair. For example, nucleic acid from a cell sample obtained from drawn blood or from other cells derived from a subject can be analyzed for mutations in the FANCD2 gene and the subject may be diagnosed to have an increased susceptibility to cancer.

We have located the FANCD2 gene at 3p25.3 on chromosome 3p in a region which correlates to a high frequency of cancer. Cytogenetic and loss of heterozygosity (LOH) studies have demonstrated that deletions of chromosome 3p occur at a high frequency in all forms of lung cancer (Todd et al., Cancer Res. Vol. 57, pp. 1344-52). For example, homozygous deletions were found in three squamous cell lines within a region of 3p21. Homozygous deletions were also found in a small cell tumor at 3p12 and a 3p14.2. (Franklin et al., Cancer Res. (1997), Vol. 57, pp. 1344-52). The present mapping of FANCD2 is supportive of the theory that this chromosomal region contains important tumor suppressor genes. Further support for this has been provided by a recent publication of Sekine et al., Human Molecular Genetics, (2001) Vol. 10, pp. 1421-1429, who reported localization of a novel susceptibility gene for familial ovarian cancer to chromosome 3p22-p25. The reduction or absence of FANCD2-L is here proposed to be diagnostic for increased risk of tumors resulting from mutations not only at the FANCD2 site (3p25.3) but also at other sites in the chromosomes possibly arising from defects in DNA repair following cell damage arising from exposure to environmental agents and normal aging processes.

As more individuals and families are screened for genetic defects in the FANCD2 gene, a data base will be developed in which population frequencies for different mutations will be gathered and correlations made between these mutations and health profile for the individuals so that the predictive value of genetic analysis will continually improve. An example of an allele specific pedigree analysis for FANCD2 is provided in FIGS. 10A-10F for two families.

Diagnosis of a mutation in the FANCD2 gene may initially be detected by a rapid immunological assay for detecting reduced amounts of FANCD2-L proteins. Positive samples may then be screened with available probes and primers for defects in any of the genes in the PA pathway. Where a defect in the FANCD2 gene is implicated, primers or probes such as provided in Table 7 may be used to detect a mutation. In those samples, where a mutation is not detected by such primers or probes, the entire FANCD2 gene may be sequenced to determine the presence and location of the mutation in the gene.

Nucleic acid screening assays for use in identifying a genetic defect in the FANCD2 gene locus may include PCR and non PCR based assays to detect mutations. There are many approaches to analyzing cell genomes for the presence of mutations in a particular allele. Alteration of a wild-type FANCD2 allele, whether, for example, by point mutation, deletion or insertions can be detected using standard methods employing probes (U.S. Pat. No. 6,033,857). Standard methods include: (a) fluorescent in situ hybridization (FISH) which may be used on whole intact cells; and (b) allele specific oligonucleotides (ASO) may be used to detect mutations using hybridization techniques on isolated nucleic acid (Conner et al., Hum. Genet., (1989) Vol. 85, pp. 55-74). Other techniques include (a) observing shifts in electrophoretic mobility of single-stranded DNA on non-denaturing polyacrylamide gels, (b) hybridizing a FANCD2 gene probe to genomic DNA isolated from the tissue sample, (c) hybridizing an allele-specific probe to genomic DNA of the tissue sample, (d) amplifying all or part of the FANCD2 gene from the tissue sample to produce an amplified sequence and sequencing the amplified sequence, (e) amplifying all or pant of the FANCD2 gene from the tissue sample using primers for a specific FANCD2 mutant allele, (f) molecular cloning all or part of the FANCD2 gene from the tissue sample to produce a cloned sequence and sequencing the cloned sequence, (g) identifying a mismatch between (i) a FANCD2 gene or a FANCD2 mRNA isolated from the tissue sample, and (ii) a nucleic acid probe complementary to the human wild-type FANCD2 gene sequence, when molecules (i) and (ii) are hybridized to each other to form a duplex, (h) amplification of FANCD2 gene sequences in the tissue sample and hybridization of the amplified sequences to nucleic acid probes which comprise wild-type FANCD2 gene sequences, (i) amplification of FANCD2 gene sequences in the tissue sample and hybridization of the amplified sequences to nucleic acid probes which comprise mutant FANCD2 gene sequences, (j) screening for a deletion mutation in the tissue sample, (k) screening for a point mutation in the tissue sample, (l) screening for an insertion mutation in the tissue sample, and (n) in situ hybridization of the FANCD2 gene of the tissue sample with nucleic acid probes which comprise the FANCD2 gene.

It is often desirable to scan a relatively short region of a gene or genome for point mutations: The large numbers of oligonucleotides needed to examine all potential sites in the sequence can be made by efficient combinatorial methods (Southern, E. M et al., Nucleic Acids Res., (1994) Vol. 22, pp. 1368-1373). Arrays may be used in conjunction with ligase or polymerase to look for mutations at all sites in the target sequence (U.S. Pat. No. 6,307,039). Analysis of mutations by hybridization can be performed for example by means of gels, arrays or dot blots.

The entire gene may be sequenced to identify mutations (U.S. Pat. No. 6,033,857). Sequencing of the FANCD2 locus can be achieved using oligonucleotide tags from a minimally cross hybridizing set which become attached to their complements on solid phase supports when attached to target sequence (U.S. Pat. No. 6,280,935).

Other approaches to detecting mutations in the FANCD2 gene include those described in U.S. Pat. No. 6,297,010, U.S. Pat. No. 6,287,772 and U.S. Pat. No. 6,300,076. It is further contemplated that the assays may employ nucleic acid microchip technology or analysis of multiple samples using laboratories on chips. Correlation of these mutations with the results of genetic studies on breast, ovarian or prostate cancer patients can then be used to determine if an identified defect within the FANC D2 gene is a cancer-associated defect according to the invention.

A subject who has developed a tumor maybe screened using nucleic acid diagnostic tests or antibody based tests to detect a FANCD2 gene mutation or a deficiency in FANCD2-L protein. On the basis of such screening samples may be obtained from subjects having a wide range of cancers including melanoma, leukemia, astocytoma, glioblastoma, lymphoma, glioma, Hodgkins lymphoma, chronic lymphocyte leukemia and cancer of the pancreas, breast, thyroid, ovary, uterus, testis, pituitary, kidney, stomach, esophagus and rectum. The clinician has an improved ability to select a suitable treatment protocol for maximizing the treatment benefit for the patient. In particular, the presence of a genetic lesion or a deficiency in FANCD2-L protein may be correlated with responsiveness to various existing chemotherapeutic drugs and radiation therapies.

New therapeutic treatments may be developed by screening for molecules that modulate the monoubiquitination of FANCD2-S to give rise to FANCD2-L in cell assays (Examples 11-12) and in knock-out mouse models (Example 10). Such molecules may include those that bind directly to FANCD2 or to molecules such as BRACA-2 that appears to interact with BRACA-1 which in turn appears to be activated by FANCD2.

In addition to screening assays that rely on defects in the FANCD2 gene or protein, an observed failure of the ubiquitination reaction that is necessary for the formation of FANCD2-L may result from a defect in the FA pathway at any point preceding the post translational modification of FANCD2 including FANCD2-S itself. Knowing the terminal step in the reactions, enables a screening assay to be formulated in which small molecules are screened in cells containing "broken FA pathway" or in vitro until a molecule is found to repair the broken pathway. This molecule can then be utilized as a probe to identify the nature of the defect. It may further be used as a therapeutic agent to repair the defect. For example, we have shown that cell cycle arrest and reduced proliferation of FA cells can be partially corrected by overexpression of a protein, SPHAR, a member of the cyclin family of proteins. This can form the basis of an assay which is suitable as a screen for identifying therapeutic small molecules.

Cells which are deficient in the posttranslational modified FANCD2 are particularly sensitive to DNA damage. These cells-may serve as a sensitive screen for determining whether a compound (including toxic molecules) has the capability for damaging DNA. Conversely, these cells also serve as a sensitive screen for determining whether a compound can protect cells against DNA damage.

FA patients and patients suffering from syndromes associated with DNA repair defects die from complications of bone marrow failure. Gene transfer is a therapeutic option to correct the defect. Multiple defects may occur throughout the FA pathway. We have shown that the terminal step is critical to proper functioning of the cell and the organism. In an embodiment of the invention, correction of defects anywhere in the FA pathway may be satisfactorily achieved by gene therapy or by therapeutic agents that target the transformation of FANCD2-S to FANCD2-L so that this transformation is successfully achieved.

Gene therapy may be carried out according to generally accepted methods, for example, as described by Friedman in "Therapy for Genetic Disease," T. Friedman, ed., Oxford University Press (1991), pp. 105-121. Targeted tissues for ex vivo or in vivo gene therapy include bone marrow for example, hematopoietic stem cells prior to onset of anemia and fetal tissues involved in developmental abnormalities. Gene therapy can provide wild-type FAND2-L function to cells which carry mutant FANCD2 alleles. Supplying such a function should suppress neoplastic growth of the recipient cells or ameliorate the symptoms of Fanconi Anemia.

The wild-type FANCD-2 gene or a part of the gene may be introduced into the cell in a vector such that the gene remains extrachromosomal. In such a situation, the gene may be expressed by the cell from the extrachromosomal location. If a gene portion is introduced and expressed in a cell carrying a mutant FANCD-2 allele, the gene portion may encode a part of the FANCD-2 protein which is required for non-neoplastic growth of the cell. Alternatively, the wild-type FANCD-2 gene or a part thereof may be introduced into the mutant cell in such a way that it recombines with the endogenous mutant FANCD-2 gene present in the cell.

Viral vectors are one class of vectors for achieving gene therapy. Viral-mediated gene transfer can be combined with direct in vivo gene transfer using liposome delivery, allowing one to direct the viral vectors to the tumor cells and not into the surrounding nondividing cells. Alternatively, a viral vector producer cell line can be injected into tumors (Culver et al., 1992). Injection of producer cells would then provide a continuous source of vector particles. This technique has been approved for use in humans with inoperable brain tumors.

The vector may be injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Vectors for introduction of genes both for recombination and for extrachromosomal maintenance are known in the art (for example as disclosed in U.S. Pat. No. 5,252,479 and PCT 93/07282, and U.S. Pat. No. 6,303,379) and include viral vectors such as retroviruses, herpes viruses (U.S. Pat. No. 6,287,557) or adenoviruses (U.S. Pat. No. 6,281,010) or a plasmid vector containing the FANCD2-L.

A vector carrying the therapeutic gene sequence or the DNA encoding the gene or piece of the gene may be injected into the patient either locally at the site of a tumor or systemically so as to reach metastasized tumor cells. Targeting may be achieved without further manipulation of the vector or the vector may be coupled to a molecule having a specificity of binding for a tumor where such molecule may be a receptor agonist or antagonist and may further include a peptide, lipid (including liposomes) or saccharide including an oligopolysaccharide or polysaccharide) as well as synthetic targeting molecules. The DNA may be conjugated via polylysine to a binding ligand. If the transfected gene is not permanently incorporated into the genome of each of the targeted tumor cells, the treatment may have to be repeated periodically.

Methods for introducing DNA into cells prior to introduction into the patient may be accomplished using techniques such as electroporation, calcium phosphate coprecipitation and viral transduction as described in the art (U.S. Pat. No. 6,033,857), and the choice of method is within the competence of the routine experimenter.

Cells transformed with the wild-type FANCD2 gene or mutant FANCD2 gene can be used as model systems to study remission of diseases resulting from defective DNA repair and drug treatments which promote such remission.

As generally discussed above, the FANCD2 gene or fragment, where applicable, may be employed in gene therapy methods in order to increase the amount of the expression products of such genes in abnormal cells. Such gene therapy is particularly appropriate for use in pre-cancerous cells, where the level of FANCD2-L polypeptide may be absent or diminished compared to normal cells and where enhancing the levels of FANCD2-L may slow the accumulation of defects arising from defective DNA repair and hence postpone initiation of a cancer state. It may also be useful to increase the level of expression of the FANCD2 gene even in those cells in which the mutant gene is expressed at a "normal" level, but there is a reduced level of the FANCD2-L isoform. The critical role of FANCD2-L in normal DNA repair provides an opportunity for developing therapeutic agents to correct a defect that causes a reduction in levels of FANCD2-L. One approach to developing novel therapeutic agents is through rational drug design. Rational drug design can provide structural analogs of biologically active polypeptides of interest or of small molecules with which they interact (e.g., agonists, antagonists, inhibitors or enhancers) in order to fashion more active or stable forms of the polypeptide, or to design small molecules which enhance or interfere with the function of a polypeptide in vivo (Hodgson, 1991). Rational drug design may provide small molecules or modified polypeptides which have improved FANCD2-L activity or stability or which act as enhancers, inhibitors; agonists or antagonists of FANCD2-L activity. By virtue of the availability of cloned FANCD2 sequences, sufficient amounts of the FANCD2-L polypeptide may be made available to perform such analytical studies as x-ray crystallography. In addition, the knowledge of the FANCD2-L protein sequence provided herein will guide those employing computer modeling techniques in place of, or in addition to x-ray crystallography.

Peptides or other molecules which have FANCD2-L activity can be supplied to cells which are deficient in the protein in a therapeutic formulation. The sequence of the FANCD2-L protein is disclosed for several organisms (human, fly and plant) (SEQ ID NO:1-3). FANCD2 could be produced by expression of the cDNA sequence in bacteria, for example, using known expression vectors with additional posttranslational modifications. Alternatively, FANCD2-L polypeptide can be extracted from FANCD2-L-producing mammalian cells. In addition, the techniques of synthetic chemistry can be employed to synthesize FANCD2-L protein. Other molecules with FANCD2-L activity (for example, peptides, drugs or organic compounds) may also be used as a therapeutic agent. Modified polypeptides having substantially similar function are also used for peptide therapy.

Similarly, cells and animals which carry a mutant FANCD2 allele or make insufficient levels of FANCD2-L can be used as model systems to study and test for substances which have potential as therapeutic agents. The cells which may be either somatic or germline can be isolated from individuals with reduced levels of FANCD2-L. Alternatively, the cell line can be engineered to have a reduced levels of FANCD2-L, as described above. After a test substance is applied to the cells, the DNA repair impaired transformed phenotype of the cell is determined.

The efficacy of novel candidate therapeutic molecules can be tested in experimental animals for efficacy and lack of toxicity. Using standard techniques, animals can be selected after mutagenesis of whole animals or after genetic engineering of germline cells or zygotes to form transgenic animals. Such treatments include insertion of mutant FANCD2 alleles, usually from a second animal species, as well as insertion of disrupted homologous genes. Alternatively, the endogenous FANCD2 gene of the animals may be disrupted by insertion or deletion mutation or other genetic alterations using conventional techniques (Capecchi, Science, (1989) Vol. 244, pp. 1288-1292) (Valancius and Smithies, 1991). After test substances have been administered to the animals, the growth of tumors must be assessed. If the test substance prevents or suppresses pathologies arising from defective DNA repair, then the test substance is a candidate therapeutic agent for the treatment of the diseases identified herein.

The subject invention provides for Fanconi Anemia/BRCA-based diagnostic assays to determine if a patient has cancer or is at an increased risk of cancer. The invention also features screening methods for the discovery of novel cancer therapeutics that are inhibitors of the Fanconi Anemia/BRCA pathway. Finally, the invention provides methods for the chemosensitization of tumor cells that have become resistant to one or more chemotherapy compounds as well as assays to determine the efficacy of chemotherapy drugs.

The practice of the present invention will employ, unless otherwise indicated, conventional techniques of molecular biology, cell biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); (Harlow, E. and Lane, D.) Using Antibodies: A Laboratory Manual (1999) Cold Spring Harbor Laboratory Press; and a series, Methods in Enzymology (Academic Press, Inc.); Short Protocols In Molecular Biology, (Ausubel et al., ed., 1995). All patents, patent applications, and publications mentioned herein, both supra and infra, are hereby incorporated by reference in their entirety.

Tissue Biopsies

The invention provides for the preparation of cellular extracts from tissue biopsies of patients including, but not limited to brain, heart, lung, lymph nodes, eyes, joints, skin and neoplasms associated with these organs. "Tissue biopsy" also encompasses the collection of biological fluids including but not limited to blood, plasma, sputum, urine, cerebrospinal fluid, lavages, and leukophoresis samples. In a preferred, embodiment, "tissue biopsies" according to the invention are taken from tumors of the breast, ovary or prostate. "Tissue biopsies" are obtained using techniques well known in the art including needle aspiration and punch biopsy of the skin.

Cisplatin

Cisplatin has been widely used to treat cancers such as metastatic testicular or ovarian carcinoma, advanced bladder cancer, head or neck cancer, cervical cancer, lung cancer or other tumors. Cisplatin can be used, alone or in combination with other agents, with efficacious doses used in clinical applications of 15-20 mg/m2 for 5 days every three weeks for a total of three courses. Exemplary doses may be 0.50 mg/m2, 1.0 mg/m2, 1.50 mg/m2, 1.75 mg/m2, 2.0 mg/m2, 3.0 mg/m2, 4.0 mg/m2, 5.0 mg/m2, 10 mg/m2. Of course, all of these dosages are exemplary, and any dosage in-between these points is also expected to be of use in the invention. Cisplatin is not absorbed orally and must therefore be delivered via injection intravenously, subcutaneously, intratumorally or intraperitoneally. Procedures for proper handling and disposal of anticancer drugs should be considered. Several guidelines on this subject have been published and are known by those in the art.

For example, PLATINOL-AQ, (cisplatin injection) NDC 0015-3220-22 (Bristol Myers Squibb) is supplied as a sterile, multidose vial without preservatives. Each multidose vial contains 50 mg of cisplatin NDC 0015-3221-22 and should be stored at 15° C.-25° C. and protected from light. The cisplatin remaining in the amber vial following initial entry is stable for 28 days protected from light or for 7 days under fluorescent room light.

The prescribing information for PLATINOL-AQ, (cisplatin injection) NDC 0015-3220-22 is available from Bristol Myers Squibb. The plasma concentrations of cisplatin decay monoexponentially with a half-life of about 20 to 30 minutes following bolus administrations of 50 or 100 mg/m2 doses. Monoexponential decay and plasma half-lives of about 0.5 hour are also seen following two hour or seven hour infusions of 100 mg/m2. After the latter, the total-body clearances and volumes of distribution at steady-state for cisplatin are about 15 to 16 L/h/m2 and 11 to 12 L/m2.

Dosage and Administration of Cisplatin

The dosage and administration of cisplatin for the treatment of cancer is known in the art.

The prescribing information of PLATINOL-AQ (Bristol Myers Squibb) recommends the following guidelines for dosage and administration: "Needles or intravenous sets containing aluminum parts that may come in contact with PLATINOL-AQ should not de used for preparation or administration. Aluminum reacts with PLATINOL-AQ, causing precipitate formation and a loss of potency".

Metastatic Testicular Tumors: The usual PLATINOL-AQ dose for the treatment of testicular cancer in combination with other approved chemotherapeutic agents is 20 mg/m2 I.V. daily for 5 days per cycle.

Metastatic Ovarian Tumors: The usual PLATINOL-AQ dose for the treatment of metastatic ovarian tumors in combination with CYTOXAN (cy-clophosphamide) is 75-100 mg/m2 I.V. per cycle once every 4 weeks, (Day 1). The dose of CYTOXAN when used in combination with PLATINOL-AQ is 600 mg/m2 I.V. once every 4 weeks, (Day 1). For directions for the administration of CYTOXAN, refer to the CYTOXAN package insert. In combination therapy, PLATINOL-AQ and CYTOXAN are administered sequentially. As a single agent, PLATINOL-AQ should be administered at a dose of 100 mg/m2 I.V. per cycle once every 4 weeks.

Advanced Bladder Cancer: PLATINOL-AQ (cisplatin injection) should be administered as a single agent at a dose of 50-70 mg/m2. I.V. per cycle once every 3 to 4 weeks depending on the extent of prior exposure to radiation therapy and/or prior chemotherapy. For heavily pretreated patients an initial dose of 50 mg/m2 per cycle repeated every four weeks is recommended. Pretreatment hydration with 1 to 2 liters of fluid infused for 8 to 12 hours prior to a PLATINOL-AQ dose is recommended. The drug is then diluted in 2 liters of 5% Dextrose in ½ or ⅓ normal saline containing 37.5 g of mannitol, and infused over a 6- to 8-hour period. If diluted solution is not to be used within 6 hours, protect solution from light. Do not dilute PLATINOL-AQ in just 5% Dextrose Injection. Adequate hydration and urinary output must be maintained during the following 24 hours. A repeat course of PLATINOL-AQ should not be given until the serum creatinine is below 1.5 mg/100 mL, and/or the BUN is below 25 mg/100 mL. A repeat course should not be given until circulating blood elements are at an acceptable level (platelets>100,000/mm2, WBC>4,000/mm2). Subsequent doses of PLATINOL-AQ should not be given until an audiometric analysis indicates that auditory acuity is within normal limits. As with other potentially toxic compounds, caution should be exercised in handling the aqueous solution. Skin reactions associated with accidental exposure to cisplatin may occur. The use of gloves is recommended. The aqueous solution should be used intravenously only and should be administered by I.V. infusion over a 6- to 8-hour period.

Dosage and Administration of a Chemosensitizing Agent

Methods of cancer chemosensitization are reported in U.S. Pat. No. 5,776,925, which is incorporated herein in its entirety. Cancer treatment according to the present invention envisions the use of one or more anti-neoplastic agents in conjunction with compounds that are not necessarily cytotoxic in themselves, but modify the host or tumor so as to enhance anticancer therapy. Such agents are called chemosensitizers.

Treatment with a chemosensitizing agent is therapeutically effective in a cancer patient, according to the invention, if tumor size is decreased by 10%, preferably 25%, preferably 50%, more preferably 75%, most preferably 100% in the presence of an antineoplastic agent and corresponding chemosensitizing agent as compared to tumor size after treatment with the anti-neoplastic agent but in the absence of the corresponding chemosenziting agent.

The present invention provides for pharmaceutical compositions comprising a therapeutically effective amount of a chemosensitizing agent, as disclosed herein, in combination with a pharmaceutically acceptable carrier or excipient. The chemosensitizers in accordance with the invention, may be administered to a patient locally or in any systemic fashion, whether intravenous, subcutaneous, intramuscular, parenteral, intraperitoneal or oral. Preferably, administration will be systemic in conjunction with or before the administration of one or more anti-neoplastic agents. In a preferred embodiment, the anti-neoplastic agent is cisplatin that is administered according to protocols well known in the art and as described herein.

For oral administration, the chemosensitizing agents useful in the invention will generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For subcutaneous and intravenous use, the chemosensitizing agents of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The chemosensitizing agents useful according to the invention may also be presented as liposome formulations.

In general a suitable dose will be in the range of 0.01 to 100 mg per kilogram body weight of the recipient per day, preferably in the range of 0.2 to 10 mg per kilogram body weight per day. The desired dose is preferably presented once daily, but may be dosed as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form. Dosages of chemosensitizing agents useful according to the invention will vary depending upon the condition to be treated or prevented and on the identity of the chemosensitizing agent being used. Estimates of effective dosages and in vivo half-lives for the individual compounds encompassed by the invention can be made on the basis of in vivo testing using an animal model, such as the mouse model described herein or an adaptation of such method to larger mammals.

In addition to their administration singly, the compounds useful according to the invention can be administered in combination with other known chemosensitizing agents and antineoplastic agents, as described herein. In any event, the administering physician can adjust the amount and timing of drug administration on the basis of results observed using standard measures of cancer activity known in the art.

Anti-Neoplastic Agents

Nonlimiting examples of anti-neoplastic agents include, e.g., antimicrotubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate, i.e., PALA, pentostatin, 5-azacitidine, 5-Aza 2'-deoxycytidine, ara-A, cladribine, 5-fluoromidine, FUDR, tiazofurin, N-[5-[N-(3,4-dihydro-2-methyl-4-oxoquinazolin-6-ylmethyl)-N-methyl amino]-2-thenoyl]-L-glutami c acid; alkylating agents, e.g., cisplatin, carboplatin, mitomycin C, BCNU, i.e., Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and antihormones, for example anti-estrogens such as tamoxifen or, for example antiandrogens such as 4'-cyano-3-(4-fluorophenylsulphony1)-2-hydroxy-2-methyl-3'-(trifluoromethyl) propionanilide.

An anti-neoplastic agent is therapeutic in a cancer patient, according to the invention, if tumor size is decreased by 10%, preferably 25%, preferably 50%, more preferably 75%, most preferably 100% when compared to tumor size prior to the initiation of treatment with an anti-neoplastic agent.

In a further embodiment, an anti-neoplastic agent, according to the invention, is therapeutically effective if the cancer patient remains cancer free, i.e., without any detectable tumors, for preferably 6 months, preferably 1 year, more preferably 2 years and most preferably 5 years or more after initiation of cancer therapy.

Inhibitors of the Fanconi Anemia/BRCA Pathway According to the Invention

Potential inhibitors of the Fanconi Anemia/BRCA pathway include, but are not limited to, biomolecules that disrupt the expression or function of Fanconi Anemia/BRCA pathway genes or proteins as defined herein. Potential inhibitors of the Fanconi Anemia/BRCA pathway include, but are not limited, to Fanconi Anemia/BRCA pathway gene antisense nucleic acids (antisense Fanconi Anemia/BRCA pathway gene RNAs, oligonucleotides, modified oligonucleotides, RNAi), dominant negative mutants of the Fanconi Anemia/BRCA pathway gene pathway as well as inhibitors of Fanconi Anemia/BRCA pathway gene transcription, mRNA processing, mRNA transport, protein translation, protein modification, protein transport, nuclear transport and Fanconi Anemia/BRCA protein complex formation.

In a most preferred embodiment, the present invention provides for small molecule inhibitors of the FANC-D2 ubiquitin E3 ligase.

Microarrays According to the Invention

To identify cancer therapeutics or chemosensitizing agents, the invention provides for the use of microarrays.

In one embodiment, the microarray of the invention is used to identify chemosensitizing agents.

In another embodiment, the microarray of the invention is used to test tissue biopsy samples for the presence of cancer-associated defects within the Fanconi Anemia/BRCA pathway genes.

In another embodiment, the microarrays of the invention are used to screen for inhibitors of the Fanconi Anemia/BRCA gene pathway.

In another embodiment, the microarrays of the invention are to be used to screen for inhibitors of the FANC-D2 ubiquitin E3 ligase.

In another embodiment, the invention provides for tissue microarrays comprising tissue biopsy samples from patients who have a cancer or who may be at risk of cancer that are screening for the presence of cancer associated defects within Fanconi Anemia/BRCA gene pathway as defined herein. In a preferred embodiment, the tissue microarrays of the present invention are used to screen for the presence of mon-ubiqutinated FANC D2-L.

In another embodiment, the invention provides for tissue microarrays comprising tissue biopsy samples from patients having BRCA-1 and BRCA-2/FANC D-1 cancer-associated defects.

In another embodiment, the invention provides for tissue microarrays comprising tissue biopsy samples from patients that do not have BRCA-1 and BRCA-2/FANC D-1 cancer-associated defects.

A "sequencing array" contains regions of the entire open reading frame of the genes in question, in order to look for mutations in the clinical sample. A "transcriptional profiling array" can have sequences from the 3' end of the genes in questions, in order to determine the expression of mRNAs in the clinical sample.

A transcriptional profiling array will be used to look at mRNA levels corresponding to each of the genes in the pathway. For instance, a breast or ovarian cancer which has a decrease in one of the transcripts, e.g., corresponding to FANC F would show that there is a defect in the Fanconi Anemia/BRCA pathway, due to decreased FANCF expression.

Construction of a Microarray

Substrate of the Microarray,

In one embodiment of the invention, the microarray or array comprises a substrate to facilitate handling of the microarray through a variety of molecular procedures. As used herein, "molecular procedure" refers to contact of the microarray with a test reagent or molecular probe such as an antibody, nucleic acid probe, enzyme, chromagen, label, and the like. In one embodiment, a molecular procedure comprises a plurality of hybridizations, incubations, fixation steps, changes of temperature (from −4° C. to 100° C.), exposures to solvents, and/or wash steps.

In a further embodiment of the invention, the microarray comprises a substrate to facilitate exposure of tissue biopsy samples to different potential inhibitors of the Fanconi Anemia/BRCA pathway, cancer therapeutics or chemosensitizing agents.

In one embodiment of the invention, the microarray substrate is solvent resistant. In another embodiment of the invention, the substrate is transparent. The substrate may be biological, non-biological, organic, inorganic, or a combination of any of these, existing as particles, strands, precipitates, gels, sheets, tubing, spheres, beads, containers, capillaries, pads, slices, films, plates, slides, chips, etc. The substrate is preferably flat or planar but may take on a variety of alternative surface configurations. The substrate may be a polymerized Langmuir Blodgett film, functionalized glass, Si, Ge, GaAs, GaP, SiO2, SIN4, modified silicon, or other nonporous substrate, plastic, such as polyolefin, polyamide, polyacrylamide, polyester, polyacrylic ester, polycarbonate, polytetrafluoroethylene, polyvinyl acetate, and a plastic composition containing fillers (such as glass fillers), extenders, stabilizers, and/or antioxidants; celluloid, cellophane or urea formaldehyde resins or other synthetic resins such as cellulose acetate ethylcellulose, or other transparent polymer. Other substrate materials will be readily apparent to those of skill in the art upon review of this disclosure.

In one embodiment, the microarray substrate is rigid; however, in another embodiment, the profile array substrate is semi-rigid or flexible (e.g., a flexible plastic comprising polycarbonate, cellular acetate, polyvinyl chloride, and the like). In a further embodiment, the array substrate is optically opaque and substantially non-fluorescent. Nylon or nitrocellulose membranes can also be used as array substrates and include materials such as polycarbonate, polyvinylidene fluoride (PVDF), polysulfone, mixed esters of cellulose and nitrocellulose, and the like.

The size and shape of the substrate may generally be varied. The substrate may have any convenient shape, such as a disc, square, sphere, circle, etc. However, preferably, the substrate fits entirely on the stage of a microscope. In one embodiment, the profile array substrate is planar. In one embodiment of the invention, the microarray substrate is 1 inch by 3 inches, 77×50 mm, or 22×50 mm. In another embodiment of the invention, the microarray substrate is at least 10-200 mm×10-200 mm.

Additional Features of the Substrate

In one embodiment of the invention, the substrate comprises a location for placing an identifier (e.g., a wax pencil or crayon mark, an etched mark, a label, a bar code, a microchip for transmitting radio or electronic signals, and the like). In one embodiment, the location comprises frosted glass. In one embodiment, the microchip communicates with a processor which comprises or can access stored information relating to the identity and address of sublocations on the array, and/or including information regarding the individual from whom the tissue was taken, e.g., prognosis, diagnosis, medical history, family medical history, drug treatment, age of death and cause of death, and the like.

Sublocations

The microarray comprises a plurality of sublocations. Each sublocation comprises a tissue stably associated therewith (e.g., able to retain its position relative to another sublocation after exposure to at least one molecular procedure). In one embodiment, the tissue is a tissue which has morphological features substantially intact which can be at least viewed under a microscope to distinguish subcellular features (e.g., such as a nucleus, an intact cell membrane, organells, and/or other cytological features), i.e., the tissue is not lysed.

In one embodiment of the invention, the microarray comprises from 2-1000 sublocations. In another embodiment, the microarray comprises 2, 5, 10, 20, 25, 30, 45, 50, 55, 60, 65, 75, 100, 150, 200, 250, 500, 550, 600, 650, 700, 750, 800, 850, 900, 950 or 1000 or more sublocations. In one embodiment of the invention, each sublocation is from 2-10 mm apart. In another embodiment of the invention, each sublocation comprises at least one dimension which is 20-600 mm. The sublocations can be organized in any pattern, and each sublocation can be generally any shape (square, circular, oval, elliptical, disc shaped, rectangular, triangular, and the like).

In a preferred embodiment, the sublocations are positioned in a regular repeating pattern (e.g., rows and columns) such that the identification of each sublocation as to tissue type can be ascertained by the use of an array locator. In one embodiment, the array locator is a template having a plurality of shapes, each shape corresponding to the shape of each sublocation in the array, and maintaining the same relationships as each sublocation on the array. The array locator is marked by coordinates, allowing the user to readily identify a sublocation on the array by virtue of unique coordinates. In one embodiment of the invention, the array locator is a transparent sheet (e.g., plastic, acetate, and the like). In another embodiment of the invention, the array locator is a sheet comprising a plurality of holes, each hole corresponding in shape and location to each sublocation on the array.

In one aspect, the invention provides for arrays wherein the compounds comprising the array are spotted onto a solid support, e.g., spotted using a robotic GMS 417 arrayer (Affymetrix, CA). Alternatively, spotting may be carried out using contact printing technology or other methods known in the art.

Types of Microarrays According to the Invention

Small Molecule Arrays

In the small molecule microarrays or arrays of the invention, the small molecules are stably associated with the surface of a solid support, wherein the support may be a flexible or rigid solid support. By "stably associated" is meant that each small molecule maintains a unique position relative to the solid support under binding and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the small molecules and a functional group present on the surface of the rigid support (e.g., —OH), where the functional group may be naturally occurring. The surface of the substrate can be preferably provided with a layer of linker molecules, although it will be understood that the linker molecules are not required elements of the invention. The linker molecules are preferably of sufficient length to permit small molecules of the invention and on a substrate to bind to small molecules and to interact freely with molecules exposed to the substrate.

The amount of small molecule present in each composition will be sufficient to provide for adequate binding and detection of target small molecules during the assay in which the array is employed. Generally, the amount of each small molecule stably associated with the solid support of the array is at least about 0.1 pg, preferably at least about 0.5 pg and more preferably at least about 1 pg, where the amount may be as high as 1000 pg or higher, but will usually not exceed about 100 pg. In a preferred embodiment, the microarray has a density exceeding 1, 2, 5, 7, 10, 15 or 20 or more small molecules/cm2.

Tissue Microarrays

In a preferred embodiment of the invention, the microarrays or arrays comprise human tissue samples. The microarrays according to the invention comprise a plurality of sublocations, each sublocation comprising a tissue sample having at least one known biological characteristic (e.g., such as tissue type). In a preferred embodiment of the invention, the plurality of sublocations comprise cancerous tissue at different neoplastic stages.

In one embodiment of the invention, the cancerous cells at individual sublocations are from an individual with an underlying cancer or predisposition to having a cancer.

In one embodiment of the invention, the cancerous cells at individual sublocations are from an individual with cancer-associated defects in the BRCA-1 and/or FANC D1/BRCA-2 genes.

In one embodiment, the microarray comprises at least one sublocation comprising cancerous cells from a single patient and comprises a plurality of sublocations comprising cells from other tissues and organs from the same patient. In a different embodiment, a microarray is provided comprising cells from a plurality of individuals who have all died from the same pathology, or from individuals being treated with the same drug (including those who recovered from the disease and/or those who did not).

In another embodiment of the invention, the microarray comprises a plurality of sublocations comprising cells from individuals sharing a trait in addition to cancer. In one embodiment of the invention, the trait shared is gender, age, a pathology, predisposition to a pathology, exposure to an infectious disease (e.g., HIV), kinship, death from the same illness, treatment with the same drug, exposure to chemotherapy or radiotherapy, exposure to hormone therapy, exposure to surgery, exposure to the same environmental condition, the same genetic alteration or group of alterations, expression of the same gene or sets of genes.

In a further embodiment of the invention, each sublocation of the microarray comprises cells from different members of a pedigree sharing a family history of cancer (e.g., selected from the group consisting of sibs, twins, cousins, mothers, fathers, grandmothers, grandfathers, uncles, aunts, and the like). In another embodiment of the invention, the "pedigree microarray" comprises environment-matched controls (e.g., husbands, wives, adopted children, stepparents, and the like). In still a further embodiment of the invention, the microarray is a reflection of a plurality of traits representing a particular patient demographic group of interest, e.g., overweight smokers, diabetics with peripheral vascular disease, individuals having a particular predisposition to disease (e.g., sickle cell Anemia, Tay Sachs, severe combined immunodeficiency), wherein individuals in each group have cancer.

In a preferred embodiment of the invention, the microarrays comprise human tissue biopsies.

FANG D2 −/− as disclosed herein. In one embodiment, the microarray comprises multiple tissues from such a mouse. In another embodiment of the invention, the microarray comprises tissues from mice that are FANC D2 −/− as disclosed herein, and which have been treated with a cancer therapy (e.g., drugs, antibodies, protein therapies, gene therapies, antisense therapies, and the like).

Screening of Chemosensitizing Agents and Novel Cancer Therapeutics

The microarrays of the invention are used to screen for chemosensitizing agents and cancer therapeutics. The screening procedures used are disclosed in Examples 15 and 16.

Measurement of Resistance to a Chemotherapy Agent

Methylation of the FANG F gene within tumor cells that are treated with cisplatin results in the repression of FANC F gene expression and thereby causes a disruption in the tumor cell's DNA damage repair mechanisms and resulting in resistance to cisplatin. The invention therefore provides for the determination of the methylation state of any of the Fanconi Anemia/BRCA pathway genes (see Example 19). In a preferred embodiment, the invention provides microarrays of tissue biopsy samples from patients being treated with one or more chemotherapy compounds for the determination of the methylation state of the Fanconi Anemia/BRCA genes as a measurement of the degree of a tumor's resistance to one or more chemotherapy compounds. Methods of measuring DNA methylation of genes are well known in the art (see U.S. Pat. Nos. 6,200,756; 6,331,393; 6,251,594).

Kits According to the Invention

The invention provides for kits useful for screening for chemosensitizers and cancer therapeutics, as well as kits useful for diagnosis of cancer or predisposition toward cancer involving cancer-associated defects in the Fanconi Anemia/BRCA gene pathway. Kits, useful according to the invention include isolated FANC D2 polynucleotide primer pairs, probes, inhibitors of the Fanconi Anemia/BRCA pathway and a FANC D2-specific antibody. In addition, kits can contain control unmethylated FANC D2 genes. In a further embodiment, a kit according to the invention can contain an ovary cancer tumor cell line. All kits according to the invention will comprise the stated items or combinations of items and packaging materials therefore. Kits will also include instructions for use.

The present invention is described by reference to the following Examples, which are offered by way of illustration and are not intended to limit the invention in any manner. Standard techniques well known in the art or the techniques specifically described below were utilized.

EXAMPLES

Example 1

Experimental Protocols Used in Examples 2-8

Cell Lines and Culture Conditions. Epstein-Barr virus (EBV) transformed lymphoblasts were maintained in RPMI media supplemented with 15% heat-inactivated fetal calf serum (FCS) and grown in a humidified 5% CO2-containing atmosphere at 37° C. A control lymphoblast line (PD7) and FA lymphoblast lines (FA-A (HSC72), FA-C (PD-4), FA-D (PD-20), FA-F (EUFA121), and FA-G (EUFA316)) have been previously described (de Winter et al., Nat. Genet., (1998) Vol. 20, pp. 281-283) (Whitney et al., Nat. Genet., (1995) Vol. 11, pp. 341-343) (Yamashita et al., P.N.A.S., (1994) Vol. 91, pp. 6712-6716) (de Winter et al., Am. J. Hum. Genet., (2001), Vol. 57, pp. 1306-1308). PD81 is a lymphoblast cell line from an FA-A patient. The SV40-transformed FA fibroblasts, GM6914, PD426, FAG326SV and PD20F, as well as HeLa cells, were grown in DMEM supplemented with 15% FCS. FA cells (both lymphoblasts and fibroblasts) were functionally complemented with pMMP retroviral vectors containing the corresponding FANC cDNAs, and functional complementation was confirmed by the MMC assay (Garcia- Higuera et al., Mol. Cell. Biol., (1999) Vol. 19, pp. 4866-4873) (Kuang et al., Blood, (2000), Vol. 96, pp. 1625-1632).

Cell Cycle Synchronization. HeLa cells, GM6914 cells, and GM6914 cells corrected with the pMMP-FANCA retrovirus were synchronized by the double thymidine block method as previously described, with minor modifications (Kupfer et al., Blood, (1997) Vol. 90, pp. 1047-1054). Briefly, cells were treated with 2 mM thymidine for 18 hours, thymidine-free media for 10 hours, and additional 2 mM thymidine for 18 hours to arrest the cell cycle at the G1/S boundary. Cells were washed twice with PBS and then released in DMEM+ 15% FCS and analyzed at various time intervals.

Alternatively, HeLa cells were treated with 0.5 mM mimosine (Sigma) for 24 hours for synchronization in late G1 phase (Krude, 1999), washed twice with PBS, and released into DMEM+15% FCS. For synchronization in M phase, a nocodazole block was used (Ruffner et al., Mol. Cell. Biol., (1999) Vol. 19, pp. 4843-4854). Cells were treated with 0.1 µg/ml nocodazole (Sigma) for 15 hours, and the non-adherent cells were washed twice with PBS and replated in DMEM+ 15%.

Cell Cycle Analysis. Trypsinized cells were resuspended in 0.5 ml of PBS and fixed by adding 5 ml of ice-cold ethanol. Cells were next washed twice with PBS with 1% bovine serum albumin fractionV (1% BSA/PBS) (Sigma), and resuspended in 0.24 ml of 1% BSA/PBS. After adding 30 µl of 500 µl/ml propidium iodide (Sigma) in 38 mM sodium citrate (pH7.0) and 30 µl of 10 mg/ml DNase free RNaseA (Sigma), samples were incubated at 37° C. for 30 min. DNA content was measured by FACScan (Beckton Dickinson), and data were analyzed by the CellQuest and Modfit LT program (Becton Dickinson).

Generation of an anti-FANCD2 antiserum. A rabbit polyclonal antiserum against FANCD2 was generated using a GST-FANCD2 (N-terminal) fusion protein as an antigen source. A 5' fragment was amplified by polymerase chain reaction (PCR) from the full length FANCD2 cDNA with the primers (SEQ ID NO:95) DF4EcoRI (5' AGCCTCgaattcGTTTCCAA AAGAAGACTGTCA-3') and (SEQ ID NO:96) DR816Xh (5'-GGTATCctcgagTCAAGACGA CAACTTATCCATCA-3'). The resulting PCR product of 841 bp, encoding the amino-terminal 272 amino acids of the FANCD2 polypeptide was digested with EcoRI/XhoI and subcloned into the EcoRI/XhoI sites of the plasmid pGEX4T-1 (Pharmacia). A GST-FANCD2 (N-terminal) fusion protein of the expected size (54 kD) was expressed in E. coli strain DH5γ, purified over glutathione-S-sepharose, and used to immunize a New Zealand White rabbit. An FANCD2-specific immune antiserum was affinity-purified by passage over an AminoLink Plus column (Pierce) loaded with GST protein and by passage over an AminoLink Plus column loaded with the GST-FANCD2 (N-terminal) fusion protein.

Generation of anti-FANCD2 MoAbs. Two anti-FANCD2 monoclonal antibodies were generated as follows. Balb/c mice were immunized with a GST-FANCD2 (N-terminal) fusion protein, which was the same fusion protein used for the generation, of the rabbit polyclonal antiserum (E35) against FANCD2. Animals were boosted with immunogen for the four days before fusion, splenocytes were harvested, and hybridization with myeloma cells was performed. Hybridoma supernatants were collected and assayed using standard ELISA assay as the initial screen and immunoblot analysis of FANCD2 as the secondary screen. Two anti-human FANCA2 monoclonal antibodies (MoAbs) (FI17 and FL14) were selected for further study. Hybridoma supernatants from the two positive cell lines were clarified by centrifugation. Supernatants were used as MoAbs for western blotting. MoAbs were purified using an affinity column for IgG. MoAbs were stored as 0.5 mg/ml stocks in phosphate buffered saline (PBS). Anti-HA antibody (HA. 11) was from Babco.

Immunoblotting. Cells were lysed with 1× sample buffer (50 mM Tris-HCl pH6.8, 86 mM 2-mercaptoethanol, 2% sodium dodecyl sulfate (SDS), boiled for 5 min, and subjected to 7.5% polyacrylamide SAS gel electrophoresis. After electrophoresis, proteins were transferred to nitrocellulose using a submerged transfer apparatus (BioRad) filled with 25 mM Tris base, 200 mM glycine, 20% methanol. After blocking with 5% non-fat dried milk in TBS-T (50 mM Tris-HCl, pH 8.0, 150 mM NaCl, 0.1% Tween 20) the membrane was incubated with the primary antibody diluted in TBS-T (1:1000 dilution for the affinity-purified anti-FANCD2 polyclonal antibody (E35) or anti-HA (HA. 11), 1:200 dilution for the anti-FANCD2 mouse monoclonal antibody FI17), washed extensively and incubated with the appropriate horseradish peroxidase-linked secondary antibody (Amersham). Chemiluminescence was used for detection.

Generation of DNA Damage. Gamma irradiation was delivered using a Gamma cell 40 apparatus. UV exposure was achieved using a Stratalinker (Stratagene) after gently aspirating the culture medium. For Mitomycin C treatment cells were continuously exposed to the drug for the indicated time. Hydroxyurea (Sigma) was added to a final concentration of 1 mM for 24 hours.

Detection of Monoubiquitinated FANCD2. HeLa cells (or the FA-G fibroblasts, FAG326SV) were transfected using FuGENE6 (Roche), following the manufacturer's protocol. HeLa cells were plated onto 15 cm tissue culture dishes and were transfected with 15 µg of a HA-tagged ubiquitin expression vector (pMT 123) (Treier et al., Cell, (1994) Vol. 78, pp. 787-798) per dish. Twelve hours following transfection, cells were treated with the indicated concentration of MMC (0, 10, 40, 160 ng/ml) or the indicated dose of IR (0, 5, 10, 10, 20 Gy). After 24 hour-incubation with MMC, or two hours after IR treatment, whole cell extracts were prepared in Lysis Buffer (50 mM TrisHCl pH7.4, 150 mM NaCl, 1% (v/v) Triton X-100) supplemented with protease inhibitors (1 µg/ml leupeptin and pepstatin, 2 µg/ml aprotinin, 1 mM phenyhnethylsulfonylfluoride) and phosphatase inhibitors (1 mM sodium orthovanadate, 10 mM sodium fluoride). Using the polyclonal antibody to FANCD2 (E35), immunoprecipitation (IP) was performed essentially as described (Kupfer et al., 1997) except that each IP was normalized to contain 4 mg of protein. As a negative control, preimmune serum from the same rabbit was used in IP reaction. Immunoblotting was done using anti-HA (HA. 11), or anti-FANCD2 (FI17) monoclonal antibody.

Ubiquitin Aldehyde Treatment. HeLa cells were treated with 1 mM hydroxyurea for 24 hours, and whole cell extracts were prepared in Lysis Buffer supplemented with protease inhibitors and phosphatase inhibitors. 200 µg of cell lysate in 67 µl of reaction with 6.7 µl of 25 µM ubiquitin aldehyde (BostonBiochem) in DMSO or with 6.7 µl of DMSO were incubated at 30° C. or at 37° C. for the indicated periods. Sixty-seven microliters of 2× sample buffer was added to each sample, and the samples were boiled for 5 min, separated by 7.5% SDS-PAGE, and immunoblotted for FANCD2 using the FI17 monoclonal anti-human FANCD2 antibody.

Immunofluorescence Microscopy. Cells were fixed with 2% paraformaldehyde in PBS for 20 min, followed by permeabilization with 0.3% Triton-X-100 in PBS (10 min). After blocking in 10% goat serum, 0.1% NP-40 in PBS (blocking buffer), specific antibodies were added at the appropriate dilution in blocking buffer and incubated for 2-4 hours at room temperature. FANCD2 was detected using the affinity-purified E35 polyclonal antibody (1/100). For BRCA1 detection, we used a commercial monoclonal antibody (D-9, Santa Cruz) at 2 µg/ml. Cells were subsequently washed three times in PBS+0.1% NP-40 (10-15 min each wash) and species-specific fluorescein or Texas red-conjugated secondary antibodies (Jackson Immunoresearch) were diluted in blocking buffer (anti-mouse 1/200, anti-rabbit 1/1000) and added. After 1 hour at room temperature three more 10-15 min washes were applied and the slides were mounted in Vectashield (Vector laboratories). Images were captured on a Nikon microscope and processed using Adobe Photoshop software.

Meiotic Chromosome Staining. Surface spreads of pachytene and diplotene spermatocytes from male mice between the ages of 16 and 28 days old were prepared as described by (Peters et al., 1997). A polyclonal goat antibody to the mouse SCP3 protein was used to visualize axial elements and synaptonemal complexes in the meiotic preparations. The M118 mouse monoclonal antibody against mouse BRCA1 was generated by standard techniques, by immunizing mice with murine BRCA1 protein. The affinity-purified E35 rabbit polyclonal antibody was used in 1:200 dilution to detect FANCD. Antibody incubation and detection procedures were a modification of the protocol of (Moens et al., J. Cell. Biol., (1987) Vol. 105, pp. 93-103) as described by (Keegan et al., Genes Dev., (1996) Vol. 10, pp. 2423-2437). Combinations of donkey-anti mouse IgG-FITC-conjugated, Donkey-anti rabbit IgG-TRITC-conjugated, and Donkey-anti goat IgGCy5-conjugated secondary antibodies were used for detection (Jackson ImmunoResearch Laboratories). All preparations were counterstained with 4', 6' diamino-2-phenylindole (DAPI, Sigma) and mounted in a DABCO (Sigma) antifade solution. The preparations were examined on a Nikon E1000 microscope (60× CFI Plan Apochromat and 100× CR Plan Fluor oil-immersion objectives). Each fluorochrome (FITC, TRITC, Cy5 and DAPI) image was captured separately as an 800×1000 pixel 12-bit source image via IPLab software (Scanalytics) controlling a cooled-CCD camera (Princeton Instruments MicroMax) and the separate 12 bit grey scale images were resampled, 24-bit pseudocolored and merged using Adobe Photoshop.

Example 2

The FA Genes Interact in a Common Cellular Pathway

Normal lymphoblasts express two isoforms of the FANCD2 protein, a short form (FANCD2-S, 155 kD) and a long form (FANCD2-L, 162 kD). FIG. 1 shows what happened when whole cell extracts were prepared from a lymphoblast line and cellular, proteins were immunoprecipitated with an anti-FANCD2 antiserum. Normal wild type cells expressed two isoforms of the FANCD2 protein—a low molecular weight isoform FANCD2-S (155 kD isoform) and a high molecular weight isoform (FANCD2-L) (162 kD isoform). FANCD2-S is the primary translation product of the cloned FANCD2 cDNA. We next evaluated a large series of FA lymphoblasts and fibroblasts for expression of the FANCD2 isoforms (Table 5). Correction of these FA cell lines with the corresponding FA cDNA resulted in functional complementation and restoration of the high molecular weight isoform, FANCD2-L.

As previously described, FA cells are sensitive to the DNA crosslinking agent, MMC, and in some cases, to ionizing radiation (IR). Interestingly, FA cells from multiple complementation groups (A, C, G, and F) only expressed the FANCD2-S isoform (FIG. 1A, lanes 3, 7, 9, 11). FA cells from complementation groups B and E also express only the FANCD2-S. Functional correction of the MMC and IR sensitivity of these FA cells with the corresponding FANC cDNA restored the FA protein complex (Garcia-Higuera et al., 1999) and restored the high molecular weight isoform (FANCD2-L) (FIG. 1A, lanes 4, 8, 10, 12). Taken together, these results demonstrate that the FA protein complex, containing FANCA, FANCC, FANCF, and FANCG, directly or indirectly regulates the expression of the two isoforms of FANCD2. The six cloned FA genes therefore appear to interact in a common pathway.

Example 3

The FA Protein Complex is Required for the Monoubiquitination of FANCD2

The high molecular weight isoform of FANCD2 could result from one or more mechanisms, including alternative splicing of the FANCD2 mRNA or post-translational modification(s) of the FANCD2 protein. Treatment with phosphatase did not convert FANCD2-L to FANCD2-S, demonstrating that phosphorylation alone does not account for the observed difference in their molecular mass.

Figure 1B:
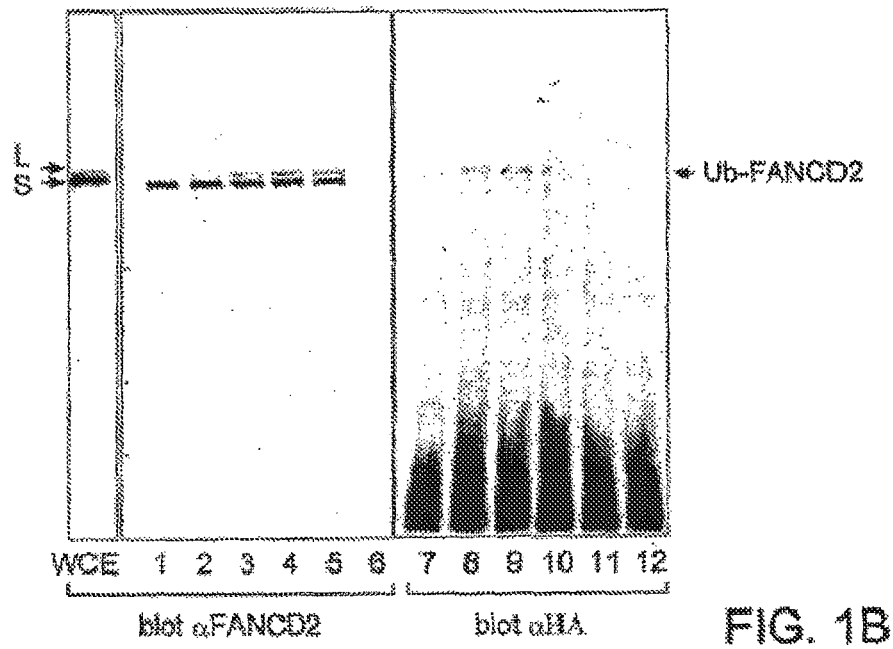
FIG. 1B shows a Western blot obtained after HeLa cells were transfected with a cDNA encoding HA-ubiquitin. After transfection, cells were treated with the indicated dose of mitomycin C (MMC). Cellular proteins were immunoprecipitated with a polyclonal antibody (E35) to FANCD2, as indicated. FANCD2 was immunoprecipitated, and immune complexes were blotted with anti-FANCD2 or anti-HA monoclonal antibody.
Figure 1C:
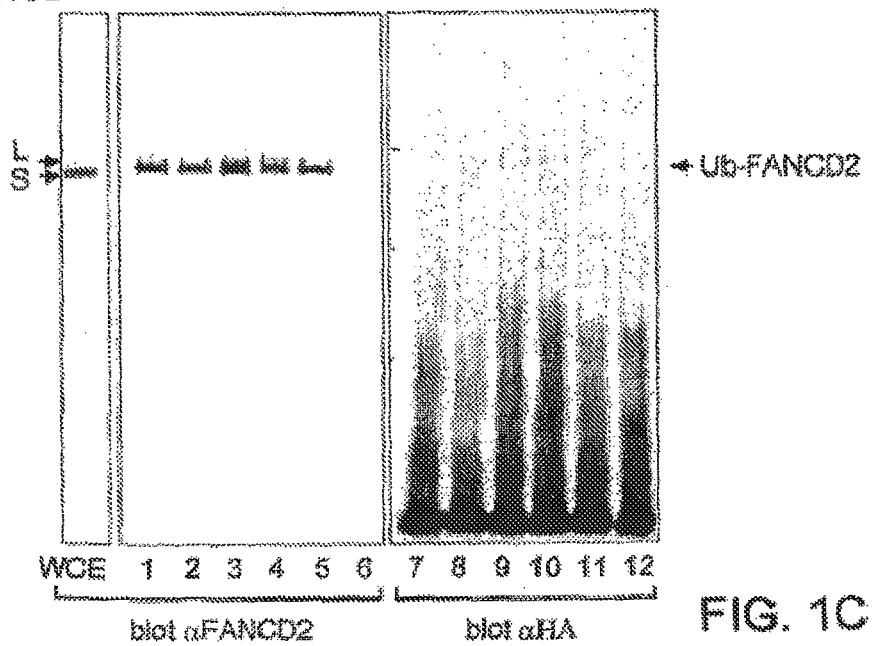
FIG. 1C shows a Western blot obtained after HeLa cells were transfected with a cDNA encoding HA-ubiquitin. After transfection, cells were treated with the indicated dose of ionizing radiation (IR). FANCD2 was immunoprecipitated, and immune complexes were blotted with anti-FANCD2 or anti-HA monoclonal antibody.
Figure 1D:
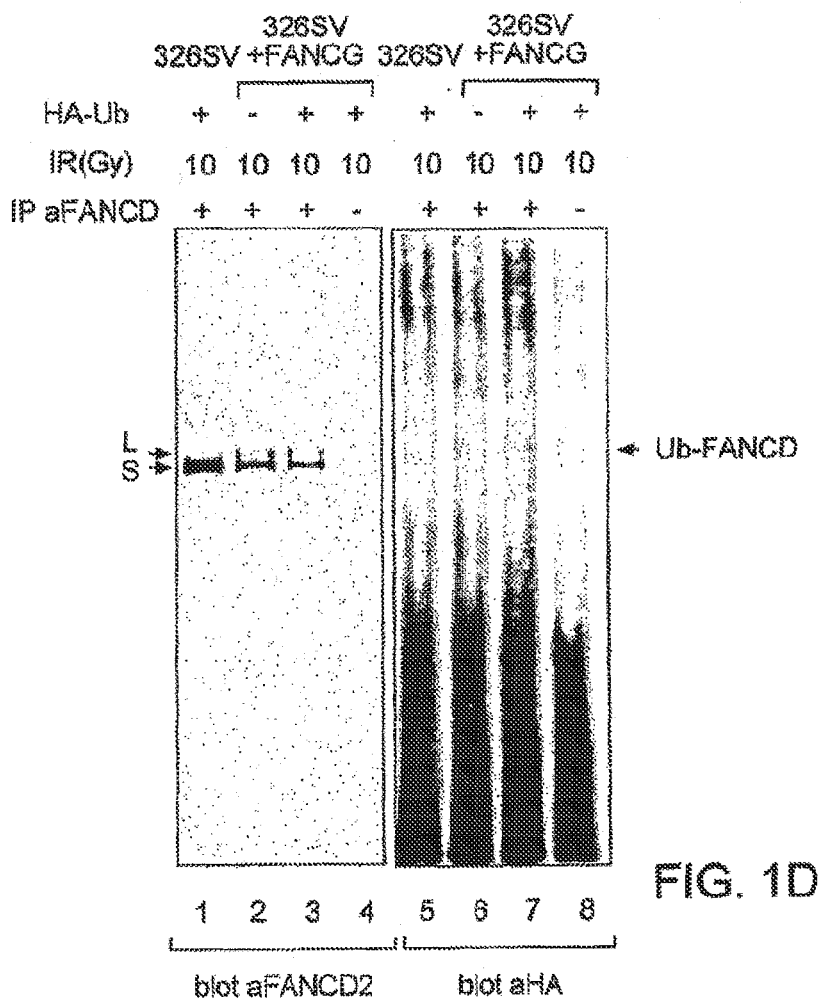
FIG. 1D shows a Western blot obtained after PA-G fibroblast line (FAG326SV) or corrected cells (FAG326SV plus FANCG cDNA) were transfected with the HA-Ub cDNA, FANCD2 was immunoprecipitated, and immune complexes were blotted with anti-FANCD2 or anti-HA antisera.
Figure 1E:
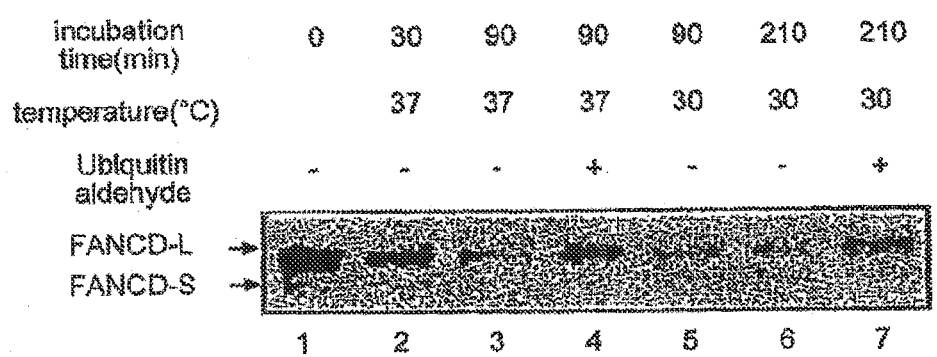
FIG. 1E shows a Western blot obtained after treatment of HeLa cells with 1 mM hydroxyurea for 24 hours. HeLa cell lysates were extracted and incubated at the indicated temperature for the indicated time period with or without 2.5 µM ubiquitin aldehyde. The FANCD2 protein was detected by immunoblot with monoclonal anti-FANCD2 (F117).

In order to identify other possible post-translational modifications of FANCD2, we initially sought cellular conditions which regulate the conversion of FANCD2-S to FANCD2-L (FIGS. 1B, C). Since FA cells are sensitive to MMC and IR, we reasoned that these agents might regulate the conversion of FANCD2-S to FANCD2-L in normal cells. Interestingly, HeLa cells treated with MMC (FIG. 1B, lanes 1-6) or IR. (FIG. 1 C, lanes 1-6) demonstrated a dose-dependent increase in the expression of the FANCD2-L isoform.

To determine whether FANCD2-L is a ubiquitinated isoform of FANCD2-S, we transfected HeLa cells with a cDNA encoding HA-ubiquitin (Treier et al., 1994). Cellular exposure to MMC (FIG. 1B, lanes 7-10) or IR (Figure IC, lanes 7-10) resulted in a dose-dependent increase in the HA-ubiquitin conjugation of FANCD2. Only the FANCD2-L isoform, and not the FANCD2-S isoform, was immunoreactive with an anti-HA antibody. Although FANCD2 was not ubiquinated in FA cells, FANCD2 ubiquination was restored upon functional complementation of these cells. Although FANCD2 was, not ubiquitinated in FA cells, FANCD2 ubiquitination was restored upon functional complementation of these cells. Since the FANCD2-S and FANCD2-L isoforms differ by 7 kD, the FANCD2-L probably contains a single ubiquitin moiety (76 amino acids) covalently bound by an amide linkage to an internal lysine residue of FANCD2.

To confirm the monoubiquitination, we isolated FANCD2-L protein from HeLa cells and analyzed its tryptic fragments by mass spectrometry (Wu et al., Science, (2000), Vol. 289, p. 11a). Ubiquitin tryptic fragments were unambiguously identified, and a site of monoubiquitination (K561 of FANCD2) was also identified. Interestingly, this lysine residue is conserved among FANCD2 sequences from human, *Drosophila*, and *C. elegans*, suggesting that the ubiquitination of this site is critical to the FA pathway in multiple organisms. Mutation of this lysine residue, FANCD2 (K561R), resulted in loss of FANCD2 monoubiquitination.

Example 4

Formation of Nuclear Foci Containing FANCD2 Requires an Intact FA Pathway

We examined the immunofluorescence pattern of the FANCD2 protein in uncorrected, MMC-sensitive FA fibroblasts and functionally-complemented fibroblasts (FIG. 2).

The corrected FA cells expressed both the FANCD2-S and FANCD2-L isoforms (FIG. 2A, lanes 2, 4, 6, 8). The endogenous FANCD2 protein was observed exclusively in the nucleus of human cells, and no cytoplasmic staining was evident (FIG. 2B, a-h). The PD-20 (FA-D) cells have decreased nuclear immunofluorescence (FIG. 2B, d), consistent with the decreased expression of FANCD2 protein in these cells by immunoblot (FIG. 2A, lane 7). In PD20 cells functionally-corrected with the FANCD2 gene by chromosome transfer, the FANCD2 protein stained in two nuclear patterns. Most corrected cells had a diffuse nuclear pattern of staining, and a minor fraction of cells stained for nuclear foci (see dots, panel, h). Both nuclear patterns were observed with three independently-derived anti-FANCD2 antisera (1 polyclonal, 2 monoclonal antisera). FA fibroblasts from subtypes A, G, and C showed only the diffuse pattern of FANCD2 nuclear immunofluorescence. Functional complementation of these cells with the FANCA, FANCG, or FANCC cDNA, respectively, restored the MMC resistance of these cells (Table 6), and restored the nuclear foci in some cells. The presence of the high molecular weight FANCD2-L isoform therefore correlates with the presence of FANCD2 nuclear foci, suggesting that only the monoubiquitinated FANCD2-L isoform is selectively localized to these foci.

Example 5

Figure 3A:
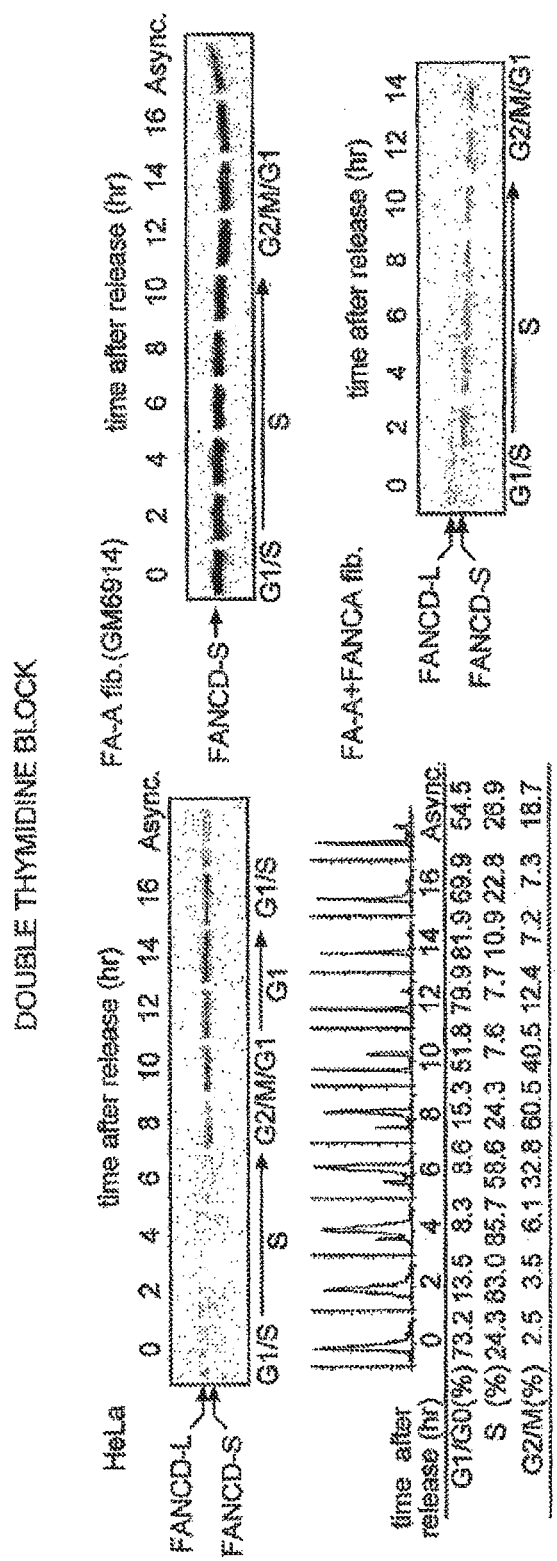
Figure 3D:
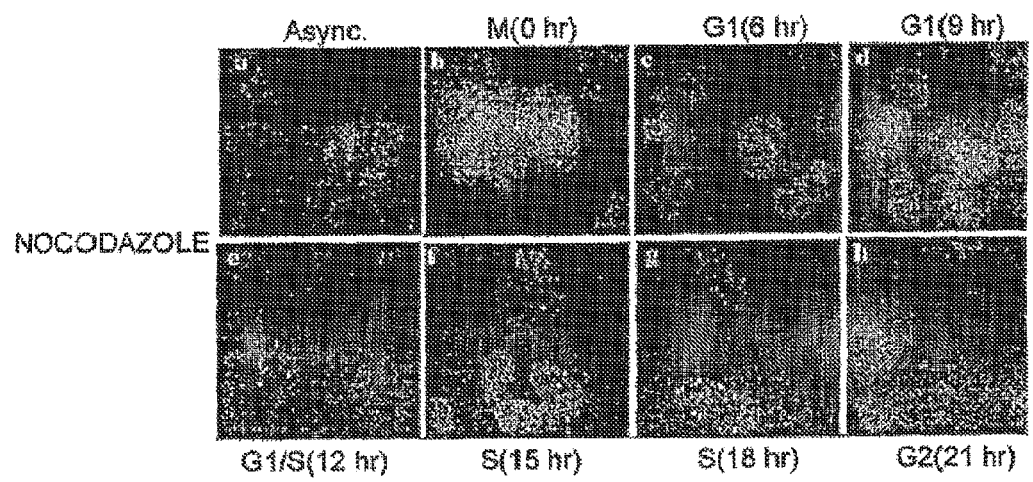
Figure 3E:
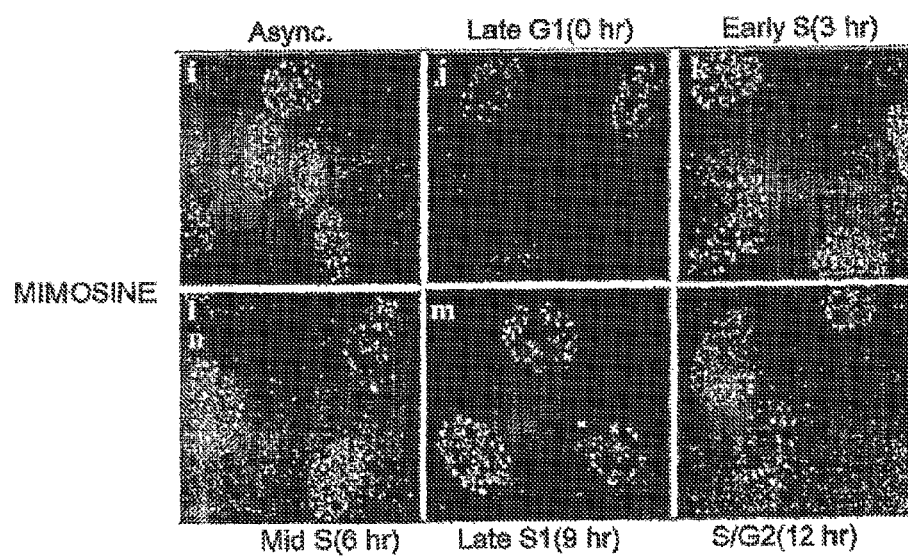

The FANCD2 Protein is Localized to Nuclear Foci During S Phase of the Cell Cycle Since only a fraction of the asynchronous functionally-complemented cells contained FANCD2 nuclear foci, we reasoned that these foci might assemble at discrete times during the cell cycle. To test this hypothesis, we examined the formation of the FANCD2-L isoform and FANCD2 nuclear foci in synchronized cells (FIG. 3A-3E). HeLa cells were synchronized at the G1/S boundary, released into S phase, and analyzed for formation of the FANCD2-L isoform (FIG. 3A). The FANCD2-L isoform was expressed specifically during late G1 phase and throughout S phase. Synchronized, uncomplemented FA cells (FA-A fibroblasts, GM6914) expressed normal to increased levels of FANCD2-S protein but failed to express FANCD2-L at any time during the cell cycle. Functional complementation of these FA-A cells by stable transfection with the FANCA cDNA restored S phase-specific expression of FANCD2-L. The S phase specific expression of the FANCD2-L isoform was confirmed when HeLa cells were synchronized by other methods, such as nocodazole arrest (FIG. 3B) or mimosine exposure (FIG. 3B). Cells arrested in mitosis did not express FANCD2-L, suggesting that the FANCD2-L isoform is removed or degraded prior to cell division (FIG. 3B, mitosis). Taken together, these results demonstrate that the monoubiquitination of the FANCD2 protein is highly regulated during the cell cycle, and that this modification requires an intact FA pathway.

The cell cycle dependent expression of the FANCD2-L isoform also correlated with the formation of FANCD2 nuclear foci (FIG. 3C). Nocodazole arrested (mitotic) cells express no FANCD2-L isoform and exhibit no FANCD2 nuclear foci (FIG. 3C, 0 hour). When these synchronized cells were allowed to traverse S phase (15 to 18 hours), an increase in FANCD2 nuclear foci was observed.

Example 6

The FANCD2 Protein is Localized to Nuclear Foci in Response to DNA Damage

Figure 4F:
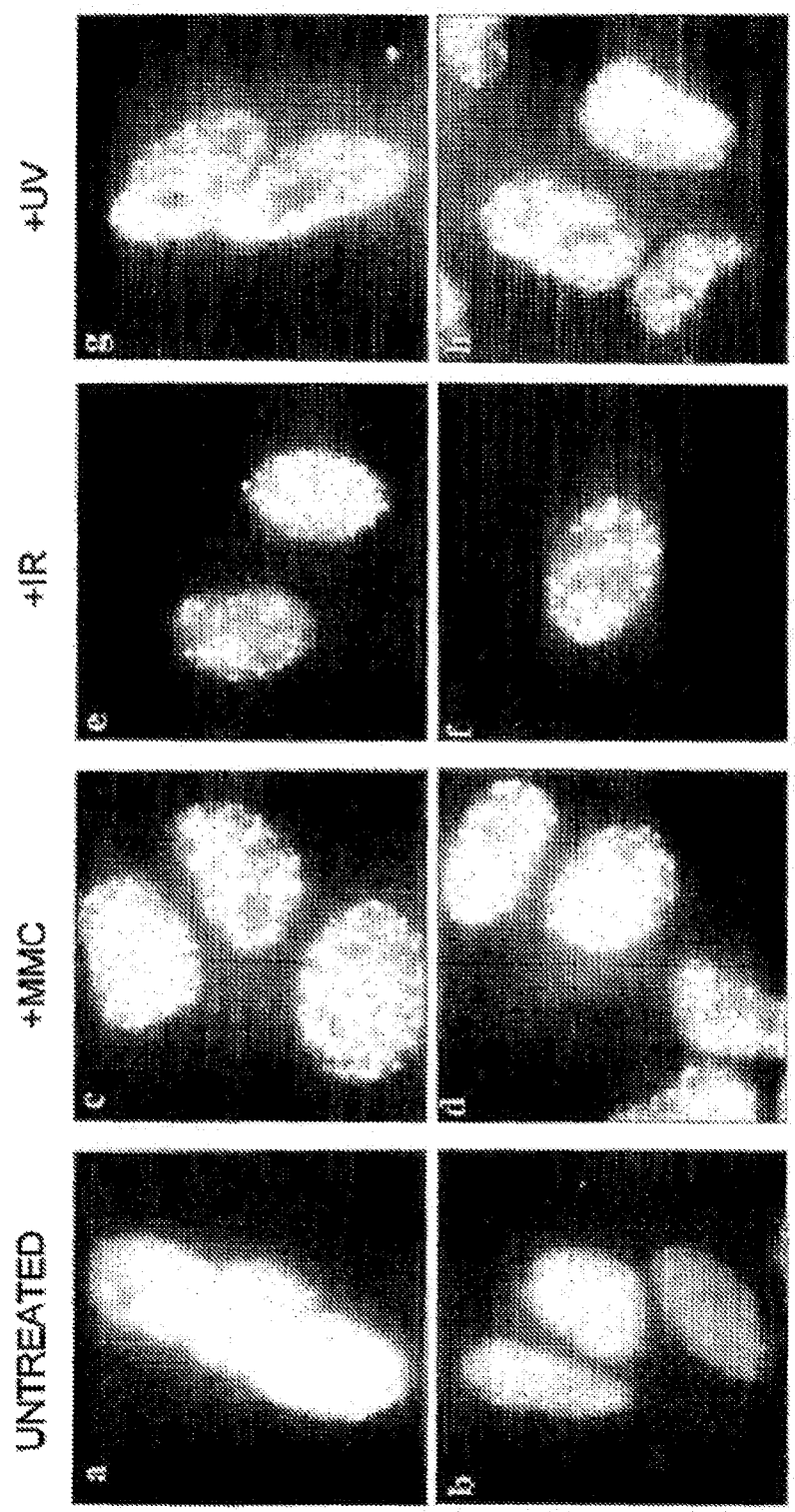
Figure 4J:
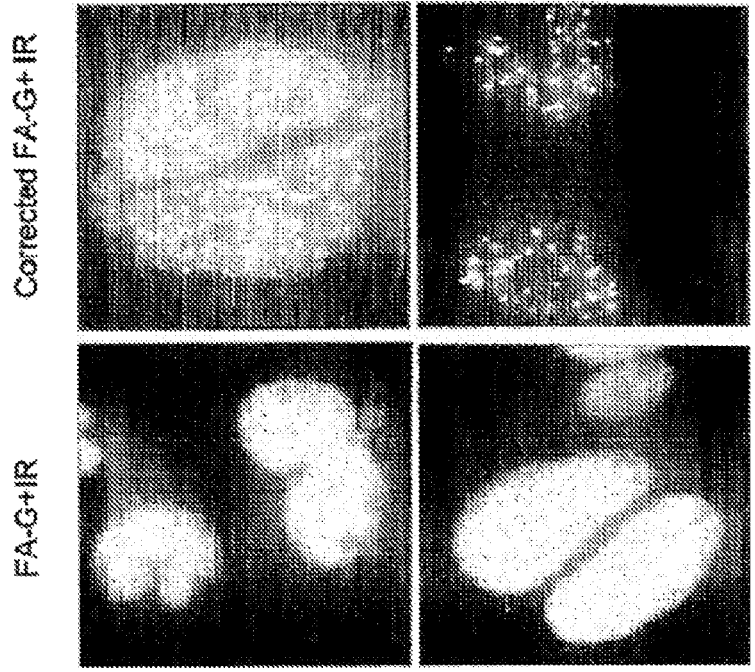
Figure 4G:
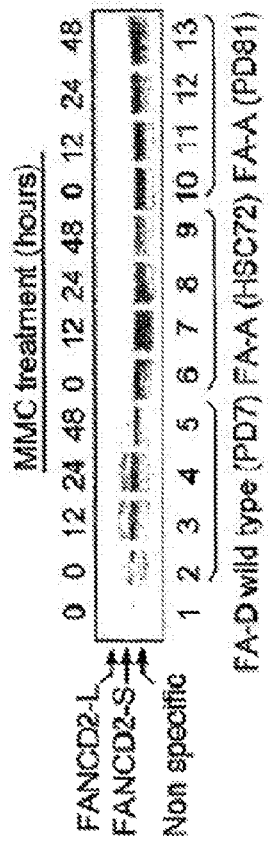
Figure 4H:
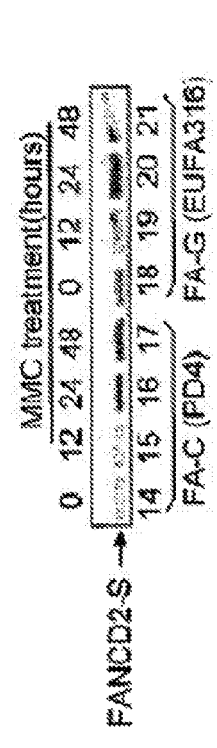
Figure 4I:
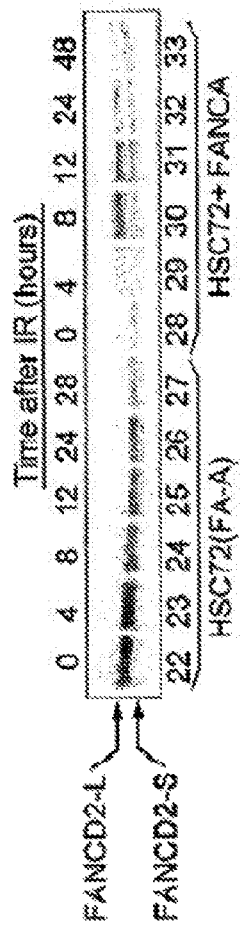

We examined the accumulation of the FANCD2-L isoform and FANCD2 nuclear foci in response to DNA damage (FIGS. 4A-4J). Previous studies have shown that FA cells are sensitive to agents which cause DNA interstrand crosslinks (MMC) or double strand breaks (IR) but are relatively resistant to ultraviolet light (UV) and monofunctional alkylating agents. MMC activated the conversion of FANCD2-S to FANCD2-L in asynchronous HeLa cells (FIG. 4A). Maximal conversion to FANCD2-L occurred 12-24 hours after MMC exposure, correlating with the time of maximal FANCD2 nuclear focus formation. There was an increase in FANCD2 nuclear foci corresponding to the increase in FANCD2-L., Ionizing radiation also activated a time-dependent and dose-dependent increase in FANCD2-L in HeLa cells, with a corresponding increase in FANCD2 foci (FIGS. 4B and 4D). Surprisingly, ultraviolet (UV) light activated a time-dependent and dose-dependent conversion of FANCD2-S to FANCD2-L, with a corresponding increase in FANCD2 foci (FIGS. 4C and 4E).

We tested the effect of DNA damage on FA cells (FIG. 4F). FA cells from multiple complementation groups (A, C, and G) failed to activate the FANCD2-L isoform and failed to activate FANCD2 nuclear foci in response to MMC or IR exposure. These data suggest that the cellular sensitivity of FA cells results, at least in part, from their failure to activate FANCD2-L and FANCD2 nuclear foci.

Example 7

Co-Localization of Activated FANCD2 and BRCA1 Protein

Like FANCD2, the breast cancer susceptibility protein, BRCA1, is upregulated in proliferating cells and is activated by post-translational modifications during S phase or in response to DNA damage. BRCA has a carboxy terminus 20 amino acids which contain a highly acidic HMG-like domain suggesting a possible mechanism for chromatin repair. The BRCA1 protein co-localizes in IR-inducible foci (IRIFs) with other proteins implicated in DNA repair, such as RAD51 or the NBS/Mre11/RAD50 complex. Cells with biallelic mutations in BRCA1 have a defect in DNA repair and are sensitive to DNA damaging agents such as IR and MMC (Table 5). Taken together, these data suggest a possible functional interaction between the FANCD2 and BRCA1 proteins. BRCA foci are large (2 mDa) multiprotein complexes including ATM and ATM substrates involved in DNA repair (BRCA1) and checkpoint functions (NBS).

Figure 5B:
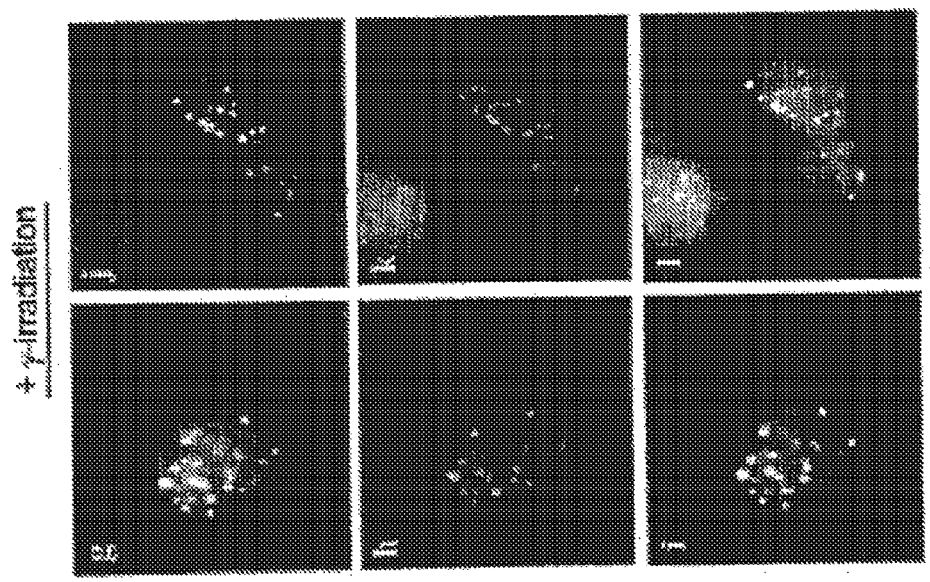
FIGS. 5A-5C show co-localization of activated FANCD2 and BRCA1 in Discrete Nuclear Foci following DNA damage. HeLa cells were untreated or exposed to Ionizing Radiation (10 Gy) as indicated, and fixed 8 hours later. Cells were double-stained with the D-9 monoclonal anti-BRCA1 antibody (FIGS. 5A and 5B, panels designated a, d, g, h) and the rabbit polyclonal anti-FANCD2 antibody (FIGS. 5A and 5B, panels designated b, e, h, k), and stained cells were analyzed by immunofluorescence. BRCA1 and FANCD2 signals overlap (Merge, panels designated c, f, i, 1 in FIGS. 5A and 5B), indicating co-localization of BRCA1 and FANCD2. Co-immunoprecipitation of FANCD2 and BRCA1 (FIG. 5C). HeLa cells were untreated (+IR) or exposed to 15 Gy of γ-irradiation (+IR) and collected 12 hours later. Cell lysates were prepared, and cellular proteins were immunoprecipitated with either the monoclonal FANCD2 antibody (FIG. 5C, FI-17, lanes 9-10), or any one of three independently-derived monoclonal antibodies to human BRCA1 (FIG. 5C, lanes 3-8): D-9 (Santa Cruz), Ab-1 and Ab-3 (Oncogene Research Products). The same amount of purified mouse IgG (Sigma) was used in control samples (lanes 1-2). Immune complexes were resolved by SDS-PAGE and were immunoblotted with anti-FANCD2 or anti-BRCA1 antisera. The FANCD-L isoform preferentially coimmunoprecipitated with BRCA1.
Figure 5A:
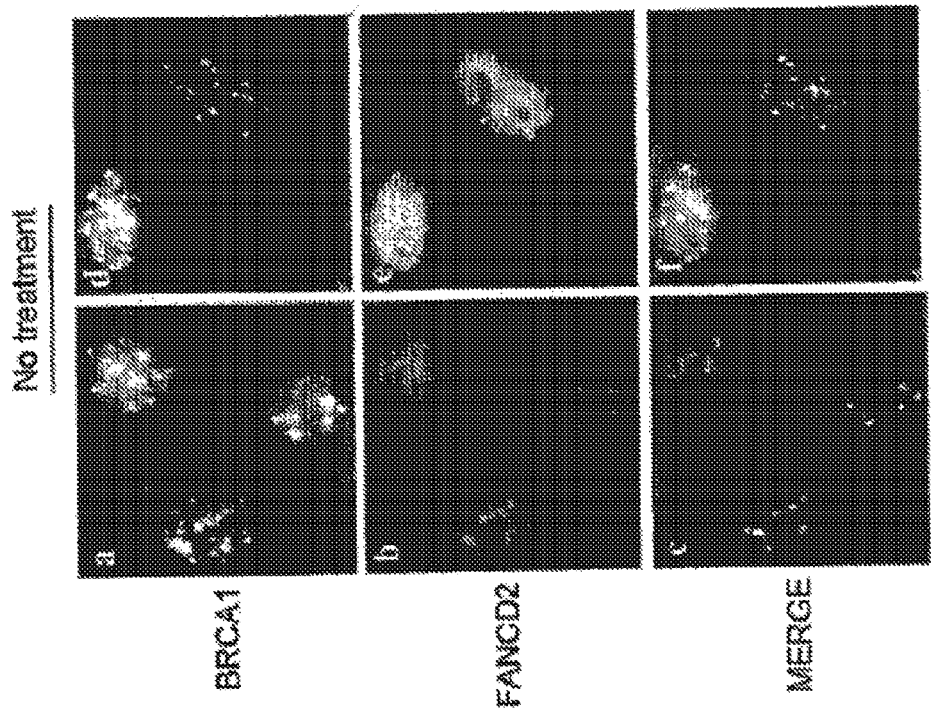
Figure 5C:
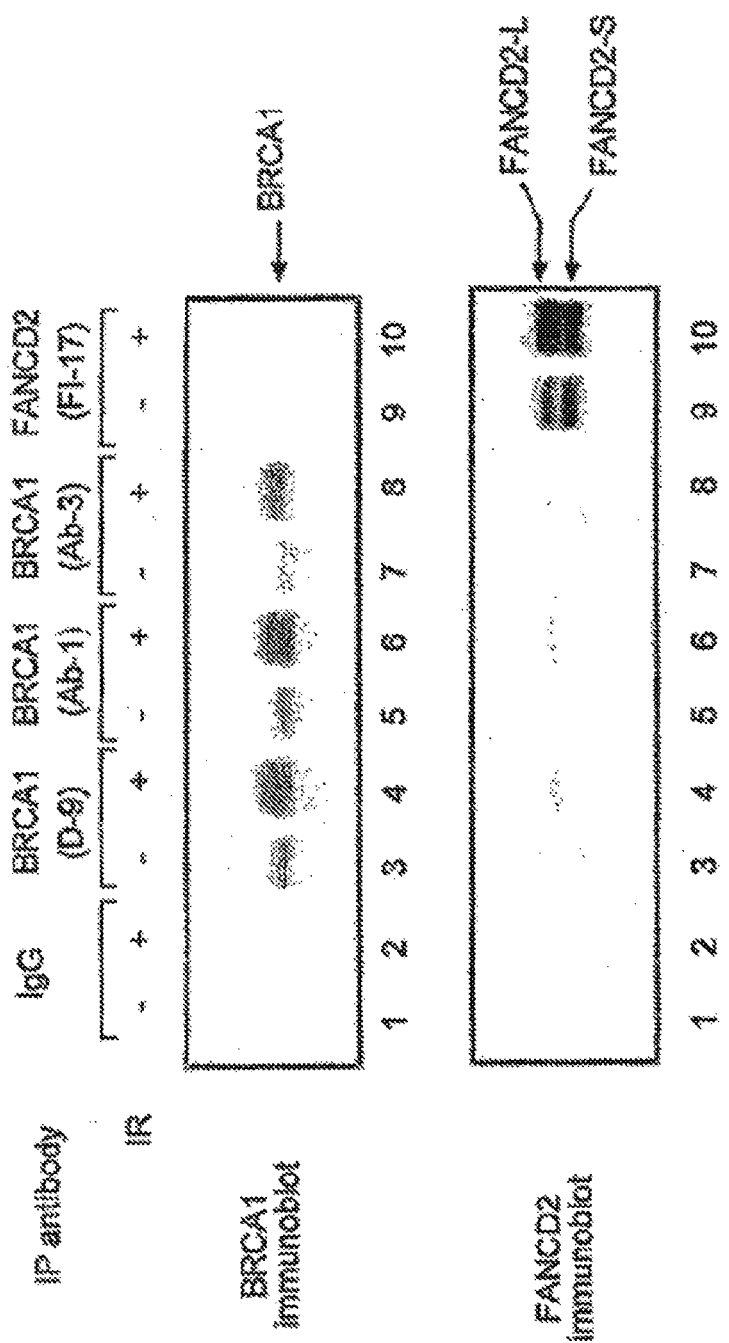

In order to determine whether the activated FANCD2 protein co-localizes with the BRCA1 protein, we performed double immunolabeling of HeLa cells (FIGS. 5A and 5B). In the absence of ionizing radiation, approximately 30-50% of cells contained BRCA1 nuclear foci (FIGS. 5A and 5B). In contrast, only rare cells traversing S phase contained FANCD2 dots (FIG. 5A, panels b, e). These nuclear foci were also immunoreactive with antisera to both BRCA1 and FANCD2 (FIG. 5A, panels c, f). Following IR exposure, there was an increase in the number of cells containing nuclear foci and the number of foci per cell. These nuclear foci were larger and more fluorescent than foci observed in the absence of IR. Again, these foci contained both BRCA1 and FANCD2 protein (FIG. 5B, panels i, 1). An interaction of FANCD2-L and BRCA1 was further confirmed by coimmunoprecipitation of the proteins (FIG. 5C) from exponentially growing HeLa cells exposed to IR.

Figures 6A, 6B:
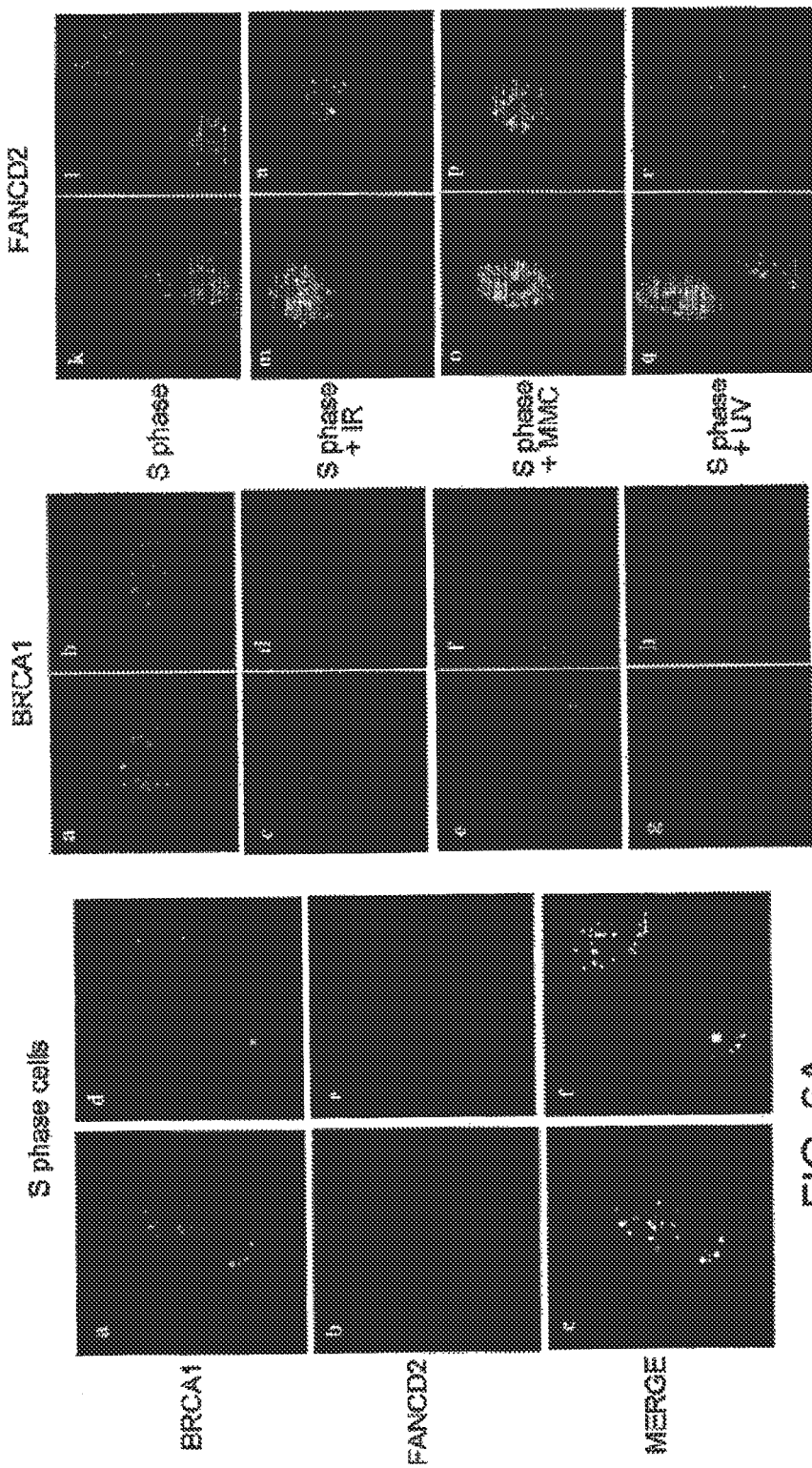
FIG. 6 shows the co-localization of activated FANCD2 and BRCA1 in discrete nuclear foci during S phase. (a) HeLa cells were synchronized in late G1 with mimosine and released into S phase. S phase cells were double-stained with the monoclonal anti-BRCA1 antibody (green, panels a, d) and the rabbit polyclonal anti-FANCD2 antibody (red, panels b, e), and stained cells were analyzed by immunofluorescence. Where green and red signals overlap (merge, panels c, f), a yellow pattern is seen, indicating co-localization of BRCA1 and FANCD2. (b) HeLa cells synchronized in S phase were either untreated (a, b, k, 1) or exposed to IR (50 Gy, panels c, d, m, n), MMC (20 µg/ml, panels e, f, o, p), or UV (100 j/m2, panels g, h, q, r) as indicated and fixed 1 hour later. Cells were subsequently immunostained with an antibody specific for FANCD2 or BRCA1

We examined the effect of BRCA1 expression on the formation of FANCD2-L and nuclear foci (FIG. 6); The BRCA1 (−/−) cell line, HCC1937, expresses a mutant form of the BRCA1 protein with a carboxy terminal truncation. Although these cells expressed a low level of FANCD2-L (FIG. 6A), IR failed to activate an increase in FANCD2-L levels. Also, these cells had a decreased number of IR-inducible FANCD2 foci (FIG. 6B, panels c, d). Correction of these BRCA1 (−/−) cells by stable transfection with the BRCA1 cDNA restored IR-inducible FANCD2 ubiquitination and nuclear foci (FIG. 6B, panels k, 1). These data suggest that the wild-type BRCA1 protein is required as an "organizer" for IR-inducible FANCD2 dot formation and further suggests a functional interaction between the proteins.

Example 8

Co-Localization of FANCD2 and BRCA1 on Meiotic Chromosomes

The association of FANCD2 and BRCA1 in mitotic cells suggested that these proteins might also co-localize during meiotic prophase. Previous studies have demonstrated that the BRCA1 protein is concentrated on the unsynapsed/axial elements of human synaptonemal complexes in zygotene and pachytene spermatocytes. To test for a possible colocalization of FANCD2 and BRCA1 in meiotic cells, we examined surface spreads of late pachytene and early diplotene mouse spermatocytes for the presence of FANCD2 and BRCA1 protein (FIG. 7). We found that the rabbit polyclonal anti-FANCD2 antibody E35 specifically stained the unpaired axes of the X and Y chromosomes in late pachynema (FIG. 7a) and in diplonema (FIGS. 7d, 7e and 7g). Under the same experimental conditions, preimmune serum did not stain symptonemal complexes (FIGS. 7b and 7c). The M118 anti-BRCA1 antibody stained the unpaired sex chromosomes in mouse pachytene and diplotene spermatocytes (FIGS. 7f and 7h). FANCD2 Ab staining of the unsynapsed axes of the sex chromosomes was interrupted, giving a beads-on-a-string appearance (FIG. 7g). A consecutive examination of 20 pachytene nuclei indicated that most (~65%) of these anti-FANCD2 foci co-localized with regions of intense anti-BRCA1 staining, further supporting an interaction between these proteins (FIGS. 7g, 7h, and 7i). These results provide the first example of a FANC protein (activated FANCD2) which binds to chromatin.

Example 9

Experimental Protocols for Obtaining and Analyzing the DNA and Protein Sequence for FANCD2

Northern Hybridizations. Human adult and fetal multi-tissue mRNA blots were purchased from Clontech (Palo Alto, Calif.). Blots were probed with 32P labeled DNA from EST clone SGC34603. Standard hybridization and washing conditions were used. Equal loading was confirmed by re-hybridizing the blot with an actin cDNA probe.

Mutation Analysis. Total cellular RNA was reverse transcribed using a commercial kit (Gibco/BRL). The 5' end section of FANCD2 was amplified from the resulting patient and control cDNA with a nested PCR protocol. The first round was performed with primers (SEQ ID NO:97) MG471 5'-AATCGAAAACTACGGGCG-3' and (SEQ ID NO:98) MG457 5'-GAGAACACATGAATGAACGC-3'. The PCR product from this round was diluted 1:50 for a subsequent round using primers (SEQ ID NO:99) MG492 5'-GGC-GACGGCTTCTCGG AAGTAATTTAAG-3' and (SEQ ID NO:100) MG472 5'-AGCGGCAGGAGGTTTATG-3'. The PCR conditions were as follows: 94° C. for 3 min, 25 cycles of 94° C. for 45 sec, 50° C. for 45 sec, 72° C. for 3 min and 5 min of 72° C. at the end. The 3' portion of the gene was amplified as described above but with primers, (SEQ ID NO:101) MG474 5'-TGGCGGCAGACAGAAGTG-3' and (SEQ ID NO:102) MG475 5'-TGGCGGCAGACA-GAAGTG-3'. The second round of PCR was performed with (SEQ ID NO:103) MG491 5'-AGAGAGCCAACCT-GAGCGA TG-3' and (SEQ ID NO:104) MG476 5'-GTGC-CAGACTCTGGTGGG-3'. The PCR products were gel-purified, cloned into the pT-Adv vector (Clontech) and sequenced using internal primers.

Allele specific assays. Allele specific assays were performed in the PD20 family and 290 control samples (=580 chromosomes). The PD20 family is of mixed Northern European descent and VU008 is a Dutch family. Control DNA samples were from unrelated individuals in CEPH families (n=95), samples from unrelated North American families with either ectodermal dysplasia (n=95) or Fanconi Anemia (n=94). The maternal nt376a→g mutation in the PD20 family created a novel MspI restriction site. For genomic DNA, the assay involved amplifying genomic DNA using the primers (SEQ ID NO:105) MG792 5'-AGGAGACACCCTTC-CTATCC-3' located in exon 4 and (SEQ ID NO:106) M0803 5'-GAAGTTGGCAAAACAGAC TG-3' which is in intron 5. The size of the PCR product was 340 bp, yielding two fragments of 283 bp and 57 bp upon MspI digestion if the mutation was present. For analysis of the reverted cDNA clones, PCR was performed using primers (SEQ ID NO:107) MG924 5'-TGTCTTGTGA GCGTCTGCAGG-3' and (SEQ ID NO:108) MG753 5'-AGGTT TTGATAATGGCAGGC-3'. The paternal exon 37 mutation (R1236H) in PD20 and exon 12 missense mutation (R302W) in VU008 were tested by allele specific oligonucleotide (ASO) hybridization (Wu et al., DNA, (1989) Vol. 8, pp. 135-142). For the exon 12 assay, genomic DNA was amplified with primers (SEQ ID NO:109) MG979 5'-ACTGGACTGTGCCTACCCACTATG-3' and (SEQ ID NO:110) MG984 5'-CCTGTGTGAGGAT-GAGCTCT-3'. Primers (SEQ ID NO:171) MG818 5'-AGAG-GTAGGGAAGGAAGCTAC-3' and (SEQ ID NO:172) MG813 5'-CCAAAGTCCA CTTCTTGAAG-3' were used for exon 37. Wild-type (SEQ ID NO:111) (5'-TTCTC-CCGAAG CTCAG-3' for R302W and (SEQ ID NO: 112) 5'-TTTCTTCCGTGTGATGA-3' for R1236H and mutant SEQ ID. NO: 351 (5'-TTCTCCCAAAGCTGAG-3' R302W and SEQ ID NO: 352 (5'-TYTCTTCCATGTGATGA-3' for R1236H) oligonucleotides were end-labeled with γ32P-[ATP] and hybridized to dot-blotted target PCR products as previously ss novel DdeI site. The wild-type PCR product digests into a 117 and 71 bp product, whereas the mutant allele yields three fragments of 56, 61 and 71 bps in length. PCR in all of the above assays was performed with 50 ng of genomic DNA for 37 cycles of 94° C. for 25 sec, 50° C. for 25 sec and 72° C. for 35 sec.

Generation of an anti-FANCD2 antiserum. A rabbit polyclonal antiserum against FANCD2 was generated using a GST-FANCD2 (N-terminal) fusion protein as an antigen source. A 5' fragment was amplified by polymerase chain reaction (PCR) from the full length FANCD2 CDNA with the primers (SEQ ID NO: 113) DF4EcoRJ (5'-AGCCTCgaat-tcGUTCC AAAAGAAGACTGTCA-3') and (SEQ ID NO: 114) DR816Xh (5'-GGTATCctcgagTCAAGA CGACAACT-TATCCATCA-3'). The resulting PCR product of 841 bp, encoding the amino-terminal 272 amino acids of the FANCD2 polypeptide was digested with EcoRI/XhoI and subcloned into the EcoRI/XhoI sites of the plasmid pGEX4T-1 (Pharmacia). A GST-FANCD2 (N-terminal) fusion protein of the expected size (54 kD) was expressed in E. coli strain DH5a, purified over glutathione-S-sepharose, and used to immunize a New Zealand White rabbit. An FANCD2-specific immune antiserum was affinity-purified over an AminoLink Plus column (Pierce) loaded with GST protein and over an AminoLink Plus column loaded with the GST-FANCD2 (N-terminal) fusion protein.

Immunoblotting is as in Example 1.

Cell Lines and Transfections. PD20i is an immortalized and PD733 a primary FA fibroblast cell line generated by the Oregon Health Sciences Fanconi Anemia cell repository (Jakobs et al., Somet. Cell. Mol. Genet., (1996), Vol. 22, pp. 151-157). PD20 lymphoblasts were derived from bone marrow samples. VU008 is a lymphoblast and VU423 a fibroblast line generated by the European Fanconi Anemia Registry (EUFAR). VU423i was an immortalized line derived by transfection with SV40 T-antigen (Jakobs et al., 1996) and telomerase (Bodnar et al., Science, (1998) Vol. 279, pp. 349-352). The other FA cell lines have been previously described. Human fibroblasts were cultured in MEM and 20% fetal calf serum. Transformed lymphoblasts were cultured in RPMI 1640 supplemented with 15% heat-inactivated fetal calf serum.

To generate FANCD2 expression constructs, the full-length cDNA was assembled from cloned RT-PCR products in pBluescript and the absence of PCR induced mutations was confirmed by sequencing. The expression vectors pIRES-Neo, pEGFP-N1, pRevTRE and pRevTet-off were from ClonTech (Palo Alto, Calif.). The FANCD2 was inserted into the appropriate multi-cloning site of these vectors. Expression constructs were electroporated into cell line PD20 and a normal control fibroblast cell line, GM639 using standard conditions (van den Hoff et al., 1992). Neomycin selection was carried out with 400 ug/ml active G418 (Gibco).

Whole cell fusions. For the whole cell fusion experiments, a PD20 cell line (PD20i) resistant to hygromycin B and deleted for the HPRT locus was used (Jakobs et al, Somet. Cell. Mol. Genet., (1997) Vol. 23, pp. 1-7). Controls included PD24 (primary fibroblasts from affected sibling of PD20) and PD319i (Jakobs et al., 1997) (immortal fibroblasts from a non-A, C, D or G FA patient). 2.5×105 cells from each cell line were mixed in a T25 flask and allowed to recover for 24 hours. The cells were washed with serum-free medium and then fused with 50% PEG for 1 min. After removal of the PEG, the cells were washed 3× with serum-free medium and allowed to recover overnight in complete medium without selection. The next day, cells were split 1:10 into selective medium containing 400 µg/ml hygromycin B (Roche Molecular) and 1× HAT. After the selection was complete, hybrids were passaged once and then analyzed as described below.

Retroviral. Transduction of FA-D2 cells and complementation analysis. The full length FANCD2 cDNA was subcloned into the vector, pMMP-puro (Pulsipher et al., 1998). Retroviral supernatants were used to transduce PD20F, and puromycin resistant cells were selected. Cells were analyzed for MMC sensitivity by the crystal violet assay (Naf et al., 1998).

Chromosome Breakage Analysis. Chromosome breakage analysis was performed by the Cytogenetics Core Lab at OHSU (Portland, Oreg.), For the analysis (Cohen et al., 1982) cells were plated into T25 flasks, allowed to recover and then treated with 300 ng/ml of DEB for two days. After treatment, the cells were exposed to colcemid for 3 hours and harvested using 0.075 M KCl and 3:1 methanol:acetic acid. Slides were stained with Wright's stain and 50-100 metaphases were scored for radials.

Example 10

Mouse Models for FA for Use in Screening Potential Therapeutic Agents

Murine models of FANCD2 can be made using homologous recombination in embryonic stem cells or targeted disruption as described in D'Andrea et al., (1997) 90:1725-1736, and Yang et al., Blood, (2001) Vol. 98, pp. 1-6. The knockout of FANCD2 locus in mice is not a lethal mutation. These knock-out animals have increased susceptibility to cancer and furthermore display other symptoms characteristic of FA. It is expected that administering certain therapeutic agents to the knock-out mice will reduce their susceptibility to cancer. Moreover, it is expected that certain established chemotherapeutic agents will be identified that are more effective for treating knock-out mice who have developed cancers as a result of the particular genetic defect and this will also be useful in treating human subjects with susceptibility to cancer or who have developed cancers as a result of a mutation in the FANCD2 locus.

We can generate experimental mice models with targeted disruptions of FANCD2 using for example the approach described by Chen et al, Nat. Genet., (1996) Vol. 12, pp. 448-451, for FANCC who created a disruption in an exon of the gene, and by Whitney et al., (1996) Vol. 88, pp. 49-58, who used homologous recombination to create a disruption of an exon of the gene. In both animal models, spontaneous chromosome breakage and an increase in chromosome breaks in splenic lymphocytes in. response to bifunctional alkylating agents are observed. In both models, FANCD2 −/− mice have germ cell defects and decreased fertility. The FANCD2 marine knockout model is useful in examining (1) the role of the FANCD2 gene in the physiologic response of hematopoietic cells to DNA damage, (2) the in vivo effects of inhibitory cytokines on FA marrow cells, and (3) the efficacy of gene therapy and (4) for screening candidate therapeutic molecules.

The availability of other FA gene disruptions will allow the generation and characterization of mice with multiple FA gene knockouts. For instance, if 2 FA genes function exclusively in the same cellular pathway, a double knockout should have the same phenotype as the single FA gene knockout.

The murine FANCD2 gene can be disrupted by replacing exons with an FRT-flanked neomycin cassette via homologous recombination in 129/SvJae embryonic stem cells. Mice homozygous for the FANCD2 mutation within a mixed genetic background of 129/Sv and C57BL can be generated following standard protocols. Mouse tail genomic DMA can be prepared as previously described and used as a template for polymerase chain reaction (PCR) genotyping.

Splenocytes can be prepared from 6-week-old mice of known FANCD2 genotype. The spleen is dissected, crushed in RPMI medium into a single-cell suspension, and filtered through a 70 µm filter. Red cells are lysed in hypotonic ammonium chloride. The remaining splenic lymphocytes are washed in phosphate-buffered saline and resuspended in RPMI/10% fetal bovine serum plus phytohemagglutinin. Cells are tested for viability by the trypan blue exclusion assay. Cells are cultured for 24 hours in media and exposed to MMC or DEB for an additional 48 hours. Alternatively, cells are cultured for 50 hours, exposed to IR (2 or 4 Gy, as indicated), and allowed to recover for 12 hours before chromosome breakage or trypan blue exclusion (viability) analysis.

Mononuclear cells can be isolated from the femurs and tibiae of 4- to 6-week-old FANCD2 +/− or FANCD2 −/− mice, as previously described. A total of 2×104 cells were cultured in 1 mL of MethoCult M343 media (StemCell Technologies, Vancouver, BC) with or without MMC treatment. Colonies are scored at day 7, when most of the colonies belong to the granulocyte-macrophage colony-forming unit or erythroid burst-forming unit lineages. Each number are averaged from duplicate plates, and the data derived from 2 independent experiments.

Lymphocytes isolated from thymus, spleen, and peripheral lymph nodes are stained for T- or B-lymphocyte surface molecules with fluorescein isothiocyanate-conjugated anti-CD3, CD4, and CD19 and PE-conjugated anti-CD8, CD44, CD 45B, immunoglobulin M, and B220 (BD PharMingen, CA). Stained cells were analyzed on a Counter Epics XL flow cytometry system.

Mice ovaries and testes were isolated and fixed in 4% paraformaldehyde and further processed by the core facility of the Department of Pathology at Massachusetts General Hospital.

Example 11

Screening Assays Using Antibody Reagents for Detecting Increased Cancer Susceptibility in Human Subjects Blood samples or tissue samples can be taken from subjects for testing for the relative amounts of FANCD2-S compared to FANCD2-L and the presence or absence of FANCD2-L. Using antibody reagents specific for FANCD2-S and FANCD2-L proteins (Example 1), positive samples can be identified on Western blots as shown in FIG. 14. Other antibody assays may be utilized such as, for example, one step migration binding banded assays described in U.S. Pat. Nos. 5,654,162 and 5,073,484. Enzyme linked immunosorbent assays (ELISA), sandwich assays, radioimmune assays and other immunodiagnostic assays known in the art may be used to determine relative binding concentrations of FANCD2-S and FANCD2-L.

The feasibility of this approach is illustrated by the following: FANCD2 Diagnostic Western Blot for Screening Human Cancer Cell Lines Human cancer cell lines were treated with or without ionizing radiation (as indicated in FIG. 14) and total cell proteins were electrophoresed, transferred to nitrocellulose and immunoblotted with the anti-FANCD2 monoclonal antibody of Example 1. Ovarian cancer cell line (TOV21G) expressed FANCD2-S but not FANCD2-L (see lanes 9, 10). This cell line has a deletion of human chromosome 3p overlapping the FANCD2 gene and is hemizygous for FANCD2 and is predicted to have a mutation in the second FANCD2 allele which therefore fails to be monoubiquinated by the PA complex hence no FANCD2-L (lanes 9, 10). This example demonstrates that antibody based tests are suited for determining lesions in the FANCD2 gene which lead to increased cancer susceptibility.

Example 12

Screening Assays Using Nucleic Acid Reagents for Detecting Increased Cancer Susceptibility in Human Subjects Blood samples or tissue samples can be taken from subjects and screened using sequencing techniques or nucleic acid probes to determine the size and location of the genetic lesion if any in the genome of the subject. The screening method may include sequencing the entire gene or by using sets of probes or single probes to identify lesions. It is expected that a single lesion may predominant in the population but that other lesions may arise throughout the gene with low frequency as is the case for other genetic conditions such as cystic fibrosis and the P53 tumor suppressor gene.

The feasibility of this approach is illustrated by the following:

Peripheral blood lymphocytes are isolated from the patient using standard Ficoll-Hypaque gradients and genomic DNA is isolated from these lymphocytes. We use genomic PCR to amplify 44 exons of the human FANCD2 gene (see primer Table 7) and sequence the two FANCD2 alleles to identify mutations. Where such mutations are found, we distinguish these from benign polymorphisms by their ability to ablate the functional complementation of an FA-D2 indicator cell line.

Example 13

Measurement of Mono-Ubiquitinated FANG D2-L in Tissue Biopsies

Tissue biopsies were obtained by needle aspiration or skin punch biopsy. Cells, resuspended in appropriate culture media in microtiter plates are then treated with the indicated concentration of MMC (0, 10, 40, 160 ng/ml) or the indicated dose of IR (0, 5, 10, 10, 20 Gy). After 24 hour-incubation with MMC, or two hours after IR treatment, whole cell extracts were prepared in Lysis Buffer (50 mM TrisHC1 pH 7.4, 150 mM NaCl, 1% (v/v) Triton X-100) supplemented with protease inhibitors (1 μg/ml leupeptin and pepstatin, 2 μg/ml aprotinin, 1 mM phenylmethylsulfonylfluoride) and phosphatase inhibitors (1 mM sodium orthovanadate, 10 mM sodium fluoride). Samples are then tested for the presence of the FANC D2-L isoform using the anti-FANCD2-L-specific monoclonal antibody, as disclosed herein, and conventional immunoassays such as the enzyme linked immunosorbent assay (ELISA) that are commonly used to quantitate the levels of proteins in cell samples (see Harlow, E. and Lane, D. Using Antibodies; A Laboratory Manual (1999) Cold Spring Harbor Laboratory Press).

Example 14

Diagnosis of Cancer Associated Defects in a Fanconi Anemia/BRCA Gene or Protein

PCR amplification and sequencing of the human FANCD2 gene—
cDNA and genomic DNA templates
Genomic DNA Sequencing In the course of sequencing the FANCD2 gene, it became apparent that there, are at least eight pseudogene sequences for FANCD2 in the human genome, all located on human chromosome 3p (see attached Table 8). Accordingly, it was important to design a specific genomic PCR assay, designed to specifically amplify the FANCD2 sequence and to exclude the pseudogenes. It is not possible to design PCR primers close to exons 1, 2, 3, 7-14, 19-22, 23-29, 30-32, 33-36 and 43.-44 of the functional FANCD2 gene that do not also amplify one or more of the non-functional copies of those exons. By first generating large PCR products that are unique to these regions of the functional gene, then using those unique products as templates in subsequent amplification reactions to produce exonic PCR products with primers that are not unique to the functional gene, a vast excess of the PCR products from the functional gene over the PCR products from the copies was generated. In this manner, mutations in the functional gene are made detectable.

Superamplicon PCR

As indicated above, the purpose of these PCR reactions is to generate large amplicons (superamplicons) that are unique to certain regions of the functional FANCD2 gene. The components of the PCR are: 60 mM Tris-S04 (pH8.9), 18 mM (NH4)2SO4, 2.0 mM MgSO$_4$, 0.2 mM in each of dATP, dCTP, dGTP, TTP, 0.1 µM of each primer, 5 ng/µl DNA, 0.05 units/µl Platinum Taq DNA Polymerase High Fidelity (GIBCO BRL, Gaithersburg, Md.).

The thermocycling conditions are: 94° C., 4 min, followed by 11 cycles, each with a denaturing step at 94° C. for 20 seconds and an extension step at 72° C. for 300 seconds, and with a 20 second annealing step that decreased 1° C./cycle, beginning at 64° C. in the first cycle and decreasing to 54° C. in the eleventh cycle; the eleventh cycle was then repeated 25 times; a 6 minute incubation at 72° C. followed by a 4° C. soak completed program.

The primer identities are as follows (the primer sequences are in the table 9):

| Exons | FwdPrimer | RevPrimer | Amplicon Length | Amplicon Name |
|---|---|---|---|---|
| x1-x2 | exon 2 F | super-1-2 R | 2097 | 1 super |
|  | exon 1 F | super-1-2 R | 4346 | 2 super |
| x3 | super-3-F | exon 3 R | 2323 | 3 super |
| x7-x14 | exon-10-F | super-7-14-R | 5635 | 4 super |
|  | super-7-14-F | exon-9-R | 4595 | 5 super |
| x19-x22 | exon-21-F | super-19-22 R | 1015 | 6 super |
|  | super-19-22-F | exon-20-R | 2749 | 7 super |
| x23-x29 | exon-27 F | super-23-29 R | 3371 | 9 super |
|  | super-23-29 F | exon 26 R | 3252 | 10 super |
| xX30-x32 | exon 31 F | super-30-32 R | 2895 | 11 super |
|  | super-30-32 F | eExon 30 R | 299 | 12 super |
| x33-36 | exon 35 F | super-33-36 R | 2186 | 13 super |
|  | super-33-36 F | exon 34 R | 3457 | 14 super |
| x43-x44 | exon 44 F | super-43-44 R | 464 | 15 super |
|  | super-43-44 F | exon 43a R | 2040 | 16 super |

Exonic PCR

These PCR's are of 2 types: (1) the superamplicon PCR is used as the DNA template; exons 1-3, 7-14, 19-22, 23-29, 30-32, 33-36 and 43-44 are in this group, and (2) unamplified genomic DNA is used as the DNA template; exons 4-6, 15-18 and 37-42 are in this group.

One primer (designated "—F") in each pair was synthesized with an 18base M13-21 forward sequence (SEQ ID NO: 192) (TGTAAAACGACGGCCAGT) at its 5' end, and the other primer (designated "—R") was synthesized with an 18 base M13-28) reverse sequence (SEQ ID NO: 193) (CAGGAAACAGCTATGACC) at its 5' end. For exon 15, two overlapping amplicons were designed.

The components of the 10 ul PCR reaction are: 20 mM Tris-HCl(pH8.4), 50 mM KCl, 1.5 mM MgCl$_2$, 0.1 mM in each of dATP, dCTP, dGTP, TTP, 0.1 µM of each primer, either 1 ul of a 1:100 dilution of the superamplicon PCR or 5 ng/ul of unamplified genomic DNA, 0.05 units/µl Taq polymerase (Taq Platinum, GIBCO BRL, Gaithersburg, Md.). The thermocycling conditions are: 94° C., 4 min, followed by 130 seconds each with a denaturing step at 94° C. for 30 seconds and an extension step at 72° C. for 20 seconds, and with a 20 second annealing step that decreased 1° C./cycle, beginning at 60° C. in the first cycle and decreasing to 50° C. in the eleventh cycle; the eleventh cycle was then repeated 25 times; a 6 minute incubation at 72° C. followed by a 4° C. soak completed the program.

cDNA Sequencing

Two micrograms of total RNA is converted into cDNA using Superscript First-Strand Synthesis System for RT-PCR (GIBCO/BRL) according to the manufacturer's instructions. One twentieth of the RT-PCR reaction is used as the DNA template in each of 18 PCR reactions; these PCR reactions amplify the coding region of the cDNA in overlapping framents. The primers are shown in the table below.

One primer (designated "-F") in each pair was synthesized with an 18base M13-21 forward sequence (TGTAAAAC-GACGGCCAGT) at its 5' end, and the other primer (designated "-R") was synthesized with an 18 base M13-28 reverse sequence (CAGGAAACAGCTATGACC) at its 5' end.

The components of the 10 ul PCR reaction are: 20 mM Tris-HCl(pH8.4), 50 mM KCl, 1.5 mM MgC 12, 0.1 mM in each of dATP, dCTP, dGTP, TTP, 0.1 M of each primer, either 1 ul of a 1:100 dilution of the superamplicon PCR or 5 ng/ul of unamplified genomic DNA, 0.05 units/µl Taq polymerase (Taq Platinum, GIBCO BRL, Gaithersburg, Md.).

The thermocycling conditions are: 94° C., 4 min, followed by 11 cycles, each with a denaturing step. at 94° C. for 30 seconds and an extension step at 72° C. for 20 seconds, and with a 20 second annealing step that decreased 1° C./cycle, beginning at 60° C. in the first cycle and decreasing to 50° C. in the eleventh cycle; the eleventh cycle was then repeated 25 times; a 6 minute incubation at 72° C. followed by a 4° C. soak completed the program.

| Primer | 5' Position | Sequence(5' to 3') | Length (bp) | |
|---|---|---|---|---|
| D1F | 24 | TGTAAAACGACGGCCAGT CGACGGCTTCTCGGAAGTAA | | (SEQ ID NO: 194) |
| D1R | 408 | AGGAAACAGCTATGACCAT GCAGACGCTCACAAGACAAA | 407 | (SEQ ID NO: 195) |
| D2F | 322 | TGTAAAACGACGGCCAGT GACACCCTTCCTATCCCAAAA | | (SEQ ID NO: 196) |
| D2R | 689 | AGGAAACAGCTATGACCAT CAGGTTCTCTGGAGCAATAC | 368 | (SEQ ID NO: 197) |
| D3F | 612 | TGTAAAACGACGGCCAGT TGGCTTGACAGAGTTGTGGAT | | (SEQ ID NO: 198) |
| D3R | 1019 | AGGAAACAGCTATGACCAT CTGTAACCGTGATGGCAAAAC | 408 | (SEQ ID NO: 199) |
| D4F | 855 | TGTAAAACGACGGCCAGT CGCCAGTTGGTGATGGATAAG | | (SEQ ID NO: 200) |
| D4R | 1223 | AGGAAACAGCTATGACCAT AAGCATCACCAGGTCAAACAC | 369 | (SEQ ID NO: 201) |
| D5F | 1081 | TGTAAAACGACGGCCAGT GCGGTCAGAGCTGTATTATTC | | (SEQ ID NO: 202) |
| D5R | 1461 | AGGAAACAGCTATGACCAT CTGCTGGCAGTACGTGTCAA | 401 | (SEQ ID NO: 203) |
| D6F | 1377 | TGTAAAACGACGGCCAGT TCGCTGGCTCAGAGTTTGCTT | | (SEQ ID NO: 204) |
| D6R | 1765 | AGGAAACAGCTATGACCAT GTGCTAGAGAGCTGCTTTCTT | 389 | (SEQ ID NO: 205) |
| D7F | 1641 | TGTAAAACGACGGCCAGT CCCCTCAGCAAATACGAAAAC | | (SEQ ID NO: 206) |
| D7R | 2065 | AGGAAACAGCTATGACCAT ACTACGAAGGCATCCTGGAAA | 424 | (SEQ ID NO: 207) |
| D8F | 1947 | TGTAAAACGACGGCCAGT GCCTCTGCACTTTACTATGATG | | (SEQ ID NO: 208) |
| D8R | 2301 | AGGAAACAGCTATGACCAT CTCCTCCAAGTTTCCGTTATG | 375 | (SEQ ID NO: 209) |
| D9F | 2210 | TGTAAAACGACGGCCAGT GGTGACCTCACAGGAATCAG | | (SEQ ID NO: 210) |
| D9R | 2573 | AGGAAACAGCTATGACCATTTTCCAAGAGGAGGGACATAG | 384 | (SEQ ID NO: 211) |
| D10F | 2438 | TGTAAAACGACGGCCAGT CAACTGGTTCCGAGAGATTGT | | (SEQ ID NO: 212) |
| D10R | 2859 | AGGAAACAGCTATGACCAT CAATGTCCAGCTCTCGGAAAAA | 422 | (SEQ ID NO: 213) |

-continued

| Primer | 5' Position | Sequence(5' to 3') | Length (bp) | |
|---|---|---|---|---|
| D11F | 2746 | TGTAAAACGACGGCCAGT GTGACCCTACGCCATCTCATA | | (SEQ ID NO: 214) |
| D11R | 3138 | AGGAAACAGCTATGACCAT ACATTGGGGTCAGCAGTTGAA | 393 | (SEQ ID NO: 215) |
| D12F | 3027 | TGTAAAACGACGGCCAGT AGAGTCCCCTTTCTCAAGAACA | | (SEQ ID NO: 216) |
| D12R | 3413 | AGGAAACAGCTATGACCAT GACGCTCTGGCTGAGTAGTT | 387 | (SEQ ID NO: 217) |
| D13F | 3334 | TGTAAAACGACGGCCAGT CAGCCCTCCATGTCCTTAGT | | (SEQ ID NO: 218) |
| D13R | 3742 | AGGAAACAGCTATGACCAT AGGGAATGTGGAGGAAGATG | 407 | (SEQ ID NO: 219) |
| D14F | 3637 | TGTAAAACGACGGCCAGT TGGAGCACACAGAGAGCATT | | (SEQ ID NO: 220) |
| D14R | 4010 | AGGAAACAGCTATGACCAT GTCTAGGAGCGGCATACATT | 374 | (SEQ ID NO: 221) |
| D15F | 3830 | TGTAAAACGACGGCCAGT AGCAGACTCGCAGCAGATTCA | | (SEQ ID NO: 222) |
| D15R | 4225 | AGGAAACAGCTATGACCAT AGCCAGAAAGCCTCTCTACA | 396 | (SEQ ID NO: 223) |
| D16F | 4117/4112 | TGTAAAACGACGGCCAGT ACACGAGACTCACCCAACAT | | (SEQ ID NO: 224) |
| D16R-L | 4477 | AGGAAACAGCTATGACCAT GGGAATGGAAATGGGCATAGA | 361 | (SEQ ID NO: 225) |
| D16R-S | 4451 | AGGAAACAGCTATGACCAT GACACAGAAGCAGGCAACAA | 340 | (SEQ ID NO: 226) |
| D17F-(L) | 4333 | TGTAAAACGAGGGCCAGT AGAGCAAAGCCACTGAGGTAT | | (SEQ ID NO: 227) |
| D17R-(L) | 4768 | AGGAAACAGCTATGACCAT GACTCTGTGCTTTGGCTTTCA | 436 | (SEQ ID NO: 228) |

DNA Sequencing

An aliquot of each. PCR reaction was diluted 1:10 with water. The diluted PCR product was sequenced on both strands using an M13 Forward and an M13 Reverse Big Dye Primer kit (Applied Biosystems, Foster City, Calif.) according to the manufacturer's recommendations. The sequencing products were separated on a fluorescent sequencer (model 377 from Applied Biosystems, Foster City, Calif.). Base calls were made by the instrument software, and reviewed by visual inspection. Each sequence was compared to the corresponding normal sequence using Sequencher 3.0 software (LifeCodes).

Example 15

Method of Screening for a Chemosensitizing Agent

As shown in the model of the FA/BRCA pathway, the enzymatic monoubiquitination of FANCD2 is a critical regulatory event. This event requires an intact FA protein complex (A/C/E/F/G complex) and requires BRCA1 and BRCA2. While the actual catalytic subunit required for FANCD2 monoubiquitination remains unknown, it still remains possible to screen for antagonists of monoubiquitination, As described elsewhere in this text, an inhibitor of the FA pathway could, in principal, function as a chemosensitizer of cisplatin in the treatment of ovarian cancer or other cancers. The screening of an inhibitor of FANCD2 monoubiquitination can be performed as a simple mammalian cell-based screen. A mammalian tissue culture cell line, e.g., Hela calls are first preincubated with random candidate small molecules. Cell clones are then screened using anti-FANCD2 western blots. An inhibitor (antagonist) of the FA pathway will block FANCD2 monoubiquitination.

As described in Garcia-Higuera et al, 2001, BRCA1 may in fact be the enzyme which monoubiquitinates FANCD2. Accordingly, BRCA1 has a ubiquitin ligase (Ring Finger) catalytic domain. Therefore, an in vitro assay will be devised to screen for BRCA1-mediated monoubiquitination of FANCD2. An inhibitor will be screened directly for its ability to inhibit this in vitro reaction. Once inhibitors are identified, such drugs could be used in animal studies or phase 1 human studies to determine their functions as cisplatin sensitizers.

Example 16

Method of Screening for a Potential Cancer Therapeutic

Cells and animals which carry a Fanconi Anemia/BRCA pathway gene having one Or more cancer associated defects can be used as model systems to study and test for substances which have potential as therapeutic agents. The cells are typically cultured epithelial cells. These may be isolated from individuals with Fanconi Anemia/BRCA pathway gene having one or more cancer associated defects, either somatic or germline. Alternatively, the cell line can be engineered to carry the mutation in a gene of the Fanconi Anemia/BRCA pathway gene having one or more cancer associated defects.

After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant Fanconi Anemia/BRCA pathway genes having one or more cancer associated defects, usually from a second animal species, as well as insertion of disrupted homologous genes. Alternatively, the endogenous Fanconi Anemia/BRCA pathway gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992) as outlined in Example 10. After test substances have been administered to the animals, the growth of tumors must be assessed. If the test substance prevents or suppresses the growth of tumors, then the test substance is a candidate therapeutic agent for the treatment of the cancers identified herein.

Example 17

Method of Treatment of a Cancer that is Resistant to an Anti-Neoplastic Agent

The present example describes the treatment of a patient with a cancer that is resistant to an anti-neoplastic agent such as cisplatin. The protocol provides for the administration of cisplatin as described herein with an increasing dosage of an inhibitor of the ubiquitination of the FANC D2 protein as a chemosensitizing agent. Cisplatin and the chemosensitizing agent can be administered intravenously, subcutaneously, intratumorally or intraperitoneally. The administering physician can adjust the amount and timing of drug administration on the basis of results observed using standard measures of cancer activity known in the art. Suppression of tumor growth and metastasis is indicative of effective treatment of the cancer.

Example 18

A Method of Measuring the Future Efficacy of a Therapeutic Agent

Tissue biopsies of neoplasms from cancer patients being treated with a therapeutic agent are obtained by needle aspiration or skin punch biopsy. Cells, resuspended in appropriate culture media in microtiter plates are then treated with the indicated concentration of MMC (0, 10, 40, 160 ng/ml) or the indicated dose of IR (0, 5, 10, 10, 20 Gy). After 24 hour-incubation with MMC, or two hours after IR treatment, it induce DNA damage, whole cell extracts were prepared in Lysis Buffer (50 mM TrisHC1 pH 7.4, 150 mM NaCl, 1% (v/v) Triton X-100) supplemented with protease inhibitors (1 μg/ml leupeptin and pepstatin, 2 μg/ml aprotinin, 1 mM phenylmethylsulfonylfluoride) and phosphatase inhibitors (1 mM sodium orthovanadate, 10 mM sodium fluoride). Samples are then tested for the presence of the FANC D2-L isoform using the anti-FANCD2-L-specific monoclonal antibody, as disclosed herein, and conventional immunoassays such as the enzyme linked immunosorbent assay (ELISA) that are commonly used to quantitate the levels of proteins in cell samples (see Harlow, E. and Lane, D. Using Antibodies: A Laboratory Manual (1999) Cold Spring Harbor Laboratory Press). Detection of the mono-ubiquitinated FANC D2-L isoform is considered indicative of a reduced efficacy of the therapeutic agent being used to treat the cancer patient.

Example 19

A Method of Determining Resistance to a Chemotherapy Agent

Figure 21:
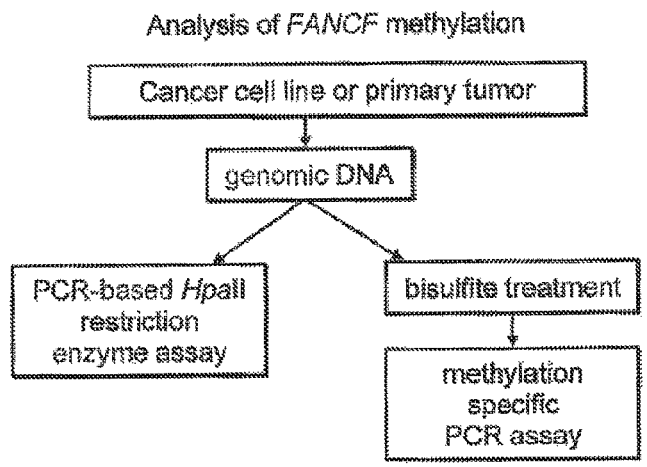
FIG. 21 depicts protocol used to analyze the methylation state of the FANC F gene.
Figure 22:
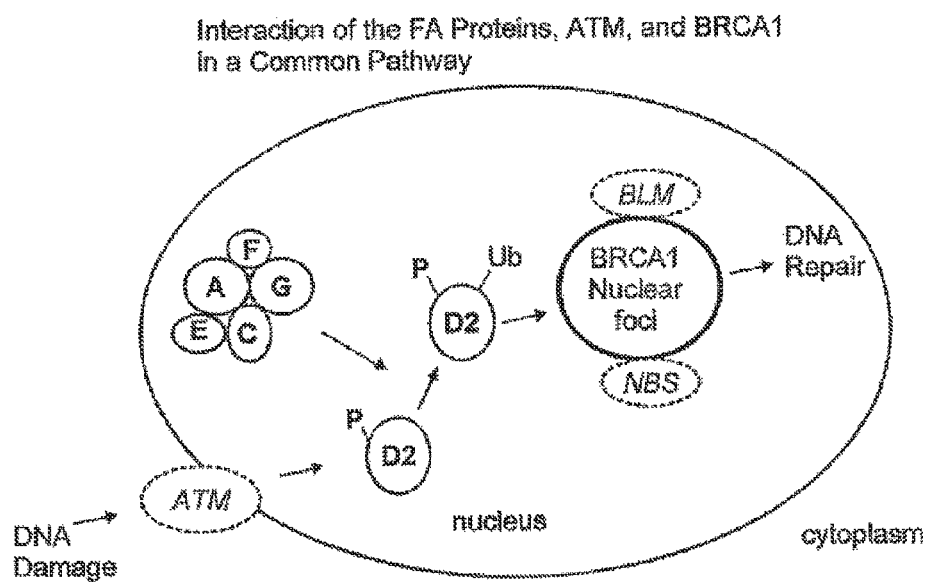
FIG. 22 depicts the Fanconi Anemia/BRCA pathway.

A flow chart describing the protocol used to determine the methylation state of the Fanconi Anemia/BRCA pathway genes is depicted in FIG. 21.

Analysis of FANCF Methylation.

DNA methylation patterns in FANCF gene were determined by methylation specific PCR or PCR-based HpaII restriction enzyme assay. Genomic DNA was isolated from indicated cell lines using QIAamp DNA Blood Mini Kit (QIAGEN).

PCR-Based HpaII Restriction Enzyme Assay 250 ng of genomic DNA was digested with 30 unit of HpaII or MspI for 12 hr at 37° C. 12.5 ng of DNA from each digest was analyzed by PCR in 10 μl reactions containing 1×PCR buffer, 200 μM each of the four deoxynucleotide triphosphates, 0.5 units of AmpliTaq DNA polymerase (Roche), and 0.2 μM of each primer. PCR was run for 33 cycles, and each cycle constituted denaturation (45 sec at 94° C., first cycle 4 min 45 sec), annealing (1 min at 61° C.), and extension (2 min at 72° C., last cycle 9 min). PCR reaction was subjected to electrophoresis on a 1.2% agarose gel containing ethidium bromide. Primers used were (SEQ ID NO:229)_FPF6 (5'-GCACCTCATGGAATCCCTTC-3')(forward) and (SEQ ID NO:230) FR343 (5'-GTTGCTGCACCAGGTGGTAA-3') (reverse): These primers were designed using nt –6-14 for the forward primer and nt 403-432 for the reverse primer.

Methylation-Specific PCR.

Bisulfite modification of genomic DNA was performed as previously described (Herman J G et al. Proc Natl Acad Sci USA 93 (18) 9821-6 (1996)). The bisulfite-treated DNA was amplified with either a methylation-specific or unmethylation-specific primer set. PCR was run for 40 cycles, and each cycle constituted denaturation (45 sec at 94° C., first cycle 4 min 45 sec), annealing (1 min' at 65° C.), and extension (2 min at 72° C., last cycle 9 min). PCR reaction was subjected to electrophoresis on a 3% Separide (Gibco) gel containing ethidium bromide. The methylation-specific primers were FF280M (SEQ ID NO:231) (5'-TTTTGCGTTTGTTG-GAGAATCGGGTTTTC-3') (forward) and FR432M (SEQ ID NO:232) (5'-ATACACCGCAAACCGCCGACGAA-CAAAACG-3') (reverse). The unmethylation-specific primers were FF280U (SEQ ID NO:233).(5'-TTTTTGT-GTTTGTTGGAGAATTGGGTTTTT-3') (forward) and FR432U (SEQ ID NO:234) (5'-ATACACCACAAACCAC-CAACAAACAAAACA-3')(reverse). These primers were designed using nt 280-309 for the forward primers and nt 403-432 for the reverse primers.

TABLE 1

Complementation Groups and Responsible Genes of Fanconi Anemia

| Subtype | Estimated percentage of patients | Responsible gene | Chromosome location | Number of exons | Protein product |
| --- | --- | --- | --- | --- | --- |
| A | 66% | FANCA | 16q24.3 | 43 | 163 Kd |
| B | 4.3% | FANCB | — | — | — |
| C | –12.7% | FANCC | 9q22.3 | 14 | 63 Kd |
| D1 | rare | FANCD1 | — | — | — |
| D2 | rare | FANCD2 | 3p25.3 | 44 | 155,162 kD |
| E | 12.7% | FANCE | 6p21.2-21.3 | 10 | 60 kD |
| F | rare | FANCF | 11p15 | 1 | 42 kD |
| G | rare | FANCG (XRCC9) | 9p13 | 14 | 68 kD |

TABLE 2

Diseases of Genomic Instability

| Disease | Damaging Agent | Neoplasm | Function |
| --- | --- | --- | --- |
| FA | Cross-linking agents | Acute myeloblastic leukemia, hepatic, gastrointestinal, and gynecological tumors | Unknown |
| XP | UV light | Squamous cell carcinomas | Excision repair |
| AT | Ionizing radiation | Lymphoma | Afferent pathway to p53 |
| Bloom's Syndrome | Alkylating agents | Acute lymphoblastic leukemia | Cell-cycle regulation |

TABLE 2-continued

Diseases of Genomic Instability

| Disease | Damaging Agent | Neoplasm | Function |
|---|---|---|---|
| Cockayne's Syndrome | UV light | Basal cell carcinoma | Transcription coupled repair |
| Hereditary non-polyposis colon cancer (HNPCC) | Unknown | Adenocarcinoma of colon, ovarian cancer | DNA mismatch repair |

TABLE 3

FANCD2 Sequence Alterations

Mutations

| | | |
|---|---|---|
| PD20 | nt376a→g | S126G/splice |
| | nt3707g→a | R1236H |
| VU008 | nt904c→t | R302W |
| | nt958c→t | Q320X |
| PD733 | | deletion of exon 17 |

Polymorphisms

| | | |
|---|---|---|
| | nt1122a→g | V374V |
| | nt1440t→c* | H480H |
| | nt1509c→t† | N503N |
| | nt2141c→t*† | L714P |
| | nt2259t→c | D753D |
| | nt4098t→g*† | L1366L |
| | nt4453g→a† | 3UTR |

*PD20 is heterozygous;
†VU008 is heterozygous.

TABLE 4

Chromosome Breakage Analysis of Whole-cell Fusions

| Cell line/hybrids | DEB (ng/ml) | MMC (ng/ml) | % of Cells with radials | Phenotype |
|---|---|---|---|---|
| PD20i | 300 | | 58 | S |
| PD24p | 300 | | na* | S |
| VU423p | 300 | | na* | S |
| PD319i | 300 | | 52 | S |
| PD20i/VU423p | 300 | | 6 | R |
| PD20i/PD24p | 300 | | 30 | S |
| PD20i/PD319i | 300 | | 0 | R |
| PD20i | | 40 | 48 | S |
| VU423i | | 40 | 78 | S |
| PD20i/VU423i | | 40 | 10 | R |
| VU423i + chr. 3, clone 1 | | 40 | 74 | S |
| VU423i + chr. 3, clone 2 | | 40 | 68 | S |
| VU423i + chr. 3, clone 3 | | 40 | 88 | S |
| PD20i + empty vector | 0 | 0 | 2 | |
| | | 40 | 24 | S |
| | 200 | | 62 | S |
| PD20i + FANCD2 vector | 0 | 0 | 0 | |
| | | 40 | 2 | R |
| | 200 | | 10 | R |

Groups of experiments are separated by line spaces. S, cross-linker sensitive; R, cross-linker-resistant; i = immortal fibroblast line; p = primary fibroblasts.
*Cell viability at this concentration was too low to score for radial formation, indicating the exquisite sensitivity of primary fibroblasts to interstrand DNA-crosslinks.

TABLE 5

| Cell line/plasmid | | FA Group | FA protein complex (1) | MMC sensitivity (2) | IR/Bleomycin sensitivity (3) |
|---|---|---|---|---|---|
| Lymphoblasts | PD7 | Wt | + | R | R |
| | HSC72 | A | − | S | |
| | HSC72 + A | A | + | R | |
| | PD4 | C | − | S | |
| | PD4 + C | C | + | R | |
| | EUFA316 | G | − | S | |
| | EUFA316 + G | G | + | R | |
| | EUFA121 | F | − | S | S |
| | EUFA121 + F | F | + | R | R |
| | PD20 | D | + | S | S |
| | PD20(R) | D | + | R | R |
| Fibroblasts | GM0637 | Wt | + | R | R |
| | GM6914 | A | − | S | S |
| | GM694 + A | A | + | R | R |
| | PD426 | C | − | S | |
| | PDF426 + C | C | + | R | |
| | FAG326SV | G | − | S | |
| | FAG326SV + G | G | + | R | |
| | PD20F | D | + | S | S |
| | 20-3-15(+D) | D | + | R | R |
| | NBS (—/—) | NBS | + | S | S |
| | ATM (—/—) | ATM | + | S | S |
| | BRCA1 (—/—) | BRCA1 | + | S | S |

(1) The presence of the FA protein complex (FANCA/FANCG/FANCC) was determined as previously described (Garcia-Higuera et al., MCB 19: 4866-4873, 1999)
(2) MMC sensitivity for determined by the XTT assay for lymphoblasts or by the crystal violet assay for fibroblasts.
(3) IR/Bleomycin sensitivity was determined by analysis of chromosome breakage. (See Materials and Methods).

TABLE 6

The Intron/Exon Junctions of FANCD

| Exon | Size | SEQ ID NO. | 5'-Donor site | Score | Intron | SEQ ID NO. | 3'-Acceptor site | Score | Exon |
|---|---|---|---|---|---|---|---|---|---|
| 1 | 30 | 9 | TCG gtgagtaagtg | 87 | | 52 | gtttcccgattttgctctag GAA | 85 | 2 |
| 2 | 97 | 10 | CCA gtaagtatcta | 83 | | 53 | gaaaattttctattttcag AAA | 83 | 3 |
| 3 | 141 | 11 | TAG gtaatatttta | 78 | | 54 | ctcttcttttttctgcatag CTG | 88 | 4 |
| 4 | 68 | 12 | AAA gtatgtatttt | 81 | 159 | 55 | attttaaatccctaag ATA | 78 | 5 |

TABLE 6-continued

The Intron/Exon Junctions of FANCD

| Exon | Size | SEQ ID NO. | 5'-Donor site | Score | Intron | SEQ ID NO. | 3'-Acceptor site | Score | Exon |
|---|---|---|---|---|---|---|---|---|---|
| 5 | 104 | 13 | CAG gtgtggagagg | 86 | 375 | 56 | gatttcttttttttttacag TAT | 91 | 6 |
| 6 | 61 | 14 | CAG gtaagactgtc | 89 | | 57 | ccctatgtcttcttttttag CCT | 86 | 7 |
| 7 | 53 | 15 | AAA gtaagtggcgt | 87 | | 58 | ttctcttcctaacattttag CAA | 80 | 8 |
| 8 | 79 | 16 | AAG gtaggcttatg | 83 | 364 | 59 | aatagtgtcttctactgcag GAC | 85 | 9 |
| 9 | 125 | 17 | CAG gtggataaacc | 80 | | 60 | tcttttttctaccattcacag TGA | 86 | 10 |
| 10 | 88 | 18 | AAG gtagaaaagac | 76 | | 61 | tctgtgcttttaattttttag GTT | 85 | 31 |
| 11 | 105 | 19 | GAG gtatgctctta | 80 | 387 | 62 | ctaatatttactttctgcag GTA | 87 | 12 |
| 12 | 101 | 20 | AAG gtaaagagctc | 85 | 342 | 63 | ttcctctctgctacttgtag TTC | 84 | 13 |
| 13 | 101 | 21 | AAG gtgagatottt | 89 | 237 | 64 | actctctcctgtttttcag GCA | 92 | 14 |
| 14 | 36 | 22 | AAG gtaatgttcat | 82 | | 65 | tgcatatttattgacaatag GTG | 73 | 15 |
| 15 | 144 | 23 | TTA gtaagtgtcag | 80 | | 66 | tctactcttccccactcaag GTT | 86 | 16 |
| 16 | 135 | 24 | CAG gtatgttgaaa | 85 | | 67 | gttgactctcccctgtatag GAA | 84 | 17 |
| 17 | 132 | 25 | AAG gtatcttattg | 77 | | 68 | tggcatcattttttccacag GGC | 89 | 18 |
| 18 | 111 | 26 | CAG gttagaggcaa | 83 | | 69 | tcttcatcatctcattgcag GAT | 87 | 19 |
| 19 | 110 | 27 | CAG gtacacgtgga | 82 | | 70 | aaaaaattctttgttttttag AAG | 79 | 20 |
| 20 | 61 | 28 | CAG gtgagttcttt | 93 | | 71 | acttcctctttgctccag GTG | 93 | 21 |
| 21 | 120 | 29 | CTG gtaaagccaat | 81 | 445 | 72 | tgtttgtttgcttcctgaag GAA | 85 | 22 |
| 22 | 74 | 30 | AGG gtaggtattgt | 84 | 300 | 73 | attctggttttctccgcag TGA | 88 | 23 |
| 23 | 147 | 31 | AAA gtcagtatagt | 73 | | 74 | aatttatttctccttctcag ATT | 89 | 24 |
| 24 | 101 | 32 | TAG gtatgggatga | 84 | 370 | 75 | aaatgtttgttctctctcag ATT | 86 | 25 |
| 25 | 116 | 33 | GAG gtgagcagagt | 88 | | 76 | atgtaatttgtactttgcag ATT | 82 | 26 |
| 26 | 109 | 34 | CAG gtaagagaagt | 89 | | 77 | cagcctgctgtttgtttcag TCA | 81 | 27 |
| 27 | 111 | 35 | TAG gtaagtatgtt | 90 | 272 | 78 | ttctcttttttaatataaaag AAA | 73 | 28 |
| 28 | 110 | 36 | AAG gtattggaatg | 78 | | 79 | ttgctgtgacttccccatag GAG | 85 | 29 |
| 29 | 144 | 37 | GAA gtaagtgacag | 85 | | 80 | toctttcctccatgtgacag GCT | 84 | 30 |
| 30 | 117 | 38 | AAG gttagtgtagg | 86 | | 81 | taactctgcatttattatag AAC | 80 | 31 |
| 31 | 129 | 39 | CAG gtcagaagcct | 82 | 118 | 82 | aaaatcattttttattttttag TGT | 79 | 32 |
| 32 | 119 | 40 | TTG gtaagtatgtg | 85 | | 83 | tcttaccttgacttccttag GAG | 85 | 33 |
| 33 | 111 | 41 | CAG gtgagtcataa | 90 | | 84 | tttttcttgtctccttacag CCA | 91 | 34 |
| 34 | 131 | 42 | TTG gtgatgggcct | 73 | | 85 | tttgtcttcttttctaacag CTT | 89 | 35 |
| 35 | 94 | 43 | CTG gtgagatgttt | 84 | 286 | 86 | atatttgactctcaatgcag TAT | 78 | 36 |
| 36 | 123 | 44 | CAG gtaagggagtt | 92 | | 87 | atgottttcccgtcttctag GCA | 88 | 37 |
| 37 | 94 | 45 | CAG gtgagtaagat | 92 | | 88 | catatatttggctgccccag ATT | 81 | 38 |
| 38 | 72 | 46 | AAG gtgagtatgga | 93 | | 89 | cttgtctttcacctctccag GTA | 93 | 39 |
| 39 | 39 | 47 | AAG gtgagagattt | 89 | | 90 | agtgtgtctctcttottcag TAT | 86 | 40 |
| 40 | 75 | 48 | CGG gtaagagctaa | 86 | | 91 | tataaacttattggttatag GAA | 77 | 41 |
| 41 | 75 | 49 | AAG gtaagaagggg | 91 | | 92 | tgttatttatttccattcag ATT | 86 | 42 |
| 42 | 147 | 50 | CAG gtaagccttgg | 91 | | 93 | ottggtccattcacattag GGT | 80 | 43 |
| 43 | 228 | | CCA taa + 3'UTR | | | 94 | atttattctttgccccttag GAT | | 44 |
| | 96 | 51 | GAG gtatctctaca | | | | | | |
| 44 | 72 | | GAT tag + 3'UTR | | | | | | |

TABLE 7

PCR Primers to Amplify the 44 Exons of FANCD

| Exon | Primer Name | SEQ ID NO. | Primer Sequence (5' -> 3') | Product Size (bp) | Annealing Temp |
|---|---|---|---|---|---|
| 1 | MG914 | 115 | F: CTAGCACAGAACTCTGCTGC | 372 | 54 |
| | MG837 | 116 | R: CTAGCACAGAACTCTGCTGC | | |
| 2 | MG746 | 117 | F: CTTCAGCAACAGCGAAGTAGTCTG | 422 | 50 |
| | MG747 | 118 | R: ATTCTCAGCACTTGAAAAGCAGG | | |
| 3 | MG773 | 119 | F: GGACACATCAGTTTTCCTCTC | 309 | 50 |
| | MG789 | 120 | R: GAAAACCCATGATTCAGTCC | | |
| 4-5 | MG816 | 121 | F: TCATCAGGCAAGAAACTTGG | 467 | 50 |
| | MG803 | 122 | R: GAAGTTGGCAAAACAGACTG | | |
| 6 | MG804 | 123 | F: GAGCCATCTGCTCATTTCTG | 283 | 50 |
| | MG812 | 124 | R: CCCGCTATTTAGACTTGAGC | | |
| 7 | MG775 | 125 | F: CAAAGTGTTTATTCCAGGAGC | 343 | 50 |
| | MG802 | 126 | R: CATCAGGGTACTTTTGAACATTC | | |
| 8-9 | MG727 | 127 | F: TTGACCAGAAAGGCTCAGTTCC | 640 | 50 |
| | MG915 | 128 | R: AGATGATGCCAGAGGGTTTATCC | | |
| 10 | MG790 | 129 | F: TGCCCAGCTCTGTTCAAACC | 222 | 50 |
| | MG774 | 130 | R: AGGCAATGACTGACTGACAC | | |
| 11 | MG805 | 131 | F: TGCCCGTCTATTTTTGATGAAGC | 392 | 50 |
| | MG791 | 132 | R: TCTCAGTTAGTCTGGGGACAG | | |
| 12 | MG751 | 133 | F: TCATGGTAGAGAGACTGGACTGTGC | 432 | 50 |
| | MG972 | 134 | R: ACCCTGGAGCAAATGACAACC | | |
| 13-14 | MG973 | 135 | F: ATTTGCTCCAGGGTACATGGC | 555 | 50 |
| | MG974 | 136 | R: GAAAGACAGTGGGAAGGCAAGC | | |

TABLE 7-continued

PCR Primers to Amplify the 44 Exons of FANCD

| Exon | Primer Name | SEQ ID NO. | Primer Sequence (5' -> 3') | Product Size (bp) | Annealing Temp |
|---|---|---|---|---|---|
| 15 | MG975 | 137 | F: GGGAGTGTGTGGAACAAATGAGC | 513 | 50 |
|  | MG976 | 138 | R: AGTTTCTACAGGCTGGTCCTATTCC |  |  |
| 16 | MG775 | 139 | F: AACGTGGAATCCCATTGATGC | 379 | 48 |
|  | MG730 | 140 | R: TTTCTGTGTTCCCTCCTTGC |  |  |
| 17 | MG794 | 141 | F: GATGGTCAAGTTACACTGGC | 382 | 50 |
|  | MG778 | 142 | R: CACCTCCCACCAATTATAGTATTC |  |  |
| 18 | MG808 | 143 | F: CTATGTGTGTCTCTTTTACAGGG | 234 | 48 |
|  | MG817 | 144 | R: AATCTTTCCCACCATATTGC |  |  |
| 19 | MG779 | 145 | F: CATACCTTCTTTTGCTGTGC | 199 | 48 |
|  | MG795 | 146 | R: CCACAGAAGTCAGAATCTCCACG |  |  |
| 20 | MG731 | 147 | F: TGTAACAAACCTGCACGTTG | 632 | 56 |
|  | MG732 | 148 | R: TGCTACCCAAGCCAGTAGTTCC |  |  |
| 21 | MG788 | 149 | F: GAGTTTGGGAAAGATTGGCAGC | 232 | 50 |
|  | MG772 | 150 | R: TGTAGTAAAGCAGCTCTCATGC |  |  |
| 22-23 | MG733 | 151 | F: CAAGTACACTCTGCACTGCC | 652 | 50 |
|  | MG758 | 152 | R: TGACTCAACTTCCCCACCAAGAG |  |  |
| 24-25 | MG736 | 153 | F: CTCCCTATGTACGTGGAGTAATAC | 732 | 50 |
|  | MG737 | 154 | R: GGGAGTCTTGTGGGAACTAAG |  |  |
| 26 | MG780 | 155 | F: TTCATAGACATCTCTCAGCTCTG | 284 | 50 |
|  | MG759 | 156 | R: GTTTTGGTATCAGGGAAAGC |  |  |
| 27-28 | MG760 | 157 | F: AGCCATGCTTGGAATTTTGG | 653 | 50 |
|  | MG781 | 158 | R: CTCACTGGGATGTCACAAAC |  |  |
| 29 | MG740 | 159 | F: GGTCTTGATGTGTGACTTGTATCCC | 447 | 50 |
|  | MG741 | 160 | R: CCTCAGTGTCACAGTGTTCTTTGTG |  |  |
| 30 | MG809 | 161 | F: CATGAAATGACTAGGACATTCC | 281 | 48 |
|  | MG797 | 162 | R: CTACCCAGTGACCCAAACAC |  |  |
| 31-32 | MG761 | 163 | F: CGAACCCTTAGTTTCTGAGACGC | 503 | 50 |
|  | MG742 | 164 | R: TCAGTGCCTTGGTGACTGTC |  |  |
| 33 | MG916 | 165 | F: TTGATGGTACAGACTGGAGGC | 274 | 50 |
|  | MG810 | 166 | R: AAGAAAGTTGCCAATCCTGTTCC |  |  |
| 34 | MG762 | 167 | F: AGCACCTGAAAATAAGGAGG | 343 | 50 |
|  | MG743 | 168 | R: GCCCAAAGTTTGTAAGTGTGAG |  |  |
| 35-36 | MG787 | 169 | F: AGCAAGAATGAGGTCAAGTTC | 590 | 50 |
|  | MG806 | 170 | R: GGGAAAAACTGGAGGAAAGAACTC |  |  |
| 37 | MG818 | 171 | F: AGAGGTAGGGAAGGAAGCTAC | 233 | 50 |
|  | MG813 | 172 | R: CCAAAGTCCACTTGAAG |  |  |
| 38 | MG834 | 173 | F: GATGCACTGGTTGCTACATC | 275 | 50 |
|  | MG836 | 174 | R: CCAGGACACTTGGTTTCTGC |  |  |
| 39 | MG839 | 175 | F: ACACTCCCAGTTGGAATCAG | 370 | 50 |
|  | MG871 | 176 | R: CTTGTGGGCAAGAAATTGAG |  |  |
| 40 | MG829 | 177 | F: TGGGCTGGATGAGACTATTC | 223 | 50 |
|  | MG870 | 178 | R: CCAAGGSVSYSYVYYVYHSHVSSC |  |  |
| 41 | MG820 | 179 | F: TGATTATCAGCATAGGCTGG | 271 | 50 |
|  | MG811 | 180 | R: GATCCCCCAATAGGAACTGC |  |  |
| 42 | MG763 | 181 | F: CATTCAGATTCACCAGGACAC | 227 | 50 |
|  | MG782 | 182 | R: CCTTACATGCCATCTGATGC |  |  |
| 43 3'UTR | MG764 | 183 | F: AACCTTCTCCCCTATTACCC | 435 | 50 |
|  | MG835 | 184 | R: GGAAAATGAGAGGCTATAATGC |  |  |
| 44 3'UTR | MG1006 | 185 | F: TGTATTCCAGAGGTCACCCAGAGC | 234 | 50 |
|  | MG1005 | 186 | R: CCAGTAAGAAAGGCAAACAGCG |  |  |

TABLE 8

FANDCD2 LOCI on Human Chromosome 3p

| Exon | Copy region 1 | Copy region 2 | Copy region 3 | FANCD2 | Copy region 4 | Copy region 5 |
|---|---|---|---|---|---|---|
| 1 | 201,110 | 344,395 |  | 8,170,539 |  |  |
| 2 |  |  |  |  |  |  |
| 3 |  |  |  |  |  |  |
| 4 |  |  |  |  |  |  |
| 5 |  |  |  |  |  |  |
| 6 |  |  |  |  |  |  |
| 7 |  |  |  |  |  |  |
| 8 |  |  |  |  |  |  |
| 9 |  |  |  |  |  |  |
| 10 |  |  |  |  |  |  |
| 11 |  |  |  |  |  |  |
| 12 |  |  | 6,126,244 | 8,209,073 |  |  |
| 13 |  |  |  |  |  |  |
| 14 |  |  |  |  |  |  |
| 15 |  |  |  |  |  |  |
| 16 |  |  |  |  | 8,202,791 |  |
| 17 |  |  |  |  |  |  |
| 18 |  |  |  |  |  |  |
| 19 |  |  |  |  |  |  |
| 20 |  |  |  |  |  |  |
| 21 |  |  |  |  |  |  |
| 22 |  |  |  |  |  |  |
| 23 |  |  |  |  |  |  |
| 24 |  |  |  |  |  | 18,201,854 |
| 25 |  |  |  |  |  |  |
| 26 |  |  |  |  |  |  |
| 27 |  |  |  |  |  |  |
| 28 |  |  | 6,094,448 |  |  |  |

TABLE 8-continued

FANDCD2 LOCI on Human Chromosone 3p

| Exon | Copy region 1 | Copy region 2 | Copy region 3 | FANCD2 | Copy region 4 | Copy region 5 |
|---|---|---|---|---|---|---|
| 29 | | | | | | |
| 30 | | | | | | |
| 31 | | | | | | |
| 32 | 186,164 | | | | | |
| 33 | | | | | | |
| 34 | | | | | | |
| 35 | | | | | | |
| 36 | | | | | | 18,178,589 |
| 37 | | | | | | |

TABLE 8-continued

FANDCD2 LOCI on Human Chromosone 3p

| Exon | Copy region 1 | Copy region 2 | Copy region 3 | FANCD2 | Copy region 4 | Copy region 5 |
|---|---|---|---|---|---|---|
| 38 | | | | | | |
| 39 | | | | | | |
| 40 | | | | | | |
| 41 | | | | | | |
| 42 | | | | | | |
| 43 | | | | | | |
| 44 | | | | 8,095,780 | | |

TABLE 9

| Primer Name | Sequence | Length of Product | SEQ ID NO: |
|---|---|---|---|
| hFANCD2_super_1_2_R | GGCCCACAGTTTCCGTTTCT | — | (SEQ ID NO: 235) |
| hFANCD2_super_1_2_F | CAAGGAAGCTAGAAATGAAGAAC | — | (SEQ ID NO: 236) |
| hFANCD2_super_3_3_R | CTGGGACTACAGACACGTTTT | — | (SEQ ID NO: 237) |
| hFANCD2_super_3_3_F | GTGTCACGTGTCTGTAATCTC | — | (SEQ ID NO: 238) |
| hFANCD2_super_7_14_R | TTAAGACCCAGCGAGGTATTC | — | (SEQ ID NO: 239) |
| hFANCD2_super_7_14_F | TGGGTTTGGTAGGGTAATGTC | — | (SEQ ID NO: 240) |
| hFANCD2_super_19_22_R | TGGAAAGTCACTGCGGAGAAA | — | (SEQ ID NO: 241) |
| hFANCD2_super_19_22_F | ACGTAATCACCCCTGTAATCC | — | (SEQ ID NO: 242) |
| hFANCD2_super_23_29_R | CACTGCAAACTGCTCACTCAA | — | (SEQ ID NO: 243) |
| hFANCD2_super_23_29_F | GGCCTTGTGCTAAGTGCTTTT | — | (SEQ ID NO: 244) |
| hFANCD2_super_30_32_R | ACCCTGGTGGACATACCTTTT | — | (SEQ ID NO: 245) |
| hFANCD2_super_30_32_F | CCAAAGTACTGGGAGTTTGAG | — | (SEQ ID NO: 246) |
| hFANCD2_super_33_36_R | TCTGGGCAACAGAACAAGCAA | — | (SEQ ID NO: 247) |
| hFANCD2_super_33_36_P | GAGCAATTTAGCCTGTGGTTTT | — | (SEQ ID NO: 248) |
| hFANCD2_super_43_44_R | ACCATCTGGCCGACATGGTA | — | (SEQ ID NO: 249) |
| hFANCD2_super_43_44_F | AGGGTCCTGAGACTATATACC | — | (SEQ ID NO: 250) |
| hFANCD2_exon1_R | TCCCATCTCAGGGCAGATGA | 324 | (SEQ ID NO: 251) |
| hFANCD2_exon1_F | TATGCCCGGCTAGCACAGAA | | (SEQ ID NO: 252) |
| hFANCD2_exon2_R | TCTCTCACATGCCTCACACAT | 258 | (SEQ ID NO: 253) |
| hFANCD2_exon2_F | CCCCTCTGATTTTGGATAGAG | | (SEQ ID NO: 254) |
| hFANCD2_exon3_R | AAGATGGATGGCCCTCTGATT | 354 | (SEQ ID NO: 255) |
| hFANCD2_exon3_F | GACACATCAGTTTTCCTCTCAT | | (SEQ ID NO: 256) |
| hFANCD2_exon4_R | AATCATTCTAGCCCACTCAACT | 253 | (SEQ ID NO: 257) |
| hFANCD2_exon4_F | TGGTTTCATCAGGCAAGAAACT | | (SEQ ID NO: 258) |
| hFANCD2_exon5_R | AGCCCCATGAAGTTGGCAAAA | 298 | (SEQ ID NO: 259) |
| hFANCD2_exon5_F | GCTTGTGCCAGCATAACTCTA | | (SEQ ID NO: 260) |
| hFANCD2_exon6_R | GCTGTGCTAAAGCTGCTACAA | 341 | (SEQ ID NO: 261) |
| hFANCD2_exon6_F | GAGCCATCTGCTCATTTCTGT | | (SEQ ID NO: 262) |
| hFANCD2_exon7_R | CAGAGAAACCAATAGTTTTCAG | 280 | (SEQ ID NO: 263) |
| hFANCD2_exon7_F | AATCTCGGCTCACTGCAATCT | | (SEQ ID NO: 264) |
| hFANCD2_exon8_R | AGCTAATGGATGGATGGAAAAG | 333 | (SEQ ID NO: 265) |
| hFANCD2_exon8_F | TAGTGCAGTGCCGAATGCATA | | (SEQ ID NO: 266) |
| hFANCD2_exon9_R | TACTCATGAAGGGGGGTATCA | 323 | (SEQ ID NO: 267) |
| hFANCD2_exon9_F | TTCACACGTAGGTAGTCTTTCT | | (SEQ ID NO: 268) |
| hFANCD2_exon10_R | CATTACTCCCAAGGCAATGAC | 229 | (SEQ ID NO: 269) |
| hFANCD2_exon10_F | GCCCAGCTCTGTTCAAACCA | | (SEQ ID NO: 270) |
| hFANCD2_exon11_R | AGCTCCATTCTCTCCTCTGAA | 341 | (SEQ ID NO: 271) |
| hFANCD2_exon11_F | GTGGGAAGATGGAGTAAGAGA | | (SEQ ID NO: 272) |
| hFANCD2_exon12_R | TCTGACAGTGGGATGTCAGAA | 211 | (SEQ ID NO: 273) |
| hFANCD2_exon12_F | TGCCTACCCACTATGAATGAG | | (SEQ ID NO: 274) |
| hFANCD2_exon13_R | ATGTGTCCATCTGGCAACCAT | 321 | (SEQ ID NO: 275) |
| hFANCD2_exon13_F | CAGGAACTCCGATCTTGTAAG | | (SEQ ID NO: 276) |
| hFANCD2_exon14_R | TGGAGGGGGGAGAAAGAAAG | 186 | (SEQ ID NO: 277) |
| hFANCD2_exon14_F | CGTGTTTCGCTGATGTGTCAT | | (SEQ ID NO: 278) |
| hFANCD2_exon15a_R | GGAAGGCCAGTTTGTCAAAGT | 325 | (SEQ ID NO: 279) |
| hFANCD2_exon15a_F | GTGTTTGACCTGGTGATGCTT | | (SEQ ID NO: 280) |
| hFANCD2_exon15b_R | CTTATTTCTTAGCACCCTGTCAA | 204 | (SEQ ID NO: 281) |
| hFANCD2_exon15b_F | GTGGAACAAATGAGCATTATCC | | (SEQ ID NO: 282) |
| hFANCD2_exon16_R | TTCCCCTTCAGTGAGTTCCAA | 332 | (SEQ ID NO: 283) |
| hFANCD2_exon16_F | AGGGAGGAGAAGTCTGACATT | | (SEQ ID NO: 284) |
| hFANCD2_exon17_R | GATTAGCCTGTAGGTTAGGTAT | 422 | (SEQ ID NO: 285) |
| hFANCD2_exon17_F | GATGGGTTTGGGTTGATTGTG | | (SEQ ID NO: 286) |
| hFANCD2_exon18_R | CCAGTCTAGGAGACAGAGCT | 282 | (SEQ ID NO: 287) |
| hFANCD2_exon18_F | GGCTATCTATGTGTGTCTCTTT | | (SEQ ID NO: 288) |
| hFANCD2_exon19_R | ACGATTAGAAGGGAACATGGAA | 328 | (SEQ ID NO: 289) |
| hFANCD2_exon19_F | CGATATCCATACCTTCTTTTGC | | (SEQ ID NO: 290) |
| hFANCD2_exon20_R | TGACAGAGCGAGACTCTCTAA | 239 | (SEQ ID NO: 291) |
| hFANCD2_exon20_F | CACACCAACATGGCACATGTA | | (SEQ ID NO: 292) |
| hFANCD2_exon21_R | GAGACAGGGTAGGGCAGAAA | 339 | (SEQ ID NO: 293) |

TABLE 9-continued

| Primer Name | Sequence | Length of Product | SEQ ID NO: |
|---|---|---|---|
| hFANCD2_exon21_F | AAAGGGGCGAGTGCAGTTTG | | (SEQ ID NO: 294) |
| hFANCD2_exon22_R | GTAACTTCACCAGTGCAACCAA | 279 | (SEQ ID NO: 295) |
| hFANCD2_exon22_F | ATGCACTCTCTCTTTTCTACTT | | (SEQ ID NO: 296) |
| hFANCD2_exon23_R | ACAAGGAATCTGCCCCATTCT | 356 | (SEQ ID NO: 297) |
| hFANCD2_exon23_F | TTCCCTGTAGCCTTGCGTATT | | (SEQ ID NO: 298) |
| hFANCD2_exon24_R | CCCCACATACACCATGTATTG | 258 | (SEQ ID NO: 299) |
| hFANCD2_exon24_F | GTCCCTATGTACGTGGAGTAA | | (SEQ ID NO: 300) |
| hFANCD2_exon25_R | GTGGGACATAACAGCTAGAGA | 350 | (SEQ ID NO: 301) |
| hFANCD2_exon25_F | AGGGGAAAGTAAATAGCAAGGA | | (SEQ ID NO: 302) |
| hFANCD2_exon26_R | TCAGGGATATTGGCCTGAGAT | 324 | (SEQ ID NO: 303) |
| hFANCD2_exon26_F | GACATCTCTCAGCTCTGGATA | | (SEQ ID NO: 304) |
| hFANCD2_exon27_R | CCAATTACTGATGCCATGATAC | 324 | (SEQ ID NO: 305) |
| hFANCD2_exon27_F | GCATTCAGCCATGCTTGGTAA | | (SEQ ID NO: 306) |
| hFANCD2_exon28_R | GATTACTCCAACGCCTAAGAG | 354 | (SEQ ID NO: 307) |
| hFANCD2_exon28_F | TCTACCTCTAGGCAGTTTCCA | | (SEQ ID NO: 308) |
| hFANCD2_exon29_R | TCTCCTCAGTCACAGTGTT | 384 | (SEQ ID NO: 309) |
| hFANCD2_exon29_F | CTTGGGCTAGAGGAAGTTGTT | | (SEQ ID NO: 310) |
| hFANCD2_exon30_R | TACCCAGTGACCCAAACACAA | 348 | (SEQ ID NO: 311) |
| hFANCD2_exon30_F | GAGTTCAAGGCTGGAATAGCT | | (SEQ ID NO: 312) |
| hFANCD2_exon31_R | ACCGTGATTCTCAGCAGCTAA | 341 | (SEQ ID NO: 313) |
| hFANCD2_exon31_F | CCATTGCGAACCCTTAGTTTC | | (SEQ ID NO: 314) |
| hFANCD2_exon32_R | AGTGCCTTGGTGACTGTCAAA | 336 | (SEQ ID NO: 315) |
| hFANCD2_exon32_F | CCACCTGGAGAACATTCACAA | | (SEQ ID NO: 316) |
| hFANCD2_exon33_R | TACTGAAAGACACCCAGGTTAT | 340 | (SEQ ID NO: 317) |
| hFANCD2_exon33_F | CACGCCCGACCTCTCAATTC | | (SEQ ID NO: 318) |
| hFANCD2_exon34_R | TATAGCAAGAGGGCCTATCCA | 349 | (SEQ ID NO: 319) |
| hFANCD2_exon34_F | TTGGGCACGTCATGTGGATTT | | (SEQ ID NO: 320) |
| hFANCD2_exon35_R | GTCCAGTCTCTGACAAACAAC | 300 | (SEQ ID NO: 321) |
| hFANCD2_exon35_F | TTAGACCGGGAACGTCTTAGT | | (SEQ ID NO: 322) |
| hFANCD2_exon36_R | GGCAAGTGGGTCTCAAAAC | 398 | (SEQ ID NO: 323) |
| hFANCD2_exon36_F | CCTCTGGTTCTGTTTTATACTG | | (SEQ ID NO: 324) |
| hFANCD2_exon37_R | TCTGGGCAACAGAACAAGCAA | 277 | (SEQ ID NO: 325) |
| hFANCD2_exon37_F | CTTCCCAGGTAGTTCTAAGCA | | (SEQ ID NO: 326) |
| hFANCD2_exon38_R | AAGCCAGGACACTTGGTTTCT | 274 | (SEQ ID NO: 327) |
| hFANCD2_exon38_F | GCACTGGTTGCTACATCTAAG | | (SEQ ID NO: 328) |
| hFANCD2_exon39_R | GCATCCATTGCCTTCCCTAAA | 236 | (SEQ ID NO: 329) |
| hFANCD2_exon39_F | TGCTCAAAGGAGCAGATCTCA | | (SEQ ID NO: 330) |
| hFANCD2_exon40_R | CAGTCCAATTTGGGGATCTCT | 309 | (SEQ ID NO: 331) |
| hFANCD2_exon40_F | CCTTGGGCTGGATGAGACTA | | (SEQ ID NO: 332) |
| hFANCD2_exon41_R | CCCCAATAGCAACTGCAGATT | 214 | (SEQ ID NO: 333) |
| hFANCD2_exon41_F | GATTGCAAGGGTATCTTGAATC | | (SEQ ID NO: 334) |
| hFANCD2_exon42_R | GCTTAGGTGACCTTCCTTACA | 356 | (SEQ ID NO: 335) |
| hFANCD2_exon42_F | AACATACCGTTGGCCCATACT | | (SEQ ID NO: 336) |
| hFANCD2_exon43a_R | AGCATGATCTCGGCTCACCA | 366 | (SEQ ID NO: 337) |
| hFANCD2_exon43a_F | GTGGCTCATGCTTGTAATCCT | | (SEQ ID NO: 338) |
| hFANCD2_exon43b_R | TCAGTAGAGATGGGGTTTCAC | 358 | (SEQ ID NO: 339) |
| hFANCD2_exon43b_F | CTGCCACCTTAGAGAACTGAA | | (SEQ ID NO: 340) |
| hFANCD2_exon43c_R | CTCAAGCAATCCTCCTACCTT | 405 | (SEQ ID NO: 341) |
| hFANCD2_exon43c_F | TAGAATCACTCCTGAGTATCTC | | (SEQ ID NO: 342) |
| hFANCD2_exon43d_R | CAGCTTCTGACTCTGTGCTTT | 367 | (SEQ ID NO: 343) |
| hFANCD2_exon43d_F | AGTTGGTGGAGCAGAACTTTG | | (SEQ ID NO: 344) |
| hFANCD2_exon43e_R | CTCGAGATACTCAGGAGTGAT | 381 | (SEQ ID NO: 345) |
| hFANCD2_exon43e_F | TCAACCTTCTCCCCTATTACC | | (SEQ ID NO: 346) |
| hFANCD2_exon43f_R | AGTTCTGCTCCACCAACTTAG | 306 | (SEQ ID NO: 347) |
| hFANCD2_exon43f_F | GGTATCCATGTTTGCTGTGTTT | | (SEQ ID NO: 348) |
| hFANCD2_exon44_R | GAAAGGCAAACAGCGGATTTC | 213 | (SEQ ID NO: 349) |
| hFANCD2_exon44_F | CACCCAGAGCAGTAACCTAAA | | (SEQ ID NO: 350) |

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

We claim:

1. An in vitro method of predicting the efficacy of a therapeutic agent in a cancer patient, comprising the steps of:
   a) taking a tissue sample from said cancer patient who is being treated with said therapeutic agent;
   b) inducing DNA damage in the cells of said tissue sample; and
   c) detecting the presence of FANCD2-L protein in said cells,
   wherein the presence of FANCD2-L protein is indicative of a reduced efficacy of said therapeutic agent in said cancer patient, and wherein said therapeutic agent is cisplatin.

2. The method of claim 1, wherein said cancer is breast cancer, ovarian cancer, or prostate cancer.

* * * * *

SEQUENCE LISTING

<160> NUMBER OF SEQ ID NOS: 352

<210> SEQ ID NO 1
<211> LENGTH: 1451
<212> TYPE: PRT
<213> ORGANISM: Homo sapiens

<400> SEQUENCE: 1

-continued

```
Met Val Ser Lys Arg Leu Ser Lys Ser Glu Asp Lys Glu Ser Leu
1               5                   10                  15

Thr Glu Asp Ala Ser Lys Thr Arg Lys Gln Pro Leu Ser Lys Lys Thr
            20                  25                  30

Lys Lys Ser His Ile Ala Asn Ala Val Glu Glu Asn Asp Ser Ile Phe
        35                  40                  45

Val Lys Leu Leu Lys Ile Ser Gly Ile Ile Leu Lys Thr Gly Glu Ser
    50                  55                  60

Gln Asn Gln Leu Ala Val Asp Gln Ile Ala Phe Gln Lys Lys Leu Phe
65                  70                  75                  80

Gln Thr Leu Arg Arg His Pro Ser Tyr Pro Lys Ile Ile Glu Glu Phe
                85                  90                  95

Val Ser Gly Leu Glu Ser Tyr Ile Glu Asp Glu Asp Ser Phe Arg Asn
                100                 105                 110

Cys Leu Leu Ser Cys Glu Arg Leu Gln Asp Glu Glu Ala Ser Met Gly
            115                 120                 125

Ala Ser Tyr Ser Lys Ser Leu Ile Lys Leu Leu Gly Ile Asp Ile
130                 135                 140

Leu Gln Pro Ala Ile Ile Lys Thr Leu Phe Glu Lys Leu Pro Glu Tyr
145                 150                 155                 160

Phe Phe Glu Asn Arg Asn Ser Asp Glu Ile Asn Ile Phe Arg Leu Ile
                165                 170                 175

Val Ser Gln Leu Lys Trp Leu Asp Arg Val Val Asp Gly Lys Asp Leu
                180                 185                 190

Thr Thr Lys Ile Met Gln Leu Ile Ser Ile Ala Pro Glu Asn Leu Gln
                195                 200                 205

His Asp Ile Ile Thr Ser Lys Pro Glu Ile Leu Gly Asp Ser Gln His
210                 215                 220

Ala Asp Val Gly Lys Glu Leu Ser Asp Leu Leu Ile Glu Asn Thr Ser
225                 230                 235                 240

Leu Thr Val Pro Ile Leu Asp Val Leu Ser Ser Leu Arg Leu Asp Pro
                245                 250                 255

Asn Phe Leu Leu Lys Val Arg Gln Leu Val Met Asp Lys Leu Ser Ser
                260                 265                 270

Ile Arg Leu Glu Asp Leu Pro Val Ile Ile Lys Phe Ile Leu His Ser
                275                 280                 285

Val Thr Ala Met Asp Thr Leu Glu Val Ile Ser Glu Leu Arg Glu Lys
                290                 295                 300

Leu Asp Leu Gln His Cys Val Leu Pro Ser Arg Leu Gln Ala Ser Gln
305                 310                 315                 320

Val Lys Leu Lys Ser Lys Gly Arg Ala Ser Ser Ser Gly Asn Gln Glu
                325                 330                 335

Ser Ser Gly Gln Ser Cys Ile Ile Leu Leu Phe Asp Val Ile Lys Ser
                340                 345                 350

Ala Ile Arg Tyr Glu Lys Thr Ile Ser Glu Ala Trp Ile Lys Ala Ile
                355                 360                 365

Glu Asn Thr Ala Ser Val Ser Glu His Lys Val Phe Asp Leu Val Met
                370                 375                 380

Leu Phe Ile Ile Val Ser Thr Asn Thr Gln Thr Lys Lys Tyr Ile Asp
385                 390                 395                 400

Arg Val Leu Arg Asn Lys Ile Arg Ser Gly Cys Ile Gln Glu Gln Leu
                405                 410                 415
```

-continued

```
Leu Gln Ser Thr Phe Ser Val His Tyr Leu Val Leu Lys Asp Met Cys
            420                 425                 430

Ser Ser Ile Leu Ser Leu Ala Gln Ser Leu Leu His Ser Leu Asp Gln
            435                 440                 445

Ser Ile Ile Ser Phe Gly Ser Leu Leu Tyr Lys Tyr Ala Phe Lys Phe
            450                 455                 460

Phe Asp Thr Tyr Cys Gln Gln Glu Val Val Gly Ala Leu Val Thr His
465                 470                 475                 480

Ile Cys Ser Gly Asn Glu Ala Glu Val Asp Asp Ala Leu Asp Val Leu
            485                 490                 495

Leu Glu Leu Val Val Leu Asn Pro Ser Ala Met Met Met Asn Ala Val
            500                 505                 510

Phe Val Gln Gly Ile Leu Asp Tyr Leu Asp Asn Ile Ser Pro Gln Gln
            515                 520                 525

Ile Arg Lys Leu Phe Tyr Val Leu Ser Thr Leu Ala Phe Ser Lys Gln
            530                 535                 540

Asn Glu Ala Ser Ser His Ile Gln Asp Asp Met His Leu Val Ile Arg
545                 550                 555                 560

Lys Gln Leu Ser Ser Thr Val Phe Lys Tyr Lys Leu Ile Gly Ile Ile
            565                 570                 575

Gly Ala Val Thr Met Ala Gly Ile Met Ala Ala Asp Arg Ser Glu Ser
            580                 585                 590

Pro Ser Leu Thr Gln Glu Arg Ala Asn Leu Ser Asp Glu Gln Cys Thr
            595                 600                 605

Gln Val Thr Ser Leu Leu Gln Leu Val His Ser Cys Ser Glu Gln Ser
            610                 615                 620

Pro Gln Ala Ser Ala Leu Tyr Tyr Asp Glu Phe Ala Asn Leu Ile Gln
625                 630                 635                 640

His Glu Lys Leu Asp Pro Lys Ala Leu Glu Trp Val Gly His Thr Ile
            645                 650                 655

Cys Asn Asp Phe Gln Asp Ala Phe Val Val Asp Ser Cys Val Val Pro
            660                 665                 670

Glu Gly Asp Phe Pro Phe Pro Val Lys Ala Leu Tyr Gly Leu Glu Glu
            675                 680                 685

Tyr Asp Thr Gln Asp Gly Ile Ala Ile Asn Leu Leu Pro Leu Leu Phe
            690                 695                 700

Ser Gln Asp Phe Ala Lys Asp Gly Gly Pro Val Thr Ser Gln Glu Ser
705                 710                 715                 720

Gly Gly Lys Leu Val Ser Pro Leu Cys Leu Ala Pro Tyr Phe Arg Leu
            725                 730                 735

Leu Arg Leu Cys Val Glu Arg Gln His Asn Gly Asn Leu Glu Glu Ile
            740                 745                 750

Asp Gly Leu Leu Asp Cys Pro Ile Phe Leu Thr Asp Leu Glu Pro Gly
            755                 760                 765

Glu Lys Leu Glu Ser Met Ser Ala Lys Glu Ala Ser Phe Met Cys Ser
            770                 775                 780

Leu Ile Phe Leu Thr Leu Asn Trp Phe Arg Glu Ile Val Asn Ala Phe
785                 790                 795                 800

Cys Gln Glu Thr Ser Pro Glu Asn Lys Gly Lys Val Leu Thr Arg Leu
            805                 810                 815

Lys His Ile Val Glu Leu Gln Ile Leu Leu Glu Lys Tyr Leu Ala Val
            820                 825                 830

Thr Pro Asp Tyr Val Pro Pro Leu Gly Asn Phe Asp Val Glu Thr Leu
```

-continued

```
            835                 840                 845
Asp Ile Thr Pro His Thr Val Thr Ala Ile Ser Ala Lys Ile Arg Lys
            850                 855                 860
Lys Gly Lys Ile Glu Arg Lys Gln Lys Thr Asp Gly Ser Lys Thr Ser
865                 870                 875                 880
Ser Ser Asp Thr Leu Ser Glu Glu Lys Asn Ser Glu Cys Asp Pro Thr
                885                 890                 895
Pro Ser His Arg Gly Gln Leu Asn Lys Glu Phe Thr Gly Lys Glu Glu
                900                 905                 910
Lys Thr Ser Leu Leu His Asn Ser His Ala Phe Phe Arg Glu Leu
            915                 920                 925
Asp Ile Glu Val Phe Ser Ile Leu His Cys Gly Leu Val Thr Lys Phe
            930                 935                 940
Ile Leu Asp Thr Glu Met His Thr Glu Ala Thr Glu Val Val Gln Leu
945                 950                 955                 960
Gly Pro Pro Glu Leu Leu Phe Leu Leu Glu Asp Leu Ser Gln Lys Leu
                965                 970                 975
Glu Ser Met Leu Thr Pro Pro Ile Ala Arg Arg Val Pro Phe Leu Lys
            980                 985                 990
Asn Lys Gly Ser Arg Asn Ile Gly Phe Ser His Leu Gln Gln Arg Ser
            995                 1000                1005
Ala Gln Glu Ile Val His Cys Val Glu Gln Leu Leu Thr Pro Met
        1010                1015                1020
Cys Asn His Leu Glu Asn Ile His Asn Tyr Ile Gln Cys Leu Ala
        1025                1030                1035
Ala Glu Asn His Gly Val Val Asp Gly Pro Gly Val Lys Val Gln
        1040                1045                1050
Glu Tyr His Ile Met Ser Ser Cys Tyr Gln Arg Leu Leu Gln Ile
        1055                1060                1065
Phe His Gly Leu Phe Ala Trp Ser Gly Phe Ser Gln Pro Glu Asn
        1070                1075                1080
Gln Asn Leu Leu Tyr Ser Ala Leu His Val Leu Ser Ser Arg Leu
        1085                1090                1095
Lys Gln Gly Glu His Ser Gln Pro Leu Glu Glu Leu Leu Ser Gln
        1100                1105                1110
Ser Val His Tyr Leu Gln Asn Phe His Gln Ser Ile Pro Ser Phe
        1115                1120                1125
Gln Cys Ala Leu Tyr Leu Ile Arg Leu Leu Met Val Ile Leu Glu
        1130                1135                1140
Lys Ser Thr Ala Ser Ala Gln Asn Lys Glu Lys Ile Ala Ser Leu
        1145                1150                1155
Ala Arg Gln Phe Leu Cys Arg Val Trp Pro Ser Gly Asp Lys Glu
        1160                1165                1170
Lys Ser Asn Ile Ser Asn Asp Gln Leu His Ala Leu Leu Cys Ile
        1175                1180                1185
Tyr Leu Glu His Thr Glu Ser Ile Leu Lys Ala Ile Glu Glu Ile
        1190                1195                1200
Ala Gln Val Gly Val Pro Glu Leu Ile Asn Ser Pro Lys Asp Ala
        1205                1210                1215
Ser Ser Ser Thr Phe Pro Leu Thr Arg His Thr Pro Val Val
        1220                1225                1230
Phe Phe Arg Val Met Met Ala Glu Leu Glu Lys Ile Val Lys Lys
        1235                1240                1245
```

Ile Glu Pro Gly Thr Ala Ala Asp Ser Gln Gln Ile His Glu Glu
1250                1255                1260

Lys Leu Leu Tyr Trp Asn Met Ala Val Arg Asp Phe Ser Ile Leu
1265                1270                1275

Ile Asn Leu Ile Lys Val Phe Asp Ser His Pro Val Leu His Val
        1280                1285                1290

Cys Leu Lys Val Gly Arg Leu Phe Val Glu Ala Phe Leu Lys Gln
        1295                1300                1305

Cys Met Pro Leu Leu Asp Ile Ser Phe Arg Lys His Arg Glu Asp
        1310                1315                1320

Val Leu Ser Leu Leu Glu Thr Phe Gln Leu Asp Thr Arg Leu Leu
        1325                1330                1335

His His Leu Cys Gly His Ser Lys Ile His Gln Asp Thr Arg Leu
        1340                1345                1350

Thr Gln His Val Pro Leu Leu Lys Lys Thr Leu Glu Leu Leu Val
        1355                1360                1365

Cys Arg Val Lys Ala Met Leu Thr Leu Asn Asn Cys Arg Glu Ala
        1370                1375                1380

Phe Trp Leu Gly Asn Leu Lys Asn Arg Asp Leu Gln Gly Glu Glu
        1385                1390                1395

Ile Lys Ser Gln Asn Ser Gln Glu Ser Thr Ala Asp Glu Ser Glu
        1400                1405                1410

Asp Asp Met Ser Ser Gln Ala Ser Lys Ser Lys Ala Thr Glu Asp
        1415                1420                1425

Gly Glu Glu Asp Glu Val Ser Ala Gly Glu Lys Glu Gln Asp Ser
        1430                1435                1440

Asp Glu Ser Tyr Asp Asp Ser Asp
        1445                1450

<210> SEQ ID NO 2
<211> LENGTH: 1269
<212> TYPE: PRT
<213> ORGANISM: Drosophila melanogaster

<400> SEQUENCE: 2

Met Tyr Lys Gln Phe Lys Lys Arg Ser Lys Lys Pro Leu Asn Thr Ile
1               5                   10                  15

Asp Glu Asn Ala Thr Ile Lys Val Pro Arg Leu Ala Glu Thr Thr Thr
                20                  25                  30

Asn Ile Ser Val Glu Ser Ser Gly Gly Ser Glu Gly Asn Ile Pro
            35                  40                  45

Ala Ser Gln Glu His Thr Gln Arg Phe Leu Ser Gln His Ser Val Ile
        50                  55                  60

Leu Ala Ala Thr Leu Gly Ala Thr Gly Glu Ser Ser Arg Asp Ile Ala
65                  70                  75                  80

Thr Leu Ser Arg Gln Pro Asn Asn Phe Phe Glu Leu Val Leu Val Arg
                85                  90                  95

Ala Gly Val Gln Leu Asp Gln Gly Asp Ser Leu Ile Leu Ala Cys Asp
                100                 105                 110

His Val Pro Ile Val Ser Lys Leu Ala Glu Ile Phe Thr Ser Ala Ser
            115                 120                 125

Ser Tyr Thr Asp Lys Met Glu Thr Phe Lys Thr Gly Leu Asn Ala Ala
        130                 135                 140

Met Ala Pro Gly Ser Lys Leu Val Gln Lys Leu Leu Thr Gly Cys Thr

```
                145                 150                 155                 160
            Val Asp Ala Ala Gly Glu Glu Gln Ile Tyr Gln Ser Gln Asn Ser Met
                            165                 170                 175

Phe Met Asn Phe Leu Met Ile Asp Phe Met Arg Asp Ala Cys Val Glu
                            180                 185                 190

Val Leu Leu Asn Lys Ile Glu Val Ala Lys Ser Asp Arg Val Ile
                        195                 200                 205

Met Gly Lys Ala Ala Ile Pro Leu Pro Leu Leu Pro Leu Met Leu Thr
                        210                 215                 220

Gln Leu Arg Tyr Leu Thr Ala Ser His Lys Val Glu Ile Tyr Ser Arg
            225                 230                 235                 240

Ile Glu Val Ile Phe Asn Arg Ala Thr Glu Ser Ala Lys Leu Asp Ile
                            245                 250                 255

Ile Ala Asn Ala Glu Leu Ile Leu Asp Ala Ser Met His Asp Glu Phe
                        260                 265                 270

Val Glu Leu Leu Asn Thr Glu Asp Leu Phe His Met Thr Thr Val Gln
                        275                 280                 285

Thr Leu Gly Asn Leu Ser Leu Ser Asp Arg Thr Gln Ala Lys Leu Arg
                        290                 295                 300

Val Arg Ile Leu Asp Phe Ala Thr Ser Gly Gln Cys Ser Asp Ala Ile
            305                 310                 315                 320

Leu Pro His Leu Ile Arg Leu Leu Leu Asn Val Leu Lys Ile Asp Thr
                            325                 330                 335

Asp Asp Ser Val Arg Asp Leu Arg Arg Arg Ile Lys Leu Glu His
                        340                 345                 350

Ile Thr Val Ser Ile Leu Glu Glu Ile Gln His Tyr Arg His Ile Leu
                        355                 360                 365

Glu Gln His Ile Thr Thr Leu Met Asn Ile Leu His Asp Phe Met Arg
                        370                 375                 380

Glu Lys Asn Arg Ile Val Ser Asp Phe Ala Lys Ser Ser Tyr Ser Ile
            385                 390                 395                 400

Leu Phe Lys Ile Phe Asn Ser Ile Gln Lys Asn Ile Leu Lys Lys Leu
                            405                 410                 415

Leu Glu Leu Thr Cys Asp Lys Ser Ser Pro His Leu Thr Thr His Ala
                        420                 425                 430

Leu Glu Leu Leu Arg Glu Leu Gln Arg Lys Ser Ala Lys Asp Val Gln
                        435                 440                 445

Asn Cys Ala Thr Leu Leu Ile Pro Met Leu Asp Arg Thr Ser Asp Leu
                        450                 455                 460

Ser Leu Thr Gln Thr Arg Val Ala Met Asp Leu Leu Cys His Val Ala
            465                 470                 475                 480

Phe Pro Asp Pro Asn Leu Ser Pro Cys Leu Gln Leu Gln Glu Gln Val
                            485                 490                 495

Asp Met Val Val Lys Lys Gln Leu Ile Asn Ser Ile Asp Asn Ile Lys
                        500                 505                 510

Lys Gln Gly Ile Ile Gly Cys Val Gln Leu Ile Asp Ala Met Ala Arg
                        515                 520                 525

Ile Ala Asn Asn Gly Val Asp Arg Asp Phe Phe Ile Ala Ser Val Glu
                        530                 535                 540

Asn Val Asp Ser Leu Pro Asp Gly Arg Gly Lys Met Ala Ala Asn Leu
            545                 550                 555                 560

Ile Ile Arg Thr Glu Ala Ser Ile Gly Asn Ser Thr Glu Ser Leu Ala
                            565                 570                 575
```

```
Leu Phe Phe Glu Glu Leu Ala Thr Val Phe Asn Gln Arg Asn Glu Gly
                580                 585                 590

Thr Ser Gly Cys Glu Leu Asp Asn Gln Phe Ile Ala Trp Ala Cys Asp
            595                 600                 605

Leu Val Thr Phe Arg Phe Gln Ala Ser Phe Val Thr Glu Asn Val Pro
        610                 615                 620

Glu Thr Lys Ala Cys Asp Ser Ile Tyr Val Leu Ala Pro Leu Phe Asn
625                 630                 635                 640

Tyr Val Arg Val Leu Tyr Lys His Arg His Gln Asp Ser Leu Glu Ser
                645                 650                 655

Ile Asn Ala Leu Leu Gly Cys Ala Ile Val Leu Pro Ser Phe Phe Glu
            660                 665                 670

Asp Asp Asn Tyr Val Ser Val Phe Glu Asn Phe Glu Ala Glu Gln Gln
        675                 680                 685

Lys Asp Ile Leu Ser Ile Tyr Phe His Thr Val Asn Trp Met Arg Val
690                 695                 700

Ser Ile Ser Ala Phe Ala Ser Gln Arg Asp Pro Thr Arg Arg Arg
705                 710                 715                 720

Val Leu Ser Arg Leu Gly Glu Leu Ile Arg Ile Glu Gln Arg Met Lys
                725                 730                 735

Pro Leu Leu Ala Arg Ala Pro Val Asp Phe Val Ala Pro Pro Tyr Gln
            740                 745                 750

Phe Leu Thr Asn Val Lys Leu Ser Asn Gln Asn Gln Lys Arg Pro Gly
        755                 760                 765

Pro Lys Pro Ala Ala Lys Leu Asn Ala Thr Leu Pro Glu Pro Asp Leu
770                 775                 780

Thr Gly Asn Gln Pro Ser Ile Ala Asp Phe Thr Ile Lys Val Gly Gln
785                 790                 795                 800

Cys Lys Thr Val Lys Thr Lys Thr Asp Phe Glu Gln Met Tyr Gly Pro
                805                 810                 815

Arg Glu Arg Tyr Arg Pro Met Glu Val Glu Ile Ile Met Leu Leu Val
            820                 825                 830

Glu Gln Lys Phe Val Leu Asn His Gln Leu Glu Glu Gln Met Gly
        835                 840                 845

Glu Phe Leu Gly Leu Leu Glu Leu Arg Phe Leu Leu Glu Asp Val Val
850                 855                 860

Gln Lys Leu Glu Ala Ala Val Leu Arg His His Asp Ser Tyr Asp Ala
865                 870                 875                 880

Asp Ser Phe Arg Pro His Leu Ala Lys Pro Glu Asp Phe Ile Cys Asp
                885                 890                 895

Leu Leu Pro Cys Leu His Glu Val Asn Asn His Leu Ile Thr Leu Gly
            900                 905                 910

Glu Ala Ile Asp Asn Gln Leu Thr Glu Val Ser Ser His Val Tyr Ser
        915                 920                 925

Asn Leu Asp Leu Phe Lys Asp Gln Phe Cys Tyr Ile Lys Ser Cys Phe
930                 935                 940

Gly Leu Cys Val Arg Leu Phe Ala Leu Tyr Phe Ala Trp Ser Glu Trp
945                 950                 955                 960

Ser Asp Lys Ser Gln Glu Gln Leu Leu His Arg Ile Leu Cys Gly Thr
                965                 970                 975

Leu Leu Arg Arg Lys Trp Phe His Tyr Ser Gly Thr Leu Asp Lys Gly
            980                 985                 990
```

Gly Gln Cys Asn Ile Tyr Leu Asp Glu Leu Val Lys Gly Phe Leu Lys
              995                 1000                1005

Lys Ser Asn Ala Lys Ser Gln Thr Glu Leu Leu Thr Glu Leu Val
     1010                1015                1020

Lys Gln Cys Ser Ile Leu Asn Thr Lys Asp Lys Ala Leu Thr Ser
     1025                1030                1035

Phe Pro Asn Phe Lys Lys Ala Asn Phe Pro Leu Leu Phe Arg Gly
     1040                1045                1050

Leu Cys Glu Val Leu Ile His Ser Leu Ser Gly Gln Val Ser Val
     1055                1060                1065

Asp Ser Arg Gly Asp Lys Leu Lys Leu Trp Glu Ser Ala Val Asp
     1070                1075                1080

Leu Leu Asn Gly Leu Leu Ser Ile Val Gln Gln Val Glu Gln Pro
     1085                1090                1095

Arg Asn Phe Gly Leu Phe Leu Lys His Ser Leu Leu Phe Leu Lys
     1100                1105                1110

Leu Leu Leu Gln His Gly Met Ser Ala Leu Glu Ser Ile Val Arg
     1115                1120                1125

Glu Asp Pro Glu Arg Leu Thr Arg Phe Leu His Glu Leu Gln Lys
     1130                1135                1140

Val Thr Arg Phe Leu His Gln Leu Cys Cys His Ser Lys Ser Ile
     1145                1150                1155

Lys Asn Thr Ala Ile Ile Ser Tyr Ile Pro Ser Leu Arg Glu Thr
     1160                1165                1170

Ile Glu Thr Leu Val Phe Arg Val Lys Ala Leu Leu Ala Ala Asn
     1175                1180                1185

Asn Cys His Ser Ala Phe His Met Gly Asn Met Ile Asn Arg Asp
     1190                1195                1200

Leu His Gly Asp Ser Ile Ile Thr Pro Arg Ser Ser Phe Ala Gly
     1205                1210                1215

Glu Glu Asn Ser Asp Asp Glu Leu Pro Ala Asp Asp Thr Ser Val
     1220                1225                1230

Asp Glu Thr Val Leu Gly Asp Asp Met Gly Ile Thr Ala Val Ser
     1235                1240                1245

Val Ser Thr Arg Pro Ser Asp Gly Ser Arg Arg Ser Lys Ser Ser
     1250                1255                1260

Ser Arg Ser Lys Cys Phe
     1265

<210> SEQ ID NO 3
<211> LENGTH: 1286
<212> TYPE: PRT
<213> ORGANISM: Arabidopsis thaliana

<400> SEQUENCE: 3

Met Val Phe Leu Ser Arg Lys Lys Pro Pro Pro Ser Ser Ser
1               5                   10                  15

Ser Ala Ala Pro Ser Leu Lys Ile Pro Gln Pro Gln Lys Glu Ser Val
                20                  25                  30

Glu Phe Asp Ala Val Glu Lys Met Thr Ala Ile Leu Ala Glu Val Gly
            35                  40                  45

Cys Thr Leu Met Asn Pro Tyr Gly Pro Pro Cys Leu Pro Ser Asp Leu
        50                  55                  60

His Ala Phe Arg Arg Asn Leu Thr Gly Arg Leu Ser Phe Ser Ala
65                  70                  75                  80

-continued

Asn Ser Gly Glu Arg Asp Asn Val Gly Ala Leu Cys Ser Val Phe Val
              85                  90                  95

Ala Gly Phe Ser Leu Tyr Ile Gln Ser Pro Ser Asn Leu Arg Arg Met
            100                 105                 110

Leu Ser Ser Ser Thr Thr Lys Arg Asp Glu Ser Leu Val Arg Asn
        115                 120                 125

Leu Leu Leu Val Ser Pro Ile Gln Leu Asp Ile Gln Glu Met Leu Leu
    130                 135                 140

Glu Lys Leu Pro Glu Tyr Phe Asp Val Val Thr Gly Cys Ser Leu Glu
145                 150                 155                 160

Glu Asp Val Ala Arg Leu Ile Ile Asn His Phe Arg Thr Leu Asp Phe
                165                 170                 175

Ile Val Asn Pro His Val Phe Thr Asp Lys Leu Met Gln Val Leu Ser
            180                 185                 190

Ile Cys Pro Leu Glu Leu Lys Lys Glu Ile Gly Ser Leu Pro Glu
        195                 200                 205

Ile Ile Gly Asp His Asn Cys Gln Ala Val Val Asp Ser Leu Glu Lys
    210                 215                 220

Met Leu Gln Glu Asp Ser Ala Val Val Val Ala Val Leu Asp Ser Phe
225                 230                 235                 240

Ser Asn Leu Asn Leu Asp Asp Gln Leu Gln Glu Gln Ala Ile Thr Val
                245                 250                 255

Ala Ile Ser Cys Ile Arg Thr Ile Asp Gly Glu His Met Pro Tyr Leu
            260                 265                 270

Leu Arg Phe Leu Leu Leu Ala Ala Thr Pro Val Asn Val Arg Arg Ile
        275                 280                 285

Ile Ser Gln Ile Arg Glu Gln Leu Lys Phe Thr Gly Met Ser Gln Pro
    290                 295                 300

Cys Ala Ser Gln Asn Lys Leu Lys Gly Lys Val Pro Ala Tyr Asn Ala
305                 310                 315                 320

Glu Gly Ser Ile Leu His Ala Leu Arg Ser Ser Leu Arg Phe Lys Asn
                325                 330                 335

Ile Leu Cys Gln Glu Ile Ile Lys Glu Leu Asn Ser Leu Glu Lys Pro
            340                 345                 350

Arg Asp Phe Lys Val Ile Asp Val Trp Leu Leu Ile Asp Met Tyr Met
        355                 360                 365

Asn Gly Asp Pro Val Arg Lys Ser Ile Glu Lys Ile Phe Lys Lys Lys
    370                 375                 380

Val Val Asp Glu Cys Ile Gln Glu Ala Leu Leu Asp Gln Cys Ile Gly
385                 390                 395                 400

Gly Asn Lys Glu Phe Val Lys Ile Leu Gly Ala Leu Val Thr His Val
                405                 410                 415

Gly Ser Asp Asn Lys Phe Glu Val Ser Ser Val Leu Glu Met Met Thr
            420                 425                 430

Ala Leu Val Lys Lys Tyr Ala Gln Gln Leu Leu Pro Phe Ser Ser His
        435                 440                 445

Ile Asn Gly Ile Ser Gly Thr Cys Ile Leu Asp Tyr Leu Glu Gly Phe
    450                 455                 460

Thr Ile Asp Asn Leu His Lys Thr Tyr Ser Gln Val Tyr Glu Val Phe
465                 470                 475                 480

Ser Leu Leu Ala Leu Ser Ala Arg Ala Ser Gly Asp Ser Phe Arg Ser
                485                 490                 495

```
Ser Thr Ser Asn Glu Leu Met Met Ile Val Arg Lys Gln Leu Thr Pro
                500                 505                 510

Ser Cys Leu Val Leu Tyr Trp Gln Val Ser His Pro Asp Leu Lys Tyr
    515                 520                 525

Lys Lys Met Gly Leu Val Gly Ser Leu Arg Ile Val Ser Ser Leu Gly
    530                 535                 540

Asp Ala Lys Ser Val Pro Asp Phe Ser Ser Gln Val Glu Arg Leu
545                 550                 555                 560

Thr Asn Asp Gly Ser Leu Ala Gly Val Asp Ala Leu Leu Gly Cys Pro
                565                 570                 575

Leu His Leu Pro Ser Ser Lys Leu Val Gly Ser Leu Trp Gly Arg Ser
                580                 585                 590

Arg Lys Lys Ser Ser Pro Ser Arg Tyr Ile Met Leu Gln Thr Gly Tyr
                595                 600                 605

Glu Asn Ser Leu Val Thr Leu Pro Cys Ile Phe Cys Asp Leu Leu Asn
            610                 615                 620

Ala Phe Ser Ser Gln Ile Asp Glu Lys Ile Gly Cys Ile Ser Gln Ala
625                 630                 635                 640

Thr Val Lys Asp Val Thr Thr Lys Leu Leu Lys Arg Leu Arg Asn Leu
                645                 650                 655

Val Phe Leu Glu Ser Leu Leu Ser Asn Leu Ile Thr Leu Ser Pro Gln
                660                 665                 670

Ser Leu Pro Glu Leu His Pro Tyr Ser Glu Ser His Val Glu His Pro
                675                 680                 685

Arg Lys Lys Asn Glu Lys Arg Lys Leu Asp Asp Ala Ser Gln Arg
                690                 695                 700

Lys Val Ser Met Lys Asn Asn Leu Lys Lys Ser Lys His Ser Asp Val
705                 710                 715                 720

Asn Glu Lys Leu Arg Gln Pro Thr Ile Met Asp Ala Phe Lys Lys Ala
                725                 730                 735

Gly Ala Val Met Ser His Ser Gln Thr Gln Leu Arg Gly Thr Pro Ser
                740                 745                 750

Leu Pro Ser Met Asp Gly Ser Thr Ala Ala Gly Ser Met Asp Glu Asn
                755                 760                 765

Cys Ser Asp Asn Glu Ser Leu Ile Val Lys Ile Pro Gln Val Ser Ser
                770                 775                 780

Ala Leu Glu Ala Gln Pro Phe Lys Phe Arg Pro Leu Leu Pro Gln Cys
785                 790                 795                 800

Leu Ser Ile Leu Asn Phe Pro Lys Val Leu Ser Gln Asp Met Gly Ser
                805                 810                 815

Pro Glu Tyr Arg Ala Glu Leu Pro Leu Tyr Leu Tyr Leu Leu His Asp
                820                 825                 830

Leu His Thr Lys Leu Asp Cys Leu Val Pro Pro Gly Lys Gln His Pro
                835                 840                 845

Phe Lys Arg Gly Ser Ala Pro Gly Tyr Phe Gly Arg Phe Lys Leu Val
    850                 855                 860

Glu Leu Leu Asn Gln Ile Lys Arg Leu Phe Pro Ser Leu Asn Ile Lys
865                 870                 875                 880

Leu Asn Ile Ala Ile Ser Leu Leu Ile Arg Gly Asp Glu Thr Ser Gln
                885                 890                 895

Thr Thr Trp Arg Asp Glu Phe Ala Leu Ser Gly Asn Pro Asn Thr Ser
                900                 905                 910

Ser Ile Val Val Ser Glu Ser Leu Val Tyr Thr Met Val Cys Lys Glu
```

```
                915                 920                 925
Val Leu Tyr Cys Phe Ser Lys Ile Leu Thr Leu Pro Glu Phe Glu Thr
                930                 935                 940
Asp Lys Ser Leu Leu Leu Asn Leu Leu Glu Ala Phe Gln Pro Thr Glu
945                 950                 955                 960
Ile Pro Val Ala Asn Phe Pro Asp Phe Gln Pro Phe Pro Ser Pro Gly
                965                 970                 975
Thr Lys Glu Tyr Leu Tyr Ile Gly Val Ser Tyr Phe Phe Glu Asp Ile
                980                 985                 990
Leu Asn Lys Gly Asn Tyr Phe Cys Ser Phe Thr Asp Asp Phe Pro Tyr
                995                 1000                1005
Pro Cys Ser Phe Ser Phe Asp Leu Ala Phe Glu Cys Leu Leu Thr
    1010                1015                1020
Leu Gln Leu Val Val Thr Ser Val Gln Lys Tyr Leu Gly Lys Val
    1025                1030                1035
Ser Glu Glu Ala Asn Arg Lys Arg Asn Pro Gly His Phe His Gly
    1040                1045                1050
Leu Val Pro Asn Leu His Ala Lys Leu Gly Thr Ser Ala Glu Lys
    1055                1060                1065
Leu Leu Arg His Lys Trp Val Asp Glu Ser Thr Asp Asn Lys Gly
    1070                1075                1080
Leu Lys Asn Lys Val Cys Pro Phe Val Ser Asn Leu Arg Ile Val
    1085                1090                1095
Gln Phe Thr Gly Glu Met Val Gln Thr Ile Leu Arg Ile Tyr Leu
    1100                1105                1110
Glu Ala Ser Gly Ser Thr Ser Asp Leu Leu Asp Glu Leu Ala Cys
    1115                1120                1125
Thr Ile Leu Pro Gln Ala Ser Leu Ser Lys Ser Thr Gly Glu Asp
    1130                1135                1140
Asp Asp Ala Arg Asp His Glu Phe Pro Thr Leu Cys Ala Ala Thr
    1145                1150                1155
Phe Arg Gly Trp Tyr Lys Thr Leu Leu Glu Glu Asn Leu Ala Ile
    1160                1165                1170
Leu Asn Lys Leu Val Lys Thr Val Ser Ser Glu Lys Arg Gly Asn
    1175                1180                1185
Cys Gln Pro Lys Thr Thr Glu Ala His Leu Lys Asn Ile Gln Lys
    1190                1195                1200
Thr Val Asn Val Val Ser Leu Val Asn Leu Cys Arg Ser His
    1205                1210                1215
Glu Lys Val Thr Ile His Gly Met Ala Ile Lys Tyr Gly Gly Lys
    1220                1225                1230
Tyr Val Asp Ser Phe Leu Lys Gly Ser Leu Lys His Lys Asp Leu
    1235                1240                1245
Arg Gly Gln Ile Val Ser Ser Gln Ala Tyr Ile Asp Asn Glu Ala
    1250                1255                1260
Asp Glu Val Glu Glu Thr Met Ser Gly Glu Glu Glu Pro Met Gln
    1265                1270                1275
Glu Asp Glu Leu Pro Leu Thr Pro
    1280                1285

<210> SEQ ID NO 4
<211> LENGTH: 1471
<212> TYPE: PRT
<213> ORGANISM: Homo sapiens
```

<400> SEQUENCE: 4

```
Met Val Ser Lys Arg Leu Ser Lys Ser Glu Asp Lys Glu Ser Leu
1               5                   10                  15

Thr Glu Asp Ala Ser Lys Thr Arg Lys Gln Pro Leu Ser Lys Lys Thr
                20                  25                  30

Lys Lys Ser His Ile Ala Asn Ala Val Glu Glu Asn Asp Ser Ile Phe
            35                  40                  45

Val Lys Leu Leu Lys Ile Ser Gly Ile Ile Leu Lys Thr Gly Glu Ser
        50                  55                  60

Gln Asn Gln Leu Ala Val Asp Gln Ile Ala Phe Gln Lys Lys Leu Phe
65                  70                  75                  80

Gln Thr Leu Arg Arg His Pro Ser Tyr Pro Lys Ile Ile Glu Glu Phe
                85                  90                  95

Val Ser Gly Leu Glu Ser Tyr Ile Glu Asp Glu Asp Ser Phe Arg Asn
            100                 105                 110

Cys Leu Leu Ser Cys Glu Arg Leu Gln Asp Glu Ala Ser Met Gly
        115                 120                 125

Ala Ser Tyr Ser Lys Ser Leu Ile Lys Leu Leu Leu Gly Ile Asp Ile
    130                 135                 140

Leu Gln Pro Ala Ile Ile Lys Thr Leu Phe Glu Lys Leu Pro Glu Tyr
145                 150                 155                 160

Phe Phe Glu Asn Arg Asn Ser Asp Glu Ile Asn Ile Phe Arg Leu Ile
                165                 170                 175

Val Ser Gln Leu Lys Trp Leu Asp Arg Val Val Asp Gly Lys Asp Leu
            180                 185                 190

Thr Thr Lys Ile Met Gln Leu Ile Ser Ile Ala Pro Glu Asn Leu Gln
        195                 200                 205

His Asp Ile Ile Thr Ser Lys Pro Glu Ile Leu Gly Asp Ser Gln His
    210                 215                 220

Ala Asp Val Gly Lys Glu Leu Ser Asp Leu Leu Ile Glu Asn Thr Ser
225                 230                 235                 240

Leu Thr Val Pro Ile Leu Asp Val Leu Ser Ser Leu Arg Leu Asp Pro
                245                 250                 255

Asn Phe Leu Leu Lys Val Arg Gln Leu Val Met Asp Lys Leu Ser Ser
            260                 265                 270

Ile Arg Leu Glu Asp Leu Pro Val Ile Ile Lys Phe Ile Leu His Ser
        275                 280                 285

Val Thr Ala Met Asp Thr Leu Glu Val Ile Ser Glu Leu Arg Glu Lys
    290                 295                 300

Leu Asp Leu Gln His Cys Val Leu Pro Ser Arg Leu Gln Ala Ser Gln
305                 310                 315                 320

Val Lys Leu Lys Ser Lys Gly Arg Ala Ser Ser Ser Gly Asn Gln Glu
                325                 330                 335

Ser Ser Gly Gln Ser Cys Ile Ile Leu Leu Phe Asp Val Ile Lys Ser
            340                 345                 350

Ala Ile Arg Tyr Glu Lys Thr Ile Ser Glu Ala Trp Ile Lys Ala Ile
        355                 360                 365

Glu Asn Thr Ala Ser Val Ser Glu His Lys Val Phe Asp Leu Val Met
    370                 375                 380

Leu Phe Ile Ile Val Ser Thr Asn Thr Gln Thr Lys Lys Tyr Ile Asp
385                 390                 395                 400

Arg Val Leu Arg Asn Lys Ile Arg Ser Gly Cys Ile Gln Glu Gln Leu
```

```
            405                 410                 415
Leu Gln Ser Thr Phe Ser Val His Tyr Leu Val Leu Lys Asp Met Cys
            420                 425                 430

Ser Ser Ile Leu Ser Leu Ala Gln Ser Leu Leu His Ser Leu Asp Gln
            435                 440                 445

Ser Ile Ile Ser Phe Gly Ser Leu Leu Tyr Lys Tyr Ala Phe Lys Phe
            450                 455                 460

Phe Asp Thr Tyr Cys Gln Gln Glu Val Val Gly Ala Leu Val Thr His
465                 470                 475                 480

Ile Cys Ser Gly Asn Glu Ala Glu Val Asp Asp Ala Leu Asp Val Leu
            485                 490                 495

Leu Glu Leu Val Val Leu Asn Pro Ser Ala Met Met Met Asn Ala Val
            500                 505                 510

Phe Val Gln Gly Ile Leu Asp Tyr Leu Asp Asn Ile Ser Pro Gln Gln
            515                 520                 525

Ile Arg Lys Leu Phe Tyr Val Leu Ser Thr Leu Ala Phe Ser Lys Gln
            530                 535                 540

Asn Glu Ala Ser Ser His Ile Gln Asp Asp Met His Leu Val Ile Arg
545                 550                 555                 560

Lys Gln Leu Ser Ser Thr Val Phe Lys Tyr Lys Leu Ile Gly Ile Ile
                565                 570                 575

Gly Ala Val Thr Met Ala Gly Ile Met Ala Ala Asp Arg Ser Glu Ser
                580                 585                 590

Pro Ser Leu Thr Gln Glu Arg Ala Asn Leu Ser Asp Glu Gln Cys Thr
                595                 600                 605

Gln Val Thr Ser Leu Leu Gln Leu Val His Ser Cys Ser Glu Gln Ser
            610                 615                 620

Pro Gln Ala Ser Ala Leu Tyr Tyr Asp Glu Phe Ala Asn Leu Ile Gln
625                 630                 635                 640

His Glu Lys Leu Asp Pro Lys Ala Leu Glu Trp Val Gly His Thr Ile
                645                 650                 655

Cys Asn Asp Phe Gln Asp Ala Phe Val Val Asp Ser Cys Val Val Pro
                660                 665                 670

Glu Gly Asp Phe Pro Phe Pro Val Lys Ala Leu Tyr Gly Leu Glu Glu
                675                 680                 685

Tyr Asp Thr Gln Asp Gly Ile Ala Ile Asn Leu Leu Pro Leu Leu Phe
                690                 695                 700

Ser Gln Asp Phe Ala Lys Asp Gly Gly Pro Val Thr Ser Gln Glu Ser
705                 710                 715                 720

Gly Gly Lys Leu Val Ser Pro Leu Cys Leu Ala Pro Tyr Phe Arg Leu
                725                 730                 735

Leu Arg Leu Cys Val Glu Arg Gln His Asn Gly Asn Leu Glu Glu Ile
                740                 745                 750

Asp Gly Leu Leu Asp Cys Pro Ile Phe Leu Thr Asp Leu Glu Pro Gly
                755                 760                 765

Glu Lys Leu Glu Ser Met Ser Ala Lys Glu Ala Ser Phe Met Cys Ser
            770                 775                 780

Leu Ile Phe Leu Thr Leu Asn Trp Phe Arg Glu Ile Val Asn Ala Phe
785                 790                 795                 800

Cys Gln Glu Thr Ser Pro Glu Asn Lys Gly Lys Val Leu Thr Arg Leu
                805                 810                 815

Lys His Ile Val Glu Leu Gln Ile Leu Leu Glu Lys Tyr Leu Ala Val
                820                 825                 830
```

```
Thr Pro Asp Tyr Val Pro Pro Leu Gly Asn Phe Asp Val Glu Thr Leu
        835                 840                 845

Asp Ile Thr Pro His Thr Val Thr Ala Ile Ser Ala Lys Ile Arg Lys
    850                 855                 860

Lys Gly Lys Ile Glu Arg Lys Gln Lys Thr Asp Gly Ser Lys Thr Ser
865                 870                 875                 880

Ser Ser Asp Thr Leu Ser Glu Glu Lys Asn Ser Glu Cys Asp Pro Thr
                885                 890                 895

Pro Ser His Arg Gly Gln Leu Asn Lys Glu Phe Thr Gly Lys Glu Glu
            900                 905                 910

Lys Thr Ser Leu Leu His Asn Ser His Ala Phe Phe Arg Glu Leu
        915                 920                 925

Asp Ile Glu Val Phe Ser Ile Leu His Cys Gly Leu Val Thr Lys Phe
    930                 935                 940

Ile Leu Asp Thr Glu Met His Thr Glu Ala Thr Glu Val Val Gln Leu
945                 950                 955                 960

Gly Pro Pro Glu Leu Leu Phe Leu Leu Glu Asp Leu Ser Gln Lys Leu
                965                 970                 975

Glu Ser Met Leu Thr Pro Pro Ile Ala Arg Arg Val Pro Phe Leu Lys
            980                 985                 990

Asn Lys Gly Ser Arg Asn Ile Gly Phe Ser His Leu Gln Gln Arg Ser
        995                 1000                1005

Ala Gln Glu Ile Val His Cys Val Glu Gln Leu Leu Thr Pro Met
    1010                1015                1020

Cys Asn His Leu Glu Asn Ile His Asn Tyr Ile Gln Cys Leu Ala
    1025                1030                1035

Ala Glu Asn His Gly Val Val Asp Gly Pro Gly Val Lys Val Gln
    1040                1045                1050

Glu Tyr His Ile Met Ser Ser Cys Tyr Gln Arg Leu Leu Gln Ile
    1055                1060                1065

Phe His Gly Leu Phe Ala Trp Ser Gly Phe Ser Gln Pro Glu Asn
    1070                1075                1080

Gln Asn Leu Leu Tyr Ser Ala Leu His Val Leu Ser Ser Arg Leu
    1085                1090                1095

Lys Gln Gly Glu His Ser Gln Pro Leu Glu Glu Leu Leu Ser Gln
    1100                1105                1110

Ser Val His Tyr Leu Gln Asn Phe His Gln Ser Ile Pro Ser Phe
    1115                1120                1125

Gln Cys Ala Leu Tyr Leu Ile Arg Leu Leu Met Val Ile Leu Glu
    1130                1135                1140

Lys Ser Thr Ala Ser Ala Gln Asn Lys Glu Lys Ile Ala Ser Leu
    1145                1150                1155

Ala Arg Gln Phe Leu Cys Arg Val Trp Pro Ser Gly Asp Lys Glu
    1160                1165                1170

Lys Ser Asn Ile Ser Asn Asp Gln Leu His Ala Leu Leu Cys Ile
    1175                1180                1185

Tyr Leu Glu His Thr Glu Ser Ile Leu Lys Ala Ile Glu Glu Ile
    1190                1195                1200

Ala Gln Val Gly Val Pro Glu Leu Ile Asn Ser Pro Lys Asp Ala
    1205                1210                1215

Ser Ser Ser Thr Phe Pro Thr Leu Thr Arg His Thr Pro Val Val
    1220                1225                1230
```

| | | | | | | | | | | | |
|---|---|---|---|---|---|---|---|---|---|---|---|
| Phe | Phe 1235 | Arg | Val | Met | Met 1240 | Ala | Glu | Leu | Glu | Lys 1245 | Ile | Val | Lys | Lys |

Phe Phe Arg Val Met Met Ala Glu Leu Glu Lys Ile Val Lys Lys
    1235            1240            1245

Ile Glu Pro Gly Thr Ala Ala Asp Ser Gln Gln Ile His Glu Glu
    1250            1255            1260

Lys Leu Leu Tyr Trp Asn Met Ala Val Arg Asp Phe Ser Ile Leu
    1265            1270            1275

Ile Asn Leu Ile Lys Val Phe Asp Ser His Pro Val Leu His Val
    1280            1285            1290

Cys Leu Lys Val Gly Arg Leu Phe Val Glu Ala Phe Leu Lys Gln
    1295            1300            1305

Cys Met Pro Leu Leu Asp Ile Ser Phe Arg Lys His Arg Glu Asp
    1310            1315            1320

Val Leu Ser Leu Leu Glu Thr Phe Gln Leu Asp Thr Arg Leu Leu
    1325            1330            1335

His His Leu Cys Gly His Ser Lys Ile His Gln Asp Thr Arg Leu
    1340            1345            1350

Thr Gln His Val Pro Leu Leu Lys Lys Thr Leu Glu Leu Leu Val
    1355            1360            1365

Cys Arg Val Lys Ala Met Leu Thr Leu Asn Asn Cys Arg Glu Ala
    1370            1375            1380

Phe Trp Leu Gly Asn Leu Lys Asn Arg Asp Leu Gln Gly Glu Glu
    1385            1390            1395

Ile Lys Ser Gln Asn Ser Gln Glu Ser Thr Ala Asp Glu Ser Glu
    1400            1405            1410

Asp Asp Met Ser Ser Gln Ala Ser Lys Ser Lys Ala Thr Glu Val
    1415            1420            1425

Ser Leu Gln Asn Pro Pro Glu Ser Gly Thr Asp Gly Cys Ile Leu
    1430            1435            1440

Leu Ile Val Leu Ser Trp Trp Ser Arg Thr Leu Pro Thr Tyr Val
    1445            1450            1455

Tyr Cys Gln Met Leu Leu Cys Pro Phe Pro Phe Pro Pro
    1460            1465            1470

<210> SEQ ID NO 5
<211> LENGTH: 5189
<212> TYPE: DNA
<213> ORGANISM: Homo sapiens

<400> SEQUENCE: 5

```
tcgaaaacta cgggcggcga cggcttctcg gaagtaattt aagtgcacaa gacattggtc      60
aaaatggttt ccaaaagaag actgtcaaaa tctgaggata agagagcct gacagaagat      120
gcctccaaaa ccaggaagca accactttcc aaaaagacaa agaaatctca tattgctaat     180
gaagttgaag aaaatgacag catctttgta agcttcttta agatatcagg aattattctt      240
aaaacgggag agagtcagaa tcaactagct gtggatcaaa tagctttcca aaagaagctc     300
tttcagaccc tgaggagaca cccttcctat cccaaaataa tagaagaatt tgttagtggc     360
ctggagtctt acattgagga tgaagacagt ttcaggaact gccttttgtc ttgtgagcgt      420
ctgcaggatg aggaagccag tatgggtgca tcttattcta agagtctcat caaactgctt     480
ctggggattg acatactgca gcctgccatt atcaaaacct atttgagaa gttgccagaa      540
tattttttg aaaacaagaa cagtgatgaa atcaacatac ctcgactcat tgtcagtcaa      600
ctaaaatggc ttgacagagt tgtggatggc aaggacctca ccaccaagat catgcagctg     660
atcagtattg ctccagagaa cctgcagcat gacatcatca ccagcctacc tgagatccta     720
```

```
gggggattccc agcacgctga tgtggggaaa gaactcagtg acctactgat agagaatact      780
tcactcactg tcccaatcct ggatgtcctt caagcctcc  gacttgaccc aaacttccta      840
ttgaaggttc gccagttggt gatggataag ttgtcgtcta ttagattgga ggatttacct      900
gtgataataa agttcattct tcattccgta acagccatgg atacacttga ggtaatttct      960
gagcttcggg agaagttgga tctgcagcat tgtgttttgc catcacggtt acaggcttcc     1020
caagtaaagt tgaaaagtaa aggacgagca agttcctcag gaaatcaaga aagcagcggt     1080
cagagctgta ttattctcct ctttgatgta ataaagtcag ctattagata tgagaaaacc     1140
atttcagaag cctggattaa ggcaattgaa aacactgcct cagtatctga acacaaggtg     1200
tttgacctgg tgatgctttt catcatctat agcaccaata ctcagacaaa gaagtacatt     1260
gacagggtgc taagaaataa gattcgatca ggctgcattc aagaacagct gctccagagt     1320
acattctctg ttcattactt agttcttaag gatatgtgtt catccattct gtcgctggct     1380
cagagtttgc ttcactctct agaccagagt ataatttcat ttggcagtct cctatacaaa     1440
tatgcattta gttttttga  cacgtactgc cagcaggaag tggttggtgc cttagtgacc     1500
catatctgca gtgggaatga agctgaagtt gatactgcct tagatgtcct tctagagttg     1560
gtagtgttaa acccatctgc tatgatgatg aatgctgtct ttgtaaaggg catttttagat     1620 tatctggata acatatcccc tcagcaaata cgaaaactct tctatgttct cagcacactg     1680
gcatttagca aacagaatga agccagcagc cacatccagg atgacatgca cttggtgata     1740
agaaagcagc tctctagcac cgtattcaag tacaagctca ttgggattat tggtgctgtg     1800
accatggctg gcatcatggc ggcagacaga agtgaatcac ctagtttgac ccaagagaga     1860
gccaacctga gcgatgagca gtgcacacag gtgacctcct tgttgcagtt ggttcattcc     1920
tgcagtgagc agtctcctca ggcctctgca ctttactatg atgaatttgc caacctgatc     1980
caacatgaaa agctggatcc aaaagccctg gaatgggttg gcataccat  ctgtaatgat     2040 ttccaggatg ccttcgtagt ggactcctgt gttgttccgg aaggtgactt tccatttcct     2100
gtgaaagcac tgtacggact ggaagaatac gacactcagg atgggattgc cataaacctc     2160
ctgccgctgc tgttttctca ggactttgca aaagatgggg gtccggtgac ctcacaggaa     2220
tcaggccaaa aattggtgtc tccgctgtgc ctggctccgt atttccggtt actgagactt     2280
tgtgtggaga acagcataa  cggaaacttg gaggagattg atggtctact agattgtcct     2340
atattcctaa ctgacctgga gcctggagag aagttggagt ccatgtctgc taaagagcgt     2400
tcattcatgt gttctctcat atttcttact ctcaactggt tccagagagat tgtaaatgcc     2460 ttctgccagg aaacatcacc tgagatgaag gggaaggtgc tcactcggtt aaagcacatt     2520
gtagaattgc aaataatcct ggaaaagtac ttggcagtca ccccagacta tgtccctcct     2580
cttggaaact ttgatgtgga aactttagat ataacacctc atactgttac tgctatttca     2640
gcaaaaatca gaaagaaagg aaaatagaa  aggaaacaaa aaacagatgg cagcaagaca     2700
tcctcctctg acacactttc agaagagaaa aattcagaat gtgacctac  gccatctcat     2760 agaggccagc taaacaagga gttcacaggg aaggaagaaa agacatcatt gttactacat     2820
aattcccatg ctttttccg  agagctggac attgaggtct tctctattct acattgtgga     2880
cttgtgacga agttcatctt agatactgaa atgcacactg aagctacaga agttgtgcaa     2940
cttgggcccc ctgagctgct tttcttgctg gaagatctct cccagaagct ggagagtatg     3000
ctgacacctc ctattgccag gagagtcccc tttctcaaga acaaaggaag ccggaatatt     3060
```

```
ggattctcac atctccaaca gagatctgcc caagaaattg ttcattgtgt tttcaactg    3120
ctgaccccaa tgtgtaacca cctggagaac attcacaact attttcagtg tttagctgct    3180
gagaatcacg gtgtagttga tggaccagga gtgaaagttc aggagtacca cataatgtct    3240
tcctgctatc agaggctgct gcagattttt catgggcttt ttgcttggag tggattttct    3300
caacctgaaa atcagaattt actgtattca gccctccatg tccttagtag ccgactgaaa    3360
cagggagaac acagccagcc tttggaggaa ctactcagcc agagcgtcca ttacttgcag    3420
aatttccatc aaagcattcc cagtttccag tgtgctcttt atctcatcag acttttgatg    3480
gttattttgg agaaatcaac agcttctgct cagaacaaag aaaaaattgc ttcccttgcc    3540
agacaattcc tctgtcgggt gtggccaagt ggggataaag agaagagcaa catctctaat    3600
gaccagctcc atgctctgct ctgtatctac ctggagcaca cagagagcat tctgaaggcc    3660
atagaggaga ttgctggtgt tggtgtccca gaactgatca actctcctaa agatgcatct    3720
tcctccacat tccctacact gaccaggcat acttttgttg ttttcttccg tgtgatgatg    3780
gctgaactag agaagacggt gaaaaaaatt gagcctggca cagcagcaga ctcgcagcag    3840
attcatgaag agaaactcct ctactggaac atggctgttc gagacttcag tatcctcatc    3900
aacttgataa aggtatttga tagtcatcct gttctgcatg tatgtttgaa gtatgggcgt    3960
ctctttgtgg aagcatttct gaagcaatgt atgccgctcc tagacttcag ttttagaaaa    4020
caccgggaag atgttctgag cttactggaa accttccagt tggacacaag gctgcttcat    4080
cacctgtgtg ggcattccaa gattcaccag gacacgagac tcacccaaca tgtgcctctg    4140
ctcaaaaaga ccctggaact tttagtttgc agagtcaaag ctatgctcac tctcaacaat    4200
tgtagagagg ctttctggct gggcaatcta aaaaaccggg acttgcaggg tgaagagatt    4260
aagtcccaaa attcccagga gagcacagca gatgagagtg aggatgacat gtcatcccag    4320
gcctccaaga gcaaagccac tgaggtatct ctacaaaacc caccagagtc tggcactgat    4380
ggttgcattt tgttaattgt tctaagttgg tggagcagaa ctttgcctac ttatgtttat    4440
tgtcaaatgc ttctatgccc atttccattc cctccataac agcttctgtg cttatataat    4500
tttgggacc cagaagaaac aacgacacaa tcttagaatc actcctgagt atctcgagtt    4560
gtggcatttg ttatagagtt gacaattttc tgcattatag cctctcattt tccatgaatt    4620
catatctgaa accattttag aagggagaag tcatcgaagt attttctgag tgttgagaag    4680
aatgagttaa accatttaaa cacatttgaa acatacaaaa atagaaatgt gaaagcattt    4740
ggtgaaagcc aaagcacaga gtcagaagct gccaccttag agaactgaaa taaaaataga    4800
agttcttacg ctttttttgtg gtacagatgc tttcgacaat ttaaagaaag ctaaataaaa    4860
atgtagacat ggctggcgca gtggctcatg cttgtaatcc tagcacttt tgaggccaag    4920
gtaggaggat tgcttgagtc cgggagctca aggcaaagct gcacaacata caagaccct    4980
atctccacaa aaaaatgaa aaataaacct gggtgcggtg gctcacacct gtaatcccag    5040
cactttggga ggccgatgtg ggcagatcac aaggtcagga ggtcaagacc agcctggcca    5100
acatagtgaa accccatctc tactgaaaat acaaaaatta gctgggtgtg gtggcacgtg    5160
cctgttatct cagctacttg ggaagctga                                      5189
```

<210> SEQ ID NO 6
<211> LENGTH: 5194
<212> TYPE: DNA
<213> ORGANISM: Homo sapiens

<400> SEQUENCE: 6

```
tagaatcgaa aactacgggc ggcgacggct tctcggaagt aatttaagtg cacaagacat    60
tggtcaaaat ggtttccaaa agaagactgt caaaatctga ggataaagag agcctgacag   120
aagatgcctc caaaaccagg aagcaaccac tttccaaaaa gacaaagaaa tctcatattg   180
ctaatgaagt tgaagaaaat gacagcatct ttgtaaagct tcttaagata tcaggaatta   240
ttcttaaaac gggagagagt cagaatcaac tagctgtgga tcaaatagct ttccaaaaga   300
agctctttca gaccctgagg agacacccct cctatcccaa aataatgaaa gaatttgtta   360
gtggcctgga gtcttacatt gaggatgaag acagtttcag gaactgcctt ttgtcttgtg   420
agcgtctgca ggatgaggaa gccagtatgg gtgcatctta ttctaagagt ctcatcaaac   480
tgcttctggg gattgacata ctgcagcctg ccattatcaa aaccttattt gagaagttgc   540
cagaatattt ttttgaaaac aagaacagtg atgaaatcaa catacctcga ctcattgtca   600
gtcaactaaa atggcttgac agagttgtgg atggcaagga cctcaccacc aagatcatgc   660
agctgatcag tattgctcca gagaacctgc agcatgacat catcaccagc ctacctgaga   720
tcctagggga ttcccagcac gctgatgtgg ggaaagaact cagtgaccta ctgatagaga   780
atacttcact cactgtccca atcctggatg tcctttcaag cctccgactt gacccaaact   840
tcctattgaa ggttcgccag ttggtgatgg ataagttgtc gtctattaga ttggaggatt   900
tacctgtgat aataaagttc attcttcatt ccgtaacagc catggataca cttgaggtaa   960
tttctgagct tcgggagaag ttggatctgc agcattgtgt tttgccatca cggttacagg  1020
cttcccaagt aaagttgaaa agtaaaggac gagcaagttc ctcaggaaat caagaaagca  1080
gcggtcagag ctgtattatt ctcctctttg atgtaataaa gtcagctatt agatatgaga  1140
aaaccatttc agaagcctgg attaaggcaa ttgaaaacac tgcctcagta tctgaacaca  1200
aggtgtttga cctggtgatg ctttttcatca tctatagcac caatactcag acaaagaagt  1260
acattgacag ggtgctaaga aataagattc gatcaggctg cattcaagaa cagctgctcc  1320
agagtacatt ctctgttcat tacttagttc ttaaggatat gtgttcatcc attctgtcgc  1380
tggctcagag tttgcttcac tctctagacc agagtataat ttcatttggc agtctcctat  1440
acaaatatgc atttaagttt tttgacacgt actgccagca ggaagtggtt ggtgccttag  1500
tgacccatat ctgcagtggg aatgaagctg aagttgatac tgccttagat gtccttctag  1560
agttggtagt gttaaaccca tctgctatga tgatgaatgc tgtctttgta aagggcattt  1620
tagattatct ggataacata tccccctcagc aaatacgaaa actcttctat gttctcagca  1680
cactggcatt tagcaaacag aatgaagcca gcagccacat ccaggatgac atgcacttgg  1740
tgataagaaa gcagctctct agcaccgtat tcaagtacaa gctcattggg attattggtg  1800
ctgtgaccat ggctggcatc atggcggcag acagaagtga atcacctagt ttgacccaag  1860
agagagccaa cctgagcgat gagcagtgca cacaggtgac ctccttgttg cagttggttc  1920
attcctgcag tgagcagtct cctcaggcct ctgcacttta ctatgatgaa tttgccaacc  1980
tgatccaaca tgaaaagctg gatccaaaag ccctggaatg ggttgggcat accatctgta  2040
atgatttcca ggatgccttc gtagtggact cctgtgttgt tccggaaggt gactttccat  2100
ttcctgtgaa agcactgtac ggactggaag aatacgacac tcaggatggg attgccataa  2160
acctcctgcc gctgctgttt tctcaggact tgcaaaaga tgggggtccg gtgacctcac  2220
aggaatcagg ccaaaaattg gtgtctccgc tgtgcctggc tccgtatttc cggttactga  2280
gactttgtgt ggagagacag cataacggaa acttggagga gattgatggt ctactagatt  2340
```

```
gtcctatatt cctaactgac ctggagcctg gagagaagtt ggagtccatg tctgctaaag      2400
agcgttcatt catgtgttct ctcatatttc ttactctcaa ctggttccga gagattgtaa      2460
atgccttctg ccaggaaaca tcacctgaga tgaaggggaa ggtgctcact cggttaaagc      2520
acattgtaga attgcaaata atcctggaaa agtacttggc agtcacccca gactatgtcc      2580
ctcctcttgg aaactttgat gtggaaactt tagatataac acctcatact gttactgcta      2640
tttcagcaaa aatcagaaag aaaggaaaaa tagaaaggaa acaaaaaaca gatggcagca      2700
agacatcctc ctctgacaca cttttcagaag agaaaaattc agaatgtgac cctacgccat      2760
ctcatagagg ccagctaaac aaggagttca cagggaagga agaaaagaca tcattgttac      2820
tacataattc ccatgctttt ttccgagagc tggacattga ggtcttctct attctacatt      2880
gtggacttgt gacgaagttc atcttagata ctgaaatgca cactgaagct acagaagttg      2940
tgcaacttgg gccccctgag ctgcttttct tgctggaaga tctctcccag aagctggaga      3000
gtatgctgac acctcctatt gccaggagag tcccctttct caagaacaaa ggaagccgga      3060
atattggatt ctcacatctc caacagagat ctgcccaaga aattgttcat tgtgttttc       3120 aactgctgac cccaatgtgt aaccacctgg agaacattca aactattttt cagtgtttag      3180
ctgctgagaa tcacggtgta gttgatggac caggagtgaa agttcaggag taccacataa      3240
tgtcttcctg ctatcagagg ctgctgcaga ttttcatgg gcttttgct tggagtggat        3300 tttctcaacc tgaaaatcag aatttactgt attcagccct ccatgtcctt agtagccgac      3360
tgaaacaggg agaacacagc cagcctttgg aggaactact cagccagagc gtccattact      3420
tgcagaattt ccatcaaagc attcccagtt ccagtgtgc tctttatctc atcagacttt       3480
tgatggttat tttggagaaa tcaacagctt ctgctcagaa caaagaaaaa attgcttccc      3540
ttgccagaca attcctctgt cgggtgtggc caagtgggga taaagagaag agcaacatct      3600
ctaatgacca gctccatgct ctgctctgta tctacctgga gcacacagag agcattctga      3660
aggccataga ggagattgct ggtgttggtg tcccagaact gatcaactct cctaaagatg      3720
catcttcctc cacattccct acactgacca ggcatacttt tgttgttttc ttccgtgtga      3780
tgatggctga actagagaag acggtgaaaa aaattgagcc tggcacagca gcagactcgc      3840
agcagattca tgaagagaaa ctcctctact ggaacatggc tgttcgagac ttcagtatcc      3900
tcatcaactt gataaaggta tttgatagtc atcctgttct gcatgtatgt ttgaagtatg      3960
ggcgtctctt tgtggaagca tttctgaagc aatgtatgcc gctcctagac ttcagttta       4020 gaaaacaccg ggaagatgtt ctgagcttac tggaaacctt ccagttggac acaaggctgc      4080
ttcatcacct gtgtgggcat tccaagattc accaggacac gagactcacc caacatgtgc      4140
ctctgctcaa aaagaccctg gaactttag tttgcagagt caaagctatg ctcactctca       4200
acaattgtag agaggctttc tggctgggca atctaaaaaa ccgggacttg cagggtgaag      4260
agattaagtc ccaaaattcc caggagagca cagcagatga gagtgaggat gacatgtcat      4320
cccaggcctc caagagcaaa gccactgagg tatctctaca aaaccaccacca gagtctggca    4380 ctgatggttg cattttgtta attgttctaa gttggtggag cagaactttg cctacttatg      4440
tttattgtca aatgcttcta tgcccatttc cattccctcc ataacagctt ctgtgcttat      4500
ataatttttg ggacccagaa gaaacaacga cacaatctta gaatcactcc tgagtatctc      4560
gagttgtggc atttgttata gagttgacaa ttttctgcat tatagcctct cattttccat      4620 gaattctat ctgaaaccat tttagaaggg agaagtcatc gaagtattt ctgagtgttg        4680 agaagaatga gttaaaccat ttaaacacat ttgaaacata caaaaataga aatgtgaaag      4740
```

| | |
|---|---|
| catttggtga aagccaaagc acagagtcag aagctgccac cttagagaac tgaaataaaa | 4800 |
| atagaagttc ttacgctttt ttgtggtaca gatgctttcg acaatttaaa gaaagctaaa | 4860 |
| taaaaatgta gacatggctg gcgcagtggc tcatgcttgt aatcctagca cttttttgagg | 4920 |
| ccaaggtagg aggattgctt gagtccggga gctcaaggca aagctgcaca acataacaag | 4980 |
| accctatctc cacaaaaaaa atgaaaaata aacctgggtg cggtggctca cacctgtaat | 5040 |
| cccagcactt tgggaggccg atgtgggcag atcacaaggt caggagttca agaccagcct | 5100 |
| ggccaacata gtgaaacccc atctctactg aaaatacaaa aattagctgg gtgtggtggc | 5160 |
| acgtgcctgt tatctcagct acttgggaag ctga | 5194 |

<210> SEQ ID NO 7
<211> LENGTH: 4455
<212> TYPE: DNA
<213> ORGANISM: Homo sapiens

<400> SEQUENCE: 7

| | |
|---|---|
| tcgaaaacta cgggcggcga cggcttctcg gaagtaattt aagtgcacaa gacattggtc | 60 |
| aaaatggttt ccaaaagaag actgtcaaaa tctgaggata aagagagcct gacagaagat | 120 |
| gcctccaaaa ccaggaagca accactttcc aaaaagacaa agaaatctca tattgctaat | 180 |
| gaagttgaag aaaatgacag catctttgta aagcttctta agatatcagg aattattctt | 240 |
| aaaacgggag agagtcagaa tcaactagct gtggatcaaa tagcttttcca aaagaagctc | 300 |
| tttcagaccc tgaggagaca cccttcctat cccaaaataa tagaagaatt tgttagtggc | 360 |
| ctggagtctt acattgagga tgaagacagt ttcaggaact gccttttgtc ttgtgagcgt | 420 |
| ctgcaggatg aggaagccag tatgggtgca tcttattcta agagtctcat caaactgctt | 480 |
| ctggggattg acatactgca gcctgccatt atcaaaacct atttgagaa gttgccagaa | 540 |
| tattttttg aaaacaagaa cagtgatgaa atcaacatac ctcgactcat tgtcagtcaa | 600 |
| ctaaaatggc ttgacagagt tgtggatggc aaggacctca ccaccaagat catgcagctg | 660 |
| atcagtattg ctccagagaa cctgcagcat gacatcatca ccagcctacc tgagatccta | 720 |
| ggggattccc agcacgctga tgtggggaaa gaactcagtg acctactgat agagaatact | 780 |
| tcactcactg tcccaatcct ggatgtcctt tcaagcctcc gacttgaccc aaacttccta | 840 |
| ttgaaggttc gccagttggt gatggataag ttgtcgtcta ttagattgga ggatttaccc | 900 |
| gtgataataa agttcattct tcattccgta acagccatgg atacacttga ggtaatttct | 960 |
| gagcttcggg agaagttgga tctgcagcat tgtgttttgc catcacggtt acaggcttcc | 1020 |
| caagtaaagt tgaaaagtaa aggacgagca agttcctcag gaaatcaaga aagcagcggt | 1080 |
| cagagctgta ttattctcct ctttgatgta ataaagtcag ctattagata tgagaaaacc | 1140 |
| atttcagaag cctggattaa ggcaattgaa aacactgcct cagtatctga acacaaggtg | 1200 |
| tttgacctgg tgatgctttt catcatctat agcaccaata tcagacaaa gaagtacatt | 1260 |
| gacagggtgc taagaaataa gattcgatca ggctgcattc aagaacagct gctccagagt | 1320 |
| acattctctg ttcattactt agttcttaag gatatgtgtt catccattct gtcgctggct | 1380 |
| cagagtttgc ttcactctct agaccagagt ataatttcat ttggcagtct cctatacaaa | 1440 |
| tatgcattta gttttttga cacgtactgc cagcaggaag tggttggtgc cttagtgacc | 1500 |
| catatctgca gtgggaatga agctgaagtt gatactgcct tagatgtcct tctagagttg | 1560 |
| gtagtgttaa acccatctgc tatgatgatg aatgctgtct ttgtaaaggg catttagat | 1620 |

-continued

| | |
|---|---|
| tatctggata acatatcccc tcagcaaata cgaaaactct tctatgttct cagcacactg | 1680 |
| gcatttagca acagaatga agccagcagc cacatccagg atgacatgca cttggtgata | 1740 |
| agaaagcagc tctctagcac cgtattcaag tacaagctca ttgggattat tggtgctgtg | 1800 |
| accatggctg gcatcatggc ggcagacaga agtgaatcac ctagtttgac ccaagagaga | 1860 |
| gccaacctga gcgatgagca gtgcacacag gtgacctcct tgttgcagtt ggttcattcc | 1920 |
| tgcagtgagc agtctcctca ggcctctgca ctttactatg atgaatttgc caacctgatc | 1980 |
| caacatgaaa agctggatcc aaaagccctg gaatggggttg ggcataccat ctgtaatgat | 2040 |
| ttccaggatg ccttcgtagt ggactcctgt gttgttccgg aaggtgactt tccatttcct | 2100 |
| gtgaaagcac tgtacggact ggaagaatac gacactcagg atgggattgc cataaacctc | 2160 |
| ctgccgctgc tgttttctca ggactttgca aaagatgggg gtccggtgac ctcacaggaa | 2220 |
| tcaggccaaa aattggtgtc tccgctgtgc ctggctccgt atttccggtt actgagactt | 2280 |
| tgtgtggaga gacagcataa cggaaacttg gaggagattg atggtctact agattgtcct | 2340 |
| atattcctaa ctgacctgga gcctggagag aagttggagt ccatgtctgc taagagcgt | 2400 |
| tcattcatgt gttctctcat atttcttact ctcaactggt tccgagagat tgtaaatgcc | 2460 |
| ttctgccagg aaacatcacc tgagatgaag gggaaggtgc tcactcggtt aaagcacatt | 2520 |
| gtagaattgc aaataatcct ggaaaagtac ttggcagtca ccccagacta tgtccctcct | 2580 |
| cttggaaact ttgatgtgga aactttagat ataacacctc atactgttac tgctatttca | 2640 |
| gcaaaaatca gaaagaaagg aaaaatagaa aggaaacaaa aacagatgg cagcaagaca | 2700 |
| tcctcctctg acacactttc agaagagaaa aattcagaat gtgaccctac gccatctcat | 2760 |
| agaggccagc taaacaagga gttcacaggg aaggaagaaa agacatcatt gttactacat | 2820 |
| aattcccatg cttttttccg agagctggac attgaggtct tctctattct acattgtgga | 2880 |
| cttgtgacga agttcatctt agatactgaa atgcacactg aagctacaga agttgtgcaa | 2940 |
| cttgggcccc ctgagctgct tttcttgctg gaagatctct cccagaagct ggagagtatg | 3000 |
| ctgacacctc ctattgccag gagagtcccc tttctcaaga caaaggaag ccggaatatt | 3060 |
| ggattctcac atctccaaca gagatctgcc caagaaattg ttcattgtgt ttttcaactg | 3120 |
| ctgacccaa tgtgtaacca cctggagaac attcacaact attttcagtg tttagctgct | 3180 |
| gagaatcacg gtgtagttga tggaccagga gtgaaagttc aggagtacca cataatgtct | 3240 |
| tcctgctatc agaggctgct gcagattttt catgggcttt ttgcttggag tggatttttct | 3300 |
| caacctgaaa atcagaattt actgtattca gccctccatg tccttagtag ccgactgaaa | 3360 |
| cagggagaac acagccagcc tttggaggaa ctactcagcc agagcgtcca ttacttgcag | 3420 |
| aatttccatc aaagcattcc cagtttccag tgtgctcttt atctcatcag acttttgatg | 3480 |
| gttattttgg agaaatcaac agcttctgct cagaacaaag aaaaaattgc ttcccttgcc | 3540 |
| agacaattcc tctgtcgggt gtggccaagt ggggataaag agaagagcaa catctctaat | 3600 |
| gaccagctcc atgctctgct ctgtatctac ctggagcaca cagagagcat tctgaaggcc | 3660 |
| atagaggaga ttgctggtgt tggtgtccca gaactgatca actctcctaa agatgcatct | 3720 |
| tcctccacat tccctacact gaccaggcat acttttgttg ttttcttccg tgtgatgatg | 3780 |
| gctgaactag agaagacggt gaaaaaaatt gagcctggca cagcagcaga ctcgcagcag | 3840 |
| attcatgaag agaaactcct ctactggaac atggctgttc gagacttcag tatcctcatc | 3900 |
| aacttgataa aggtatttga tagtcatcct gttctgcatg tatgtttgaa gtatgggcgt | 3960 |
| ctctttgtgg aagcatttct gaagcaatgt atgccgctcc tagacttcag ttttagaaaa | 4020 |

| | |
|---|---|
| caccgggaag atgttctgag cttactggaa accttccagt tggacacaag gctgcttcat | 4080 |
| cacctgtgtg ggcattccaa gattcaccag gacacgagac tcacccaaca tgtgcctctg | 4140 |
| ctcaaaaaga ccctggaact tttagtttgc agagtcaaag ctatgctcac tctcaacaat | 4200 |
| tgtagagagg ctttctggct gggcaatcta aaaaaccggg acttgcaggg tgaagagatt | 4260 |
| aagtcccaaa attcccagga gagcacagca gatgagagtg aggatgacat gtcatcccag | 4320 |
| gcctccaaga gcaaagccac tgaggatggt gaagaagacg aagtaagtgc tggagaaaag | 4380 |
| gagcaagata gtgatgagag ttatgatgac tctgattaga ccccagataa attgttgcct | 4440 |
| gcttctgtgt ctcaa | 4455 |

<210> SEQ ID NO 8
<211> LENGTH: 5516
<212> TYPE: DNA
<213> ORGANISM: Mus musculus

<400> SEQUENCE: 8

| | |
|---|---|
| ggaaagtcga aaacgaaggg aagcaactgg cgggtcccca ggaagtaata taagtggcag | 60 |
| aagacgttag tcaaaatgat ttccaaaaga cgtcggctag attctgagga taaagaaaac | 120 |
| ctgacagaag atgcctccaa aaccatgccc ctttccaagc tggcaaagaa gtctcacaat | 180 |
| tctcatgaag ttgaagaaaa tggcagtgtc tttgtaaagc ttcttaaggc ttcaggactc | 240 |
| actcttaaaa ctggagagaa ccaaaatcag ctaggtgtgg atcaggtaat cttccaaagg | 300 |
| aagctctttc aggccttgag gaagcatcct gcttatccca agtaataga agagtttgtt | 360 |
| aatggcctgg agtcctacac tgaggacagt gagagtctca ggaactgcct gctgtcttgt | 420 |
| gagcgcctgc aggatgagga agccagcatg ggcacatttt actccaagag tctgatcaag | 480 |
| ctacttctgg ggattgacat tttacagcct gccattatca aaatgttatt tgaaaaagtg | 540 |
| cctcagtttc tttttgaaag tgagaacaga gatggaatca acatggccag actcattatc | 600 |
| aatcaactaa aatggctgga tagaattgtg gatggcaagg acctcacggc ccagatgatg | 660 |
| cagttgatca gtgttgctcc cgtgaactta cagcatgact tcatcacgag ccttcctgaa | 720 |
| atcctagggg attcccagca tgctaatgtg gggaaagagc ttggcgagct gctggtgcag | 780 |
| aatacttccc tgactgttcc aattttggat gtcttttcca gtctccgact tgaccccaac | 840 |
| ttcctgtcca agatccgcca gttggtgatg ggcaagctgt catctgtccg tctagaggat | 900 |
| ttccctgtga ttgtaaagtt ccttcttcat tctgtaacag acaccacttc ccttgaggtc | 960 |
| attgccgagc ttcgggagaa cttgaacgtc cagcagttta ttttgccgtc acgaattcag | 1020 |
| gcttcccaaa gcaaattgaa aagtaaagga ctagcaagct cttcaggaaa tcaagagaac | 1080 |
| agtgataaag actgtattgt tcttgtcttt gatgtaataa agtcagccat tagatatgag | 1140 |
| aaaaccattt cagaggcctg gtttaaggca attgaacgca ttgagtccgc ggctgaacat | 1200 |
| aaggctttgg acgtggtcat gctgctcatc atctacagca ccagcacgca gaccaagaag | 1260 |
| ggcgtggaga agctgctgag aaacaagatt cagtcagact gcattcaaga acagctgctt | 1320 |
| gacagtgcgt tctctacaca ttacctggtt cttaaggata tttgcccatc tattcttttg | 1380 |
| ctggctcaga ctttgtttca ctctcaagac cagaggatca ttttgtttgg cagtcttctg | 1440 |
| tacaaatatg cttttaagtt ttttgatact tactgccagc aggaagtggt tggtgcccta | 1500 |
| gtcacccatg tctgcagtgg gactgaggct gaagtcgaca ctgcactgga tgtcctcctg | 1560 |
| gagctgattg tgctaaacgc ctctgctatg aggctcaatg ctgcttttgt taagggcatc | 1620 |

```
ttagattatt tggaaaatat gtcccctcag caaatacgaa aaatcttctg tattctcagc   1680
actcttgcat ttagccaaca gcccggaacc agcaaccata tccaggacga catgcacctg   1740
gtgatccgga agcagctctc tagcactgtg ttcaagtaca agctcattgg gatcattggt   1800
gcagtcacca tggccggcat catggcggaa gacagaagtg taccatctaa ctcatcccag   1860
aggagcgcca atgtgagcag tgagcagcgc acacaggtga cttctttgct acaactagtt   1920
cattcttgca ctgagcactc tccttgggcc tcttctctgt attatgatga atttgccaac   1980
ctgatccaag aaggaagtt ggctccaaaa accttggagt gggttgggca gaccatcttc    2040
aatgatttcc aagatgcctt tgtggtagac ttctgtgctg ctccagaggg tgactttcca   2100
tttcctgtga agcgctcta tggactggaa gagtacagca ctcaagacgg cattgtcatc    2160
aacctcctgc cgctgttcta tcaggaatgt gcaaaagatg ccagtcgagc gacatcacaa   2220
gaatcgagcc agagatcaat gtcttctttg tgcctggctt cccatttccg gctgctgaga   2280 cttttgcgtgg caagacaaca tgatggaaac ttggatgaga tcgatggtct cttagattgt   2340
cccctgttcc tccctgacct ggaacctgga gagaaactgg agtccatgtc tgctaaagac   2400
cgttcgctta tgtgttcgct cacattccta actttcaact ggttccgaga ggttgtgaat   2460
gccttctgcc aacaaacatc tcctgagatg aagggcaagg ttcttagtcg gctaaaggac   2520
cttgtagaac ttcagggaat cctagagaag tacttggcag tcatcccaga ctatgttccg   2580
cctttcgcaa gcgttgactt ggacacttta gatatgatgc ctaggagcag ttctgctgtt   2640
gcagcaaaaa acagaaacaa gggaaagacg gggggaaaga acaaaaaagc tgatagcaac   2700
aaagcatcct gttcggacac acttctaaca gaagacactt cagagtgtga catggcgcca   2760
tctgggagaa gccacgtaga caaggagtcc acagggaagg aaggaaagac gtttgtgtca   2820
ctgcagaatt accgcgcttt tttccgagag ctggacattg aggtcttctc tattctacat   2880
tctggacttg tgaccaagtt catcttagac actgaaatgc acactgaagc tacagaggtc   2940
gtacagctgg ggcctgctga gctgctcttc ttgctggaag atctttccca gaagctagag   3000
aatatgctga ctgctccttt tgccaagaga atctgctgct ttaagaataa aggaaggcag   3060
aatattggct tctcacatct tcatcagaga tctgtccagg acattgtgca ctgtgtggtt   3120
cagctgctaa ccccgatgtg taaccatctg gagaacattc acaacttctt tcagtgctta   3180
ggtgctgagc atctcagtgc agatgacaag gcgagagcga cagctcagga gcagcacacc   3240
atggcctgct gctaccagaa gctgctgcag gtcttgcacg cgctctttgc gtggaaggga   3300
tttactcacc aatcaaagca ccgcctcctg cactcagccc ttgaggtcct ctcgaaccga   3360
ctaaagcaga tggaacagga ccagcccttg gaggaactgg tcagccagag cttcagttac   3420
ttgcagaact tccaccatag tgttcccagt ttccagtgtg gtctctacct tctcagactt   3480
ctgatggccc ttctggagaa gtctgcagta cctaaccaga agaaagaaaa acttgcctct   3540
ctggccaaac agctgctttg ccgagcatgg cctcatgggg aaaaagagaa gaacccccact  3600 tttaatgacc acctgcatga tgtgcttac atctacttgg agcacacaga caatgttctg    3660
aaggccatag aggagatyac tggtgttggt gtcccagaac tggtcagtgc tccgaaagac   3720
gccgcctcct ctacattccc tacgttgacc grgcacacct ttgtcatatt cttccgtgtg   3780
atgatggctg aactcgagaa gacggtgaag ggtctycagg ctggcacagc agcagattcg   3840
cagcaggttc acgaagagaa gctcctctat tkgaacatgg ctgtccgaga tttcagyatc   3900
cttytcaatc tgatgaaagt atttgacagt tatcctgttc tgcatgtgtg tttaaagtat   3960
ggccgtcgct ttgtggaggc atttctgaag caatgtatgc cactcctcga cttcagcttt   4020
```

```
agaaagcatc gggaagatgt tctgagcttg ctgcaaaccc ttcagttgaa cacgaggcta    4080
cttcatcacc tttgtggaca ctccaagatt cgccaggaca caagactcac caagcaygtg    4140
cctttactca aaaagtcact ggaactgtta gtttgcagag tcaaagccat gcttgtcctc    4200
aacaactgta gagaggcttt ctggtttggg t actctcaaaa accgagactt acagggtgaa    4260
gaaattattt cccaggatcc ctcttcctca gagagcaatg cagaggacag tgaggatggc    4320
gtgacatctc acgtctccag gaacagagca acagaggatg gggaagatga agcaagtgat    4380
gaacagaagg accaggacag tgatgaaagt gacgacagct ccagttagag ccgagtggca    4440
tggctgccct gctcacctct gacagactct catctctttg gggtttgaag tcagatgtct    4500 gttttttctag tcagaagcat cctgtttgtc catcaagaag gggtgtttat ttaattcccc    4560
agtgggtttc acaggttgtc taacctccag gtccctggtt caggagtcca gtgtagcatc    4620
catcgttgac taggaygaac atggctgggc tgcagtgcag tkcagtgcag gtgccctagc    4680
tgggccttgg ggttttgaaa ctaaaattta ggcttataat agctttgtaa ataaatctgt    4740
ttcagagttt tgcctcagct accttttttcc tcactttaga tgtgattatt caaggatctc    4800
attattcaag gattaggtaa tattgagttg aggtttgtgc aatcgtactg gtggcctaaa    4860
agtatgttcc gtactgttat cttcctggag gaatgaccca actttcttat caatgatcaa    4920
gtgtttggtt tggtctgtgt cagggtctct ttacatagtc ctggctggtg tgttattaga    4980
tatgttgacc aggagggtct tgaacattac ttttgaattt taaacatttt tgtacatatg    5040
tgtatgggca tatatgtgcc actgtgcata tgtgtaggtc agaggatagc ttatgggagt    5100
gagctctctc cttccaccat gtgggttcca gggttcaaac tctagacctt cacctgctca    5160
gccaccttac cctttaaaa tgtttggtta ttaatatata aaggaagga agacaacatc    5220 aaacatgtgc tggctttgta tgtatatata gttttttattt ccacattaat ttgaattatg    5280
cctataatat atttgtaata atcatacaaa ataattgtaa tttattagaa atagaacatc    5340
aggagttaaa ataggggatt cttctgtctt ctgccaggaa gcccagtctc agagatgctg    5400
ccaggctctt cctcgctgtg ccattaagat tatttaattt ttgttaatat ttttactcat    5460
accggtatta aagttatgtt ttgttggaaa aaaaaaaaa aaaaaaaaa aaaaaa         5516
```

<210> SEQ ID NO 9
<211> LENGTH: 14
<212> TYPE: DNA
<213> ORGANISM: Homo sapiens

<400> SEQUENCE: 9
tcggtgagta agtg                                                       14

<210> SEQ ID NO 10
<211> LENGTH: 14
<212> TYPE: DNA
<213> ORGANISM: Homo sapiens

<400> SEQUENCE: 10
ccagtaagta tcta                                                       14

<210> SEQ ID NO 11
<211> LENGTH: 14
<212> TYPE: DNA
<213> ORGANISM: Homo sapiens

<400> SEQUENCE: 11

-continued taggtaatat ttta                                              14

<210> SEQ ID NO 12
<211> LENGTH: 14
<212> TYPE: DNA
<213> ORGANISM: Homo sapiens

<400> SEQUENCE: 12
aaagtatgta tttt                                              14

<210> SEQ ID NO 13
<211> LENGTH: 14
<212> TYPE: DNA
<213> ORGANISM: Homo sapiens

<400> SEQUENCE: 13
caggtgtgga gagg                                              14

<210> SEQ ID NO 14
<211> LENGTH: 14
<212> TYPE: DNA
<213> ORGANISM: Homo sapiens

<400> SEQUENCE: 14
caggtaagac tgtc                                              14

<210> SEQ ID NO 15
<211> LENGTH: 14
<212> TYPE: DNA
<213> ORGANISM: Homo sapiens

<400> SEQUENCE: 15
aaagtaagtg gcgt                                              14

<210> SEQ ID NO 16
<211> LENGTH: 14
<212> TYPE: DNA
<213> ORGANISM: Homo sapiens

<400> SEQUENCE: 16
aaggtaggct tatg                                              14

<210> SEQ ID NO 17
<211> LENGTH: 14
<212> TYPE: DNA
<213> ORGANISM: Homo sapiens

<400> SEQUENCE: 17
caggtggata aacc                                              14

<210> SEQ ID NO 18
<211> LENGTH: 14
<212> TYPE: DNA
<213> ORGANISM: Homo sapiens

<400> SEQUENCE: 18
aaggtagaaa agac                                              14

<210> SEQ ID NO 19
<211> LENGTH: 14
<212> TYPE: DNA
<213> ORGANISM: Homo sapiens

<400> SEQUENCE: 19

```
gaggtatgct ctta                                                        14

<210> SEQ ID NO 20
<211> LENGTH: 14
<212> TYPE: DNA
<213> ORGANISM: Homo sapiens

<400> SEQUENCE: 20
aaggtaaaga gctc                                                        14

<210> SEQ ID NO 21
<211> LENGTH: 14
<212> TYPE: DNA
<213> ORGANISM: Homo sapiens

<400> SEQUENCE: 21
aaggtgagat cttt                                                        14

<210> SEQ ID NO 22
<211> LENGTH: 14
<212> TYPE: DNA
<213> ORGANISM: Homo sapiens

<400> SEQUENCE: 22
aaggtaatgt tcat                                                        14

<210> SEQ ID NO 23
<211> LENGTH: 14
<212> TYPE: DNA
<213> ORGANISM: Homo sapiens

<400> SEQUENCE: 23
ttagtaagtg tcag                                                        14

<210> SEQ ID NO 24
<211> LENGTH: 14
<212> TYPE: DNA
<213> ORGANISM: Homo sapiens

<400> SEQUENCE: 24
caggtatgtt gaaa                                                        14

<210> SEQ ID NO 25
<211> LENGTH: 14
<212> TYPE: DNA
<213> ORGANISM: Homo sapiens

<400> SEQUENCE: 25
aaggtatctt attg                                                        14

<210> SEQ ID NO 26
<211> LENGTH: 14
<212> TYPE: DNA
<213> ORGANISM: Homo sapiens

<400> SEQUENCE: 26
caggttagag gcaa                                                        14

<210> SEQ ID NO 27
<211> LENGTH: 14
<212> TYPE: DNA
<213> ORGANISM: Homo sapiens
```

```
<400> SEQUENCE: 27
caggtacacg tgga                                              14

<210> SEQ ID NO 28
<211> LENGTH: 14
<212> TYPE: DNA
<213> ORGANISM: Homo sapiens

<400> SEQUENCE: 28
caggtgagtt cttt                                              14

<210> SEQ ID NO 29
<211> LENGTH: 14
<212> TYPE: DNA
<213> ORGANISM: Homo sapiens

<400> SEQUENCE: 29
ctggtaaagc caat                                              14

<210> SEQ ID NO 30
<211> LENGTH: 14
<212> TYPE: DNA
<213> ORGANISM: Homo sapiens

<400> SEQUENCE: 30
agggtaggta ttgt                                              14

<210> SEQ ID NO 31
<211> LENGTH: 14
<212> TYPE: DNA
<213> ORGANISM: Homo sapiens

<400> SEQUENCE: 31
aaagtcagta tagt                                              14

<210> SEQ ID NO 32
<211> LENGTH: 14
<212> TYPE: DNA
<213> ORGANISM: Homo sapiens

<400> SEQUENCE: 32
taggtatggg atga                                              14

<210> SEQ ID NO 33
<211> LENGTH: 14
<212> TYPE: DNA
<213> ORGANISM: Homo sapiens

<400> SEQUENCE: 33
gaggtgagca gagt                                              14

<210> SEQ ID NO 34
<211> LENGTH: 14
<212> TYPE: DNA
<213> ORGANISM: Homo sapiens

<400> SEQUENCE: 34
caggtaagag aagt                                              14

<210> SEQ ID NO 35
<211> LENGTH: 14
<212> TYPE: DNA
<213> ORGANISM: Homo sapiens
```

```
<400> SEQUENCE: 35
taggtaagta tgtt                                                        14

<210> SEQ ID NO 36
<211> LENGTH: 14
<212> TYPE: DNA
<213> ORGANISM: Homo sapiens

<400> SEQUENCE: 36
aaggtattgg aatg                                                        14

<210> SEQ ID NO 37
<211> LENGTH: 14
<212> TYPE: DNA
<213> ORGANISM: Homo sapiens

<400> SEQUENCE: 37
gaagtaagtg acag                                                        14

<210> SEQ ID NO 38
<211> LENGTH: 14
<212> TYPE: DNA
<213> ORGANISM: Homo sapiens

<400> SEQUENCE: 38
aaggttagtg tagg                                                        14

<210> SEQ ID NO 39
<211> LENGTH: 14
<212> TYPE: DNA
<213> ORGANISM: Homo sapiens

<400> SEQUENCE: 39
caggtcagaa gcct                                                        14

<210> SEQ ID NO 40
<211> LENGTH: 14
<212> TYPE: DNA
<213> ORGANISM: Homo sapiens

<400> SEQUENCE: 40
ttggtaagta tgtg                                                        14

<210> SEQ ID NO 41
<211> LENGTH: 14
<212> TYPE: DNA
<213> ORGANISM: Homo sapiens

<400> SEQUENCE: 41
caggtgagtc ataa                                                        14

<210> SEQ ID NO 42
<211> LENGTH: 14
<212> TYPE: DNA
<213> ORGANISM: Homo sapiens

<400> SEQUENCE: 42
ttggtgatgg gcct                                                        14

<210> SEQ ID NO 43
<211> LENGTH: 14
<212> TYPE: DNA
```

```
<213> ORGANISM: Homo sapiens

<400> SEQUENCE: 43
ctggtgagat gttt                                                        14

<210> SEQ ID NO 44
<211> LENGTH: 14
<212> TYPE: DNA
<213> ORGANISM: Homo sapiens

<400> SEQUENCE: 44
caggtaaggg agtt                                                        14

<210> SEQ ID NO 45
<211> LENGTH: 14
<212> TYPE: DNA
<213> ORGANISM: Homo sapiens

<400> SEQUENCE: 45
caggtgagta agat                                                        14

<210> SEQ ID NO 46
<211> LENGTH: 14
<212> TYPE: DNA
<213> ORGANISM: Homo sapiens

<400> SEQUENCE: 46
aaggtgagta tgga                                                        14

<210> SEQ ID NO 47
<211> LENGTH: 14
<212> TYPE: DNA
<213> ORGANISM: Homo sapiens

<400> SEQUENCE: 47
aaggtgagag attt                                                        14

<210> SEQ ID NO 48
<211> LENGTH: 14
<212> TYPE: DNA
<213> ORGANISM: Homo sapiens

<400> SEQUENCE: 48
cgggtaagag ctaa                                                        14

<210> SEQ ID NO 49
<211> LENGTH: 14
<212> TYPE: DNA
<213> ORGANISM: Homo sapiens

<400> SEQUENCE: 49
aaggtaagaa gggg                                                        14

<210> SEQ ID NO 50
<211> LENGTH: 14
<212> TYPE: DNA
<213> ORGANISM: Homo sapiens

<400> SEQUENCE: 50
caggtaagcc ttgg                                                        14

<210> SEQ ID NO 51
<211> LENGTH: 14
```

```
<212> TYPE: DNA
<213> ORGANISM: Homo sapiens

<400> SEQUENCE: 51
gaggtatctc taca                                                         14

<210> SEQ ID NO 52
<211> LENGTH: 23
<212> TYPE: DNA
<213> ORGANISM: Homo sapiens

<400> SEQUENCE: 52
gtttcccgat tttgctctag gaa                                               23

<210> SEQ ID NO 53
<211> LENGTH: 23
<212> TYPE: DNA
<213> ORGANISM: Homo sapiens

<400> SEQUENCE: 53
gaaaattttt ctattttcag aaa                                               23

<210> SEQ ID NO 54
<211> LENGTH: 23
<212> TYPE: DNA
<213> ORGANISM: Homo sapiens

<400> SEQUENCE: 54
ctcttctttt ttctgcatag ctg                                               23

<210> SEQ ID NO 55
<211> LENGTH: 23
<212> TYPE: DNA
<213> ORGANISM: Homo sapiens

<400> SEQUENCE: 55
attttttaaa tctccttaag ata                                               23

<210> SEQ ID NO 56
<211> LENGTH: 23
<212> TYPE: DNA
<213> ORGANISM: Homo sapiens

<400> SEQUENCE: 56
gatttctttt tttttacag tat                                                23

<210> SEQ ID NO 57
<211> LENGTH: 23
<212> TYPE: DNA
<213> ORGANISM: Homo sapiens

<400> SEQUENCE: 57
ccctatgtct tcttttttag cct                                               23

<210> SEQ ID NO 58
<211> LENGTH: 23
<212> TYPE: DNA
<213> ORGANISM: Homo sapiens

<400> SEQUENCE: 58
ttctcttcct aacatttag caa                                                23

<210> SEQ ID NO 59
```

```
<211> LENGTH: 23
<212> TYPE: DNA
<213> ORGANISM: Homo sapiens

<400> SEQUENCE: 59
aatagtgtct tctactgcag gac                                              23

<210> SEQ ID NO 60
<211> LENGTH: 23
<212> TYPE: DNA
<213> ORGANISM: Homo sapiens

<400> SEQUENCE: 60 tcttttcta ccattcacag tga                                               23

<210> SEQ ID NO 61
<211> LENGTH: 23
<212> TYPE: DNA
<213> ORGANISM: Homo sapiens

<400> SEQUENCE: 61
tctgtgcttt taattttag gtt                                               23

<210> SEQ ID NO 62
<211> LENGTH: 23
<212> TYPE: DNA
<213> ORGANISM: Homo sapiens

<400> SEQUENCE: 62
ctaatattta ctttctgcag gta                                              23

<210> SEQ ID NO 63
<211> LENGTH: 23
<212> TYPE: DNA
<213> ORGANISM: Homo sapiens

<400> SEQUENCE: 63
ttcctctctg ctacttgtag ttc                                              23

<210> SEQ ID NO 64
<211> LENGTH: 23
<212> TYPE: DNA
<213> ORGANISM: Homo sapiens

<400> SEQUENCE: 64
actctctcct gtttttcag gca                                               23

<210> SEQ ID NO 65
<211> LENGTH: 23
<212> TYPE: DNA
<213> ORGANISM: Homo sapiens

<400> SEQUENCE: 65
tgcatattta ttgacaatag gtg                                              23

<210> SEQ ID NO 66
<211> LENGTH: 23
<212> TYPE: DNA
<213> ORGANISM: Homo sapiens

<400> SEQUENCE: 66
tctactcttc cccactcaag gtt                                              23
```

```
<210> SEQ ID NO 67
<211> LENGTH: 23
<212> TYPE: DNA
<213> ORGANISM: Homo sapiens

<400> SEQUENCE: 67
gttgactctc ccctgtatag gaa                                              23

<210> SEQ ID NO 68
<211> LENGTH: 23
<212> TYPE: DNA
<213> ORGANISM: Homo sapiens

<400> SEQUENCE: 68
tggcatcatt ttttccacag ggc                                              23

<210> SEQ ID NO 69
<211> LENGTH: 23
<212> TYPE: DNA
<213> ORGANISM: Homo sapiens

<400> SEQUENCE: 69
tcttcatcat ctcattgcag gat                                              23

<210> SEQ ID NO 70
<211> LENGTH: 23
<212> TYPE: DNA
<213> ORGANISM: Homo sapiens

<400> SEQUENCE: 70
aaaaaattct ttgtttttag aag                                              23

<210> SEQ ID NO 71
<211> LENGTH: 23
<212> TYPE: DNA
<213> ORGANISM: Homo sapiens

<400> SEQUENCE: 71
attcttcctc tttgctccag gtg                                              23

<210> SEQ ID NO 72
<211> LENGTH: 23
<212> TYPE: DNA
<213> ORGANISM: Homo sapiens

<400> SEQUENCE: 72
tgtttgtttg cttcctgaag gaa                                              23

<210> SEQ ID NO 73
<211> LENGTH: 23
<212> TYPE: DNA
<213> ORGANISM: Homo sapiens

<400> SEQUENCE: 73
attctggttt ttctccgcag tga                                              23

<210> SEQ ID NO 74
<211> LENGTH: 23
<212> TYPE: DNA
<213> ORGANISM: Homo sapiens

<400> SEQUENCE: 74
aatttatttc tccttctcag att                                              23
```

```
<210> SEQ ID NO 75
<211> LENGTH: 23
<212> TYPE: DNA
<213> ORGANISM: Homo sapiens

<400> SEQUENCE: 75
aaatgtttgt tctctctcag att                                    23

<210> SEQ ID NO 76
<211> LENGTH: 23
<212> TYPE: DNA
<213> ORGANISM: Homo sapiens

<400> SEQUENCE: 76
atgtaatttg tactttgcag att                                    23

<210> SEQ ID NO 77
<211> LENGTH: 23
<212> TYPE: DNA
<213> ORGANISM: Homo sapiens

<400> SEQUENCE: 77
cagcctgctg tttgtttcag tca                                    23

<210> SEQ ID NO 78
<211> LENGTH: 23
<212> TYPE: DNA
<213> ORGANISM: Homo sapiens

<400> SEQUENCE: 78 ttctctttt aatataaaag aaa                                     23

<210> SEQ ID NO 79
<211> LENGTH: 23
<212> TYPE: DNA
<213> ORGANISM: Homo sapiens

<400> SEQUENCE: 79
ttgctgtgac ttccccatag gag                                    23

<210> SEQ ID NO 80
<211> LENGTH: 23
<212> TYPE: DNA
<213> ORGANISM: Homo sapiens

<400> SEQUENCE: 80
tcctttcctc catgtgacag gct                                    23

<210> SEQ ID NO 81
<211> LENGTH: 23
<212> TYPE: DNA
<213> ORGANISM: Homo sapiens

<400> SEQUENCE: 81
taactctgca tttattatag aac                                    23

<210> SEQ ID NO 82
<211> LENGTH: 23
<212> TYPE: DNA
<213> ORGANISM: Homo sapiens

<400> SEQUENCE: 82
aaaatcattt ttatttttag tgt                                    23
```

```
<210> SEQ ID NO 83
<211> LENGTH: 23
<212> TYPE: DNA
<213> ORGANISM: Homo sapiens

<400> SEQUENCE: 83
tcttaccttg acttccttag gag                                              23

<210> SEQ ID NO 84
<211> LENGTH: 23
<212> TYPE: DNA
<213> ORGANISM: Homo sapiens

<400> SEQUENCE: 84
tttttcttgt ctccttacag cca                                              23

<210> SEQ ID NO 85
<211> LENGTH: 23
<212> TYPE: DNA
<213> ORGANISM: Homo sapiens

<400> SEQUENCE: 85
tttgtcttct tttctaacag ctt                                              23

<210> SEQ ID NO 86
<211> LENGTH: 23
<212> TYPE: DNA
<213> ORGANISM: Homo sapiens

<400> SEQUENCE: 86
atatttgact ctcaatgcag tat                                              23

<210> SEQ ID NO 87
<211> LENGTH: 23
<212> TYPE: DNA
<213> ORGANISM: Homo sapiens

<400> SEQUENCE: 87
atgcttttcc cgtcttctag gca                                              23

<210> SEQ ID NO 88
<211> LENGTH: 23
<212> TYPE: DNA
<213> ORGANISM: Homo sapiens

<400> SEQUENCE: 88
catatatttg gctgccccag att                                              23

<210> SEQ ID NO 89
<211> LENGTH: 23
<212> TYPE: DNA
<213> ORGANISM: Homo sapiens

<400> SEQUENCE: 89
cttgtctttc acctctccag gta                                              23

<210> SEQ ID NO 90
<211> LENGTH: 23
<212> TYPE: DNA
<213> ORGANISM: Homo sapiens

<400> SEQUENCE: 90
```
agtgtgtctc tcttcttcag tat 23

<210> SEQ ID NO 91
<211> LENGTH: 23
<212> TYPE: DNA
<213> ORGANISM: Homo sapiens

<400> SEQUENCE: 91
tataaactta ttggttatag gaa 23

<210> SEQ ID NO 92
<211> LENGTH: 23
<212> TYPE: DNA
<213> ORGANISM: Homo sapiens

<400> SEQUENCE: 92
tgttatttat ttccattcag att 23

<210> SEQ ID NO 93
<211> LENGTH: 23
<212> TYPE: DNA
<213> ORGANISM: Homo sapiens

<400> SEQUENCE: 93
cttggtccat tcacatttag ggt 23

<210> SEQ ID NO 94
<211> LENGTH: 23
<212> TYPE: DNA
<213> ORGANISM: Homo sapiens

<400> SEQUENCE: 94
atttattctt tgccccttag gat 23

<210> SEQ ID NO 95
<211> LENGTH: 33
<212> TYPE: DNA
<213> ORGANISM: Artificial sequence
<220> FEATURE:
<223> OTHER INFORMATION: Primer

<400> SEQUENCE: 95
agcctcgaat tcgtttccaa aagaagactg tca 33

<210> SEQ ID NO 96
<211> LENGTH: 35
<212> TYPE: DNA
<213> ORGANISM: Artificial sequence
<220> FEATURE:
<223> OTHER INFORMATION: Primer

<400> SEQUENCE: 96
ggtatcctcg agtcaagacg acaacttatc catca 35

<210> SEQ ID NO 97
<211> LENGTH: 18
<212> TYPE: DNA
<213> ORGANISM: Artificial sequence
<220> FEATURE:
<223> OTHER INFORMATION: Primer

<400> SEQUENCE: 97
aatcgaaaac tacgggcg 18

```
<210> SEQ ID NO 98
<211> LENGTH: 20
<212> TYPE: DNA
<213> ORGANISM: Artificial sequence
<220> FEATURE:
<223> OTHER INFORMATION: Primer

<400> SEQUENCE: 98
gagaacacat gaatgaacgc                                               20

<210> SEQ ID NO 99
<211> LENGTH: 28
<212> TYPE: DNA
<213> ORGANISM: Artificial sequence
<220> FEATURE:
<223> OTHER INFORMATION: Primer

<400> SEQUENCE: 99
ggcgacggct tctcggaagt aatttaag                                      28

<210> SEQ ID NO 100
<211> LENGTH: 18
<212> TYPE: DNA
<213> ORGANISM: Artificial sequence
<220> FEATURE:
<223> OTHER INFORMATION: Primer

<400> SEQUENCE: 100
agcggcagga ggtttatg                                                 18

<210> SEQ ID NO 101
<211> LENGTH: 18
<212> TYPE: DNA
<213> ORGANISM: Artificial sequence
<220> FEATURE:
<223> OTHER INFORMATION: Primer

<400> SEQUENCE: 101
tggcggcaga cagaagtg                                                 18

<210> SEQ ID NO 102
<211> LENGTH: 18
<212> TYPE: DNA
<213> ORGANISM: Artificial sequence
<220> FEATURE:
<223> OTHER INFORMATION: Primer

<400> SEQUENCE: 102
tggcggcaga cagaagtg                                                 18

<210> SEQ ID NO 103
<211> LENGTH: 21
<212> TYPE: DNA
<213> ORGANISM: Artificial sequence
<220> FEATURE:
<223> OTHER INFORMATION: Primer

<400> SEQUENCE: 103
agagagccaa cctgagcgat g                                             21

<210> SEQ ID NO 104
<211> LENGTH: 18
<212> TYPE: DNA
<213> ORGANISM: Artificial sequence
<220> FEATURE:
<223> OTHER INFORMATION: Primer
```

<400> SEQUENCE: 104
gtgccagact ctggtgggg                                              18

<210> SEQ ID NO 105
<211> LENGTH: 20
<212> TYPE: DNA
<213> ORGANISM: Artificial sequence
<220> FEATURE:
<223> OTHER INFORMATION: Primer

<400> SEQUENCE: 105
aggagacacc cttcctatcc                                             20

<210> SEQ ID NO 106
<211> LENGTH: 20
<212> TYPE: DNA
<213> ORGANISM: Artificial sequence
<220> FEATURE:
<223> OTHER INFORMATION: Primer

<400> SEQUENCE: 106
gaagttggca aaacagactg                                             20

<210> SEQ ID NO 107
<211> LENGTH: 21
<212> TYPE: DNA
<213> ORGANISM: Artificial sequence
<220> FEATURE:
<223> OTHER INFORMATION: Primer

<400> SEQUENCE: 107
tgtcttgtga gcgtctgcag g                                           21

<210> SEQ ID NO 108
<211> LENGTH: 20
<212> TYPE: DNA
<213> ORGANISM: Artificial sequence
<220> FEATURE:
<223> OTHER INFORMATION: Primer

<400> SEQUENCE: 108
aggttttgat aatggcaggc                                             20

<210> SEQ ID NO 109
<211> LENGTH: 24
<212> TYPE: DNA
<213> ORGANISM: Artificial sequence
<220> FEATURE:
<223> OTHER INFORMATION: Primer

<400> SEQUENCE: 109
actggactgt gcctacccac tatg                                        24

<210> SEQ ID NO 110
<211> LENGTH: 20
<212> TYPE: DNA
<213> ORGANISM: Artificial sequence
<220> FEATURE:
<223> OTHER INFORMATION: Primer

<400> SEQUENCE: 110
cctgtgtgag gatgagctct                                             20

<210> SEQ ID NO 111
<211> LENGTH: 16

```
<212> TYPE: DNA
<213> ORGANISM: Artificial sequence
<220> FEATURE:
<223> OTHER INFORMATION: Primer

<400> SEQUENCE: 111
ttctcccgaa gctcag                                                       16

<210> SEQ ID NO 112
<211> LENGTH: 17
<212> TYPE: DNA
<213> ORGANISM: Artificial sequence
<220> FEATURE:
<223> OTHER INFORMATION: Primer

<400> SEQUENCE: 112
tttcttccgt gtgatga                                                      17

<210> SEQ ID NO 113
<211> LENGTH: 33
<212> TYPE: DNA
<213> ORGANISM: Artificial sequence
<220> FEATURE:
<223> OTHER INFORMATION: Primer

<400> SEQUENCE: 113
agcctcgaat tcgtttccaa aagaagactg tca                                    33

<210> SEQ ID NO 114
<211> LENGTH: 35
<212> TYPE: DNA
<213> ORGANISM: Artificial sequence
<220> FEATURE:
<223> OTHER INFORMATION: Primer

<400> SEQUENCE: 114
ggtatcctcg agtcaagacg acaacttatc catca                                  35

<210> SEQ ID NO 115
<211> LENGTH: 20
<212> TYPE: DNA
<213> ORGANISM: Artificial sequence
<220> FEATURE:
<223> OTHER INFORMATION: Primer

<400> SEQUENCE: 115
ctagcacaga actctgctgc                                                   20

<210> SEQ ID NO 116
<211> LENGTH: 20
<212> TYPE: DNA
<213> ORGANISM: Artificial sequence
<220> FEATURE:
<223> OTHER INFORMATION: Primer

<400> SEQUENCE: 116
ctagcacaga actctgctgc                                                   20

<210> SEQ ID NO 117
<211> LENGTH: 24
<212> TYPE: DNA
<213> ORGANISM: Artificial sequence
<220> FEATURE:
<223> OTHER INFORMATION: Primer

<400> SEQUENCE: 117
```
cttcagcaac agcgaagtag tctg                      24

<210> SEQ ID NO 118
<211> LENGTH: 24
<212> TYPE: DNA
<213> ORGANISM: Artificial sequence
<220> FEATURE:
<223> OTHER INFORMATION: Primer

<400> SEQUENCE: 118
gattctcagc acttgaaaag cagg                      24

<210> SEQ ID NO 119
<211> LENGTH: 21
<212> TYPE: DNA
<213> ORGANISM: Artificial sequence
<220> FEATURE:
<223> OTHER INFORMATION: Primer

<400> SEQUENCE: 119
ggacacatca gttttcctct c                         21

<210> SEQ ID NO 120
<211> LENGTH: 20
<212> TYPE: DNA
<213> ORGANISM: Artificial sequence
<220> FEATURE:
<223> OTHER INFORMATION: Primer

<400> SEQUENCE: 120
gaaaacccat gattcagtcc                           20

<210> SEQ ID NO 121
<211> LENGTH: 20
<212> TYPE: DNA
<213> ORGANISM: Artificial sequence
<220> FEATURE:
<223> OTHER INFORMATION: Primer

<400> SEQUENCE: 121
tcatcaggca agaaacttgg                           20

<210> SEQ ID NO 122
<211> LENGTH: 20
<212> TYPE: DNA
<213> ORGANISM: Artificial sequence
<220> FEATURE:
<223> OTHER INFORMATION: Primer

<400> SEQUENCE: 122
gaagttggca aaacagactg                           20

<210> SEQ ID NO 123
<211> LENGTH: 20
<212> TYPE: DNA
<213> ORGANISM: Artificial sequence
<220> FEATURE:
<223> OTHER INFORMATION: Primer

<400> SEQUENCE: 123
gagccatctg ctcatttctg                           20

<210> SEQ ID NO 124
<211> LENGTH: 20
<212> TYPE: DNA
<213> ORGANISM: Artificial sequence

```
<220> FEATURE:
<223> OTHER INFORMATION: Primer

<400> SEQUENCE: 124
cccgctattt agacttgagc                                               20

<210> SEQ ID NO 125
<211> LENGTH: 21
<212> TYPE: DNA
<213> ORGANISM: Artificial sequence
<220> FEATURE:
<223> OTHER INFORMATION: Primer

<400> SEQUENCE: 125
caaagtgttt attccaggag c                                             21

<210> SEQ ID NO 126
<211> LENGTH: 22
<212> TYPE: DNA
<213> ORGANISM: Artificial sequence
<220> FEATURE:
<223> OTHER INFORMATION: Primer

<400> SEQUENCE: 126
catcagggta ctttgaacat tc                                            22

<210> SEQ ID NO 127
<211> LENGTH: 22
<212> TYPE: DNA
<213> ORGANISM: Artificial sequence
<220> FEATURE:
<223> OTHER INFORMATION: Primer

<400> SEQUENCE: 127
ttgaccagaa aggctcagtt cc                                            22

<210> SEQ ID NO 128
<211> LENGTH: 23
<212> TYPE: DNA
<213> ORGANISM: Artificial sequence
<220> FEATURE:
<223> OTHER INFORMATION: Primer

<400> SEQUENCE: 128
agatgatgcc agagggttta tcc                                           23

<210> SEQ ID NO 129
<211> LENGTH: 20
<212> TYPE: DNA
<213> ORGANISM: Artificial sequence
<220> FEATURE:
<223> OTHER INFORMATION: Primer

<400> SEQUENCE: 129
tgcccagctc tgttcaaacc                                               20

<210> SEQ ID NO 130
<211> LENGTH: 20
<212> TYPE: DNA
<213> ORGANISM: Artificial sequence
<220> FEATURE:
<223> OTHER INFORMATION: Primer

<400> SEQUENCE: 130
aggcaatgac tgactgacac                                               20
```

<210> SEQ ID NO 131
<211> LENGTH: 23
<212> TYPE: DNA
<213> ORGANISM: Artificial sequence
<220> FEATURE:
<223> OTHER INFORMATION: Primer

<400> SEQUENCE: 131
tgcccgtcta tttttgatga agc                                           23

<210> SEQ ID NO 132
<211> LENGTH: 21
<212> TYPE: DNA
<213> ORGANISM: Artificial sequence
<220> FEATURE:
<223> OTHER INFORMATION: Primer

<400> SEQUENCE: 132
tctcagttag tctggggaca g                                             21

<210> SEQ ID NO 133
<211> LENGTH: 25
<212> TYPE: DNA
<213> ORGANISM: Artificial sequence
<220> FEATURE:
<223> OTHER INFORMATION: Primer

<400> SEQUENCE: 133
tcatggtaga gagactggac tgtgc                                         25

<210> SEQ ID NO 134
<211> LENGTH: 21
<212> TYPE: DNA
<213> ORGANISM: Artificial sequence
<220> FEATURE:
<223> OTHER INFORMATION: Primer

<400> SEQUENCE: 134
accctggagc aaatgacaac c                                             21

<210> SEQ ID NO 135
<211> LENGTH: 21
<212> TYPE: DNA
<213> ORGANISM: Artificial sequence
<220> FEATURE:
<223> OTHER INFORMATION: Primer

<400> SEQUENCE: 135
atttgctcca gggtacatgg c                                             21

<210> SEQ ID NO 136
<211> LENGTH: 22
<212> TYPE: DNA
<213> ORGANISM: Artificial sequence
<220> FEATURE:
<223> OTHER INFORMATION: Primer

<400> SEQUENCE: 136
gaaagacagt gggaaggcaa gc                                            22

<210> SEQ ID NO 137
<211> LENGTH: 23
<212> TYPE: DNA
<213> ORGANISM: Artificial sequence
<220> FEATURE:
<223> OTHER INFORMATION: Primer

<400> SEQUENCE: 137
gggagtgtgt ggaacaaatg agc                                     23

<210> SEQ ID NO 138
<211> LENGTH: 25
<212> TYPE: DNA
<213> ORGANISM: Artificial sequence
<220> FEATURE:
<223> OTHER INFORMATION: Primer

<400> SEQUENCE: 138
agtttctaca ggctggtcct attcc                                   25

<210> SEQ ID NO 139
<211> LENGTH: 21
<212> TYPE: DNA
<213> ORGANISM: Artificial sequence
<220> FEATURE:
<223> OTHER INFORMATION: Primer

<400> SEQUENCE: 139
aacgtggaat cccattgatg c                                       21

<210> SEQ ID NO 140
<211> LENGTH: 20
<212> TYPE: DNA
<213> ORGANISM: Artificial sequence
<220> FEATURE:
<223> OTHER INFORMATION: Primer

<400> SEQUENCE: 140
tttctgtgtt ccctccttgc                                         20

<210> SEQ ID NO 141
<211> LENGTH: 20
<212> TYPE: DNA
<213> ORGANISM: Artificial sequence
<220> FEATURE:
<223> OTHER INFORMATION: Primer

<400> SEQUENCE: 141
gatggtcaag ttacactggc                                         20

<210> SEQ ID NO 142
<211> LENGTH: 24
<212> TYPE: DNA
<213> ORGANISM: Artificial sequence
<220> FEATURE:
<223> OTHER INFORMATION: Primer

<400> SEQUENCE: 142
cacctcccac caattatagt attc                                    24

<210> SEQ ID NO 143
<211> LENGTH: 23
<212> TYPE: DNA
<213> ORGANISM: Artificial sequence
<220> FEATURE:
<223> OTHER INFORMATION: Primer

<400> SEQUENCE: 143
ctatgtgtgt ctcttttaca ggg                                     23

<210> SEQ ID NO 144

```
<211> LENGTH: 20
<212> TYPE: DNA
<213> ORGANISM: Artificial sequence
<220> FEATURE:
<223> OTHER INFORMATION: Primer

<400> SEQUENCE: 144
aatctttccc accatattgc                                                  20

<210> SEQ ID NO 145
<211> LENGTH: 20
<212> TYPE: DNA
<213> ORGANISM: Artificial sequence
<220> FEATURE:
<223> OTHER INFORMATION: Primer

<400> SEQUENCE: 145
cataccttct tttgctgtgc                                                  20

<210> SEQ ID NO 146
<211> LENGTH: 23
<212> TYPE: DNA
<213> ORGANISM: Artificial sequence
<220> FEATURE:
<223> OTHER INFORMATION: Primer

<400> SEQUENCE: 146
ccacagaagt cagaatctcc acg                                              23

<210> SEQ ID NO 147
<211> LENGTH: 20
<212> TYPE: DNA
<213> ORGANISM: Artificial sequence
<220> FEATURE:
<223> OTHER INFORMATION: Primer

<400> SEQUENCE: 147
tgtaacaaac ctgcacgttg                                                  20

<210> SEQ ID NO 148
<211> LENGTH: 23
<212> TYPE: DNA
<213> ORGANISM: Artificial sequence
<220> FEATURE:
<223> OTHER INFORMATION: Primer

<400> SEQUENCE: 148
tgctacccaa gccagtagtt tcc                                              23

<210> SEQ ID NO 149
<211> LENGTH: 22
<212> TYPE: DNA
<213> ORGANISM: Artificial sequence
<220> FEATURE:
<223> OTHER INFORMATION: Primer

<400> SEQUENCE: 149
gagtttggga aagattggca gc                                               22

<210> SEQ ID NO 150
<211> LENGTH: 22
<212> TYPE: DNA
<213> ORGANISM: Artificial sequence
<220> FEATURE:
<223> OTHER INFORMATION: Primer

<400> SEQUENCE: 150
```
tgtagtaaag cagctctcat gc                                              22

<210> SEQ ID NO 151
<211> LENGTH: 20
<212> TYPE: DNA
<213> ORGANISM: Artificial sequence
<220> FEATURE:
<223> OTHER INFORMATION: Primer

<400> SEQUENCE: 151
caagtacact ctgcactgcc                                                 20

<210> SEQ ID NO 152
<211> LENGTH: 23
<212> TYPE: DNA
<213> ORGANISM: Artificial sequence
<220> FEATURE:
<223> OTHER INFORMATION: Primer

<400> SEQUENCE: 152
tgactcaact tccccaccaa gag                                             23

<210> SEQ ID NO 153
<211> LENGTH: 24
<212> TYPE: DNA
<213> ORGANISM: Artificial sequence
<220> FEATURE:
<223> OTHER INFORMATION: Primer

<400> SEQUENCE: 153
ctccctatgt acgtggagta atac                                            24

<210> SEQ ID NO 154
<211> LENGTH: 21
<212> TYPE: DNA
<213> ORGANISM: Artificial sequence
<220> FEATURE:
<223> OTHER INFORMATION: Primer

<400> SEQUENCE: 154
gggagtcttg tgggaactaa g                                               21

<210> SEQ ID NO 155
<211> LENGTH: 23
<212> TYPE: DNA
<213> ORGANISM: Artificial sequence
<220> FEATURE:
<223> OTHER INFORMATION: Primer

<400> SEQUENCE: 155
ttcatagaca tctctcagct ctg                                             23

<210> SEQ ID NO 156
<211> LENGTH: 20
<212> TYPE: DNA
<213> ORGANISM: Artificial sequence
<220> FEATURE:
<223> OTHER INFORMATION: Primer

<400> SEQUENCE: 156
gttttggtat cagggaaagc                                                 20

<210> SEQ ID NO 157
<211> LENGTH: 20
<212> TYPE: DNA

<213> ORGANISM: Artificial sequence
<220> FEATURE:
<223> OTHER INFORMATION: Primer

<400> SEQUENCE: 157
agccatgctt ggaattttgg                                              20

<210> SEQ ID NO 158
<211> LENGTH: 20
<212> TYPE: DNA
<213> ORGANISM: Artificial sequence
<220> FEATURE:
<223> OTHER INFORMATION: Primer

<400> SEQUENCE: 158
ctcactggga tgtcacaaac                                              20

<210> SEQ ID NO 159
<211> LENGTH: 25
<212> TYPE: DNA
<213> ORGANISM: Artificial sequence
<220> FEATURE:
<223> OTHER INFORMATION: Primer

<400> SEQUENCE: 159
ggtcttgatg tgtgacttgt atccc                                        25

<210> SEQ ID NO 160
<211> LENGTH: 25
<212> TYPE: DNA
<213> ORGANISM: Artificial sequence
<220> FEATURE:
<223> OTHER INFORMATION: Primer

<400> SEQUENCE: 160
cctcagtgtc acagtgttct ttgtg                                        25

<210> SEQ ID NO 161
<211> LENGTH: 22
<212> TYPE: DNA
<213> ORGANISM: Artificial sequence
<220> FEATURE:
<223> OTHER INFORMATION: Primer

<400> SEQUENCE: 161
catgaaatga ctaggacatt cc                                           22

<210> SEQ ID NO 162
<211> LENGTH: 20
<212> TYPE: DNA
<213> ORGANISM: Artificial sequence
<220> FEATURE:
<223> OTHER INFORMATION: Primer

<400> SEQUENCE: 162
ctacccagtg acccaaacac                                              20

<210> SEQ ID NO 163
<211> LENGTH: 23
<212> TYPE: DNA
<213> ORGANISM: Artificial sequence
<220> FEATURE:
<223> OTHER INFORMATION: Primer

<400> SEQUENCE: 163 cgaacccttta gtttctgaga cgc                                         23

```
<210> SEQ ID NO 164
<211> LENGTH: 20
<212> TYPE: DNA
<213> ORGANISM: Artificial sequence
<220> FEATURE:
<223> OTHER INFORMATION: Primer

<400> SEQUENCE: 164
tcagtgcctt ggtgactgtc                                               20

<210> SEQ ID NO 165
<211> LENGTH: 21
<212> TYPE: DNA
<213> ORGANISM: Artificial sequence
<220> FEATURE:
<223> OTHER INFORMATION: Primer

<400> SEQUENCE: 165
ttgatggtac agactggagg c                                             21

<210> SEQ ID NO 166
<211> LENGTH: 23
<212> TYPE: DNA
<213> ORGANISM: Artificial sequence
<220> FEATURE:
<223> OTHER INFORMATION: Primer

<400> SEQUENCE: 166
aagaaagttg ccaatcctgt tcc                                           23

<210> SEQ ID NO 167
<211> LENGTH: 20
<212> TYPE: DNA
<213> ORGANISM: Artificial sequence
<220> FEATURE:
<223> OTHER INFORMATION: Primer

<400> SEQUENCE: 167
agcacctgaa aataaggagg                                               20

<210> SEQ ID NO 168
<211> LENGTH: 22
<212> TYPE: DNA
<213> ORGANISM: Artificial sequence
<220> FEATURE:
<223> OTHER INFORMATION: Primer

<400> SEQUENCE: 168
gcccaaagtt tgtaagtgtg ag                                            22

<210> SEQ ID NO 169
<211> LENGTH: 21
<212> TYPE: DNA
<213> ORGANISM: Artificial sequence
<220> FEATURE:
<223> OTHER INFORMATION: Primer

<400> SEQUENCE: 169
agcaagaatg aggtcaagtt c                                             21

<210> SEQ ID NO 170
<211> LENGTH: 24
<212> TYPE: DNA
<213> ORGANISM: Artificial sequence
<220> FEATURE:
```

<223> OTHER INFORMATION: Primer

<400> SEQUENCE: 170
gggaaaaact ggaggaaaga actc                                        24

<210> SEQ ID NO 171
<211> LENGTH: 21
<212> TYPE: DNA
<213> ORGANISM: Artificial sequence
<220> FEATURE:
<223> OTHER INFORMATION: Primer

<400> SEQUENCE: 171
agaggtaggg aaggaagcta c                                           21

<210> SEQ ID NO 172
<211> LENGTH: 20
<212> TYPE: DNA
<213> ORGANISM: Artificial sequence
<220> FEATURE:
<223> OTHER INFORMATION: Primer

<400> SEQUENCE: 172
ccaaagtcca cttcttgaag                                             20

<210> SEQ ID NO 173
<211> LENGTH: 20
<212> TYPE: DNA
<213> ORGANISM: Artificial sequence
<220> FEATURE:
<223> OTHER INFORMATION: Primer

<400> SEQUENCE: 173
gatgcactgg ttgctacatc                                             20

<210> SEQ ID NO 174
<211> LENGTH: 20
<212> TYPE: DNA
<213> ORGANISM: Artificial sequence
<220> FEATURE:
<223> OTHER INFORMATION: Primer

<400> SEQUENCE: 174
ccaggacact tggtttctgc                                             20

<210> SEQ ID NO 175
<211> LENGTH: 20
<212> TYPE: DNA
<213> ORGANISM: Artificial sequence
<220> FEATURE:
<223> OTHER INFORMATION: Primer

<400> SEQUENCE: 175
acactcccag ttggaatcag                                             20

<210> SEQ ID NO 176
<211> LENGTH: 20
<212> TYPE: DNA
<213> ORGANISM: Artificial sequence
<220> FEATURE:
<223> OTHER INFORMATION: Primer

<400> SEQUENCE: 176
cttgtgggca agaaattgag                                             20

```
<210> SEQ ID NO 177
<211> LENGTH: 20
<212> TYPE: DNA
<213> ORGANISM: Artificial sequence
<220> FEATURE:
<223> OTHER INFORMATION: Primer

<400> SEQUENCE: 177
tgggctggat gagactattc                                              20

<210> SEQ ID NO 178
<211> LENGTH: 24
<212> TYPE: DNA
<213> ORGANISM: Artificial sequence
<220> FEATURE:
<223> OTHER INFORMATION: Primer

<400> SEQUENCE: 178
ccaaggacat atcttctgag caac                                         24

<210> SEQ ID NO 179
<211> LENGTH: 20
<212> TYPE: DNA
<213> ORGANISM: Artificial sequence
<220> FEATURE:
<223> OTHER INFORMATION: Primer

<400> SEQUENCE: 179
tgattatcag cataggctgg                                              20

<210> SEQ ID NO 180
<211> LENGTH: 20
<212> TYPE: DNA
<213> ORGANISM: Artificial sequence
<220> FEATURE:
<223> OTHER INFORMATION: Primer

<400> SEQUENCE: 180
gatcccccaa tagcaactgc                                              20

<210> SEQ ID NO 181
<211> LENGTH: 21
<212> TYPE: DNA
<213> ORGANISM: Artificial sequence
<220> FEATURE:
<223> OTHER INFORMATION: Primer

<400> SEQUENCE: 181
cattcagatt caccaggaca c                                            21

<210> SEQ ID NO 182
<211> LENGTH: 20
<212> TYPE: DNA
<213> ORGANISM: Artificial sequence
<220> FEATURE:
<223> OTHER INFORMATION: Primer

<400> SEQUENCE: 182
ccttacatgc catctgatgc                                              20

<210> SEQ ID NO 183
<211> LENGTH: 20
<212> TYPE: DNA
<213> ORGANISM: Artificial sequence
<220> FEATURE:
<223> OTHER INFORMATION: Primer
```

<400> SEQUENCE: 183
aaccttctcc cctattaccc                                              20

<210> SEQ ID NO 184
<211> LENGTH: 22
<212> TYPE: DNA
<213> ORGANISM: Artificial sequence
<220> FEATURE:
<223> OTHER INFORMATION: Primer

<400> SEQUENCE: 184
ggaaaatgag aggctataat gc                                           22

<210> SEQ ID NO 185
<211> LENGTH: 24
<212> TYPE: DNA
<213> ORGANISM: Artificial sequence
<220> FEATURE:
<223> OTHER INFORMATION: Primer

<400> SEQUENCE: 185
tgtattccag aggtcaccca gagc                                         24

<210> SEQ ID NO 186
<211> LENGTH: 22
<212> TYPE: DNA
<213> ORGANISM: Artificial sequence
<220> FEATURE:
<223> OTHER INFORMATION: Primer

<400> SEQUENCE: 186
ccagtaagaa aggcaaacag cg                                           22

<210> SEQ ID NO 187
<211> LENGTH: 1094
<212> TYPE: DNA
<213> ORGANISM: Homo sapiens

<400> SEQUENCE: 187
ggagaacaca gccagccttt ggaggaacta ctcagccaga gcgtccatta cttgcagaat    60
ttccatcaaa gcattcccag tttccagtgt gctctttatc tcatcagact tttgatggtt   120
attttggaga aatcaacagc ttctgctcag aacaaagaaa aaattgcttc ccttgccaga   180
caattcctct gtcgggtgtg gccaagtggg gataaagaga agagcaacat ctctaatgac   240
cagctccatg ctctgctctg tatctacctg gagcacacag agagcattct gaaggccata   300
gaggagattg ctggtgttgg tgtcccagaa ctgatcaact ctcctaaaga tgcatcttcc   360
tccacattcc ctacactgac caggcatact tttgttgttt cttccgtgt gatgatggct    420 gaactagaga agacggtgaa aaaaattgag cctggcacag cagcagactc gcagcagatt   480
catgaagaga aactcctcta ctggaacatg gctgttcgag acttcagtat cctcatcaac   540
ttgataaagg tatttgatag tcatcctgtt ctgcatgtat gtttgaagta tgggcgtctc   600
tttgtggaag catttctgaa gcaatgtatg ccgctcctag acttcagttt tagaaaacac   660
cgggaagatg ttctgagctt actggaaacc ttccagttgg acacaaggtg cttcatcacc   720
tgtgtgggca ttccaagatt caccaggaca cgagactcac ccaacatgtg cctctgctca   780
aaaagaccct ggaacttta gtttgcagag tcaaagctat gctcactctc aacaacaatt   840
gtagagaggc tttctggctg ggcaatctaa aaaaccggga cttgcagggt gaagagatta   900
agtcccaaaa ttcccaggag agcacagcag atgagagtga ggatgacatg tcatcccagg   960
cctccaagag caaagccact gaggatggtg aagaagacga agtaagtgct ggagaaaagg    1020
agcaagatag tgatgagagt tatgatgact ctgattagac cccagataaa ttgttgcctg    1080
cttctgtgtc tcaa                                                      1094

<210> SEQ ID NO 188
<211> LENGTH: 1115
<212> TYPE: DNA
<213> ORGANISM: Homo sapiens

<400> SEQUENCE: 188
ggagaacaca gccagccttt ggaggaacta ctcagccaga gcgtccatta cttgcagaat      60
ttccatcaaa gcattcccag tttccagtgt gctctttatc tcatcagact tttgatggtt     120
attttggaga aatcaacagc ttctgctcag aacaaagaaa aaattgcttc ccttgccaga     180
caattcctct gtcgggtgtg gccaagtggg gataaagaga agagcaacat ctctaatgac     240
cagctccatg ctctgctctg tatctacctg gagcacacag agagcattct gaaggccata     300
gaggagattg ctggtgttgg tgtcccagaa ctgatcaact ctcctaaaga tgcatcttcc     360
tccacattcc ctacactgac caggcatact tttgttgttt cttccgtgt gatgatggct      420 gaactagaga agacggtgaa aaaaattgag cctggcacag cagcagactc gcagcagatt     480
catgaagaga aactcctcta ctggaacatg gctgttcgag acttcagtat cctcatcaac     540
ttgataaagg tatttgatag tcatcctgtt ctgcatgtat gtttgaagta tgggcgtctc     600
tttgtggaag catttctgaa gcaatgtatg ccgctcctag acttcagttt tagaaaacac     660
cgggaagatg ttctgagctt actggaaacc ttccagttgg acacaaggtg cttcatcacc     720
tgtgtgggca ttccaagatt caccaggaca cgagactcac ccaacatgtg cctctgctca     780
aaaagaccct ggaacttta gtttgcagag tcaaagctat gctcactctc aacaattgta     840
gagaggcttt ctggctgggc aatctaaaaa accgggactt gcaggtgaa gagattaagt       900 cccaaaattc ccaggagagc acagcagatg agagtgagga tgacatgtca tcccaggcct     960
ccaagagcaa agccactgag gtatctctac aaaacccacc agagtctggc actgatggtt    1020
gcattttgtt aattgttcta agttggtgga gcagaacttt gcctacttat gtttattgtc    1080
aaatgcttct atgcccattt ccattccctc cataa                                1115

<210> SEQ ID NO 189
<211> LENGTH: 52
<212> TYPE: DNA
<213> ORGANISM: Homo sapiens

<400> SEQUENCE: 189
ggaagccagg tgtggagagg aggcatggaa tcttgctgaa attcagtctg tc              52

<210> SEQ ID NO 190
<211> LENGTH: 52
<212> TYPE: DNA
<213> ORGANISM: Homo sapiens

<400> SEQUENCE: 190
ggaagccggg tgtggagagg aggcatggaa tcttgctgaa attcagtctg tc              52

<210> SEQ ID NO 191
<211> LENGTH: 52
<212> TYPE: DNA
<213> ORGANISM: Homo sapiens

<400> SEQUENCE: 191
ggaagccggg tgtgaagagg aggcatggaa tcttgctgaa attcagtctg tc                 52

<210> SEQ ID NO 192
<211> LENGTH: 18
<212> TYPE: DNA
<213> ORGANISM: Artificial sequence
<220> FEATURE:
<223> OTHER INFORMATION: Primer

<400> SEQUENCE: 192
tgtaaaacga cggccagt                                                       18

<210> SEQ ID NO 193
<211> LENGTH: 18
<212> TYPE: DNA
<213> ORGANISM: Artificial sequence
<220> FEATURE:
<223> OTHER INFORMATION: Primer

<400> SEQUENCE: 193
caggaaacag ctatgacc                                                       18

<210> SEQ ID NO 194
<211> LENGTH: 38
<212> TYPE: DNA
<213> ORGANISM: Artificial sequence
<220> FEATURE:
<223> OTHER INFORMATION: Primer

<400> SEQUENCE: 194
tgtaaaacga cggccagtcg acggcttctc ggaagtaa                                 38

<210> SEQ ID NO 195
<211> LENGTH: 39
<212> TYPE: DNA
<213> ORGANISM: Artificial sequence
<220> FEATURE:
<223> OTHER INFORMATION: Primer

<400> SEQUENCE: 195
aggaaacagc tatgaccatg cagacgctca caagacaaa                                39

<210> SEQ ID NO 196
<211> LENGTH: 39
<212> TYPE: DNA
<213> ORGANISM: Artificial sequence
<220> FEATURE:
<223> OTHER INFORMATION: Primer

<400> SEQUENCE: 196
tgtaaaacga cggccagtga caccttcct atcccaaaa                                 39

<210> SEQ ID NO 197
<211> LENGTH: 39
<212> TYPE: DNA
<213> ORGANISM: Artificial sequence
<220> FEATURE:
<223> OTHER INFORMATION: Primer

<400> SEQUENCE: 197
aggaaacagc tatgaccatc aggttctctg gagcaatac                                39

<210> SEQ ID NO 198
<211> LENGTH: 39

-continued

<212> TYPE: DNA
<213> ORGANISM: Artificial sequence
<220> FEATURE:
<223> OTHER INFORMATION: Primer

<400> SEQUENCE: 198
tgtaaaacga cggccagttg gcttgacaga gttgtggat                                   39

<210> SEQ ID NO 199
<211> LENGTH: 40
<212> TYPE: DNA
<213> ORGANISM: Artificial sequence
<220> FEATURE:
<223> OTHER INFORMATION: Primer

<400> SEQUENCE: 199
aggaaacagc tatgaccatc tgtaaccgtg atggcaaaac                                  40

<210> SEQ ID NO 200
<211> LENGTH: 39
<212> TYPE: DNA
<213> ORGANISM: Artificial sequence
<220> FEATURE:
<223> OTHER INFORMATION: Primer

<400> SEQUENCE: 200
tgtaaaacga cggccagtcg ccagttggtg atggataag                                   39

<210> SEQ ID NO 201
<211> LENGTH: 40
<212> TYPE: DNA
<213> ORGANISM: Artificial sequence
<220> FEATURE:
<223> OTHER INFORMATION: Primer

<400> SEQUENCE: 201
aggaaacagc tatgaccata agcatcacca ggtcaaacac                                  40

<210> SEQ ID NO 202
<211> LENGTH: 39
<212> TYPE: DNA
<213> ORGANISM: Artificial sequence
<220> FEATURE:
<223> OTHER INFORMATION: Primer

<400> SEQUENCE: 202
tgtaaaacga cggccagtgc ggtcagagct gtattattc                                   39

<210> SEQ ID NO 203
<211> LENGTH: 39
<212> TYPE: DNA
<213> ORGANISM: Artificial sequence
<220> FEATURE:
<223> OTHER INFORMATION: Primer

<400> SEQUENCE: 203
aggaaacagc tatgaccatc tgctggcagt acgtgtcaa                                   39

<210> SEQ ID NO 204
<211> LENGTH: 39
<212> TYPE: DNA
<213> ORGANISM: Artificial sequence
<220> FEATURE:
<223> OTHER INFORMATION: Primer

<400> SEQUENCE: 204
tgtaaaacga cggccagttc gctggctcag agtttgctt            39

<210> SEQ ID NO 205
<211> LENGTH: 40
<212> TYPE: DNA
<213> ORGANISM: Artificial sequence
<220> FEATURE:
<223> OTHER INFORMATION: Primer

<400> SEQUENCE: 205
aggaaacagc tatgaccatg tgctagagag ctgctttctt           40

<210> SEQ ID NO 206
<211> LENGTH: 39
<212> TYPE: DNA
<213> ORGANISM: Artificial sequence
<220> FEATURE:
<223> OTHER INFORMATION: Primer

<400> SEQUENCE: 206
tgtaaaacga cggccagtcc cctcagcaaa tacgaaaac            39

<210> SEQ ID NO 207
<211> LENGTH: 40
<212> TYPE: DNA
<213> ORGANISM: Artificial sequence
<220> FEATURE:
<223> OTHER INFORMATION: Primer

<400> SEQUENCE: 207
aggaaacagc tatgaccata ctacgaaggc atcctggaaa           40

<210> SEQ ID NO 208
<211> LENGTH: 40
<212> TYPE: DNA
<213> ORGANISM: Artificial sequence
<220> FEATURE:
<223> OTHER INFORMATION: Primer

<400> SEQUENCE: 208
tgtaaaacga cggccagtgc ctctgcactt tactatgatg           40

<210> SEQ ID NO 209
<211> LENGTH: 40
<212> TYPE: DNA
<213> ORGANISM: Artificial sequence
<220> FEATURE:
<223> OTHER INFORMATION: Primer

<400> SEQUENCE: 209
aggaaacagc tatgaccatc tcctccaagt ttccgttatg           40

<210> SEQ ID NO 210
<211> LENGTH: 38
<212> TYPE: DNA
<213> ORGANISM: Artificial sequence
<220> FEATURE:
<223> OTHER INFORMATION: Primer

<400> SEQUENCE: 210
tgtaaaacga cggccagtgg tgacctcaca ggaatcag             38

<210> SEQ ID NO 211
<211> LENGTH: 40
<212> TYPE: DNA
<213> ORGANISM: Artificial sequence
<220> FEATURE:
<223> OTHER INFORMATION: Primer

<400> SEQUENCE: 211
aggaaacagc tatgaccatt ttccaagagg agggacatag                40

<210> SEQ ID NO 212
<211> LENGTH: 39
<212> TYPE: DNA
<213> ORGANISM: Artificial sequence
<220> FEATURE:
<223> OTHER INFORMATION: Primer

<400> SEQUENCE: 212
tgtaaaacga cggccagtca actggttccg agagattgt                 39

<210> SEQ ID NO 213
<211> LENGTH: 41
<212> TYPE: DNA
<213> ORGANISM: Artificial sequence
<220> FEATURE:
<223> OTHER INFORMATION: Primer

<400> SEQUENCE: 213
aggaaacagc tatgaccatc aatgtccagc tctcggaaaa a              41

<210> SEQ ID NO 214
<211> LENGTH: 39
<212> TYPE: DNA
<213> ORGANISM: Artificial sequence
<220> FEATURE:
<223> OTHER INFORMATION: Primer

<400> SEQUENCE: 214
tgtaaaacga cggccagtgt gaccctacgc catctcata                 39

<210> SEQ ID NO 215
<211> LENGTH: 40
<212> TYPE: DNA
<213> ORGANISM: Artificial sequence
<220> FEATURE:
<223> OTHER INFORMATION: Primer

<400> SEQUENCE: 215
aggaaacagc tatgaccata cattggggtc agcagttgaa                40

<210> SEQ ID NO 216
<211> LENGTH: 40
<212> TYPE: DNA
<213> ORGANISM: Artificial sequence
<220> FEATURE:
<223> OTHER INFORMATION: Primer

<400> SEQUENCE: 216
tgtaaaacga cggccagtag agtccccttt ctcaagaaca                40

<210> SEQ ID NO 217
<211> LENGTH: 39
<212> TYPE: DNA
<213> ORGANISM: Artificial sequence
<220> FEATURE:
<223> OTHER INFORMATION: Primer

<400> SEQUENCE: 217
aggaaacagc tatgaccatg acgctctggc tgagtagtt                 39

```
<210> SEQ ID NO 218
<211> LENGTH: 38
<212> TYPE: DNA
<213> ORGANISM: Artificial sequence
<220> FEATURE:
<223> OTHER INFORMATION: Primer

<400> SEQUENCE: 218
tgtaaaacga cggccagtca gccctccatg tccttagt                              38

<210> SEQ ID NO 219
<211> LENGTH: 39
<212> TYPE: DNA
<213> ORGANISM: Artificial sequence
<220> FEATURE:
<223> OTHER INFORMATION: Primer

<400> SEQUENCE: 219
aggaaacagc tatgaccata gggaatgtgg aggaagatg                             39

<210> SEQ ID NO 220
<211> LENGTH: 38
<212> TYPE: DNA
<213> ORGANISM: Artificial sequence
<220> FEATURE:
<223> OTHER INFORMATION: Primer

<400> SEQUENCE: 220
tgtaaaacga cggccagttg gagcacacag agagcatt                              38

<210> SEQ ID NO 221
<211> LENGTH: 39
<212> TYPE: DNA
<213> ORGANISM: Artificial sequence
<220> FEATURE:
<223> OTHER INFORMATION: Primer

<400> SEQUENCE: 221
aggaaacagc tatgaccatg tctaggagcg gcatacatt                             39

<210> SEQ ID NO 222
<211> LENGTH: 39
<212> TYPE: DNA
<213> ORGANISM: Artificial sequence
<220> FEATURE:
<223> OTHER INFORMATION: Primer

<400> SEQUENCE: 222
tgtaaaacga cggccagtag cagactcgca gcagattca                             39

<210> SEQ ID NO 223
<211> LENGTH: 39
<212> TYPE: DNA
<213> ORGANISM: Artificial sequence
<220> FEATURE:
<223> OTHER INFORMATION: Primer

<400> SEQUENCE: 223
aggaaacagc tatgaccata gccagaaagc ctctctaca                             39

<210> SEQ ID NO 224
<211> LENGTH: 38
<212> TYPE: DNA
<213> ORGANISM: Artificial sequence
<220> FEATURE:
<223> OTHER INFORMATION: Primer
```

```
<400> SEQUENCE: 224
tgtaaaacga cggccagtac acgagactca cccaacat                             38

<210> SEQ ID NO 225
<211> LENGTH: 40
<212> TYPE: DNA
<213> ORGANISM: Artificial sequence
<220> FEATURE:
<223> OTHER INFORMATION: Primer

<400> SEQUENCE: 225
aggaaacagc tatgaccatg ggaatggaaa tgggcataga                           40

<210> SEQ ID NO 226
<211> LENGTH: 39
<212> TYPE: DNA
<213> ORGANISM: Artificial sequence
<220> FEATURE:
<223> OTHER INFORMATION: Primer

<400> SEQUENCE: 226
aggaaacagc tatgaccatg acacagaagc aggcaacaa                            39

<210> SEQ ID NO 227
<211> LENGTH: 39
<212> TYPE: DNA
<213> ORGANISM: Artificial sequence
<220> FEATURE:
<223> OTHER INFORMATION: Primer

<400> SEQUENCE: 227
tgtaaaacga cggccagtag agcaaagcca ctgaggtat                            39

<210> SEQ ID NO 228
<211> LENGTH: 40
<212> TYPE: DNA
<213> ORGANISM: Artificial sequence
<220> FEATURE:
<223> OTHER INFORMATION: Primer

<400> SEQUENCE: 228
aggaaacagc tatgaccatg actctgtgct ttggctttca                           40

<210> SEQ ID NO 229
<211> LENGTH: 20
<212> TYPE: DNA
<213> ORGANISM: Artificial sequence
<220> FEATURE:
<223> OTHER INFORMATION: Primer

<400> SEQUENCE: 229
gcacctcatg gaatcccttc                                                 20

<210> SEQ ID NO 230
<211> LENGTH: 20
<212> TYPE: DNA
<213> ORGANISM: Artificial sequence
<220> FEATURE:
<223> OTHER INFORMATION: Primer

<400> SEQUENCE: 230
gttgctgcac caggtggtaa                                                 20

<210> SEQ ID NO 231
```

```
<211> LENGTH: 30
<212> TYPE: DNA
<213> ORGANISM: Artificial sequence
<220> FEATURE:
<223> OTHER INFORMATION: Primer

<400> SEQUENCE: 231
tttttgcgtt tgttggagaa tcgggttttc                                          30

<210> SEQ ID NO 232
<211> LENGTH: 30
<212> TYPE: DNA
<213> ORGANISM: Artificial sequence
<220> FEATURE:
<223> OTHER INFORMATION: Primer

<400> SEQUENCE: 232
atacaccgca aaccgccgac gaacaaaacg                                          30

<210> SEQ ID NO 233
<211> LENGTH: 30
<212> TYPE: DNA
<213> ORGANISM: Artificial sequence
<220> FEATURE:
<223> OTHER INFORMATION: Primer

<400> SEQUENCE: 233
tttttgtgtt tgttggagaa ttgggttttt                                          30

<210> SEQ ID NO 234
<211> LENGTH: 30
<212> TYPE: DNA
<213> ORGANISM: Artificial sequence
<220> FEATURE:
<223> OTHER INFORMATION: Primer

<400> SEQUENCE: 234
atacaccaca aaccaccaac aaacaaaaca                                          30

<210> SEQ ID NO 235
<211> LENGTH: 20
<212> TYPE: DNA
<213> ORGANISM: Artificial sequence
<220> FEATURE:
<223> OTHER INFORMATION: Primer

<400> SEQUENCE: 235
ggcccacagt ttccgtttct                                                     20

<210> SEQ ID NO 236
<211> LENGTH: 23
<212> TYPE: DNA
<213> ORGANISM: Artificial sequence
<220> FEATURE:
<223> OTHER INFORMATION: Primer

<400> SEQUENCE: 236
caaggaagct agaaatgaag aac                                                 23

<210> SEQ ID NO 237
<211> LENGTH: 21
<212> TYPE: DNA
<213> ORGANISM: Artificial sequence
<220> FEATURE:
<223> OTHER INFORMATION: Primer

<400> SEQUENCE: 237
```
ctgggactac agacacgttt t            21

<210> SEQ ID NO 238
<211> LENGTH: 21
<212> TYPE: DNA
<213> ORGANISM: Artificial sequence
<220> FEATURE:
<223> OTHER INFORMATION: Primer

<400> SEQUENCE: 238
gtgtcacgtg tctgtaatct c            21

<210> SEQ ID NO 239
<211> LENGTH: 21
<212> TYPE: DNA
<213> ORGANISM: Artificial sequence
<220> FEATURE:
<223> OTHER INFORMATION: Primer

<400> SEQUENCE: 239
ttaagaccca gcgaggtatt c            21

<210> SEQ ID NO 240
<211> LENGTH: 21
<212> TYPE: DNA
<213> ORGANISM: Artificial sequence
<220> FEATURE:
<223> OTHER INFORMATION: Primer

<400> SEQUENCE: 240
tgggtttggt agggtaatgt c            21

<210> SEQ ID NO 241
<211> LENGTH: 21
<212> TYPE: DNA
<213> ORGANISM: Artificial sequence
<220> FEATURE:
<223> OTHER INFORMATION: Primer

<400> SEQUENCE: 241
tggaaagtca ctgcggagaa a            21

<210> SEQ ID NO 242
<211> LENGTH: 21
<212> TYPE: DNA
<213> ORGANISM: Artificial sequence
<220> FEATURE:
<223> OTHER INFORMATION: Primer

<400> SEQUENCE: 242
acgtaatcac ccctgtaatc c            21

<210> SEQ ID NO 243
<211> LENGTH: 21
<212> TYPE: DNA
<213> ORGANISM: Artificial sequence
<220> FEATURE:
<223> OTHER INFORMATION: Primer

<400> SEQUENCE: 243
cactgcaaac tgctcactca a            21

<210> SEQ ID NO 244
<211> LENGTH: 21
<212> TYPE: DNA

```
<213> ORGANISM: Artificial sequence
<220> FEATURE:
<223> OTHER INFORMATION: Primer

<400> SEQUENCE: 244
ggccttgtgc taagtgcttt t                                              21

<210> SEQ ID NO 245
<211> LENGTH: 21
<212> TYPE: DNA
<213> ORGANISM: Artificial sequence
<220> FEATURE:
<223> OTHER INFORMATION: Primer

<400> SEQUENCE: 245
accctggtgg acataccttt t                                              21

<210> SEQ ID NO 246
<211> LENGTH: 21
<212> TYPE: DNA
<213> ORGANISM: Artificial sequence
<220> FEATURE:
<223> OTHER INFORMATION: Primer

<400> SEQUENCE: 246
ccaaagtact gggagtttga g                                              21

<210> SEQ ID NO 247
<211> LENGTH: 21
<212> TYPE: DNA
<213> ORGANISM: Artificial sequence
<220> FEATURE:
<223> OTHER INFORMATION: Primer

<400> SEQUENCE: 247
tctgggcaac agaacaagca a                                              21

<210> SEQ ID NO 248
<211> LENGTH: 22
<212> TYPE: DNA
<213> ORGANISM: Artificial sequence
<220> FEATURE:
<223> OTHER INFORMATION: Primer

<400> SEQUENCE: 248
gagcaattta gcctgtggtt tt                                             22

<210> SEQ ID NO 249
<211> LENGTH: 20
<212> TYPE: DNA
<213> ORGANISM: Artificial sequence
<220> FEATURE:
<223> OTHER INFORMATION: Primer

<400> SEQUENCE: 249
accatctggc cgacatggta                                                20

<210> SEQ ID NO 250
<211> LENGTH: 21
<212> TYPE: DNA
<213> ORGANISM: Artificial sequence
<220> FEATURE:
<223> OTHER INFORMATION: Primer

<400> SEQUENCE: 250
agggtcctga gactatatac c                                              21
```

<210> SEQ ID NO 251
<211> LENGTH: 20
<212> TYPE: DNA
<213> ORGANISM: Artificial sequence
<220> FEATURE:
<223> OTHER INFORMATION: Primer

<400> SEQUENCE: 251
tcccatctca gggcagatga                                              20

<210> SEQ ID NO 252
<211> LENGTH: 20
<212> TYPE: DNA
<213> ORGANISM: Artificial sequence
<220> FEATURE:
<223> OTHER INFORMATION: Primer

<400> SEQUENCE: 252
tatgcccggc tagcacagaa                                              20

<210> SEQ ID NO 253
<211> LENGTH: 21
<212> TYPE: DNA
<213> ORGANISM: Artificial sequence
<220> FEATURE:
<223> OTHER INFORMATION: Primer

<400> SEQUENCE: 253
tctctcacat gcctcacaca t                                            21

<210> SEQ ID NO 254
<211> LENGTH: 21
<212> TYPE: DNA
<213> ORGANISM: Artificial sequence
<220> FEATURE:
<223> OTHER INFORMATION: Primer

<400> SEQUENCE: 254
cccctctgat tttggataga g                                            21

<210> SEQ ID NO 255
<211> LENGTH: 21
<212> TYPE: DNA
<213> ORGANISM: Artificial sequence
<220> FEATURE:
<223> OTHER INFORMATION: Primer

<400> SEQUENCE: 255
aagatggatg gccctctgat t                                            21

<210> SEQ ID NO 256
<211> LENGTH: 22
<212> TYPE: DNA
<213> ORGANISM: Artificial sequence
<220> FEATURE:
<223> OTHER INFORMATION: Primer'

<400> SEQUENCE: 256
gacacatcag ttttcctctc at                                           22

<210> SEQ ID NO 257
<211> LENGTH: 22
<212> TYPE: DNA
<213> ORGANISM: Artificial sequence
<220> FEATURE:

<223> OTHER INFORMATION: Primer

<400> SEQUENCE: 257
aatcattcta gcccactcaa ct                        22

<210> SEQ ID NO 258
<211> LENGTH: 22
<212> TYPE: DNA
<213> ORGANISM: Artificial sequence
<220> FEATURE:
<223> OTHER INFORMATION: Primer

<400> SEQUENCE: 258
tggtttcatc aggcaagaaa ct                        22

<210> SEQ ID NO 259
<211> LENGTH: 21
<212> TYPE: DNA
<213> ORGANISM: Artificial sequence
<220> FEATURE:
<223> OTHER INFORMATION: Primer

<400> SEQUENCE: 259
agccccatga agttggcaaa a                         21

<210> SEQ ID NO 260
<211> LENGTH: 21
<212> TYPE: DNA
<213> ORGANISM: Artificial sequence
<220> FEATURE:
<223> OTHER INFORMATION: Primer

<400> SEQUENCE: 260
gcttgtgcca gcataactct a                         21

<210> SEQ ID NO 261
<211> LENGTH: 21
<212> TYPE: DNA
<213> ORGANISM: Artificial sequence
<220> FEATURE:
<223> OTHER INFORMATION: Primer

<400> SEQUENCE: 261
gctgtgctaa agctgctaca a                         21

<210> SEQ ID NO 262
<211> LENGTH: 21
<212> TYPE: DNA
<213> ORGANISM: Artificial sequence
<220> FEATURE:
<223> OTHER INFORMATION: Primer

<400> SEQUENCE: 262
gagccatctg ctcatttctg t                         21

<210> SEQ ID NO 263
<211> LENGTH: 22
<212> TYPE: DNA
<213> ORGANISM: Artificial sequence
<220> FEATURE:
<223> OTHER INFORMATION: Primer

<400> SEQUENCE: 263
cagagaaacc aatagttttc ag                        22

<210> SEQ ID NO 264
<211> LENGTH: 21
<212> TYPE: DNA
<213> ORGANISM: Artificial sequence
<220> FEATURE:
<223> OTHER INFORMATION: Primer

<400> SEQUENCE: 264
aatctcggct cactgcaatc t                                              21

<210> SEQ ID NO 265
<211> LENGTH: 22
<212> TYPE: DNA
<213> ORGANISM: Artificial sequence
<220> FEATURE:
<223> OTHER INFORMATION: Primer

<400> SEQUENCE: 265
agctaatgga tggatggaaa ag                                             22

<210> SEQ ID NO 266
<211> LENGTH: 21
<212> TYPE: DNA
<213> ORGANISM: Artificial sequence
<220> FEATURE:
<223> OTHER INFORMATION: Primer

<400> SEQUENCE: 266
tagtgcagtg ccgaatgcat a                                              21

<210> SEQ ID NO 267
<211> LENGTH: 21
<212> TYPE: DNA
<213> ORGANISM: Artificial sequence
<220> FEATURE:
<223> OTHER INFORMATION: Primer

<400> SEQUENCE: 267
tactcatgaa gggggtatc a                                               21

<210> SEQ ID NO 268
<211> LENGTH: 22
<212> TYPE: DNA
<213> ORGANISM: Artificial sequence
<220> FEATURE:
<223> OTHER INFORMATION: Primer

<400> SEQUENCE: 268
ttcacacgta ggtagtcttt ct                                             22

<210> SEQ ID NO 269
<211> LENGTH: 21
<212> TYPE: DNA
<213> ORGANISM: Artificial sequence
<220> FEATURE:
<223> OTHER INFORMATION: Primer

<400> SEQUENCE: 269
cattactccc aaggcaatga c                                              21

<210> SEQ ID NO 270
<211> LENGTH: 20
<212> TYPE: DNA
<213> ORGANISM: Artificial sequence
<220> FEATURE:
<223> OTHER INFORMATION: Primer

<400> SEQUENCE: 270
gcccagctct gttcaaacca                                            20

<210> SEQ ID NO 271
<211> LENGTH: 21
<212> TYPE: DNA
<213> ORGANISM: Artificial sequence
<220> FEATURE:
<223> OTHER INFORMATION: Primer

<400> SEQUENCE: 271
agctccattc tctcctctga a                                          21

<210> SEQ ID NO 272
<211> LENGTH: 21
<212> TYPE: DNA
<213> ORGANISM: Artificial sequence
<220> FEATURE:
<223> OTHER INFORMATION: Primer

<400> SEQUENCE: 272
gtgggaagat ggagtaagag a                                          21

<210> SEQ ID NO 273
<211> LENGTH: 21
<212> TYPE: DNA
<213> ORGANISM: Artificial sequence
<220> FEATURE:
<223> OTHER INFORMATION: Primer

<400> SEQUENCE: 273
tctgacagtg ggatgtcaga a                                          21

<210> SEQ ID NO 274
<211> LENGTH: 21
<212> TYPE: DNA
<213> ORGANISM: Artificial sequence
<220> FEATURE:
<223> OTHER INFORMATION: Primer

<400> SEQUENCE: 274
tgcctaccca ctatgaatga g                                          21

<210> SEQ ID NO 275
<211> LENGTH: 21
<212> TYPE: DNA
<213> ORGANISM: Artificial sequence
<220> FEATURE:
<223> OTHER INFORMATION: Primer

<400> SEQUENCE: 275
atgtgtccat ctggcaacca t                                          21

<210> SEQ ID NO 276
<211> LENGTH: 21
<212> TYPE: DNA
<213> ORGANISM: Artificial sequence
<220> FEATURE:
<223> OTHER INFORMATION: Primer

<400> SEQUENCE: 276
caggaactcc gatcttgtaa g                                          21

<210> SEQ ID NO 277
<211> LENGTH: 20

```
<212> TYPE: DNA
<213> ORGANISM: Artificial sequence
<220> FEATURE:
<223> OTHER INFORMATION: Primer

<400> SEQUENCE: 277 tggaggggggg agaaagaaag                                              20

<210> SEQ ID NO 278
<211> LENGTH: 21
<212> TYPE: DNA
<213> ORGANISM: Artificial sequence
<220> FEATURE:
<223> OTHER INFORMATION: Primer

<400> SEQUENCE: 278
cgtgtttcgc tgatgtgtca t                                             21

<210> SEQ ID NO 279
<211> LENGTH: 21
<212> TYPE: DNA
<213> ORGANISM: Artificial sequence
<220> FEATURE:
<223> OTHER INFORMATION: Primer

<400> SEQUENCE: 279
ggaaggccag tttgtcaaag t                                             21

<210> SEQ ID NO 280
<211> LENGTH: 21
<212> TYPE: DNA
<213> ORGANISM: Artificial sequence
<220> FEATURE:
<223> OTHER INFORMATION: Primer

<400> SEQUENCE: 280
gtgtttgacc tggtgatgct t                                             21

<210> SEQ ID NO 281
<211> LENGTH: 23
<212> TYPE: DNA
<213> ORGANISM: Artificial sequence
<220> FEATURE:
<223> OTHER INFORMATION: Primer

<400> SEQUENCE: 281
cttatttctt agcaccctgt caa                                           23

<210> SEQ ID NO 282
<211> LENGTH: 22
<212> TYPE: DNA
<213> ORGANISM: Artificial sequence
<220> FEATURE:
<223> OTHER INFORMATION: Primer

<400> SEQUENCE: 282
gtggaacaaa tgagcattat cc                                            22

<210> SEQ ID NO 283
<211> LENGTH: 21
<212> TYPE: DNA
<213> ORGANISM: Artificial sequence
<220> FEATURE:
<223> OTHER INFORMATION: Primer

<400> SEQUENCE: 283
```

```
ttccccttca gtgagttcca a                                              21
```

<210> SEQ ID NO 284
<211> LENGTH: 21
<212> TYPE: DNA
<213> ORGANISM: Artificial sequence
<220> FEATURE:
<223> OTHER INFORMATION: Primer

<400> SEQUENCE: 284

```
agggaggaga agtctgacat t                                              21
```

<210> SEQ ID NO 285
<211> LENGTH: 22
<212> TYPE: DNA
<213> ORGANISM: Artificial sequence
<220> FEATURE:
<223> OTHER INFORMATION: Primer

<400> SEQUENCE: 285

```
gattagcctg taggttaggt at                                             22
```

<210> SEQ ID NO 286
<211> LENGTH: 21
<212> TYPE: DNA
<213> ORGANISM: Artificial sequence
<220> FEATURE:
<223> OTHER INFORMATION: Primer

<400> SEQUENCE: 286

```
gatgggtttg ggttgattgt g                                              21
```

<210> SEQ ID NO 287
<211> LENGTH: 20
<212> TYPE: DNA
<213> ORGANISM: Artificial sequence
<220> FEATURE:
<223> OTHER INFORMATION: Primer

<400> SEQUENCE: 287

```
ccagtctagg agacagagct                                                20
```

<210> SEQ ID NO 288
<211> LENGTH: 22
<212> TYPE: DNA
<213> ORGANISM: Artificial sequence
<220> FEATURE:
<223> OTHER INFORMATION: Primer

<400> SEQUENCE: 288

```
ggctatctat gtgtgtctct tt                                             22
```

<210> SEQ ID NO 289
<211> LENGTH: 22
<212> TYPE: DNA
<213> ORGANISM: Artificial sequence
<220> FEATURE:
<223> OTHER INFORMATION: Primer

<400> SEQUENCE: 289

```
acgattagaa gggaacatgg aa                                             22
```

<210> SEQ ID NO 290
<211> LENGTH: 22
<212> TYPE: DNA
<213> ORGANISM: Artificial sequence

```
<220> FEATURE:
<223> OTHER INFORMATION: Primer

<400> SEQUENCE: 290
cgatatccat accttctttt gc                                              22

<210> SEQ ID NO 291
<211> LENGTH: 21
<212> TYPE: DNA
<213> ORGANISM: Artificial sequence
<220> FEATURE:
<223> OTHER INFORMATION: Primer

<400> SEQUENCE: 291
tgacagagcg agactctcta a                                               21

<210> SEQ ID NO 292
<211> LENGTH: 21
<212> TYPE: DNA
<213> ORGANISM: Artificial sequence
<220> FEATURE:
<223> OTHER INFORMATION: Primer

<400> SEQUENCE: 292
cacaccaaca tggcacatgt a                                               21

<210> SEQ ID NO 293
<211> LENGTH: 20
<212> TYPE: DNA
<213> ORGANISM: Artificial sequence
<220> FEATURE:
<223> OTHER INFORMATION: Primer

<400> SEQUENCE: 293
gagacagggt agggcagaaa                                                 20

<210> SEQ ID NO 294
<211> LENGTH: 20
<212> TYPE: DNA
<213> ORGANISM: Artificial sequence
<220> FEATURE:
<223> OTHER INFORMATION: Primer

<400> SEQUENCE: 294 aaagggggcga gtggagtttg                                                20

<210> SEQ ID NO 295
<211> LENGTH: 22
<212> TYPE: DNA
<213> ORGANISM: Artificial sequence
<220> FEATURE:
<223> OTHER INFORMATION: Primer

<400> SEQUENCE: 295
gtaacttcac cagtgcaacc aa                                              22

<210> SEQ ID NO 296
<211> LENGTH: 22
<212> TYPE: DNA
<213> ORGANISM: Artificial sequence
<220> FEATURE:
<223> OTHER INFORMATION: Primer

<400> SEQUENCE: 296
atgcactctc tcttttctac tt                                              22
```

```
<210> SEQ ID NO 297
<211> LENGTH: 21
<212> TYPE: DNA
<213> ORGANISM: Artificial sequence
<220> FEATURE:
<223> OTHER INFORMATION: Primer

<400> SEQUENCE: 297
acaaggaatc tgccccattc t                                              21

<210> SEQ ID NO 298
<211> LENGTH: 21
<212> TYPE: DNA
<213> ORGANISM: Artificial sequence
<220> FEATURE:
<223> OTHER INFORMATION: Primer

<400> SEQUENCE: 298
ttccctgtag ccttgcgtat t                                              21

<210> SEQ ID NO 299
<211> LENGTH: 21
<212> TYPE: DNA
<213> ORGANISM: Artificial sequence
<220> FEATURE:
<223> OTHER INFORMATION: Primer

<400> SEQUENCE: 299
ccccacatac accatgtatt g                                              21

<210> SEQ ID NO 300
<211> LENGTH: 21
<212> TYPE: DNA
<213> ORGANISM: Artificial sequence
<220> FEATURE:
<223> OTHER INFORMATION: Primer

<400> SEQUENCE: 300
ctccctatgt acgtggagta a                                              21

<210> SEQ ID NO 301
<211> LENGTH: 21
<212> TYPE: DNA
<213> ORGANISM: Artificial sequence
<220> FEATURE:
<223> OTHER INFORMATION: Primer

<400> SEQUENCE: 301
gtgggacata acagctagag a                                              21

<210> SEQ ID NO 302
<211> LENGTH: 22
<212> TYPE: DNA
<213> ORGANISM: Artificial sequence
<220> FEATURE:
<223> OTHER INFORMATION: Primer

<400> SEQUENCE: 302
aggggaaagt aaatagcaag ga                                             22

<210> SEQ ID NO 303
<211> LENGTH: 21
<212> TYPE: DNA
<213> ORGANISM: Artificial sequence
<220> FEATURE:
<223> OTHER INFORMATION: Primer
```

<400> SEQUENCE: 303
tcagggatat tggcctgaga t                                              21

<210> SEQ ID NO 304
<211> LENGTH: 21
<212> TYPE: DNA
<213> ORGANISM: Artificial sequence
<220> FEATURE:
<223> OTHER INFORMATION: Primer

<400> SEQUENCE: 304
gacatctctc agctctggat a                                              21

<210> SEQ ID NO 305
<211> LENGTH: 22
<212> TYPE: DNA
<213> ORGANISM: Artificial sequence
<220> FEATURE:
<223> OTHER INFORMATION: Primer

<400> SEQUENCE: 305
ccaattactg atgccatgat ac                                             22

<210> SEQ ID NO 306
<211> LENGTH: 21
<212> TYPE: DNA
<213> ORGANISM: Artificial sequence
<220> FEATURE:
<223> OTHER INFORMATION: Primer

<400> SEQUENCE: 306
gcattcagcc atgcttggta a                                              21

<210> SEQ ID NO 307
<211> LENGTH: 21
<212> TYPE: DNA
<213> ORGANISM: Artificial sequence
<220> FEATURE:
<223> OTHER INFORMATION: Primer

<400> SEQUENCE: 307
gattactcca acgcctaaga g                                              21

<210> SEQ ID NO 308
<211> LENGTH: 21
<212> TYPE: DNA
<213> ORGANISM: Artificial sequence
<220> FEATURE:
<223> OTHER INFORMATION: Primer

<400> SEQUENCE: 308
tctacctcta ggcagtttcc a                                              21

<210> SEQ ID NO 309
<211> LENGTH: 21
<212> TYPE: DNA
<213> ORGANISM: Artificial sequence
<220> FEATURE:
<223> OTHER INFORMATION: Primer

<400> SEQUENCE: 309
tctcctcagt gtcacagtgt t                                              21

<210> SEQ ID NO 310

```
<211> LENGTH: 21
<212> TYPE: DNA
<213> ORGANISM: Artificial sequence
<220> FEATURE:
<223> OTHER INFORMATION: Primer

<400> SEQUENCE: 310
cttgggctag aggaagttgt t                                              21

<210> SEQ ID NO 311
<211> LENGTH: 21
<212> TYPE: DNA
<213> ORGANISM: Artificial sequence
<220> FEATURE:
<223> OTHER INFORMATION: Primer

<400> SEQUENCE: 311
tacccagtga cccaaacaca a                                              21

<210> SEQ ID NO 312
<211> LENGTH: 21
<212> TYPE: DNA
<213> ORGANISM: Artificial sequence
<220> FEATURE:
<223> OTHER INFORMATION: Primer

<400> SEQUENCE: 312
gagttcaagg ctggaatagc t                                              21

<210> SEQ ID NO 313
<211> LENGTH: 21
<212> TYPE: DNA
<213> ORGANISM: Artificial sequence
<220> FEATURE:
<223> OTHER INFORMATION: Primer

<400> SEQUENCE: 313
accgtgattc tcagcagcta a                                              21

<210> SEQ ID NO 314
<211> LENGTH: 21
<212> TYPE: DNA
<213> ORGANISM: Artificial sequence
<220> FEATURE:
<223> OTHER INFORMATION: Primer

<400> SEQUENCE: 314
ccattgcgaa cccttagttt c                                              21

<210> SEQ ID NO 315
<211> LENGTH: 21
<212> TYPE: DNA
<213> ORGANISM: Artificial sequence
<220> FEATURE:
<223> OTHER INFORMATION: Primer

<400> SEQUENCE: 315
agtgccttgg tgactgtcaa a                                              21

<210> SEQ ID NO 316
<211> LENGTH: 21
<212> TYPE: DNA
<213> ORGANISM: Artificial sequence
<220> FEATURE:
<223> OTHER INFORMATION: Primer

<400> SEQUENCE: 316
```
ccacctggag aacattcaca a          21

<210> SEQ ID NO 317
<211> LENGTH: 22
<212> TYPE: DNA
<213> ORGANISM: Artificial sequence
<220> FEATURE:
<223> OTHER INFORMATION: Primer

<400> SEQUENCE: 317
tactgaaaga cacccaggtt at         22

<210> SEQ ID NO 318
<211> LENGTH: 20
<212> TYPE: DNA
<213> ORGANISM: Artificial sequence
<220> FEATURE:
<223> OTHER INFORMATION: Primer

<400> SEQUENCE: 318
cacgcccgac ctctcaattc            20

<210> SEQ ID NO 319
<211> LENGTH: 21
<212> TYPE: DNA
<213> ORGANISM: Artificial sequence
<220> FEATURE:
<223> OTHER INFORMATION: Primer

<400> SEQUENCE: 319
tatagcaaga gggcctatcc a          21

<210> SEQ ID NO 320
<211> LENGTH: 21
<212> TYPE: DNA
<213> ORGANISM: Artificial sequence
<220> FEATURE:
<223> OTHER INFORMATION: Primer

<400> SEQUENCE: 320
ttgggcacgt catgtggatt t          21

<210> SEQ ID NO 321
<211> LENGTH: 21
<212> TYPE: DNA
<213> ORGANISM: Artificial sequence
<220> FEATURE:
<223> OTHER INFORMATION: Primer

<400> SEQUENCE: 321
gtccagtctc tgacaaacaa c          21

<210> SEQ ID NO 322
<211> LENGTH: 21
<212> TYPE: DNA
<213> ORGANISM: Artificial sequence
<220> FEATURE:
<223> OTHER INFORMATION: Primer

<400> SEQUENCE: 322
ttagaccggg aacgtcttag t          21

<210> SEQ ID NO 323
<211> LENGTH: 20
<212> TYPE: DNA

```
<213> ORGANISM: Artificial sequence
<220> FEATURE:
<223> OTHER INFORMATION: Primer

<400> SEQUENCE: 323
ggccaagtgg gtctcaaaac                                                    20

<210> SEQ ID NO 324
<211> LENGTH: 22
<212> TYPE: DNA
<213> ORGANISM: Artificial sequence
<220> FEATURE:
<223> OTHER INFORMATION: Primer

<400> SEQUENCE: 324
cctctggttc tgttttatac tg                                                 22

<210> SEQ ID NO 325
<211> LENGTH: 21
<212> TYPE: DNA
<213> ORGANISM: Artificial sequence
<220> FEATURE:
<223> OTHER INFORMATION: Primer

<400> SEQUENCE: 325
tctgggcaac agaacaagca a                                                  21

<210> SEQ ID NO 326
<211> LENGTH: 21
<212> TYPE: DNA
<213> ORGANISM: Artificial sequence
<220> FEATURE:
<223> OTHER INFORMATION: Primer

<400> SEQUENCE: 326
cttcccaggt agttctaagc a                                                  21

<210> SEQ ID NO 327
<211> LENGTH: 21
<212> TYPE: DNA
<213> ORGANISM: Artificial sequence
<220> FEATURE:
<223> OTHER INFORMATION: Primer

<400> SEQUENCE: 327
aagccaggac acttggtttc t                                                  21

<210> SEQ ID NO 328
<211> LENGTH: 21
<212> TYPE: DNA
<213> ORGANISM: Artificial sequence
<220> FEATURE:
<223> OTHER INFORMATION: Primer

<400> SEQUENCE: 328
gcactggttg ctacatctaa g                                                  21

<210> SEQ ID NO 329
<211> LENGTH: 21
<212> TYPE: DNA
<213> ORGANISM: Artificial sequence
<220> FEATURE:
<223> OTHER INFORMATION: Primer

<400> SEQUENCE: 329
gcatccattg ccttccctaa a                                                  21
```

```
<210> SEQ ID NO 330
<211> LENGTH: 21
<212> TYPE: DNA
<213> ORGANISM: Artificial sequence
<220> FEATURE:
<223> OTHER INFORMATION: Primer

<400> SEQUENCE: 330
tgctcaaagg agcagatctc a                                              21

<210> SEQ ID NO 331
<211> LENGTH: 21
<212> TYPE: DNA
<213> ORGANISM: Artificial sequence
<220> FEATURE:
<223> OTHER INFORMATION: Primer

<400> SEQUENCE: 331
cagtccaatt tggggatctc t                                              21

<210> SEQ ID NO 332
<211> LENGTH: 20
<212> TYPE: DNA
<213> ORGANISM: Artificial sequence
<220> FEATURE:
<223> OTHER INFORMATION: Primer

<400> SEQUENCE: 332
ccttgggctg gatgagacta                                                20

<210> SEQ ID NO 333
<211> LENGTH: 21
<212> TYPE: DNA
<213> ORGANISM: Artificial sequence
<220> FEATURE:
<223> OTHER INFORMATION: Primer

<400> SEQUENCE: 333
ccccaatagc aactgcagat t                                              21

<210> SEQ ID NO 334
<211> LENGTH: 22
<212> TYPE: DNA
<213> ORGANISM: Artificial sequence
<220> FEATURE:
<223> OTHER INFORMATION: Primer

<400> SEQUENCE: 334
gattgcaagg gtatcttgaa tc                                             22

<210> SEQ ID NO 335
<211> LENGTH: 21
<212> TYPE: DNA
<213> ORGANISM: Artificial sequence
<220> FEATURE:
<223> OTHER INFORMATION: Primer

<400> SEQUENCE: 335
gcttaggtga ccttccttac a                                              21

<210> SEQ ID NO 336
<211> LENGTH: 21
<212> TYPE: DNA
<213> ORGANISM: Artificial sequence
<220> FEATURE:
```

<223> OTHER INFORMATION: Primer

<400> SEQUENCE: 336
aacataccgt tggcccatac t                                              21

<210> SEQ ID NO 337
<211> LENGTH: 20
<212> TYPE: DNA
<213> ORGANISM: Artificial sequence
<220> FEATURE:
<223> OTHER INFORMATION: Primer

<400> SEQUENCE: 337
agcatgatct cggctcacca                                                20

<210> SEQ ID NO 338
<211> LENGTH: 21
<212> TYPE: DNA
<213> ORGANISM: Artificial sequence
<220> FEATURE:
<223> OTHER INFORMATION: Primer

<400> SEQUENCE: 338
gtggctcatg cttgtaatcc t                                              21

<210> SEQ ID NO 339
<211> LENGTH: 21
<212> TYPE: DNA
<213> ORGANISM: Artificial sequence
<220> FEATURE:
<223> OTHER INFORMATION: Primer

<400> SEQUENCE: 339
tcagtagaga tggggtttca c                                              21

<210> SEQ ID NO 340
<211> LENGTH: 21
<212> TYPE: DNA
<213> ORGANISM: Artificial sequence
<220> FEATURE:
<223> OTHER INFORMATION: Primer

<400> SEQUENCE: 340
ctgccacctt agagaactga a                                              21

<210> SEQ ID NO 341
<211> LENGTH: 21
<212> TYPE: DNA
<213> ORGANISM: Artificial sequence
<220> FEATURE:
<223> OTHER INFORMATION: Primer

<400> SEQUENCE: 341
ctcaagcaat cctcctacct t                                              21

<210> SEQ ID NO 342
<211> LENGTH: 22
<212> TYPE: DNA
<213> ORGANISM: Artificial sequence
<220> FEATURE:
<223> OTHER INFORMATION: Primer

<400> SEQUENCE: 342
tagaatcact cctgagtatc tc                                             22

```
<210> SEQ ID NO 343
<211> LENGTH: 21
<212> TYPE: DNA
<213> ORGANISM: Artificial sequence
<220> FEATURE:
<223> OTHER INFORMATION: Primer

<400> SEQUENCE: 343
cagcttctga ctctgtgctt t                                    21

<210> SEQ ID NO 344
<211> LENGTH: 21
<212> TYPE: DNA
<213> ORGANISM: Artificial sequence
<220> FEATURE:
<223> OTHER INFORMATION: Primer

<400> SEQUENCE: 344
agttggtgga gcagaacttt g                                    21

<210> SEQ ID NO 345
<211> LENGTH: 21
<212> TYPE: DNA
<213> ORGANISM: Artificial sequence
<220> FEATURE:
<223> OTHER INFORMATION: Primer

<400> SEQUENCE: 345
ctcgagatac tcaggagtga t                                    21

<210> SEQ ID NO 346
<211> LENGTH: 21
<212> TYPE: DNA
<213> ORGANISM: Artificial sequence
<220> FEATURE:
<223> OTHER INFORMATION: Primer

<400> SEQUENCE: 346
tcaaccttct ccctattac c                                     21

<210> SEQ ID NO 347
<211> LENGTH: 21
<212> TYPE: DNA
<213> ORGANISM: Artificial sequence
<220> FEATURE:
<223> OTHER INFORMATION: Primer

<400> SEQUENCE: 347
agttctgctc caccaactta g                                    21

<210> SEQ ID NO 348
<211> LENGTH: 22
<212> TYPE: DNA
<213> ORGANISM: Artificial sequence
<220> FEATURE:
<223> OTHER INFORMATION: Primer

<400> SEQUENCE: 348
ggtatccatg tttgctgtgt tt                                   22

<210> SEQ ID NO 349
<211> LENGTH: 21
<212> TYPE: DNA
<213> ORGANISM: Artificial sequence
<220> FEATURE:
<223> OTHER INFORMATION: Primer
```

```
<400> SEQUENCE: 349
gaaaggcaaa cagcggattt c                                              21

<210> SEQ ID NO 350
<211> LENGTH: 21
<212> TYPE: DNA
<213> ORGANISM: Artificial sequence
<220> FEATURE:
<223> OTHER INFORMATION: Primer

<400> SEQUENCE: 350
cacccagagc agtaacctaa a                                              21

<210> SEQ ID NO 351
<211> LENGTH: 16
<212> TYPE: DNA
<213> ORGANISM: Artificial sequence
<220> FEATURE:
<223> OTHER INFORMATION: primer

<400> SEQUENCE: 351
ttctcccaaa gctgag                                                    16

<210> SEQ ID NO 352
<211> LENGTH: 17
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (2)..(2)
<223> OTHER INFORMATION: Y=pyrimidine

<400> SEQUENCE: 352
tytcttccat gtgatga                                                   17
```